(12) United States Patent
Verhoest et al.

(10) Patent No.: US 6,992,087 B2
(45) Date of Patent: Jan. 31, 2006

(54) SUBSTITUTED ARYL 1,4-PYRAZINE DERIVATIVES

(75) Inventors: Patrick R. Verhoest, Augusta, MI (US); Robert Louis Hoffman, Kalamazoo, MI (US); Jeffrey W. Corbett, Portage, MI (US); Michael Dalton Ennis, Mattawan, MI (US); Kristine E. Frank, Portage, MI (US); Jian-Min Fu, Kalamazoo, MI (US)

(73) Assignee: Pfizer Inc, New York, NY (US)

( * ) Notice: Subject to any disclaimer, the term of this patent is extended or adjusted under 35 U.S.C. 154(b) by 58 days.

(21) Appl. No.: 10/298,193

(22) Filed: Nov. 15, 2002

(65) Prior Publication Data

US 2003/0144297 A1 Jul. 31, 2003

Related U.S. Application Data

(60) Provisional application No. 60/332,052, filed on Nov. 21, 2001, provisional application No. 60/358,546, filed on Feb. 21, 2002, provisional application No. 60/388,285, filed on Jun. 13, 2002, and provisional application No. 60/410,378, filed on Sep. 13, 2002.

(51) Int. Cl.
*A61K 31/4965* (2006.01)
*C07D 241/00* (2006.01)
*C07D 241/02* (2006.01)
*B65D 75/80* (2006.01)

(52) U.S. Cl. .................. 514/255.05; 544/336; 206/828
(58) Field of Classification Search ............ 514/255.05; 544/336
See application file for complete search history.

(56) References Cited

U.S. PATENT DOCUMENTS

| 5,872,136 A | 2/1999 | Anthony et al. ............ 514/341 |
| 5,880,140 A | 3/1999 | Anthony ..................... 514/333 |
| 5,883,105 A | 3/1999 | Anthony ..................... 514/277 |
| 6,043,260 A | 3/2000 | Chen et al. .................. 514/348 |

FOREIGN PATENT DOCUMENTS

| WO | WO 97/35901 | 10/1997 |
| WO | WO 97/36886 | 10/1997 |
| WO | WO 97/36898 | 10/1997 |
| WO | WO 98/29119 | 7/1998 |
| WO | WO 98/38174 | 9/1998 |
| WO | WO 01/60806 A2 | 8/2001 |

OTHER PUBLICATIONS

Keller et al, "Corticotropin Releasing Hormone: Therapeutic Implications and Medicinal Chemistry Developments" Bioorganic & Medicinal Chemistry Letters, vol. 8(6), pp. 1213–123 (2000).*

Kobayashi et al, "Nucleosides, XIX. Synthesis, properties and chemical behavior of 1(3)–methyl–6, 7–diphenyl–3(1)–(beta–D–ribofuranosyl) lumazine derivatives" Chemische Berichte, vol. 109(9), pp. 3194–3207 (1976).*

Hawley's Condensed Chemical Dictionary, 12th ed., Richard J. Lewis, Sr. , © 1993 by Van Nostrand Reinhold, p. 594.*

Concise Chemical Dictionary, edited by Drs. Hans–Dieter Jakubke and Hans Jeschkelt, © 1993 by Walter de Gruyter & Co., p. 490.*

McGraw–Hill Dictionary of Chemical Terms, 3rd ed. edited by Sybil P. Parker, © 1984 McGraw–Hill, Inc., p. 200.*

Kehne and De Lombert, "Non–Peptidic CRF1 Receptor Treatment of Anxiety, Depression and Stress Disorders" Current Drug Targets, vol. 1(5), pp. 467–493 (2002).*

Dautzenberg and Hauger, "The CRF peptide family and their receptors: yet more partners discovered" Trends in Pharmacological Sciences, vol. 23(2), pp. 71–77 (Feb. 2002).*

Richard B. Silverman, The Organic Chemistry of Drug Design and Drug Action, pp. 352–400. © 1992 Academic Press, Inc.*

Hans Bundgaard, Design of Prodrugs, p. 1. © 1985 Elsevier Science Publishers.*

Al–Dabbagh and Smith, "Species differences in oxidative drug metabolism: some basic considerations." Archives of toxicology. Supplement. Archiv fur Toxikologie. supplement, vol. 7, pp. 219–231 (1984).

Petrusewitz and Kaliszan, "Antiaggregatory activity of imidazoline drugs and chemicals as a function of their structure" Agents and Actions, vol. 24 (1/2), pp. 204–209 (1988).

Jens Ahman, et al, "An Improved Method for the Palladium–Catalyzed Amination of Aryl Triflates", Tetrahedron Letters, vol. 38, No. 36, 1997, pp. 6363–6366.

Mihály Arato, et al, "Elevated CSF CRF in Suicide Victims", Society of biological Psychiatry, 1989; 25:355–359.

Csaba M. Banki, M.D., et al, "CSF Corticotropin–Releasing Factor–Like Immunoreactivity in Depression and Schizophrenia", Am J Psychiatry 144:7, 1987, pp. 873–877.

D.R. Britton, et al, "Intraventricular Corticotropin–Releasing Factor Enhances Behavioral Effects of Novelty", Life Sciences, vol. 31, 1982, pp. 363–367.

(Continued)

*Primary Examiner*—James O. Wilson
*Assistant Examiner*—Zachary C. Tucker
(74) *Attorney, Agent, or Firm*—Peter C. Richardson; Lorraine B. Ling; Andrea E. Dorigo

(57) ABSTRACT

Substituted aryl 1,4-pyrazine derivatives of formula I as defined herein

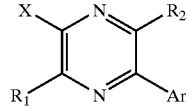

Formula I and their use in treating anxiety disorders, depression and stress related disorders are disclosed.

20 Claims, No Drawings

OTHER PUBLICATIONS

Karen Thatcher Britton, et al, "Corticotropin releasing factor and amphetamine exaggerate partial agonist properties of benzodiazepine antagonist Ro 15–1788 in the conflict test", Psychopharmacology, 94, 1988, pp. 306–311.

Adrian J. Dunn, et al, "Physiological and behavioral responses to corticotropin–releasing factor administration: is CRF a mediator of anxiety or stress responses?", Brain Research Reviews, 15, 1990, pp. 71–100.

Paul J. Fagan, et al, "Using Intelligent/Random Library Screening to Design Focused Libraries for the Optimization of Homogenous Catalysts: Ullmann Ether Formation", American Chemical Society, 122, 2000, pp. 5043–5051.

Randal D. France, et al, "CSF Corticotropin–Releasing Factor–Like Immunoactivity in Chronic Pain Patients with and without Major Depression", Society of Biological Psychiatry, 23, 1988, pp. 86–88.

Dimitri E. Grigoriadis, et al, "Effects of Chronic Antidepressant and Benzodiazepine Treatment on Corticotropin–Reseasing–Factor Receptors in Rat Brain and Pituitary", Neuropsychopharmacology, 1989, vol. 2, No. 1, pp. 53–60.

Prudencio S. Herradura, et al, "Copper–Mediated Cross–Coupling of Aryl Boronic Acids and Alkyl Thiols", Organic Letters, vol. 2, No. 14, 2000, pp. 2019–2022.

Adam F. Littke, et al, "Versatile Catalysts for the Suzuki Cross–Coupling of Arylboronic Acids with Aryl and Vinyl Halides and Triflates under Mild Conditions", American Chemical Society, 122, 2000, pp. 4020–4028.

Joseph A. Miller, et al, "Synthesis of Functionally Substituted Unsymmetrical Biaryls via a Novel Double Metal Catalyzed Coupling Reaction", Tetrahedron Letters, 39, 1998, pp. 7275–7278.

Terence N. Mitchell, "Palladium–Catalysed Reactions of Organotin Compounds", Fachbereich Chemie, 1991, pp. 803–815.

Norio Miyaura, et al, "Palladium–Catalyzed Cross–Coupling Reactions of Organoboron Compounds", Chemical Reviews, 95, 1995, pp. 2457–2483.

J. E. Morley, et al, "Neuropeptides: Conductors of the Immune Orchestra", Life Sciences, vol. 41, pp. 527–544.

Hideshi Nakamura, et al, "Synthesis and Chemiluminescence of 5–[(2–Pyridyl)–, (2–Pyrazinyl)–, and (Substituted 2–pyrazinyl)amino]–1,2,4–trioxanes", The Chemical Society of Japan, 1988, pp. 3776–3778.

Charles B. Nemeroff, et al, "Elevated Concentrations of CSF Corticotropin–Releasing Factor–Like Immunoreactivity in Depressed Patients", Science vol. 226, 1984, pp. 1342–1344.

Charles B. Nemeroff, et al, "Reduced Corticotropin Releasing Factor Binding Sites in the Frontal Cortex of Suicide Victims", Arch. Gen. Psychiatry, vol. 45, 1988, pp. 577–579.

Akihiro Ohta, et al, "Syntheses and Reactions of Some 2,5–Disubstituted Pyrazine Monoxides", Chem. Pharm. Bull. 27, 9, 1979, pp. 2027–2041.

Jean Rivier, et al, "Characterization of rat hypothalamic corticotropin–releasing factor", Proc. Natl. Acad. Sci. vol. 80, 1983, pp. 4851–4855.

Robert M. Sapolsky, "Hypercortisolism Among Socially Subordinate Wild Baboons Originates at the CNS Level", Arch. Gen. Psychiatry, vol. 46, 1989, pp. 1047–1051.

Scott E. Schaus, "Practical Synthesis of Enantiopure Cyclic 1,2–Amino Alcohols via Catalytic Asymmetric Ring Opening of Meso Epoxides", J. Org. Chem., 62, 1987, pp. 4197–4199.

Errol B. De Souza, et al, "Corticotropin–releasing Factor Receptors Are Widely Distributed within the Rat Central Nervous System: An Autoradiographic Study", The Journal of Neuroscience, vol. 5, pp. 3189–3203.

N. R. Swerdlow, et al, "Corticotropin–releasing factor potentiates acoustic startle in rats: Blockade by chlordiazepoxide", Psychopharmacology, 88, 1986, pp. 147–152.

Karen E. Torraca, et al, "An Efficient Intermolecular Palladium–Catalyzed Synthesis of Aryl Ethers", J. Am. Chem. Soc., 123, 2001, pp. 10770–10771.

Wylie Vale, et al, "Characterization of a 41–Residue Ovine Hypothalamic Peptide That Stimulates Secretion of Corticotropin and o–Endorphin", Science, vol. 213, 1981, pp. 1394–1397.

John P. Wolfe, et al, "An Ammonia Equivalent for the Palladium–Catalyzed Animation of Aryl Halides and Triflates", Tetrahedron Letters, vol. 38, No. 36, 1997, pp. 6367–6370.

John P. Wolfe, et al, "Simple, Efficient Catalyst System for the Palladium–Catalyzed Animation of Aryl Chlorides, Bromides, and Triflates", J. Org. Chem., 65, 2000, pp. 1158–1174.

XP002233213, Chemical Abstract, vol. 121, No. 28, (1994), p. 1111, column 2.

XP002233214, Chemical Abstract, vol. 127, No. 2, (1997), p. 559.

George Battaglia, et al, "Characterization of Corticotropin–Releasing Factor Receptor–Mediated Adenylate Cyclase Activity in the Rat Central Nervous System", Synapse 1:572 (1987).

Craig W. Berridge, et al, "Corticotropin Releasing Factor Antagonist Reverses the Stress–Induced Changes of Exploratory Behavior in Mice", Hormones and Behavior vol. 21, pp. 393–401 (1987).

Craig W. Berridge and Adrian J. Dunn, "Corticotropin–Releasing Factor Ellicits Naloxone Sensitive Stress–Like Alterations in Exploratory Behavior in Mice", vol. 16 pp. 83–91 (1986).

J. Edwin Blalock, "A Molecular Basis for Bidirectional Communication Between the Immune and Neuroendocrine Systems", Physiological Reviews, vol. 69:1–32 (1989).

Errol B. De Souza, "CRH Defects in Alzheimer's and Other Neurologic Diseases", Hospital Practice, vol. 23, pp. 59–71 (1988).

Philip W. Gold, et al, "Psychiatric Implications of Basic and Clinical Studies with Corticotropin–Releasing Factor", vol. 141:5, pp. 619–727, (1984).

Philip W. Gold, et al, "Response to Corticotropin–Releasing Hormone in the Hypercortisolism of Depression and Cushing's Disease", The New England Journal of Medicine, vol. 314, No. 21, pp. 1329–1335 (1986).

Florian Holsboer, et al, "ACTH and Multisteroid Responses to Corticotropin–Releasing Factor in Depressive Illness:

Relationship to Multisteroid Responses After ACTH Stimulation and Dexamethasone Suppression", vol. 9, No. 2, pp. 147–160, (1984).

George F. Koob, "Stress, Corticotropin–Releasing Factor, and Behavior", Perspectives on Behavioral Medicine, vol. 2, pp. 39–52 (1985).

Wylie Vale, et al, "Chemical and Biological Characterization of Corticotropin Releasing Factor", Recent Progress in Hormone Research, vol. 39, pp. 245–271 (1983).

* cited by examiner

SUBSTITUTED ARYL 1,4-PYRAZINE DERIVATIVES

CROSS REFERENCE TO RELATED APPLICATIONS

This application claims the benefit of U.S. provisional application Ser. No. 60/332,052 filed on 21, Nov. 2001, under 35 USC 119(e)(i); U.S. provisional application Ser. No. 60/358,546 filed on 21, Feb. 2002, under 35 USC 119(e)(i); U.S. provisional application Ser. No. 60/388,285 filed on 13, Jun. 2002, under 35 USC 119(e)(i); U.S. provisional application Ser. No. 60/410,378 filed on 13, Sep. 2002, under 35 USC 119(e)(i), which are incorporated herein by reference in their entirety.

FIELD OF THE INVENTION

This invention relates to substituted aryl 1,4-pyrazine derivatives and processes for preparing them, pharmaceutical compositions containing them, and methods of using them to treat a disorder or condition which can be effected or facilitated by antagonizing a CRF receptor, including but not limited to disorders induced or facilitated by CRF, such as anxiety disorders, and depression and stress related disorders. Additionally this invention relates to the use of such compounds as probes for the localization of $CRF_1$ receptors in cells or tissues.

BACKGROUND OF THE INVENTION

Corticotropin releasing factor (CRF) is a 41 amino acid peptide that is the primary physiological regulator of proopiomelanocortin (POMC) derived peptide secretion from the anterior pituitary gland [J. Rivier et al., *Proc. Natl. Acad. Sci (USA)* 80:4851 (1983); W. Vale et al., *Science* 213:1394 (1981)]. In addition to its endocrine role at the pituitary gland, immunohistochemical localization of CRF has demonstrated that the hormone has a broad extrahypothalamic distribution in the central nervous system and produces a wide spectrum of autonomic, electrophysiological and behavioral effects consistent with a neurotransmitter or neuromodulator role in the brain [W. Vale et al., *Rec. Prog. Horm. Res.* 39:245 (1983); .F. Koob, *Persp. Behav. Med.* 2:39 (1985); E. B. De Souza et al., *J. Neurosci.* 5:3189 (1985)]. There is also evidence that CRF plays a significant role in integrating the response in the immune system to physiological, psychological, and immunological stressors [J. E. Blalock, *Physiological Reviews* 69:1 (1989); J. E. Morley, *Life Sci.* 41:527 (1987)].

There is evidence that CRF has a role in psychiatric disorders and neurological diseases including depression, anxiety-related disorders and feeding disorders. A role for CRF has also been postulated in the etiology and pathophysiology of Alzheimer's disease, Parkinson's disease, Huntington's disease, progressive supranuclear palsy and amyotrophic lateral sclerosis, as they relate to the dysfunction of CRF neurons in the central nervous system [for a review, see: E. B. De Souze, *Hosp. Practice* 23:59 (1988)].

Anxiety disorders are a group of diseases, recognized in the art, that includes phobic disorders, anxiety states, post-traumatic stress disorder and atypical anxiety disorders [The Merck Manual of Diagnosis and Therapy, 16$^{th}$ edition (1992)]. Emotional stress is often a precipitating factor in anxiety disorders, and such disorders generally respond to medications that lower response to stress.

In affective disorder, or major depression, the concentration of CRF is significantly increased in the cerebral spinal fluid (CSF) of drug-free individuals [C. B. Nemeroff et al., *Science* 226:1342 (1984); C. M. Banki et al., *Am. J. Psychiatry* 144:873 (1987); R. D. France et al., *Biol. Psychiatry* 28:86 (1988); M. Arato et al., *Biol. Psychiatry* 25:355 (1989)]. Furthermore, the density of CRF receptors is significantly decreased in the frontal cortex of suicide victims, consistent with a hypersecretion of CRF [C. B. Memeroff et al., *Arch. Gen. Psychiatry* 45:577 (1988)]. In addition, there is a blunted adrenocorticotropin (ACTH) response to CRF (i.v. administered) observed in depressed patients [P. W. Gold et al., *Am. J. Psychiatry* 141:619 (1984); F. Holsboer et al., *Psychoneuroendocrinology* 9:147 (1984); P. W. Gold et al., *New Engl. J. Med.* 314:1129 (1986)]. Preclinical studies in rats and non-human primates provide additional support for the hypothesis that hypersecretion of CRF may be involved in the symptoms seen in human depression [R. M. Sapolsky, *Arch. Gen. Psychiatry* 46:1047 (1989)]. There is also preliminary evidence that tricyclic antidepressants can alter CRF levels and thus modulate the numbers of receptors in the brain [Grigoriadis et al., *Neuropsychopharmacology* 2:53 (1989)].

CRF has also been implicated in the etiology of anxiety-related disorders, and is known to produce anxiogenic effects in animals. Interactions between benzodiazepine/non-benzodiazepine anxiolytics and CRF have been demonstrated in a variety of behavioral anxiety models [D. R. Britton et al., *Life Sci.* 31:363 (1982); C. W. Berridge and A. J. Dunn *Regul. Peptides* 16:83 (1986)]. Preliminary studies using the putative CRF receptor antagonist α-helical ovine CRF (9–41) in a variety of behavioral paradigms demonstrates that the antagonist produces "anxiolytic-like" effects that are qualitatively similar to the benzodiazepines [C. W. Berridge and A. J. Dunn *Horm. Behav.* 21:393 (1987), *Brain Research Reviews* 15:71 (1990)].

Neurochemical, endocrine and receptor binding studies have all demonstrated interactions between CRF and benzodiazepine anxiolytics, providing further evidence for the involvement of CRF in these disorders. Chlodiazepoxide attenuates the "anxiogenic" effects of CRF both in the conflict test [K. T. Britton et al., *Psychopharmacology* 86:170 (1985); K. T. Britton et al., *Psychopharmacology* 94:306 (1988)] and in the acoustic startle test [N. R. Swerdlow et al., *Psychopharmacology* 88:147 (1986)] in rats. The benzodiazepine receptor antagonist Ro 15-1788, which was without behavioral activity alone in the operant conflict test, reversed the effects of CRF in a dose-dependent manner while the benzodiazepine inverse agonist FG 7142 enhanced the actions of CRF [K. T. Britton et al., *Psychopharmacology* 94:396 (1988)]. The mechanisms and sites of action through which conventional anxiolytics and antidepressants produce their therapeutic effects remain to be elucidated. Preliminary studies, examining the effects of a $CRF_1$ receptor antagonist peptide (α-helical $CRF_{9-41}$) in a variety of behavioral paradigms, have demonstrated that the $CRF_1$ antagonist produces "anxiolytic-like" effects qualitatively similar to the benzodiazepines [for a review, see: G. F. Koob and K. T. Britton, In: *Corticotropin-Releasing Factor: Basic and Clinical Studies of a Neuropeptide*, E. B. De Souza and C. B. Nemeroff eds., CRC Press p. 221 (1990)].

The use of $CRF_1$ antagonists for the treatment of Syndrome X has also been described in U.S. patent application Ser. No. 09/696,822, filed Oct. 26, 2000, and European Patent Application No. 003094414, filed Oct. 26, 2000, which are also incorporated in their entireties herein by reference. Methods for using $CRF_1$ antagonists to treat congestive heart failure are described in U.S. Ser. No. 09/248,073, filed Feb. 10, 1999, now U.S. Pat. No. 6,043, 260 (Mar. 28, 2000) which is also incorporated herein in its entirety by reference.

CRF is known to have a broad extrahypothalmic distribution in the CNS, contributing therein to a wide spectrum of autonomic behavioral and physiological effects [see, e.g., Vale et al., 1983; Koob, 985; and E. B. De Souze et al., 1985]. For example, CRF concentrations are significantly increased in the cerebral spinal fluid of patients afflicted with affective disorder or major depression [see, e.g., Nemeroff et al., 1984; Banki et al., 1987; France et al., 1988; Arato et al., 1989]. Moreover, excessive levels of CRF are known to produce anxiogenic effects in animal models [see, e.g., Britton et al., 1982; Berridge and Dunn, 1986 and 1987], and $CRF_1$ antagonists are known to produce anxiolytic effects; accordingly, therapeutically effective amounts of compounds provided herein are, for example, determined by assessing the anxiolytic effects of varying amounts of the compounds in such animal models.

The following patents or patent applications disclose compounds as antagonists of $CRF_1$ receptors: WO0160806, WO9735901, WO9829119, WO9736886, WO9736898, and U.S. Pat. Nos. 5,872,136, 5,880,140, and 5,883,105. The compounds are useful for treating CNS-related disorders, particularly affective disorders and acute and chronic neurological disorders.

SUMMARY OF THE INVENTION

We have found that compounds of Formula I, as well as stereoisomers thereof, pharmaceutically acceptable salts thereof, and prodrugs thereof, are $CRF_1$ antagonists and are useful in the treatment of disorders and diseases associated with $CRF_1$ receptors, including CNS-related disorders and diseases, particularly psychiatric disorders, affective disorders such as anxiety disorders, depression and stress related disorders, and acute and chronic neurological disorders and diseases. The compounds are also useful in smoking cessation programs.

Thus, in a first aspect, this invention provides a compound of Formula I,

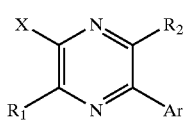

Formula I or a stereoisomer thereof, a pharmaceutically acceptable salt thereof, or a prodrug thereof, wherein in Formula I:

X is selected from $-NR_3R_4$, $-OR_3$, $-CR_3R_5R_5$, $-C(O)R_3$, $-S(O)_mR_3$, $-NR_3C(O)R_4$, or $-NR_3S(O)_mR_4$; m is 0,1 or 2;

Ar is selected from aryl, substituted aryl, heteroaryl, or substituted heteroaryl;

$R_1$, $R_2$, and $R_5$ are independently selected from halogen, $-NO_2$, $-CN$, $-R_a$, $-OR_a$, $-S(O)_mR_a$, $-NR_aR_a$, $-C(O)NR_aR_a$, $-C(S)NR_aR_a$, $-S(O)_mNR_aR_a$, $-NR_aS(O)_m R_a$, $-NR_aC(O)OR_a$, $-OC(O)NR_aR_a$, $-NR_aC(O)NR_aR_a$, $-NR_aC(S)NR_aR_a$, $-C(O)OR_a$, $-C(S)OR_a$, or $-OC(O)OR_a$;

$R_3$ and $R_4$ are independently selected from $R_a$, heterocycloalkyl, substituted heterocycloalkyl, substituted heteroaryl, substituted aryl, aryl cycloalkyl, substituted aryl cycloalkyl, heteroaryl cycloalkyl, substituted heteroaryl cycloalkyl, aryl heterocycloalkyl, substituted aryl heterocycloalkyl, heteroaryl heterocycloalkyl, or substituted heteroaryl heterocycloalkyl provided at least one of $R_3$ or $R_4$ are heteroaryl, substituted heteroaryl, aryl cycloalkyl, substituted aryl cycloalkyl, heteroaryl cycloalkyl, substituted heteroaryl cycloalkyl, aryl heterocycloalkyl, substituted aryl heterocycloalkyl, heteroaryl heterocycloalkyl, substituted heteroaryl heterocycloalkyl, heterocycloalkyl or substituted heterocycloalkyl;

$R_a$ each is selected from H, alkyl, cycloalkyl, haloalkyl, aryl, heteroaryl, or heterocycloalkyl optionally substituted with 1 to 5 of $R_t$, $-OR_t$, $-S(O)_mR_t$, $NR_tR_t$, oxo (=O), thione (=S), phenyl, heteroaryl, or heterocycloalkyl where phenyl, heteroaryl, and heterocycloalkyl are optionally substituted with 1 to 5 independently taken from $R_t$;

$R_t$ each is selected from H, halogen, $-NO_2$, $-NH_2$, $-OH$, $-SH$, $-CN$, $-C(O)NH_2$, $-C(O)-NHalkyl$, $-C(O)Nalkylalkyl$, $-Oalkyl$, NHalkyl, Nalkylalkyl, $-S(O)_malkyl$, $SO_2NH_2$, $SO_2NHalkyl$ and $SO_2Nalkylalkyl$, alkyl, cycloalkyl, haloalkyl, phenyl, benzyl, heteroaryl, or heterocycloalkyl where phenyl, benzyl heteroaryl and heterocycloalkyl may be optionally substituted with alkyl or halogen; and Aryl is either phenyl or naphthyl, provided that the compound is not:

2,5-dimethyl-3-(2,4-dichlorophenyl)-6-[(1-methylpiperidin-4-yl)oxy]pyrazine 2,5-dimethyl-3-(2,4-dichlorophenyl)-6-(tetrahydrofuran-3-yl)oxy]pyrazine 2,5-dimethyl-3-(2,4-dichlorophenyl)-6-(tetrahydro-2H-pyran-4-yloxy)pyrazine 2,5-dimethyl-3-(2,4-dichlorophenyl)-6-[(1-methylpiperidin-3-yl)oxy]pyrazine 2,5-dimethyl-3-(2,4-dichlorophenyl)-6-[(1-ethylpiperidin-3-yl)oxy]pyrazine 2,5-dimethyl-3-(2,4-dichlorophenyl)-6-(1-piperidin-4-yl)oxy]pyrazine 2,5-dimethyl-3-(2,4-dichlorophenyl)-6-piperidin-3-yl)oxy]pyrazine 2,5-dimethyl-3-(2,4-dichlorophenyl)-6-[(1-ethylpyrrolidin-3-yl)oxy]pyrazine 2,5-dimethyl-3-(2,4-dichlorophenyl)-6-[(1-methylpyrrolidin-3-yl)oxy]pyrazine 2,5-dimethyl-3-(2,4-dichlorophenyl)-6-[(pyrrolidin-3-yl)oxy]pyrazine 2,5-dimethyl-3-(2,4-dichlorophenyl)-6-[(pyridin-4-yl)oxy]pyrazine.

In another aspect, the present invention provides a novel compound of Formula I, or a stereoisomer thereof, a pharmaceutically acceptable salt thereof, or a prodrug thereof, which are useful for the treatment of the disorders or diseases that are associated with $CRF_1$ receptors, or disorders the treatment of which can be effected or facilitated by antagonizing CRF, in a mammal, particularly in a human, such as social anxiety disorder; panic disorder; obsessive-compulsive disorder; anxiety with co-morbid depressive illness; affective disorder; anxiety; and depression.

In still another aspect, the present invention provides for the use of a compound of the invention for treatment of a disorder disclosed herein above in a mammal, particularly in a human.

In still another aspect, the present invention provides for a composition comprising a compound of the invention useful for treatment of a disorder disclosed herein above in a mammal, particularly in a human.

In still another aspect, the present invention provides for the use of a compound of the invention in a binding assay, wherein one or more of the compounds may be joined to a label, where the label can directly or indirectly provide a detectable signal. Various labels include radioisotopes, fluorescers, chemiluminescers, specific binding molecules, particles, e.g. magnetic particles, and the like.

In yet another aspect, the present invention relates to the use of the compounds of the invention (particularly labeled compounds of this invention) as probes for the localization of receptors in cells and tissues and as standards and reagents for use in determining the receptor-binding characteristics of test compounds.

Labeled compounds of the invention may be used for in vitro studies such as autoradiography of tissue sections or for in vivo methods, e.g. PET or SPECT scanning. Particularly, compounds of the invention are useful as standards and reagents in determining the ability of a potential pharmaceutical to bind to the $CRF_1$ receptor.

DETAILED DESCRIPTION OF THE INVENTION

In a first aspect, this invention provides a compound of Formula I, shown and defined above.

Compounds provided herein can have one or more asymmetric centers or planes, and all chiral (enantiomeric and diastereomeric) and racemic forms of the compound are included in the present invention. Many geometric isomers of olefins, C=N double bonds, and the like can also be present in the compounds, and all such stable isomers are contemplated in the present invention. Compounds of the invention are isolated in either the racemic form, or in the optically pure form, for example, by resolution of the racemic form by conventional methods such as crystallization in the presence of a resolving agent, or chromatography, using, for example, a chiral HPLC column, or synthesized by an asymmetric synthesis route enabling the preparation of enantiomerically enriched material. The present invention encompasses all possible tautomers of the compounds represented by Formula I.

Preferred compound of the invention include those of Formula II

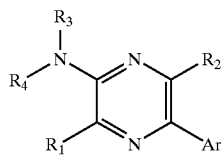

Formula II or a stereoisomer thereof, a pharmaceutically acceptable salt thereof, or a prodrug thereof, wherein in Formula II, Ar is selected from aryl, substituted aryl, heteroaryl, or substituted heteroaryl;

m is 0,1 or 2;

$R_1$ and $R_2$ are independently selected from halogen, —$NO_2$, —CN, —$R_a$, —$OR_a$, —$S(O)_mR_a$, —$NR_aR_a$, —$C(O)NR_aR_a$, —$C(S)NR_aR_a$—$S(O)_mNR_aR_a$, —$NR_aS$ $(O)_m$ $R_a$, —$NR_aC(O)OR_a$, —$OC(O)NR_aR_a$, —$NR_aC(O)$ $NR_aR_a$, —$NR_aC(S)NR_aR_a$, —$C(O)OR_a$, —$C(S)OR_a$, or —$OC(O)OR_a$;

$R_3$ and $R_4$ are independently selected from $R_a$, heterocycloalkyl, substituted heterocycloalkyl, substituted heteroaryl, substituted aryl, aryl cycloalkyl, substituted aryl cycloalkyl, heteroaryl cycloalkyl, substituted heteroaryl cycloalkyl, aryl heterocycloalkyl, substituted aryl heterocycloalkyl, heteroaryl heterocycloalkyl, or substituted heteroaryl heterocycloalkyl provided at least one of $R_3$ or $R_4$ are heteroaryl, substituted heteroaryl, aryl cycloalkyl, substituted aryl cycloalkyl, heteroaryl cycloalkyl, substituted heteroaryl cycloalkyl, aryl heterocycloalkyl, substituted aryl heterocycloalkyl, heteroaryl heterocycloalkyl, substituted heteroaryl heterocycloalkyl, heterocycloalkyl or substituted heterocycloalkyl;

$R_a$ each is independently selected from H, alkyl, cycloalkyl, haloalkyl, aryl, heteroaryl, or heterocycloalkyl optionally substituted with 1 to 5 of $R_t$, —$OR_t$, —$S(O)_mR_t$, $NR_tR_t$, oxo (=O), thione (=S), phenyl, heteroaryl, or heterocycloalkyl where phenyl, heteroaryl, and heterocycloalkyl are optionally substituted with 1 to 5 independently taken from $R_t$; and $R_t$ each is independently selected from H, halogen, —$NO_2$, —$NH_2$, —OH, —SH, —CN, —$C(O)NH_2$, —C(O)—NHalkyl, —C(O)Nalkylalkyl, —Oalkyl, NHalkyl, Nalkylalkyl, —$S(O)_m$alkyl, $SO_2NH_2$, $SO_2$NHalkyl and $SO_2$Nalkylalkyl, alkyl, cycloalkyl, haloalkyl, phenyl, benzyl, heteroaryl, or heterocycloalkyl where phenyl, benzyl heteroaryl and heterocycloalkyl may be optionally substituted with alkyl or halogen.

Other preferred compounds of the invention include those of Formula III

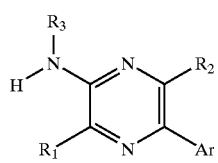

Formula III or a stereoisomer thereof, a pharmaceutically acceptable salt thereof, or a prodrug thereof, wherein in Formula III, Ar is selected from aryl, substituted aryl, heteroaryl, or substituted heteroaryl;

m is 0,1 or 2;

$R_1$ and $R_2$ are independently selected from halogen, —$NO_2$, —CN, —$R_a$, —$OR_a$, —$S(O)_mR_a$, —$NR_aR_a$, —$C(O)NR_aR_a$, —$C(S)NR_aR_a$—$S(O)_mNR_aR_a$, —$NR_aS$ $(O)_m$ $R_a$, —$NR_aC(O)OR_a$, —$OC(O)NR_aR_a$, —$NR_aC(O)$ $NR_aR_a$, —$NR_aC(S)NR_aR_a$, —$C(O)OR_a$, —$C(S)OR_a$, or —$OC(O)OR_a$;

$R_3$ is selected from heteroaryl, substituted heteroaryl, aryl cycloalkyl, substituted aryl cycloalkyl, heteroaryl cycloalkyl, substituted heteroaryl cycloalkyl, aryl heterocycloalkyl, substituted aryl heterocycloalkyl, heteroaryl heterocycloalkyl, substituted heteroaryl heterocycloalkyl, heterocycloalkyl or substituted heterocycloalkyl;

$R_a$ each is independently selected from H, alkyl, cycloalkyl, haloalkyl, aryl, heteroaryl, or heterocycloalkyl optionally substituted with 1 to 5 of $R_t$, —$OR_t$, —$S(O)_mR_t$, $NR_tR_t$, oxo (=O), thione (=S), phenyl, heteroaryl, or heterocycloalkyl where phenyl, heteroaryl, and heterocycloalkyl are optionally substituted with 1 to 5 independently taken from $R_t$; and $R_t$ each is independently selected from H, halogen, —$NO_2$, —$NH_2$, —OH, —SH, —CN, —$C(O)NH_2$, —C(O)—NHalkyl, —C(O)Nalkylalkyl, —Oalkyl, NHalkyl, Nalkylalkyl, —$S(O)_m$alkyl, $SO_2NH_2$, $SO_2$NHalkyl and $SO_2$Nalkylalkyl, alkyl, cycloalkyl, haloalkyl, phenyl, benzyl, heteroaryl, or heterocycloalkyl where phenyl, benzyl heteroaryl and heterocycloalkyl may be optionally substituted with alkyl or halogen.

Still other preferred compounds of the invention include those of Formula IV

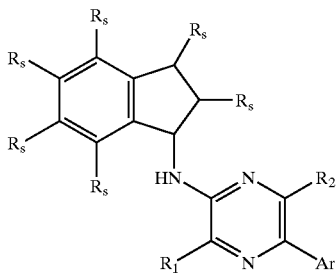

Formula IV or a stereoisomer thereof, a pharmaceutically acceptable salt thereof, or a prodrug thereof, wherein in Formula IV, Ar is selected from aryl, substituted aryl, heteroaryl, or substituted heteroaryl;

m is 0,1 or 2;

$R_1$ and $R_2$ are independently selected from halogen, —$NO_2$, —CN, —$R_a$, —$OR_a$, —$S(O)_mR_a$, —$NR_aR_a$, —$C(O)NR_aR_a$, —$C(S)NR_aR_a$—$S(O)_mNR_aR_a$, —$NR_aS(O)_m$ $R_a$, —$NR_aC(O)OR_a$, —$OC(O)NR_aR_a$, —$NR_aC(O)NR_aR_a$, —$NR_aC(S)NR_aR_a$, —$C(O)OR_a$, —$C(S)OR_a$, or —$OC(O)OR_a$;

$R_s$ each is independently selected from halogen, —$NO_2$, —CN, —$R_a$, —$OR_a$, —$S(O)_mR_a$, —$NR_aR_a$, —$C(O)NR_aR_a$, —$C(S)NR_aR_a$—$S(O)_mNR_aR_a$, —$NR_aS(O)_mR_a$, —$NR_aC(O)OR_a$, —$OC(O)NR_aR_a$, —$NR_aC(O)NR_aR_a$, —$NR_aC(S)NR_aR_a$, —$C(O)OR_a$, —$C(S)OR_a$, or —$OC(O)OR_a$;

$R_a$ each is independently selected from H, alkyl, cycloalkyl, haloalkyl, aryl, heteroaryl, or heterocycloalkyl optionally substituted with 1 to 5 of $R_t$, —$OR_t$, —$S(O)_mR_t$, $NR_tR_t$, oxo (=O), thione (=S), phenyl, heteroaryl, or heterocycloalkyl where phenyl, heteroaryl, and heterocycloalkyl are optionally substituted with 1 to 5 independently taken from $R_t$; and $R_t$ each is independently selected from H, halogen, —$NO_2$, —$NH_2$, —OH, —SH, —CN, —$C(O)NH_2$, —C(O)—NHalkyl, —C(O)Nalkylalkyl, —Oalkyl, NHalkyl, Nalkylalkyl, —$S(O)_m$alkyl, $SO_2NH_2$, $SO_2$NHalkyl and $SO_2$Nalkylalkyl, alkyl, cycloalkyl, haloalkyl, phenyl, benzyl, heteroaryl, or heterocycloalkyl where phenyl, benzyl heteroaryl and heterocycloalkyl may be optionally substituted with alkyl or halogen.

Still other preferred compounds of the invention include those of Formula V

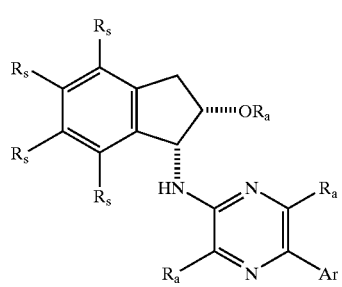

Formula V or a stereoisomer thereof, a pharmaceutically acceptable salt thereof, or a prodrug thereof, wherein in Formula V, Ar is selected from aryl, substituted aryl, heteroaryl, or substituted heteroaryl;

m is 0,1 or 2;

$R_s$ each is independently selected from halogen, —$NO_2$, —CN, —$R_a$, —$OR_a$, —$S(O)_mR_a$, —$NR_aR_a$, —$C(O)NR_aR_a$, —$C(S)NR_aR_a$—$S(O)_mNR_aR_a$, —$NR_aS(O)_mR_a$, —$NR_aC(O)OR_a$, —$OC(O)NR_aR_a$, —$NR_aC(O)NR_aR_a$, —$NR_aC(S)NR_aR_a$, —$C(O)OR_a$, —$C(S)OR_a$, or —$OC(O)OR_a$;

$R_a$ each is independently selected from H, alkyl, cycloalkyl, haloalkyl, aryl, heteroaryl, or heterocycloalkyl optionally substituted with 1 to 5 of $R_t$, —$OR_t$, —$S(O)_mR_t$, $NR_tR_t$, oxo (=O), thione (=S), phenyl, heteroaryl, or heterocycloalkyl where phenyl, heteroaryl, and heterocycloalkyl are optionally substituted with 1 to 5 independently taken from $R_t$; and $R_t$ each is independently selected from H, halogen, —$NO_2$, —$NH_2$, —OH, —SH, —CN, —$C(O)NH_2$, —C(O)—NHalkyl, —C(O)Nalkylalkyl, —Oalkyl, NHalkyl, Nalkylalkyl, —$S(O)_m$alkyl, $SO_2NH_2$, $SO_2$NHalkyl and $SO_2$Nalkylalkyl, alkyl, cycloalkyl, haloalkyl, phenyl, benzyl, heteroaryl, or heterocycloalkyl where phenyl, benzyl heteroaryl and heterocycloalkyl may be optionally substituted with alkyl or halogen.

Still other preferred compounds of the invention include those of Formula VI

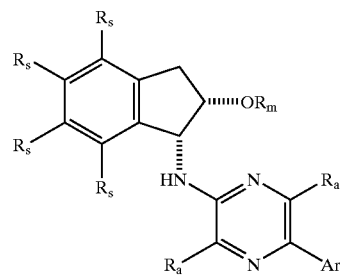

Formula VI or a stereoisomer thereof, a pharmaceutically acceptable salt thereof, or a prodrug thereof, wherein in Formula VI, Ar is selected from aryl, substituted aryl, heteroaryl, or substituted heteroaryl;

m is 0,1 or 2;

$R_s$ each is independently selected from halogen, —$NO_2$, —CN, —$R_a$, —$OR_a$, —$S(O)_mR_a$, —$NR_aR_a$, —$C(O)NR_aR_a$, —$C(S)NR_aR_a$—$S(O)_mNR_aR_a$, —$NR_aS(O)_mR_a$, —$NR_aC(O)OR_a$, —$OC(O)NR_aR_a$, —$NR_aC(O)NR_aR_a$, —$NR_aC(S)NR_aR_a$, —$C(O)OR_a$, —$C(S)OR_a$, or —$OC(O)OR_a$;

$R_a$ each is independently selected from H, alkyl, cycloalkyl, haloalkyl, aryl, heteroaryl, or heterocycloalkyl optionally substituted with 1 to 5 of $R_t$, —$OR_t$, —$S(O)_mR_t$, $NR_tR_t$, oxo (=O), thione (=S), phenyl, heteroaryl, or heterocycloalkyl where phenyl, heteroaryl, and heterocycloalkyl are optionally substituted with 1 to 5 independently taken from $R_t$;

$R_m$ is $C_1$–$C_6$ alkyl substituted with from 1–2 of halogen, —$NO_2$, —$NH_2$, —OH, —SH, —CN, —$C(O)NH_2$, —C(O)—NHalkyl, —C(O)Nalkylalkyl, —Oalkyl, NHalkyl, Nalkylalkyl, —$S(O)_m$alkyl, $SO_2NH_2$, $SO_2$NHalkyl and $SO_2$Nalkylalkyl, oxo (=O), thione (=S), heterocycloalkyl, or substituted heterocycloalkyl; and $R_t$ each is independently selected from H, halogen, —$NO_2$, —$NH_2$, —OH, —SH, —CN, —$C(O)NH_2$, —C(O)—NHalkyl, —C(O)Nalkylalkyl, —Oalkyl, NHalkyl, Nalkylalkyl, —$S(O)_m$alkyl, $SO_2NH_2$, $SO_2$NHalkyl and $SO_2$Nalkylalkyl, alkyl, cycloalkyl, haloalkyl, phenyl, benzyl, heteroaryl, or heterocycloalkyl where phenyl, benzyl heteroaryl and heterocycloalkyl may be optionally substituted with alkyl or halogen.

Still other preferred compounds of the invention include those of Formula VII

Formula VII

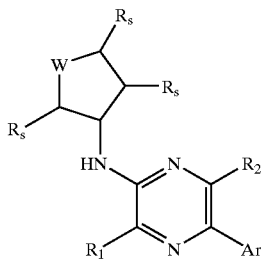

or a stereoisomer thereof, a pharmaceutically acceptable salt thereof, or a prodrug thereof, wherein in Formula VII, Ar is selected from aryl, substituted aryl, heteroaryl, or substituted heteroaryl;

W is O, $NR_p$, or $S(O)_m$;

m is 0,1 or 2;

$R_s$ each is independently selected from halogen, $-NO_2$, $-CN$, $-R_a$, $-OR_a$, $-S(O)_mR_a$, $-NR_aR_a$, $-C(O)NR_aR_a$, $-C(S)NR_aR_a-S(O)_mNR_aR_a$, $-NR_aS(O)_mR_a$, $-NR_aC(O)OR_a$, $-OC(O)NR_aR_a$, $-NR_aC(O)NR_aR_a$, $-NR_aC(S)NR_aR_a$, $-C(O)OR_a$, $-C(S)OR_a$, or $-OC(O)OR_a$;

$R_1$ and $R_2$ are independently selected from halogen, $-NO_2$, $-CN$, $-R_a$, $-OR_a$, $-S(O)_mR_a$, $-NR_aR_a$, $-C(O)NR_aR_a$, $-C(S)NR_aR_a-S(O)_mNR_aR_a$, $-NR_aS(O)_m R_a$, $-NR_aC(O)OR_a$, $-OC(O)NR_aR_a$, $-NR_aC(O)NR_aR_a$, $-NR_aC(S)NR_aR_a$, $-C(O)OR_a$, $-C(S)OR_a$, or $-OC(O)OR_a$;

$R_p$ each is independently selected from $-R_a$, $-S(O)_mR_a$, $-C(O)NR_aR_a$, $-C(S)NR_aR_a-S(O)_mNR_aR_a$, $-C(O)OR_a$, or $-C(S)OR_a$;

$R_a$ each is independently selected from H, alkyl, cycloalkyl, haloalkyl, aryl, heteroaryl, or heterocycloalkyl optionally substituted with 1 to 5 of $R_t$, $-OR_t$, $-S(O)_mR_t$, $NR_tR_t$, oxo (=O), thione (=S), phenyl, heteroaryl, or heterocycloalkyl where phenyl, heteroaryl, and heterocycloalkyl are optionally substituted with 1 to 5 independently taken from $R_t$; and $R_t$ each is independently selected from H, halogen, $-NO_2$, $-NH_2$, $-OH$, $-SH$, $-CN$, $-C(O)NH_2$, $-C(O)-NHalkyl$, $-C(O)Nalkylalkyl$, $-Oalkyl$, NHalkyl, Nalkylalkyl, $-S(O)_malkyl$, $SO_2NH_2$, $SO_2NHalkyl$ and $SO_2Nalkylalkyl$, alkyl, cycloalkyl, haloalkyl, phenyl, benzyl, heteroaryl, or heterocycloalkyl where phenyl, benzyl heteroaryl and heterocycloalkyl may be optionally substituted with alkyl or halogen.

Still other preferred compounds of the invention include those of Formula VIII

Formula VIII

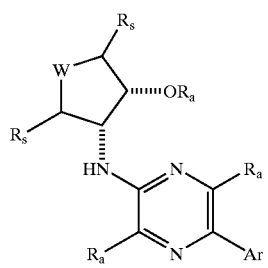

or a stereoisomer thereof, a pharmaceutically acceptable salt thereof, or a prodrug thereof, wherein in Formula VIII, Ar is selected from aryl, substituted aryl, heteroaryl, or substituted heteroaryl;

W is O, $NR_p$, or $S(O)_m$;

m is 0,1 or 2;

$R_s$ each is independently selected from halogen, $-NO_2$, $-CN$, $-R_a$, $-OR_a$, $-S(O)_mR_a$, $-NR_aR_a$, $-C(O)NR_aR_a$, $-C(S)NR_aR_a-S(O)_mNR_aR_a$, $-NR_aS(O)_mR_a$, $-NR_aC(O)OR_a$, $-OC(O)NR_aR_a$, $-NR_aC(O)NR_aR_a$, $-NR_aC(S)NR_aR_a$, $-C(O)OR_a$, $-C(S)OR_a$, or $-OC(O)OR_a$;

$R_p$ is independently selected from $-R_a$, $-S(O)_mR_a$, $-C(O)NR_aR_a$, $-C(S)NR_aR_a-S(O)_mNR_aR_a$, $-C(O)OR_a$, or $-C(S)OR_a$;

$R_a$ each is independently selected from H, alkyl, cycloalkyl, haloalkyl, aryl, heteroaryl, or heterocycloalkyl optionally substituted with 1 to 5 of $R_t$, $-OR_t$, $-S(O)_mR_t$, $NR_tR_t$, oxo (=O), thione (=S), phenyl, heteroaryl, or heterocycloalkyl where phenyl, heteroaryl, and heterocycloalkyl are optionally substituted with 1 to 5 independently taken from $R_t$; and $R_t$ each is independently selected from H, halogen, $-NO_2$, $-NH_2$, $-OH$, $-SH$, $-CN$, $-C(O)NH_2$, $-C(O)-NHalkyl$, $-C(O)Nalkylalkyl$, $-Oalkyl$, NHalkyl, Nalkylalkyl, $-S(O)_malkyl$, $SO_2NH_2$, $SO_2NHalkyl$ and $SO_2Nalkylalkyl$, alkyl, cycloalkyl, haloalkyl, phenyl, benzyl, heteroaryl, or heterocycloalkyl where phenyl, benzyl heteroaryl and heterocycloalkyl may be optionally substituted with alkyl or halogen.

Still other preferred compounds of the invention include those of Formula IX

Formula IX

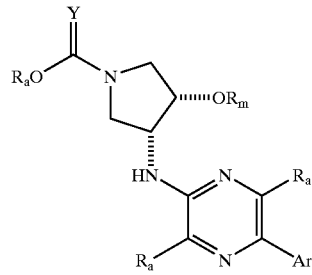

or a stereoisomer thereof, a pharmaceutically acceptable salt thereof, or a prodrug thereof, wherein in Formula IX, Ar is selected from aryl, substituted aryl, heteroaryl, or substituted heteroaryl;

m is 0,1 or 2;

Y=O or S $R_m$ is $C_1$–$C_6$ alkyl substituted with from 1–2 of halogen, $-NO_2$, $-NH_2$, $-OH$, $-SH$, $-CN$, $-C(O)NH_2$, $-C(O)-NHalkyl$, $-C(O)Nalkylalkyl$, $-Oalkyl$, NHalkyl, Nalkylalkyl, $-S(O)_malkyl$, $SO_2NH_2$, $SO_2NHalkyl$ and $SO_2Nalkylalkyl$, oxo (=O), thione (=S), heterocycloalkyl, or substituted heterocycloalkyl;

$R_a$ each is independently selected from H, alkyl, cycloalkyl, haloalkyl, aryl, heteroaryl, or heterocycloalkyl optionally substituted with 1 to 5 of $R_t$, $-OR_t$, $-S(O)_mR_t$, $NR_tR_t$, oxo (=O), thione (=S), phenyl, heteroaryl, or heterocycloalkyl where phenyl, heteroaryl, and heterocycloalkyl are optionally substituted with 1 to 5 independently taken from $R_t$; and $R_t$ each is independently selected from H, halogen, $-NO_2$, $-NH_2$, $-OH$, $-SH$, $-CN$, $-C(O)NH_2$, $-C(O)-NHalkyl$, $-C(O)Nalkylalkyl$, $-Oalkyl$, NHalkyl, Nalkylalkyl, $-S(O)_malkyl$, $SO_2NH_2$, $SO_2NHalkyl$ and $SO_2Nalkylalkyl$, alkyl, cycloalkyl, haloalkyl, phenyl, benzyl, heteroaryl, or heterocycloalkyl where phenyl, benzyl heteroaryl and heterocycloalkyl may be optionally substituted with alkyl or halogen.

Still other preferred compounds of the invention include:

compounds of Formula I where X is NR3R4;

compounds of Formula I where X is NR3R4 and one of R3 or R4 is aryl cycloalkyl or heteroaryl cycloalkyl;

compounds of Formula I where X is NR3R4 and one of R3 or R4 is aryl cycloalkyl or heteroaryl cycloalkyl and the point of attachment is the cycloalkyl ring;

compounds of Formula I where X is NR3R4 and one of R3 or R4 is aryl cycloalkyl or heteroaryl cycloalkyl and the point of attachment is the cycloalkyl ring and one of R3 or R4 is hydrogen;

compounds of Formula I where X is NR3R4 and one of R3 or R4 is heterocycloalkyl and one of R3 or R4 is hydrogen;

compounds of Formula I where X is NR3R4 and one of R3 or R4 is substituted aryl cycloalkyl or substituted heteroaryl cycloalkyl and the point of attachment is the cycloalkyl ring and one of R3 or R4 is hydrogen;

compounds of Formula I where X is NR3R4 and one of R3 or R4 is substituted aryl cycloalkyl or substituted heteroaryl cycloalkyl where the substituent is either alkyl or alkoxy and is on the cycloalkyl ring and the point of attachment is the cycloalkyl ring and one of R3 or R4 is hydrogen;

compounds of Formula I where X is NR3R4 and one of R3 or R4 is substituted heterocycloalkyl where the substituent is either alkyl or alkoxy and one of R3 or R4 is hydrogen;

compounds of Formula I where X is NR3R4 and one of R3 or R4 is substituted heterocycloalkyl where the substituent is either alkyl or alkoxy and the absolute stereochemistry of these ring substituents are either (R,R), (R,S), (S,R), or (S,S) and one of R3 or R4 is hydrogen;

compounds of Formula I where X is NR3R4 and one of R3 or R4 is substituted aryl cycloalkyl or substituted heteroaryl cycloalkyl where the substituent is either alkyl or alkoxy and is on the cycloalkyl ring and the absolute stereochemistry of these ring substituents are either (R,R), (R,S), (S,R), or (S,S) and the point of attachment is the cycloalkyl ring and one of R3 or R4 is hydrogen;

compounds of Formula I where X is NR3R4 and R3 is 2-substituted-1-indanyl and R4 is hydrogen;

compounds of Formula I where X is NR3R4 and R3 is 2-alkoxy-1-indanyl and R4 is hydrogen;

compounds of Formula I where X is NR3R4 and R3 is 2(S)-alkoxy-1(R)-indanyl and R4 is hydrogen;

compounds of Formula I where X is NR3R4 and R3 is 4-substituted-3-pyrrolidinyl and R4 is hydrogen;

compounds of Formula I where X is NR3R4 and R3 is 4-alkoxy-3-pyrrolidinyl and R4 is hydrogen; and compounds of Formula I where X is NR3R4 and R3 is 4(S)-alkoxy-3(R)-pyrrolidinyl-1-carboxylate and R4 is hydrogen.

Following are examples of particular compounds of the invention, with each compound being identified by both a chemical name and a structural formula immediately below the chemical name:

5-(2,4-dichlorophenyl)-N-[(1R,2S)-2-ethoxy-2,3-dihydro-1H-inden-1-yl]-3,6-diethylpyrazin-2-amine

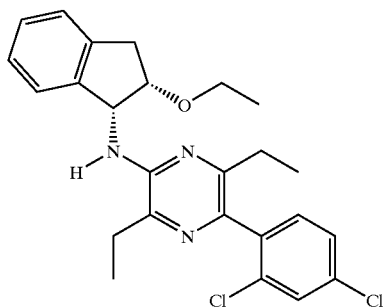

5-(2,4-dichlorophenyl)-3,6-diethyl-N-[(1R,2S)-2-methoxy-2,3-dihydro-1H-inden-1-yl]pyrazin-2-amine

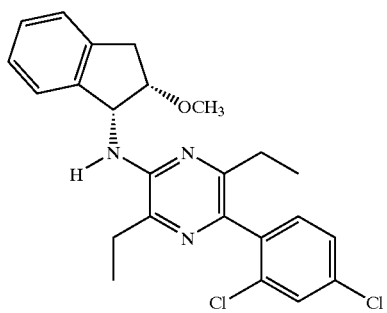

5-(2,4-dichlorophenyl)-3,6-diethyl-N-[(1R,2S)-2-isopropoxy-2,3-dihydro-1H-inden-1-yl]pyrazin-2-amine

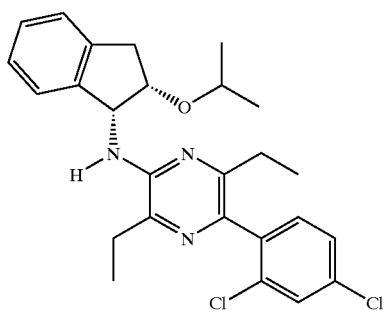

5-(2,4-dichlorophenyl)-3,6-diethyl-N-[(1S,2R)-2-methoxy-2,3-dihydro-1H-inden-1-yl]pyrazin-2-amine

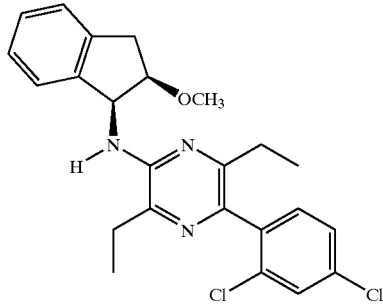

5-(2,4-dichlorophenyl)-3,6-diethyl-N-[(1S,2S)-2-methoxy-2,3-dihydro-1H-inden-1-yl]pyrazin-2-amine

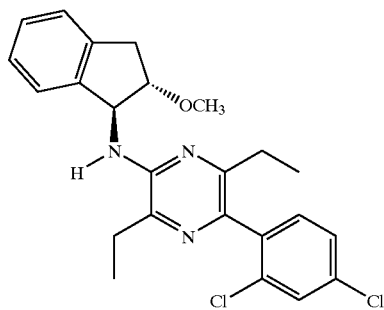

5-(2,4-dichlorophenyl)-3,6-diethyl-N-[(1R,2R)-2-methoxy-2,3-dihydro-1H-inden-1-yl]pyrazin-2-amine

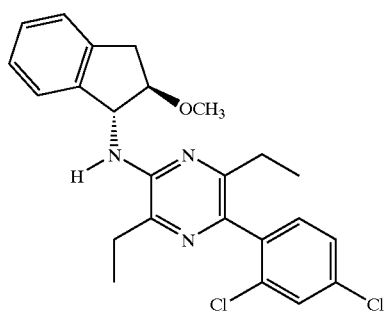

N-[(1R,2S)-2-(cyclopropylmethoxy)-2,3-dihydro-1H-inden-1-yl]-5-(2,4-dichlorophenyl)-3,6-diethylpyrazin-2-amine

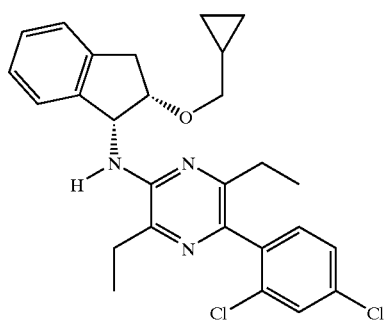

5-(2,4-dichlorophenyl)-3,6-diethyl-N-[(1R,2S)-2-(prop-2-ynyloxy)-2,3-dihydro-1H-inden-1-yl]pyrazin-2-amine

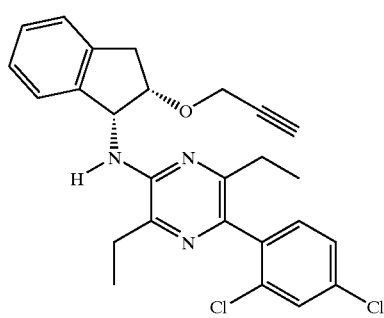

5-(2,4-dichlorophenyl)-3,6-diethyl-N-[(1R,2S)-2-(2-methoxyethoxy)-2,3-dihydro-1H-inden-1-yl]pyrazin-2-amine

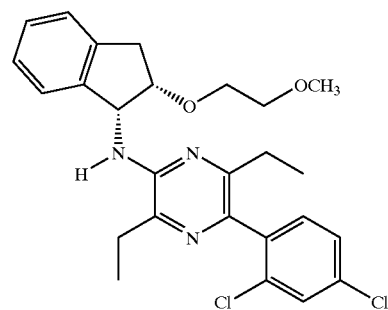

N-[(1R,2S)-2-(allyloxy)-2,3-dihydro-1H-inden-1-yl]-5-(2,4-dichlorophenyl)-3,6-diethylpyrazin-2-amine

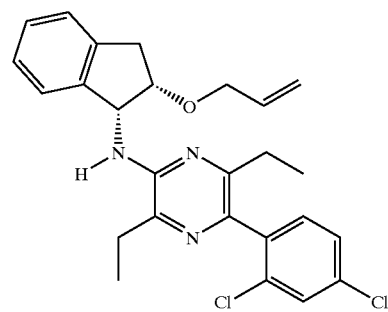

5-(2,4-dichlorophenyl)-3,6-diethyl-N-[(1R,2S)-2-(2-fluoroethoxy)-2,3-dihydro-1H-inden-1-yl]pyrazin-2-amine

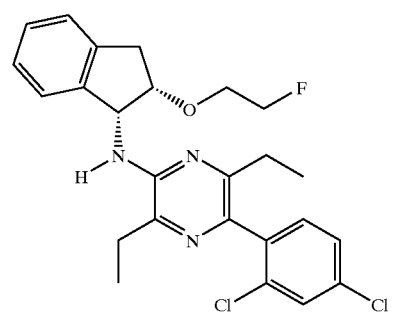

5-(2,4-dichlorophenyl)-3,6-diethyl-N-[(1R,2S)-2-propoxy-2,3-dihydro-1H-inden-1-yl]pyrazin-2-amine.

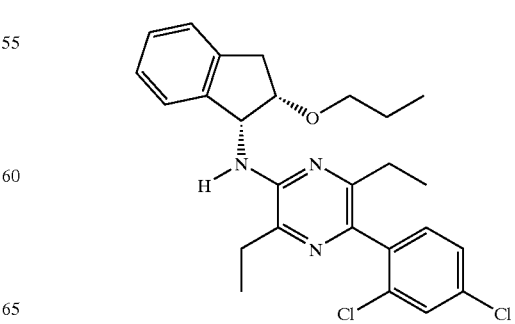

2-[((1R,2S)-1-{[5-(2,4-dichlorophenyl)-3,6-diethylpyrazin-2-yl]amino}-2,3-dihydro-1H-inden-2-yl)oxy]ethanol.

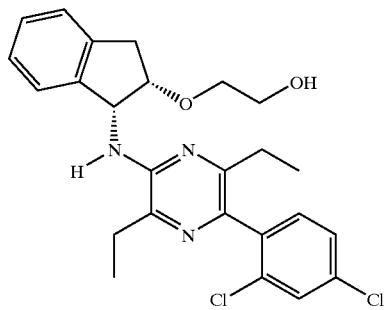

(1R,2S)-1-{[5-(2,4-dichlorophenyl)-3,6-diethylpyrazin-2-yl]amino}-2,3-dihydro-1H-inden-2-yl dimethylcarbamate.

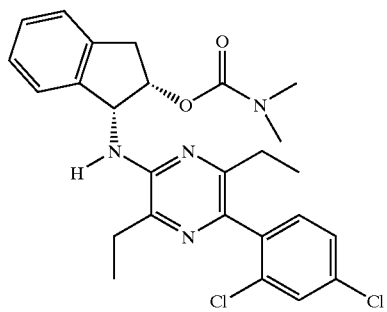

(1R,2S)-1-{[5-(2,4-dichlorophenyl)-3,6-diethylpyrazin-2-yl]amino}-2,3-dihydro-1H-inden-2-yl acetate.

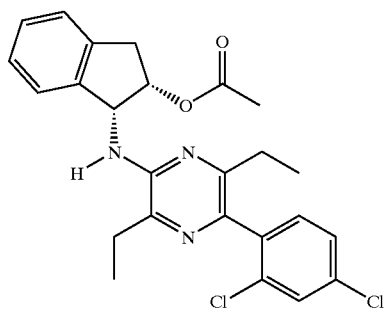

5-(2-chloro-4-methoxyphenyl)-N-[(1R,2S)-2-ethoxy-2,3-dihydro-1H-inden-1-yl]-3,6-diethylpyrazin-2-amine.

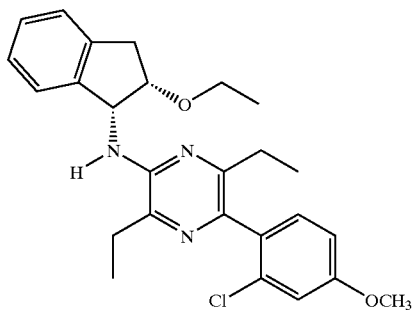

5-(2-chloro-4-methoxyphenyl)-3,6-diethyl-N-[(1R,2S)-2-(2-fluoroethoxy)-2,3-dihydro-1H-inden-1-yl]pyrazin-2-amine.

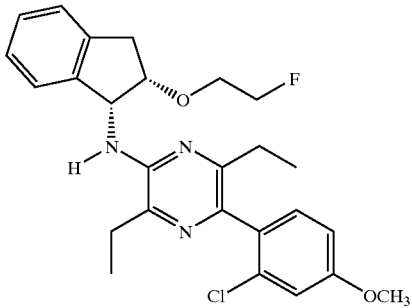

(1R,2S)-1-{[5-(2-chloro-4-methoxyphenyl)-3,6-diethylpyrazin-2-yl]amino}-2,3-dihydro-1H-inden-2-yl acetate.

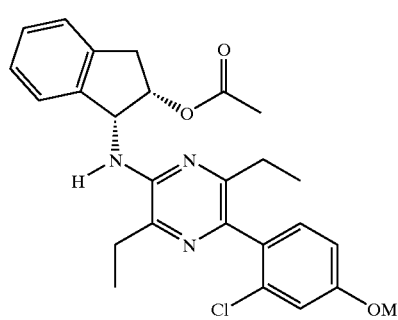

N-[(1R,2S)-2-ethoxy-2,3-dihydro-1H-inden-1-yl]-3,6-diethyl-5-(4-methoxy-2-methylphenyl)pyrazin-2-amine.

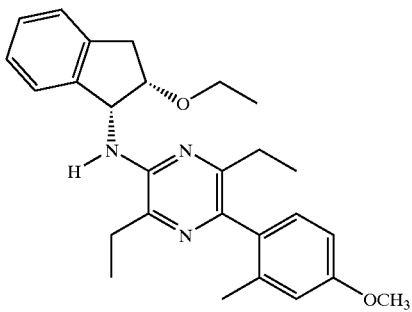

3,6-diethyl-N-[(1R,2S)-2-(2-fluoroethoxy)-2,3-dihydro-1H-inden-1-yl]-5-(4-methoxy-2-methylphenyl)pyrazin-2-amine.

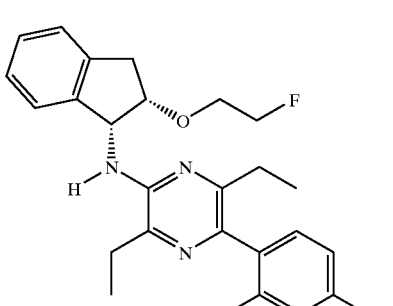

5-(2,4-dimethoxyphenyl)-N-[(1R,2S)-2-ethoxy-2,3-dihydro-1H-inden-1-yl]-3,6-diethylpyrazin-2-amine.

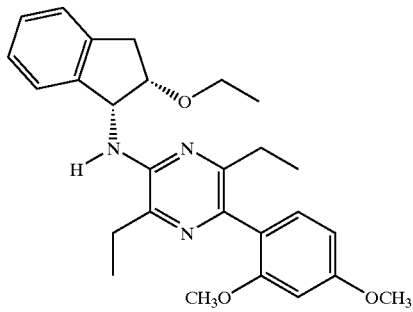

5-(2,4-dimethoxyphenyl)-3,6-diethyl-N-[(1R,2S)-2-(2-fluoroethoxy)-2,3-dihydro-1H-inden-1-yl]pyrazin-2-amine.

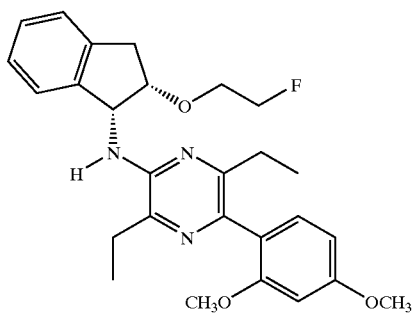

5-[2-chloro-4-(dimethylamino)phenyl]-N-[(1R,2S)-2-ethoxy-2,3-dihydro-1H-inden-1-yl]-3,6-diethylpyrazin-2-amine.

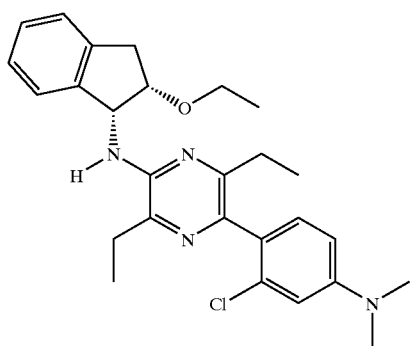

5-[2-chloro-4-(dimethylamino)phenyl]-3,6-diethyl-N-[(1R,2S)-2-(2-fluoroethoxy)-2,3-dihydro-1H-inden-1-yl]pyrazin-2-amine.

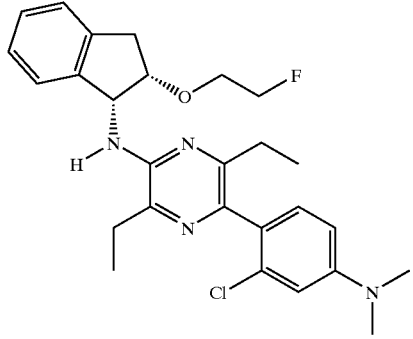

5-[6-(dimethylamino)-4-methylpyridin-3-yl]-N-[(1R,2S)-2-ethoxy-2,3-dihydro-1H-inden-1-yl]-3,6-diethylpyrazin-2-amine.

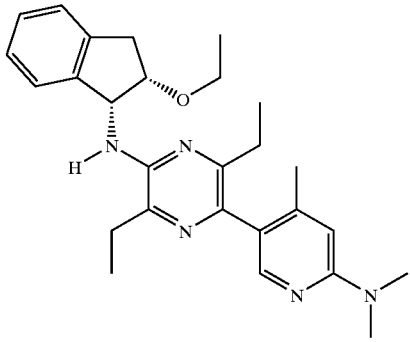

5-(2,4-dichlorophenyl)-N-(2,3-dihydro-1H-inden-1-yl)-3,6-dimethylpyrazin-2-amine

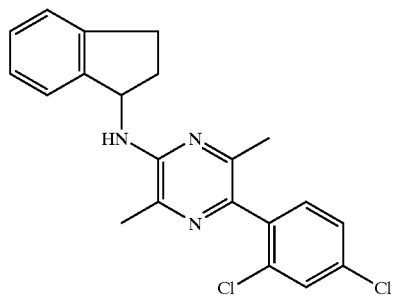

N-(2,3-dihydro-1H-inden-1-yl)-5-(4-methoxy-2-methylphenyl)-3,6-dimethylpyrazin-2-amine

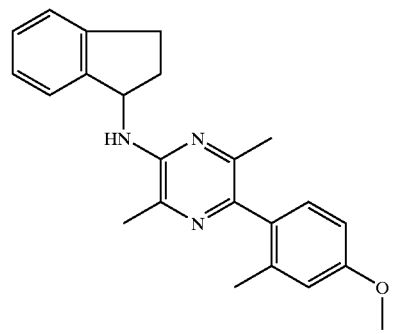

5-(2,4-dichlorophenyl)-3,6-dimethyl-N-(1,2,3,4-tetrahydronaphthalen-1-yl)pyrazin-2-amine

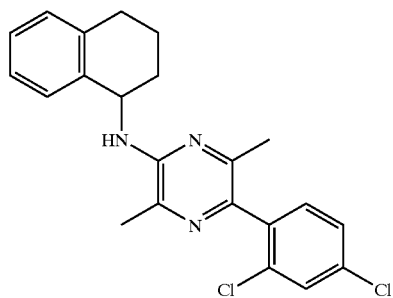

5-(4-methoxy-2-methylphenyl)-3,6-dimethyl-N-(1,2,3,4-tetrahydronaphthalen-1-yl)pyrazin-2-amine

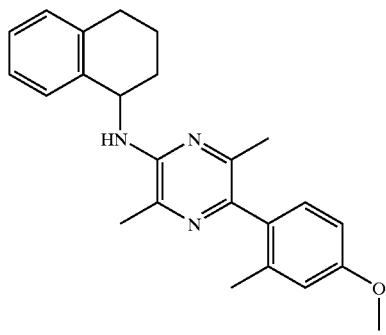

N-[5-(2,4-dichlorophenyl)-3,6-dimethylpyrazin-2-yl]isoquinolin-1-amine

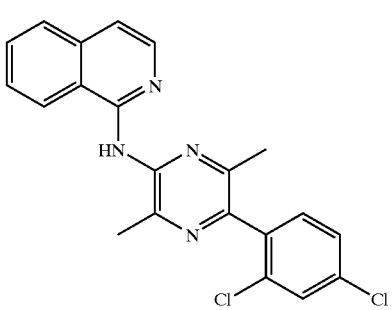

5-(2,4-dichlorophenyl)-3,6-diethyl-N-(3-ethyl-6-methylpyridin-2-yl)pyrazin-2-amine

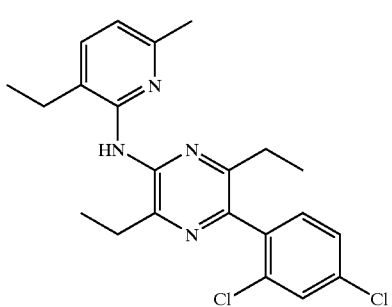

5-(2,4-dichlorophenyl)-N-(4,6-dimethylpyridin-2-yl)-3,6-diethylpyrazin-2-amine

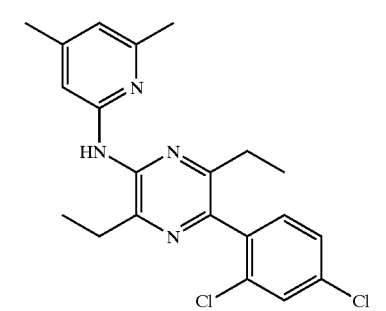

5-(2,4-dichlorophenyl)-3,6-diethyl-N-(4,5,6,7-tetrahydro-1-benzofuran-4-yl)pyrazin-2-amine

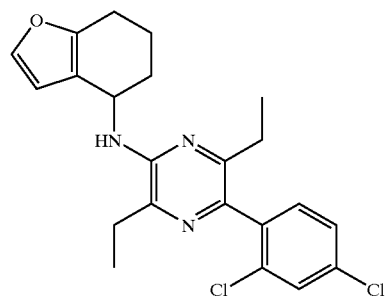

5-(2,4-dichlorophenyl)-3,6-diethyl-N-(5-methyl-4,5,6,7-tetrahydro-1-benzofuran-4-yl)pyrazin-2-amine

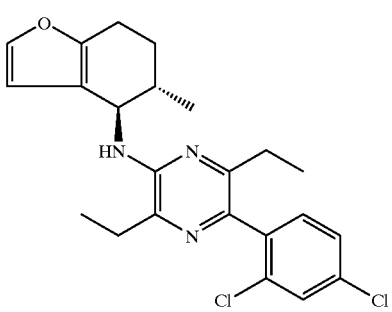

5-(2,4-dichlorophenyl)-3,6-diethyl-N-[(cis)-5-ethyl-4,5,6,7-tetrahydro-1-benzofuran-4-yl]pyrazin-2-amine

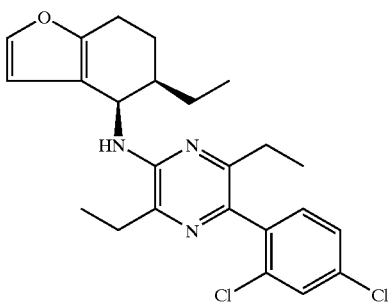

5-(2,4-dichlorophenyl)-3,6-diethyl-N-[(cis)-5-ethyl-4,5,6,7-tetrahydro-1-benzofuran-4-yl]pyrazin-2-amine

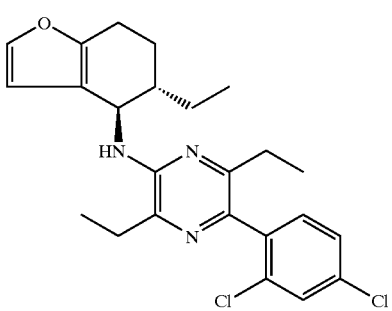

5-(2,4-dichlorophenyl)-N-(3,4-dihydro-2H-thiochromen-4-yl)-3,6-diethylpyrazin-2-amine

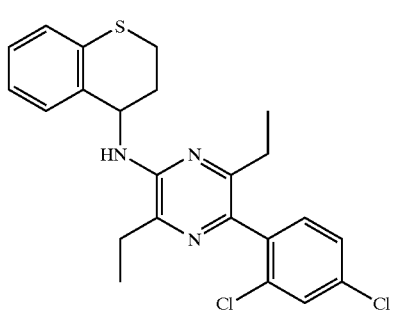

5-(2,4-dichlorophenyl)-3,6-diethyl-N-(1,2,3,4-tetrahydronaphthalen-1-yl)pyrazin-2-amine

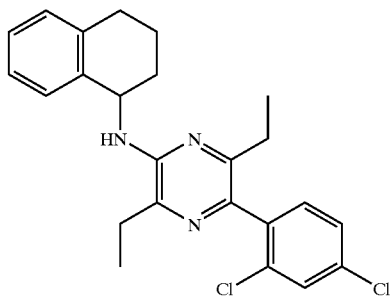

2-(2,4-dichlorophenyl)-3,6-diethyl-5-(1,2,3,4-tetrahydronaphthalen-1-yloxy)pyrazine

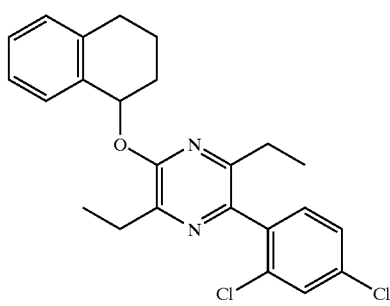

5-(2,4-dichlorophenyl)-3,6-diethyl-N-(7-methoxy-1,2,3,4-tetrahydronaphthalen-1-yl)pyrazin-2-amine

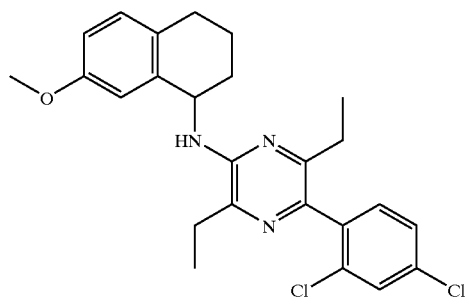

5-(2-chloro-4-methoxyphenyl)-3,6-diethyl-N-(7-methoxy-1,2,3,4-tetrahydronaphthalen-1-yl)pyrazin-2-amine

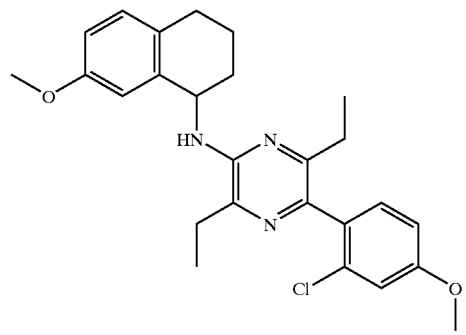

5-(2,4-dichlorophenyl)-3,6-diethyl-N-(5-methoxy-1,2,3,4-tetrahydronaphthalen-1-yl)pyrazin-2-amine

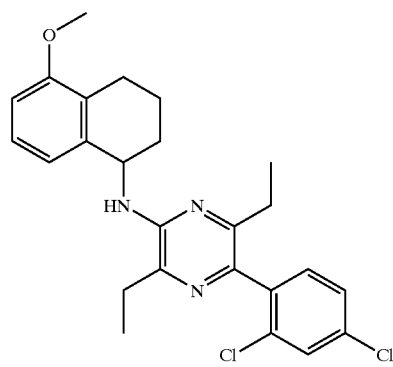

5-(2,4-dichlorophenyl)-3,6-diethyl-N-(6-methoxy-1,2,3,4-tetrahydronaphthalen-1-yl)pyrazin-2-amine

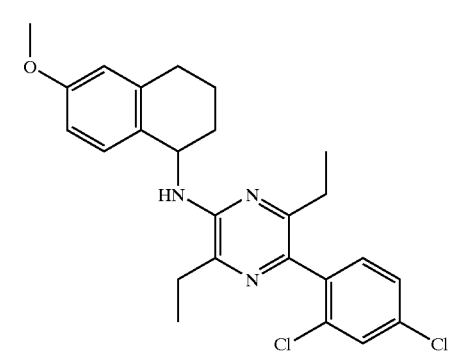

5-(2,4-dichlorophenyl)-3,6-diethyl-N-[(1R,2R) and (1S,2S)-2-methoxy-1,2,3,4-tetrahydronaphthalen-1-yl]pyrazin-2-amine

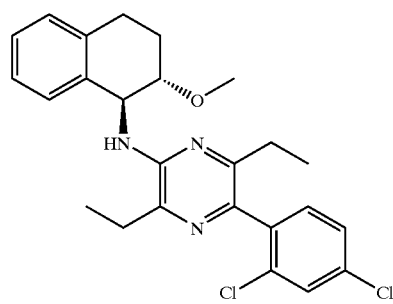

5-(2,4-dichlorophenyl)-N-[(1R,2R) and (1S,2S)-2-ethoxy-1,2,3,4-tetrahydronaphthalen-1-yl]-3,6-diethylpyrazin-2-amine

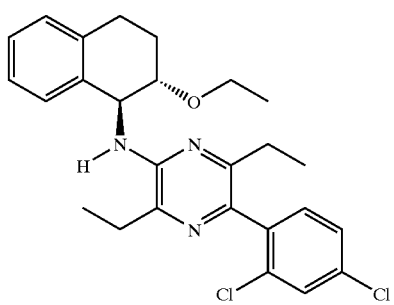

cis-1-{[5-(2,4-dichlorophenyl)-3,6-diethylpyrazin-2-yl]amino}-1,2,3,4-tetrahydronaphthalen-2-ol

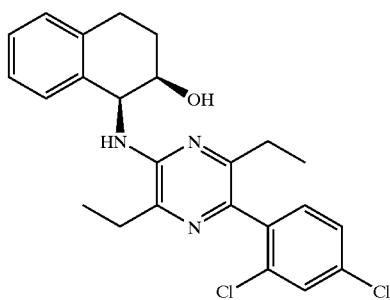

(cis)-2-methoxy-1,2,3,4-tetrahydronaphthalen-1-yl]pyrazin-2-amine

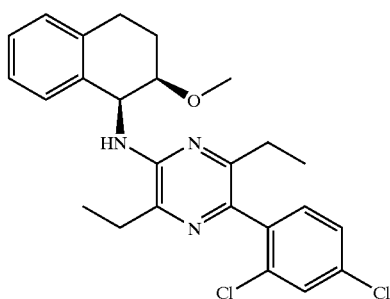

5-(2,4-dichlorophenyl)-N-[(cis)-2-ethoxy-1,2,3,4-tetrahydronaphthalen-1-yl]-3,6-diethylpyrazin-2-amine

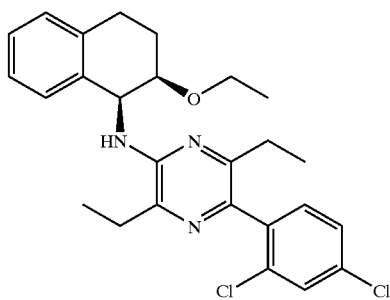

5-(2,4-dichlorophenyl)-3,6-diethyl-N-(4,5,6,7-tetrahydro-1-benzothien-4-yl)pyrazin-2-amine

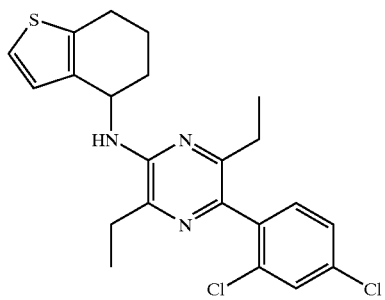

5-(2,4-dichlorophenyl)-3,6-diethyl-N-[Cis-5-methyl-4,5,6,7-tetrahydro-1-benzothien-4-yl]pyrazin-2-amine

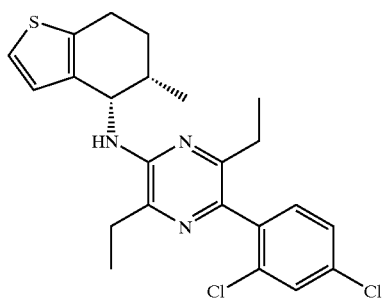

5-(2,4-dichlorophenyl)-3,6-diethyl-N-[Trans-5-methyl-4,5,6,7-tetrahydro-1-benzothien-4-yl]pyrazin-2-amine

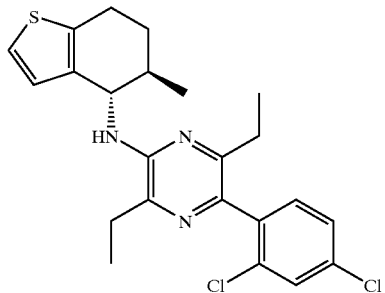

5-(2,4-dichlorophenyl)-3,6-diethyl-N-[Cis-5-ethyl-4,5,6,7-tetrahydro-1-benzothien-4-yl]pyrazin-2-amine

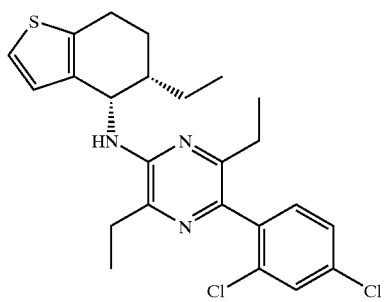

25

5-(2,4-dichlorophenyl)-3,6-diethyl-N-[Trans-5-ethyl-4,5,6,
7-tetrahydro-1-benzothien-4-yl]pyrazin-2-amine

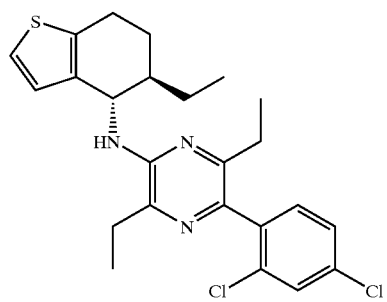

5-(2,4-dichlorophenyl)-N-(3,4-dihydro-2H-chromen-4-yl)-
3,6-diethylpyrazin-2-amine

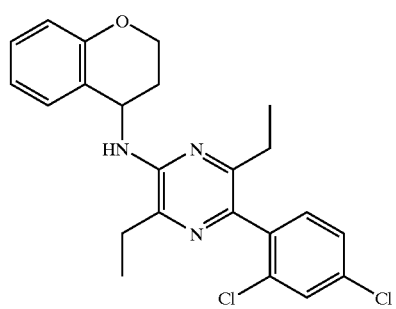

5-(2-chloro-4-methylphenyl)-N-(3,4-dihydro-2H-chromen-
4-yl)-3,6-diethylpyrazin-2-amine

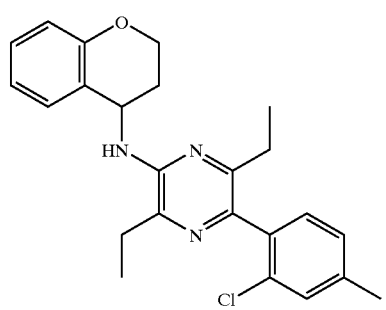

N-(3,4-dihydro-2H-chromen-4-yl)-5-(2,4-dimethylphenyl)-
3,6-diethylpyrazin-2-amine

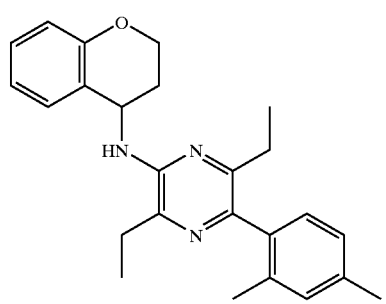

26

5-(2,4-dichlorophenyl)-3,6-diethyl-N-[Cis-5-propyl-4,5,6,
7-tetrahydro-1-benzothien-4-yl]pyrazin-2-amine

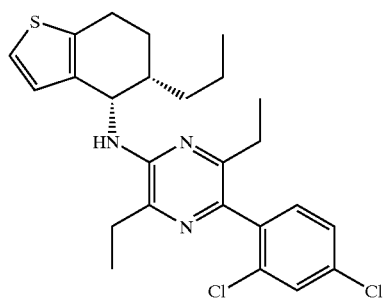

5-(2,4-dichlorophenyl)-3,6-diethyl-N-[Trans-5-propyl-4,5,
6,7-tetrahydro-1-benzothien-4-yl]pyrazin-2-amine

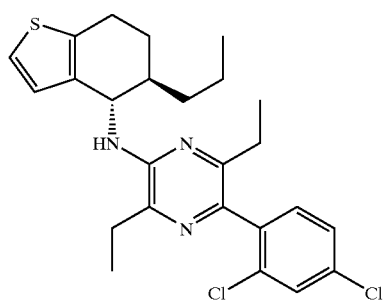

5-(2,4-dichlorophenyl)-N-[(1R,2S)-2-methoxy-2,3-
dihydro-1H-inden-1-yl]-3,6-dimethylpyrazin-2-amine

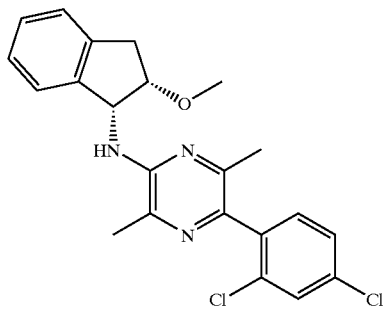

5-(2,4-dichlorophenyl)-N-[(1R,2S)-2-ethoxy-2,3-dihydro-
1H-inden-1-yl]-3,6-dimethylpyrazin-2-amine

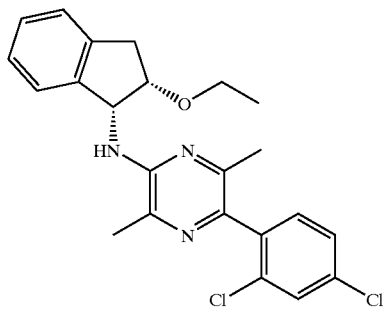

27

5-(2,4-dichlorophenyl)-N-[(1R,2S)-2-isopropoxy-2,3-dihydro-1H-inden-1-yl]-3,6-dimethylpyrazin-2-amine

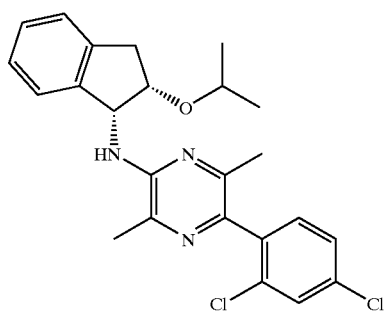

5-(2,4-dichlorophenyl)-3,6-diethyl-N-(8-methoxy-1,2,3,4-tetrahydronaphthalen-1-yl)pyrazin-2-amine

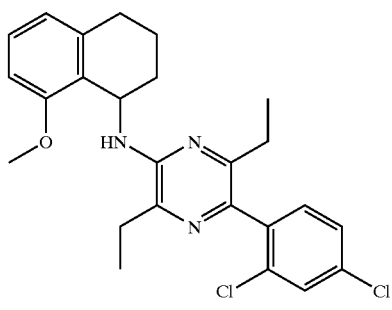

5-(2,4-dichlorophenyl)-3,6-diethyl-N-(6-methoxy-2,3-dihydro-1H-inden-1-yl)pyrazin-2-amine

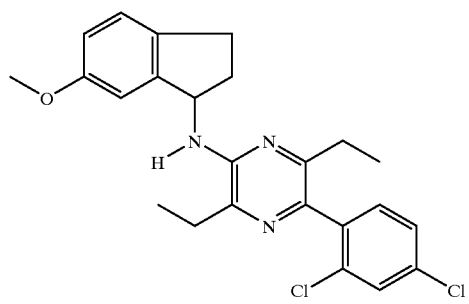

5-(2,4-dichlorophenyl)-3,6-diethyl-N-[(cis)-2-ethyl-6-methoxy-2,3-dihydro-1H-inden-1-yl]pyrazin-2-amine

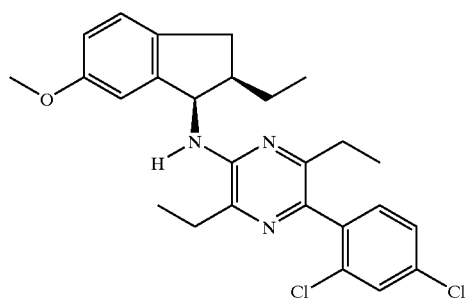

28

5-(2,4-dichlorophenyl)-3,6-diethyl-N-(5-methoxy-2,3-dihydro-1H-inden-1-yl)pyrazin-2-amine

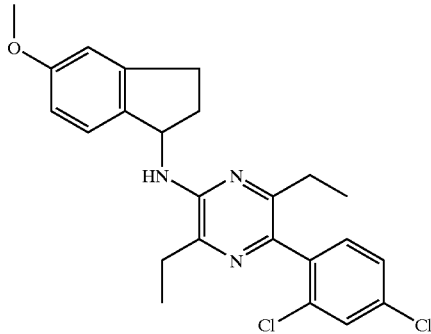

N-[5-(2,4-dichlorophenyl)-3,6-diethylpyrazin-2-yl]-6,7-dihydro-5H-cyclopenta[b]pyridin-7-amine

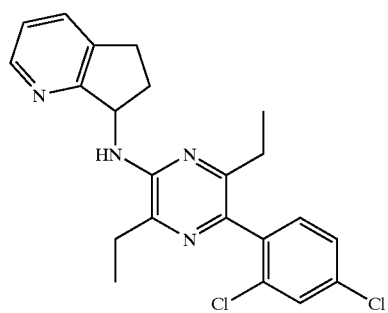

N-[5-(2,4-dichlorophenyl)-3,6-diethylpyrazin-2-yl]-6,7-dihydro-5H-cyclopenta[b]pyridin-5-amine

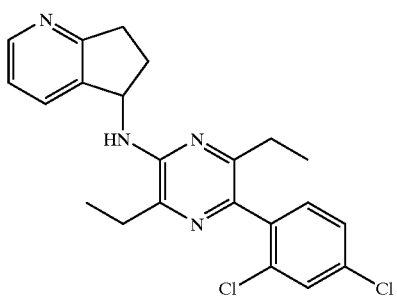

N-[5-(2-chloro-4-methoxyphenyl)-3,6-diethylpyrazin-2-yl]-6-ethyl-6,7-dihydro-5H-cyclopenta[b]pyridin-7-amine

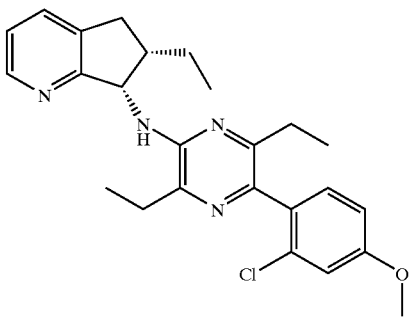

N-[5-(2-chloro-4-methoxyphenyl)-3,6-diethylpyrazin-2-yl]-6-ethyl-6,7-dihydro-5H-cyclopenta[b]pyridin-7-amine

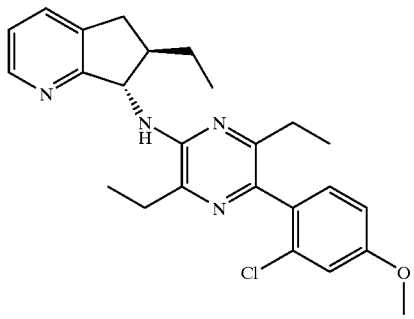

(+/−)-5-(2,4-dichlorophenyl)-3,6-diethyl-N-[cis-2-ethyl-2,3-dihydro-1H-inden-1-yl]pyrazin-2-amine

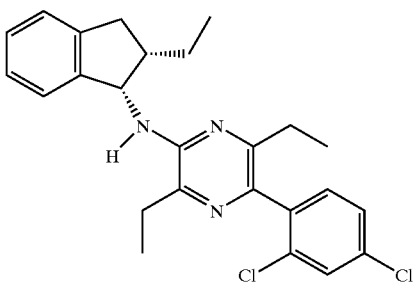

(+/−)-5-(2,4-dichlorophenyl)-3,6-diethyl-N-[trans-2-ethyl-2,3-dihydro-1H-inden-1-yl]pyrazin-2-amine

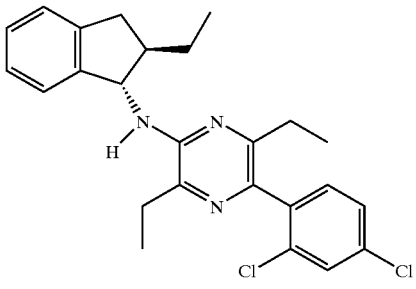

benzyl (cis)-3-{[5-(2,4-dichlorophenyl)-3,6-diethylpyrazin-2-yl]amino}-4-ethoxypyrrolidine-1-carboxylate

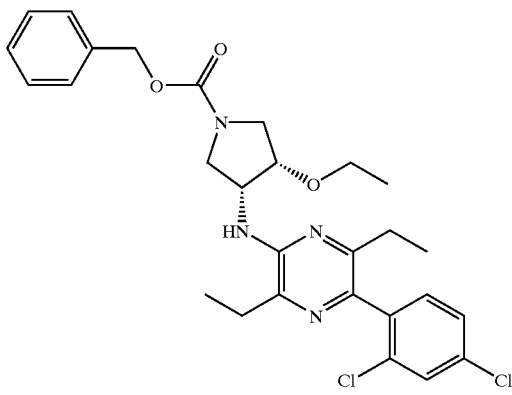

5-(2,4-dichlorophenyl)-N-[(cis)-4-ethoxypyrrolidin-3-yl]-3,6-diethylpyrazin-2-amine

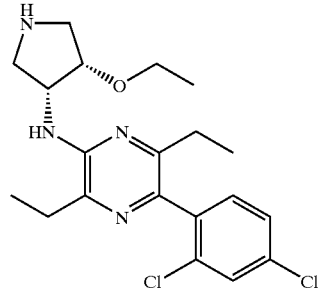

N-[(cis)-1-acetyl-4-ethoxypyrrolidin-3-yl]-5-(2,4-dichlorophenyl)-3,6-diethylpyrazin-2-amine

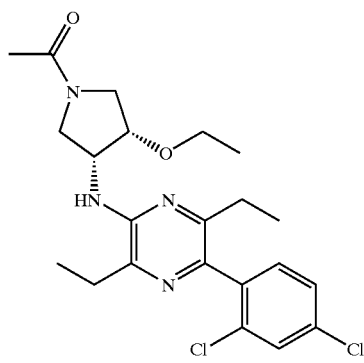

5-(2,4-dichlorophenyl)-N-[(cis)-4-ethoxy-1-propionylpyrrolidin-3-yl]-3,6-diethylpyrazin-2-amine

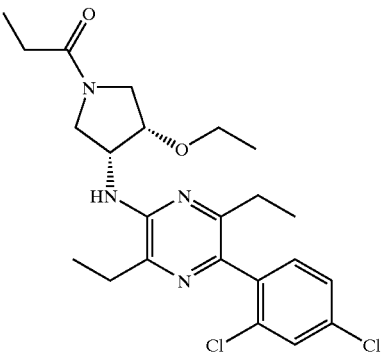

methyl (cis)-3-{[5-(2,4-dichlorophenyl)-3,6-diethylpyrazin-2-yl]amino}-4-ethoxypyrrolidine-1-carboxylate

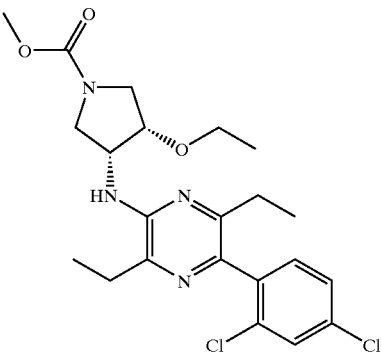

| 31 | 32 |
|---|---|
| 5-(2,4-dichlorophenyl)-N-[(cis)-4-ethoxy-1-(methylsulfonyl)pyrrolidin-3-yl]-3,6-diethylpyrazin-2-amine | (cis)-3-{[5-(2,4-dichlorophenyl)-3,6-diethylpyrazin-2-yl]amino}-4-ethoxy-N,N-dimethylpyrrolidine-1-carbothioamide |

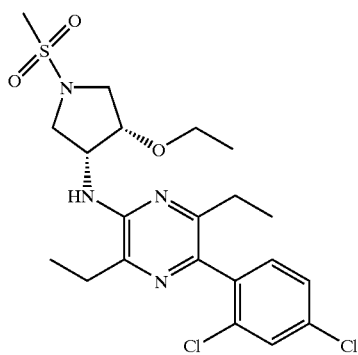

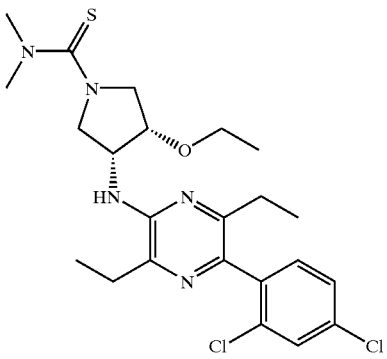

ethyl (cis)-3-{[5-(2,4-dichlorophenyl)-3,6-diethylpyrazin-2-yl]amino}-4-ethoxypyrrolidine-1-carboxylate isopropyl (cis)-3-{[5-(2,4-dichlorophenyl)-3,6-diethylpyrazin-2-yl]amino}-4-ethoxypyrrolidine-1-carboxylate

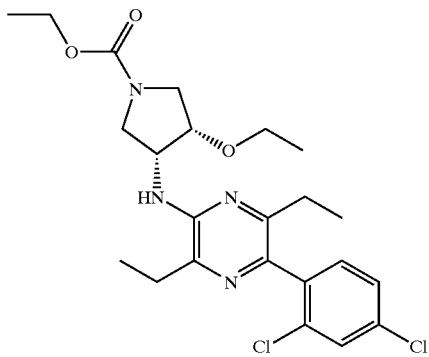

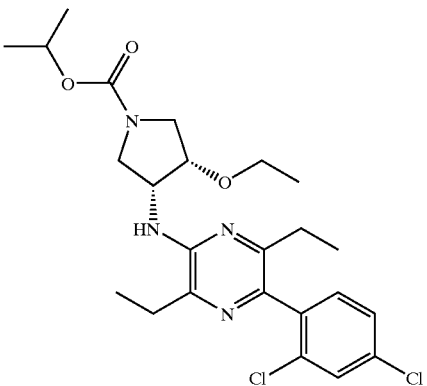

(cis)-3-{[5-(2,4-dichlorophenyl)-3,6-diethylpyrazin-2-yl]amino}-4-ethoxy-N,N-dimethylpyrrolidine-1-carboxamide (cis)-3-{[5-(2,4-dichlorophenyl)-3,6-diethylpyrazin-2-yl]amino}-4-ethoxy-N-methylpyrrolidine-1-carbothioamide

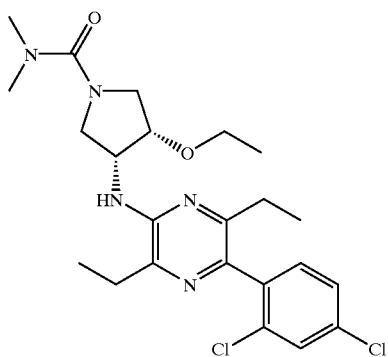

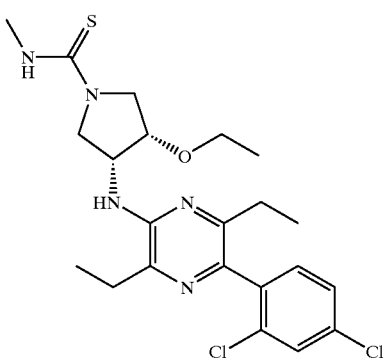

33

5-(2,4-dichlorophenyl)-N-[(cis)-4-ethoxy-1-(morpholin-4-ylcarbonyl)pyrrolidin-3-yl]-3,6-diethylpyrazin-2-amine

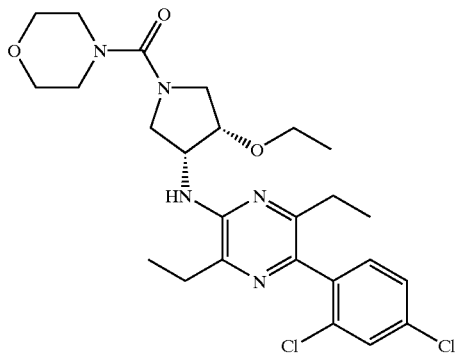

2-fluoroethyl (cis)-3-{[5-(2,4-dichlorophenyl)-3,6-diethylpyrazin-2-yl]amino}-4-ethoxypyrrolidine-1-carboxylate

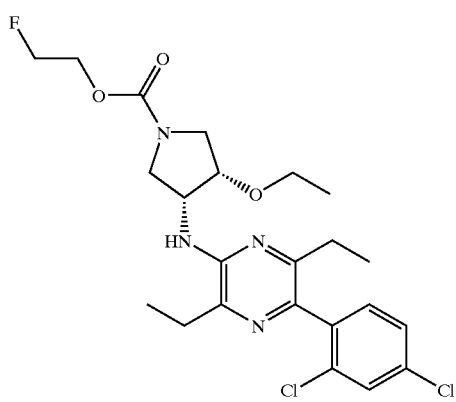

benzyl (3R,4S)-3-{[5-(2,4-dichlorophenyl)-3,6-diethylpyrazin-2-yl]amino}-4-ethoxypyrrolidine-1-carboxylate

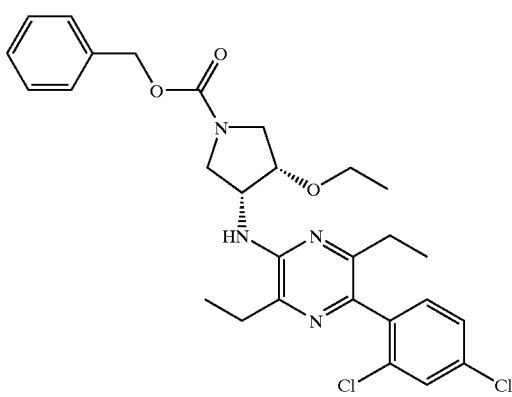

34

5-(2,4-dichlorophenyl)-N-[(3R,4S)-4-ethoxypyrrolidin-3-yl]-3,6-diethylpyrazin-2-amine

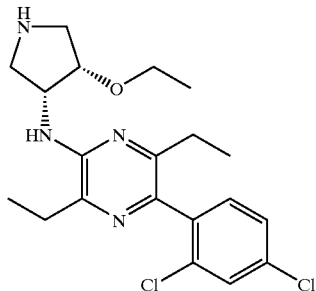

methyl (3R,4S)-3-{[5-(2,4-dichlorophenyl)-3,6-diethylpyrazin-2-yl]amino}-4-ethoxypyrrolidine-1-carboxylate

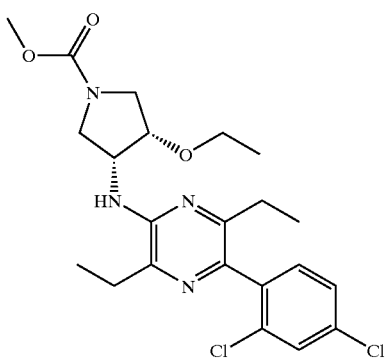

benzyl (3R,4S)-3-{[5-(2,4-dichlorophenyl)-3,6-diethylpyrazin-2-yl]amino}-4-(2-fluoroethoxy)pyrrolidine-1-carboxylate

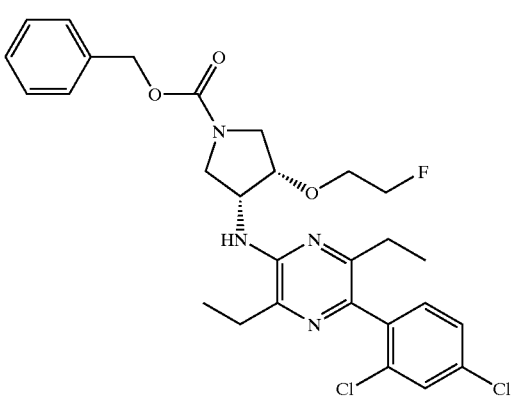

5-(2,4-dichlorophenyl)-3,6-diethyl-N-[(3R,4S)-4-(2-fluoroethoxy)pyrrolidin-3-yl]pyrazin-2-amine

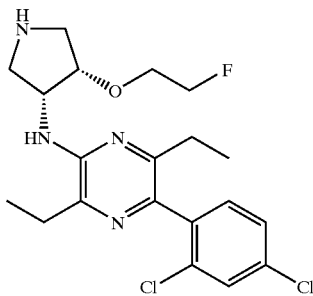

methyl (3R,4S)-3-{[5-(2,4-dichlorophenyl)-3,6-diethylpyrazin-2-yl]amino}-4-(2-fluoroethoxy)pyrrolidine-1-carboxylate

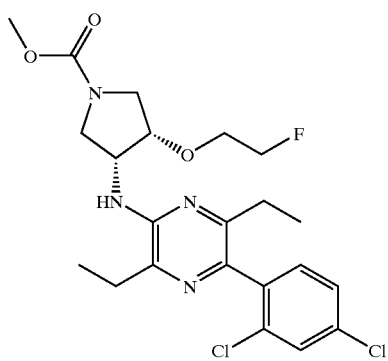

Preparation of methyl(3R,4S)-3-{[3,6-diethyl-5-(4-methoxy-2-methylphenyl)pyrazin-2-yl]amino}-4-(2-fluoroethoxy)pyrrolidine-1-carboxylate

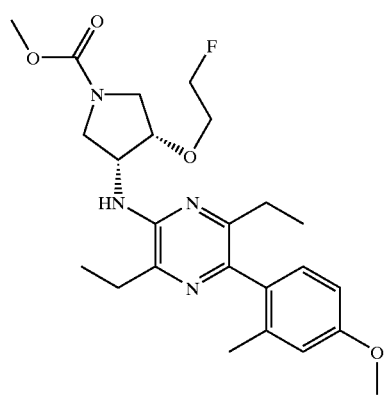

methyl (3R,4S)-3-({5-[2-chloro-4-(dimethylamino)phenyl]-3,6-diethylpyrazin-2-yl}amino)-4-(2-fluoroethoxy)pyrrolidine-1-carboxylate

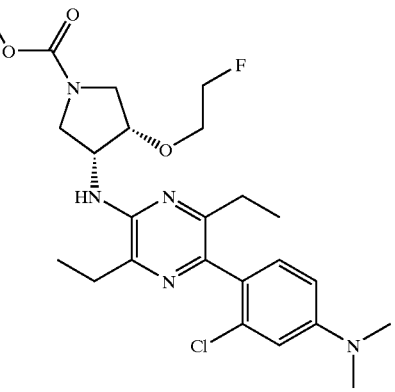

benzyl (3R,4S)-3-{[5-(2-chloro-4-methoxyphenyl)-3,6-diethylpyrazin-2-yl]amino}-4-hydroxypyrrolidine-1-carboxylate

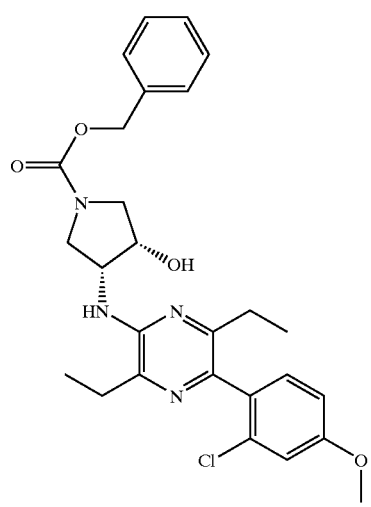

benzyl (3R,4S)-3-{[5-(2-chloro-4-methoxyphenyl)-3,6-diethylpyrazin-2-yl]amino}-4-ethoxypyrrolidine-1-carboxylate

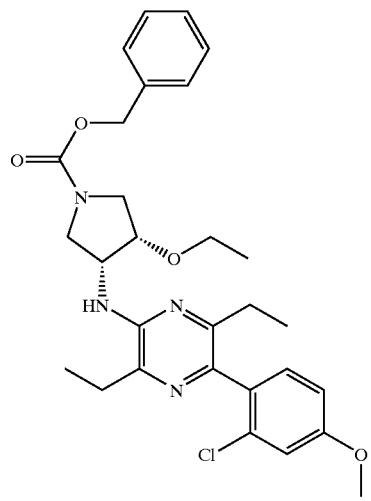

benzyl (3R,4S)-3-{[5-(2-chloro-4-methoxyphenyl)-3,6-
diethylpyrazin-2-yl]amino}-4-(2-fluoroethoxy)
pyrrolidine-1-carboxylate

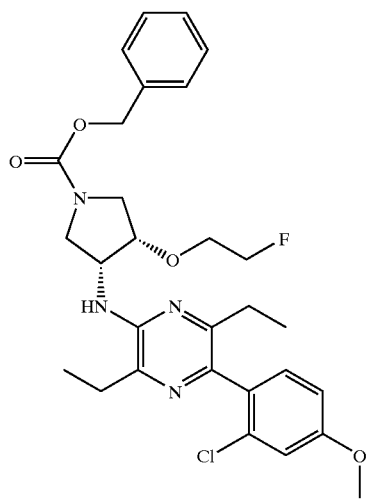

5-(2-chloro-4-methoxyphenyl)-N-[(3R,4S)-4-
ethoxypyrrolidin-3-yl]-3,6-diethylpyrazin-2-amine

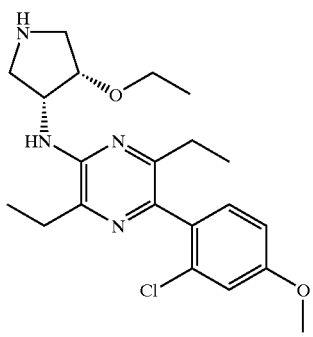

methyl (3R,4S)-3-{[5-(2-chloro-4-methoxyphenyl)-3,6-
diethylpyrazin-2-yl]amino}-4-ethoxypyrrolidine-1-
carboxylate

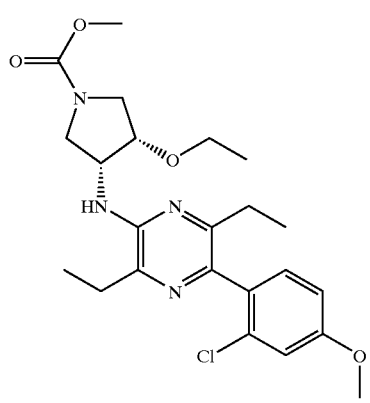

5-(2-chloro-4-methoxyphenyl)-3,6-diethyl-N-[(3R,4S)-4-
(2-fluoroethoxy)pyrrolidin-3-yl]pyrazin-2-amine

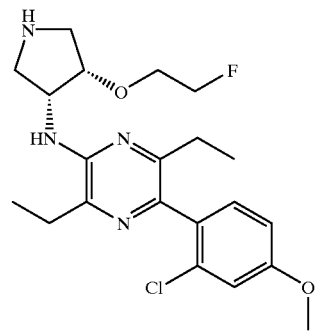

methyl (3R,4S)-3-{[5-(2-chloro-4-methoxyphenyl)-3,6-
diethylpyrazin-2-yl]amino}-4-(2-fluoroethoxy)
pyrrolidine-1-carboxylate

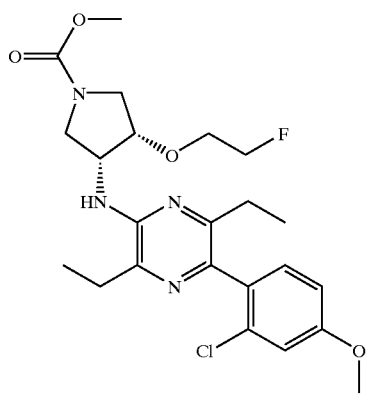

trans-(+/−)-N-[4-ethoxytetrahydrofuran-3-yl]-3,6-diethyl-5-
(4-methoxy-2-methylphenyl)pyrazin-2-amine

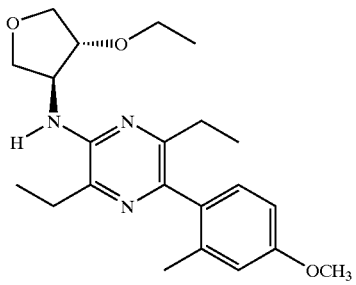

cis-(+/−)-N-[4-ethoxytetrahydrofuran-3-yl]-3,6-diethyl-5-(4-methoxy-2-methylphenyl)pyrazin-2-amine

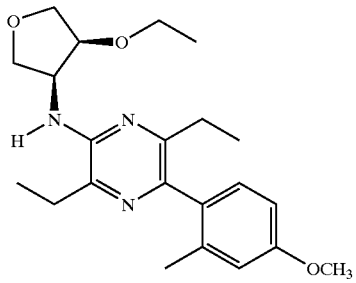

cis-(+/−)-5-(2-chloro-4-methoxyphenyl)-3,6-diethyl-N-[4-methoxytetrahydrofuran-3-yl]pyrazin-2-amine

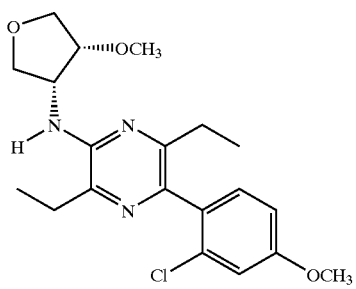

cis-(+/−)-5-(2-chloro-4-methoxyphenyl)-N-[4-ethoxytetrahydrofuran-3-yl]-3,6-diethylpyrazin-2-amine

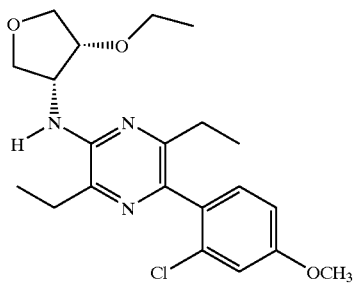

cis-(+/−)-5-(2-chloro-4-methoxyphenyl)-N-[4-propoxytetrahydrofuran-3-yl]-3,6-diethylpyrazin-2-amine

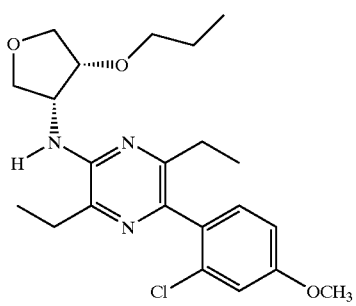

5-(2-chloro-4-methoxyphenyl)-3,6-diethyl-N-[(3S,4S)-4-propoxytetrahydrofuran-3-yl]pyrazin-2-amine

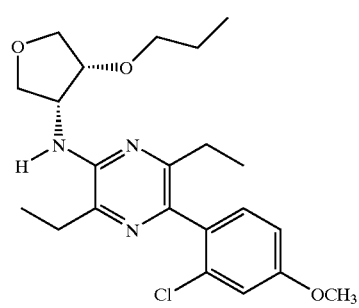

5-(2-chloro-4-methoxyphenyl)-3,6-diethyl-N-[(3S,4S)-4-propoxytetrahydrofuran-3-yl]pyrazin-2-amine

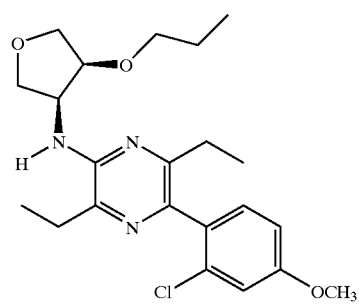

(+/−)-5-(2-chloro-4-methoxyphenyl)-3,6-diethyl-N-[cis-4-(3-fluoropropoxy)tetrahydrofuran-3-yl]pyrazin-2-amine

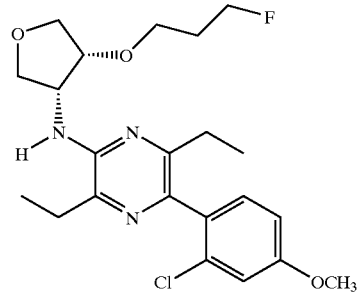

5-(2,4-dichlorophenyl)-3,6-diethyl-N-(1-propyl-1H-imidazol-2-yl)pyrazin-2-amine

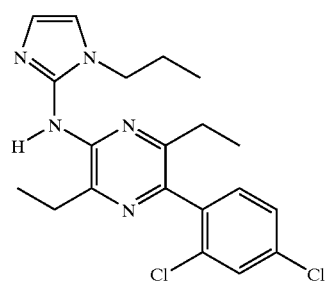

3,6-dicyclopropyl-5-(2,4-dichlorophenyl)-N-[(1R,2S)-2-
ethoxy-2,3-dihydro-1H-inden-1-yl]pyrazin-2-amine

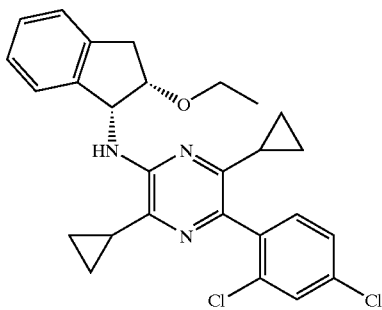

6-cyclopropyl-5-(2,4-dichlorophenyl)-N-[(1R,2S)-2-
ethoxy-2,3-dihydro-1H-inden-1-yl]-3-methylpyrazin-2-
amine

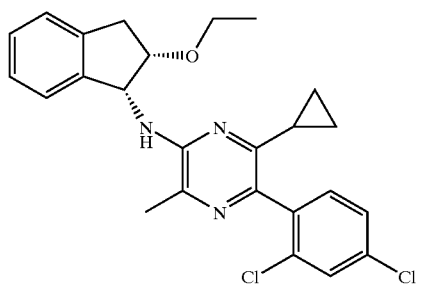

3-cyclopropyl-5-(2,4-dichlorophenyl)-N-[(1R,2S)-2-
ethoxy-2,3-dihydro-1H-inden-1-yl]-6-methylpyrazin-2-
amine

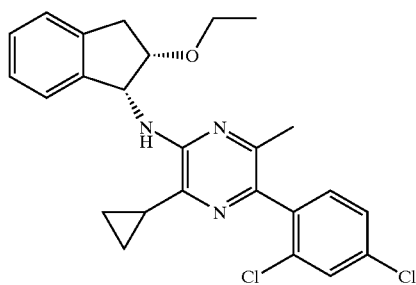

6-cyclopropyl-5-(2,4-dichlorophenyl)-N-[(1R,2S)-2-
ethoxy-2,3-dihydro-1H-inden-1-yl]-3-ethylpyrazin-2-
amine

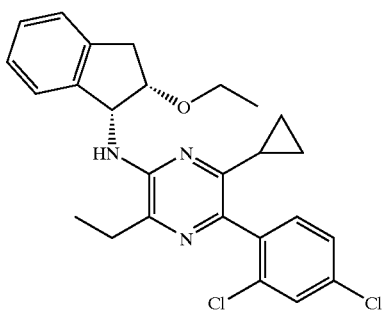

5-(2-chloro-4-methoxyphenyl)-6-cyclopropyl-N-[(1R,2S)-
2-ethoxy-2,3-dihydro-1H-inden-1-yl]-3-ethylpyrazin-2-
amine

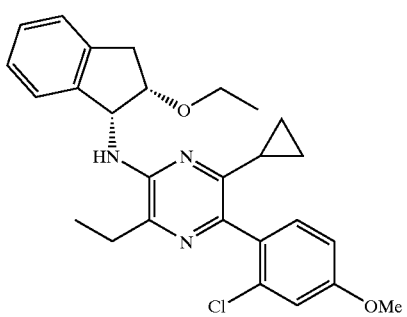

6-cyclopropyl-5-[6-(dimethylamino)-4-methylpyridin-3-
yl]-N-[(1R,2S)-2-ethoxy-2,3-dihydro-1H-inden-1-yl]-3-
ethylpyrazin-2-amine

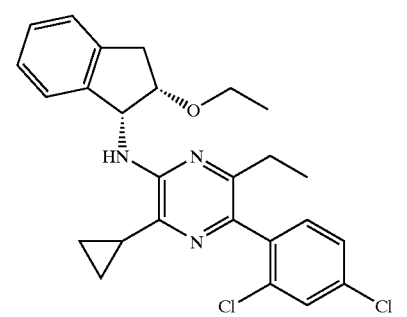

3-cyclopropyl-5-(2,4-dichlorophenyl)-N-[(1R,2S)-2-
ethoxy-2,3-dihydro-1H-inden-1-yl]-6-ethylpyrazin-2-
amine 3-cyclopropyl-5-[6-(dimethylamino)-4-methylpyridin-3-
yl]-N-[(1R,2S)-2-ethoxy-2,3-dihydro-1H-inden-1-yl]-6-
ethylpyrazin-2-amine

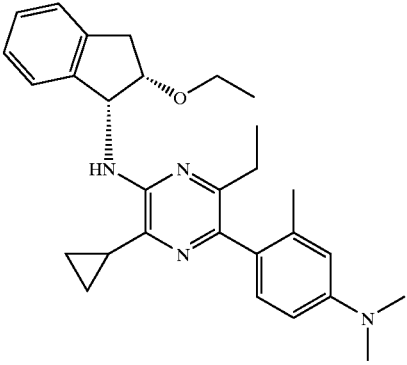

5-(2-chloro-4-methoxyphenyl)-3-cyclopropyl-N-[(1R,2S)-2-ethoxy-2,3-dihydro-1H-inden-1-yl]-6-ethylpyrazin-2-amine

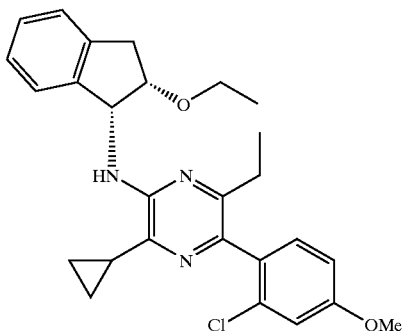

5-(2-chloro-4-methoxyphenyl)-3-cyclopropyl-N-[(1R,2S)-2-ethoxy-2,3-dihydro-1H-inden-1-yl]-6-ethylpyrazin-2-amine

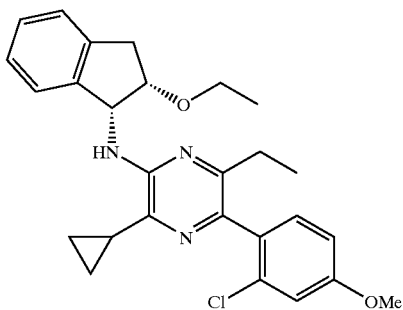

5-(2,4-dichlorophenyl)-N-[(1R,2S)-2-ethoxy-2,3-dihydro-1H-inden-1-yl]-6-ethyl-3-methylpyrazin-2-amine

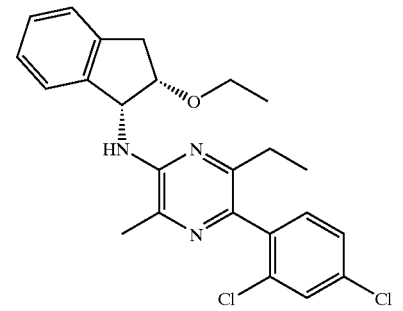

5-(2,4-dichlorophenyl)-N-[(1R,2S)-2-ethoxy-2,3-dihydro-1H-inden-1-yl]-3-ethyl-6-methylpyrazin-2-amine

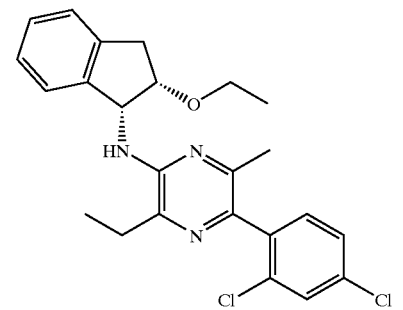

(1R,2R)-N$^1$-[3,6-dicyclopropyl-5-(2,4-dichlorophenyl)pyrazin-2-yl]-N$^2$-ethyl-2,3-dihydro-1H-indene-1,2-diamine

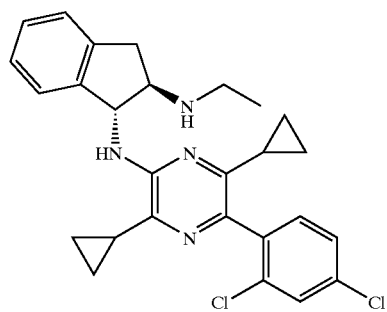

N-((1R,2R)-1-{[3,6-dicyclopropyl-5-(2,4-dichlorophenyl)pyrazin-2-yl]amino}-2,3-dihydro-1H-inden-2-yl)acetamide

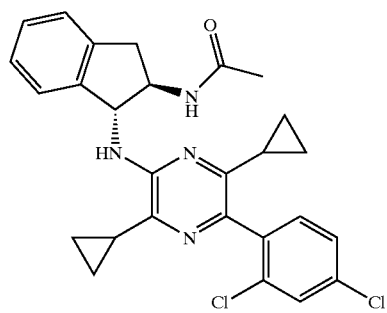

(1R,2R)-N$^1$-[3,6-dicyclopropyl-5-(2,4-dichlorophenyl)pyrazin-2-yl]-N$^2$-(2-methoxyethyl)-2,3-dihydro-1H-indene-1,2-diamine

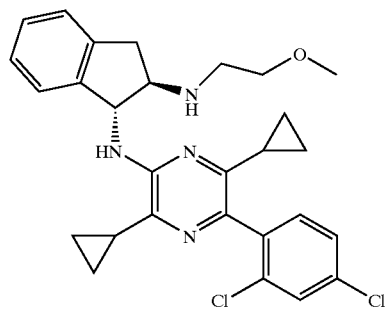

5-(2,4-dichlorophenyl)-N-[(1S,2R)-2-ethoxy-2,3-dihydro-1H-inden-1-yl]-3,6-diethylpyrazin-2-amine

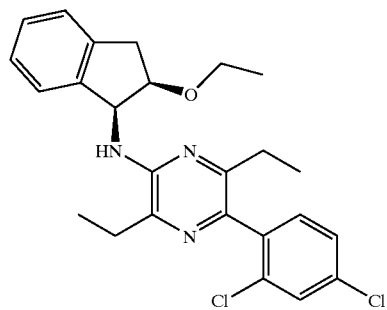

5-(2,4-dichlorophenyl)-N-[(1S,2S)-2-ethoxy-2,3-dihydro-1H-inden-1-yl]-3,6-diethylpyrazin-2-amine

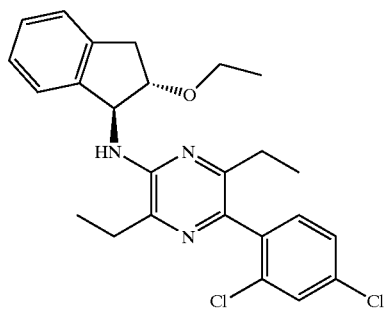

5-(2,4-dichlorophenyl)-3,6-diethyl-N-[(1S,2S)-2-(2-fluoroethoxy)-2,3-dihydro-1H-inden-1-yl]pyrazin-2-amine

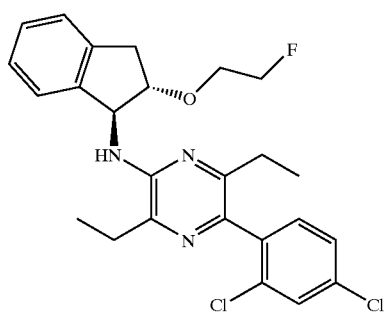

methyl 3-(2,4-dichlorophenyl)-6-{[(1R,2S)-2-ethoxy-2,3-dihydro-1H-inden-1-yl]amino}-5-methoxypyrazine-2-carboxylate

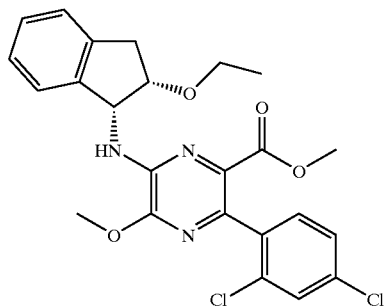

methyl 6-{[(1R,2S)-2-(acetyloxy)-2,3-dihydro-1H-inden-1-yl]amino}-3-(2,4-dichlorophenyl)-5-methoxypyrazine-2-carboxylate

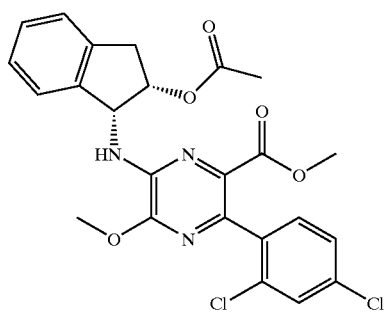

5-(2,4-dichlorophenyl)-N-[(1R,2S)-2-ethoxy-2,3-dihydro-1H-inden-1-yl]-6-methoxy-3-vinylpyrazin-2-amine

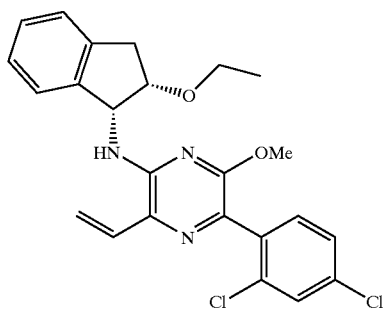

methyl (3R,4S)-3-{[5-(2,4-dichlorophenyl)-3,6-diethylpyrazin-2-yl]amino}-4-propoxypyrrolidine-1-carboxylate

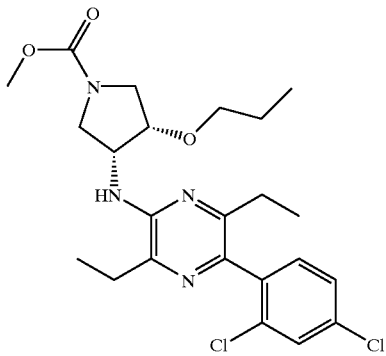

methyl (3R,4S)-3-{[5-(2,4-dichlorophenyl)-3,6-diethylpyrazin-2-yl]amino}-4-(3-fluoropropoxy)pyrrolidine-1-carboxylate

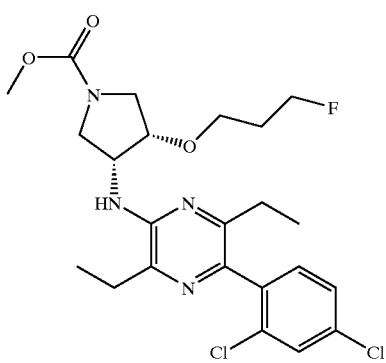

methyl (3R,4S)-3-{[5-(2-chloro-4-methoxyphenyl)-3,6-diethylpyrazin-2-yl]amino}-4-(3-fluoropropoxy)pyrrolidine-1-carboxylate

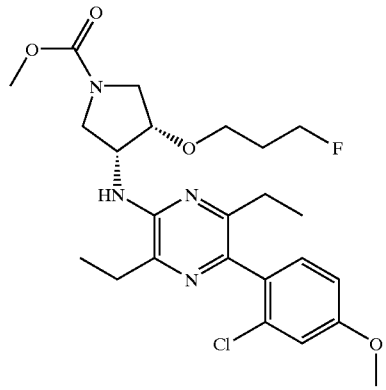

methyl (3R,4S)-3-{[5-(2-chloro-4-methoxyphenyl)-3,6-diethylpyrazin-2-yl]amino}4-propoxypyrrolidine-1-carboxylate

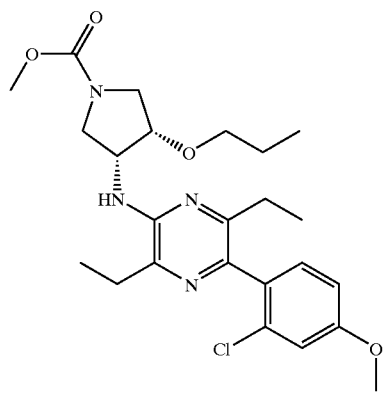

methyl (3R,4S)-3-{[5-(2-chloro-4-methoxyphenyl)-3,6-diethylpyrazin-2-yl]amino}-4-(propionyloxy)pyrrolidine-1-carboxylate

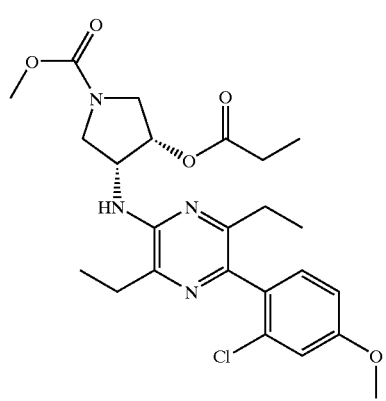

methyl (3S,4R)-3-(acetyloxy)-4-{[5-(2-chloro-4-methoxyphenyl)-3,6-diethylpyrazin-2-yl]amino}pyrrolidine-1-carboxylate

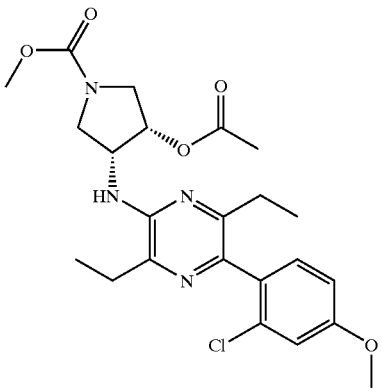

methyl (3S,4R)-3-(acetyloxy)-4-{[5-(2,4-dichlorophenyl)-3,6-diethylpyrazin-2-yl]amino}pyrrolidine-1-carboxylate

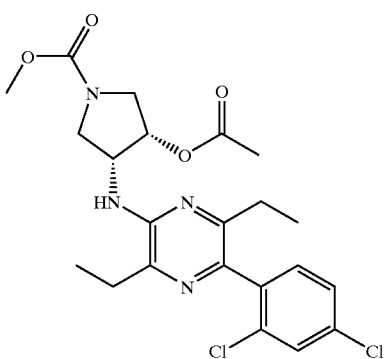

methyl (3R,4S)-3-{[5-(2,4-dichlorophenyl)-3,6-diethylpyrazin-2-yl]amino}-4-(propionyloxy)pyrrolidine-1-carboxylate

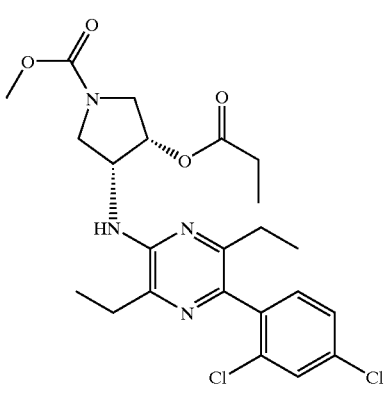

methyl (3R,4S)-3-{[5-(2,4-dichlorophenyl)-3,6-diethylpyrazin-2-yl]amino}-4-(propionylamino)pyrrolidine-1-carboxylate

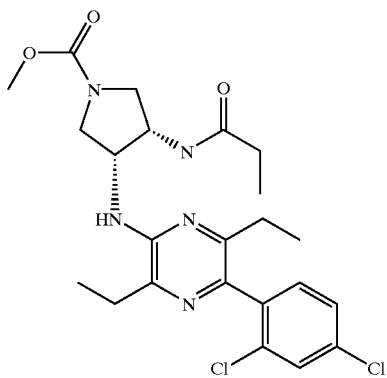

methyl (3S,4R)-3-(acetylamino)-4-{[5-(2,4-dichlorophenyl)-3,6-diethylpyrazin-2-yl]amino}pyrrolidine-1-carboxylate

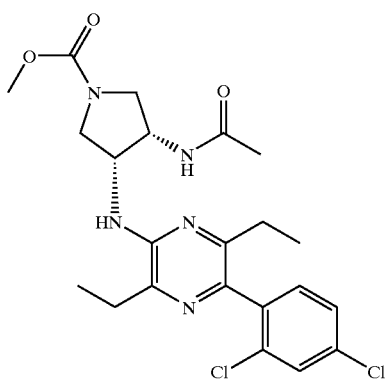

methyl (3R,4S)-3-{[5-(2,4-dichlorophenyl)-3,6-diethylpyrazin-2-yl]amino}-4-(ethylamino)pyrrolidine-1-carboxylate

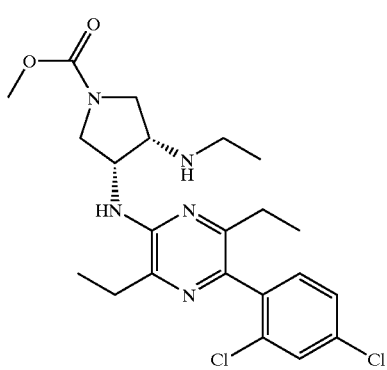

methyl (3R,4S)-3-{[5-(2,4-dichlorophenyl)-3,6-diethylpyrazin-2-yl]amino}-4-(propylamino)pyrrolidine-1-carboxylate

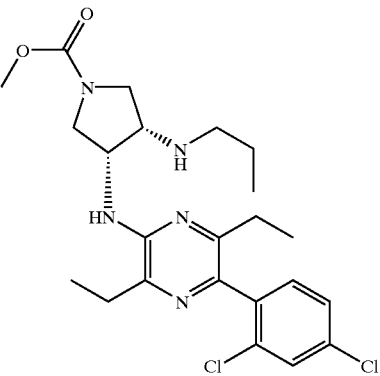

O-methyl (3R,4S)-3-{[5-(2,4-dichlorophenyl)-3,6-diethylpyrazin-2-yl]amino}-4-2-fluoroethoxy)pyrrolidine-1-carbothioate

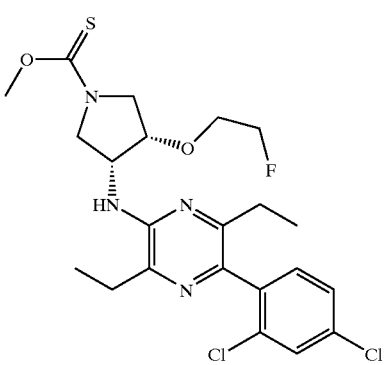

O-methyl (3R,4S)-3-{[5-(2,4-dichlorophenyl)-3,6-diethylpyrazin-2-yl]amino}-4-ethoxypyrrolidine-1-carbothioate

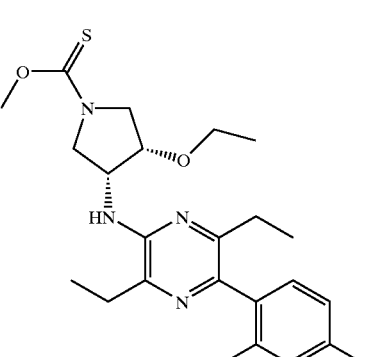

51

O-methyl (3R,4S)-3-{[5-(2-chloro-4-methoxyphenyl)-3,6-diethylpyrazin-2-yl]amino}-4-(3-fluoropropoxy)pyrrolidine-1-carbothioate

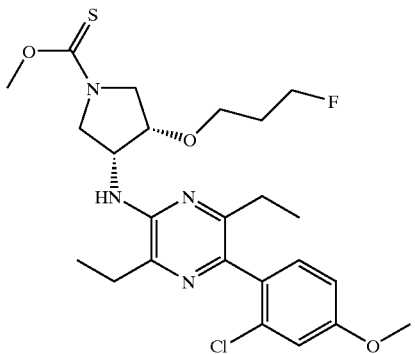

ethyl (3R,4S)-3-{[5-(2-chloro-4-methoxyphenyl)-3,6-diethylpyrazin-2-yl]amino}-4-(2-fluoroethoxy)pyrrolidine-1-carboxylate

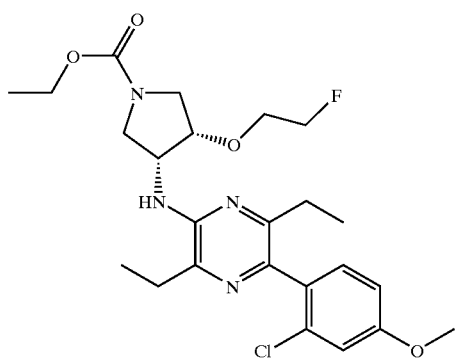

ethyl (3R,4S)-3-{[5-(2,4-dichlorophenyl)-3,6-diethylpyrazin-2-yl]amino}-4-(2-fluoroethoxy)pyrrolidine-1-carboxylate

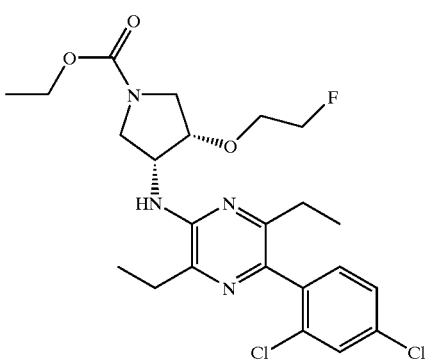

52 pyridin-2-ylmethyl (3R,4S)-3-{[5-(2,4-dichlorophenyl)-3,6-diethylpyrazin-2-yl]amino}-4-(2-fluoroethoxy)pyrrolidine-1-carboxylate

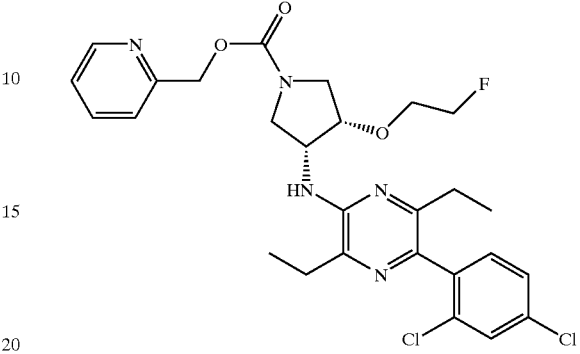

pyridin-3-ylmethyl (3R,4S)-3-{[5-(2,4-dichlorophenyl)-3,6-diethylpyrazin-2-yl]amino}-4-(2-fluoroethoxy)pyrrolidine-1-carboxylate

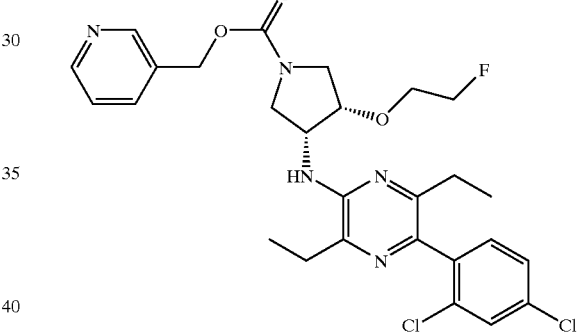

pyridin-4-ylmethyl (3R,4S)-3-{[5-(2-chloro-4-methoxyphenyl)-3,6-diethylpyrazin-2-yl]amino}-4-(2-fluoroethoxy)pyrrolidine-1-carboxylate

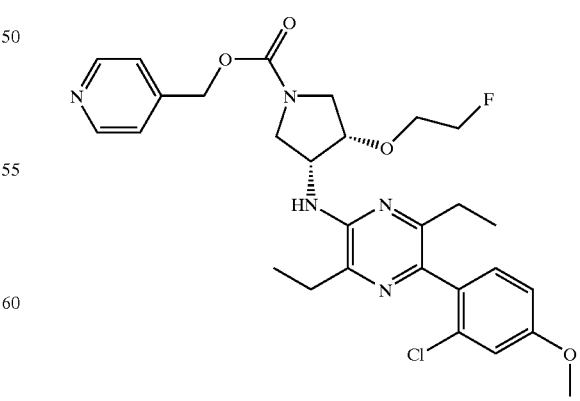

53

2-piperidin-1-ylethyl (3R,4S)-3-{[5-(2-chloro-4-methoxyphenyl)-3,6-diethylpyrazin-2-yl]amino}-4-(2-fluoroethoxy)pyrrolidine-1-carboxylate

54

2-(dimethylamino)ethyl (3R,4S)-3-{[5-(2,4-dichlorophenyl)-3,6-diethylpyrazin-2-yl]amino}-4-(3-fluoropropoxy)pyrrolidine-1-carboxylate

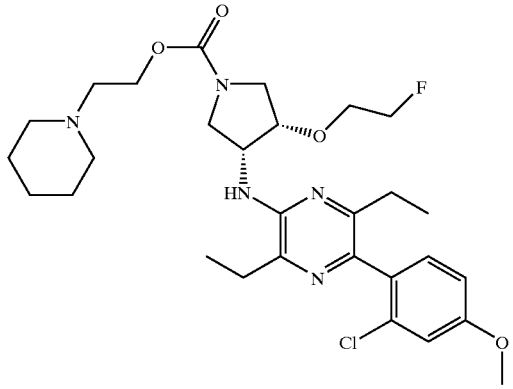

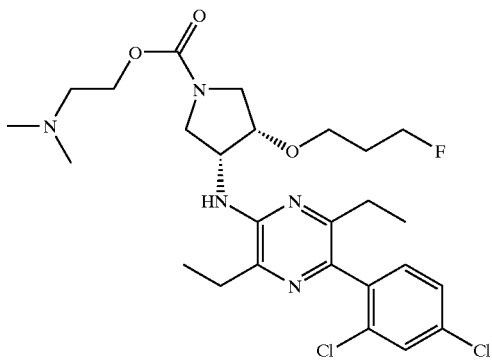

2-morpholin-4-ylethyl (3R,4S)-3-{[5-(2,4-dichlorophenyl)-3,6-diethylpyrazin-2-yl]amino}-4-(2-fluoroethoxy)pyrrolidine-1-carboxylate 2-pyrrolidin-1-ylethyl (3R,4S)-3-{[5-(2,4-dichlorophenyl)-3,6-diethylpyrazin-2-yl]amino}-4-(3-fluoropropoxy)pyrrolidine-1-carboxylate

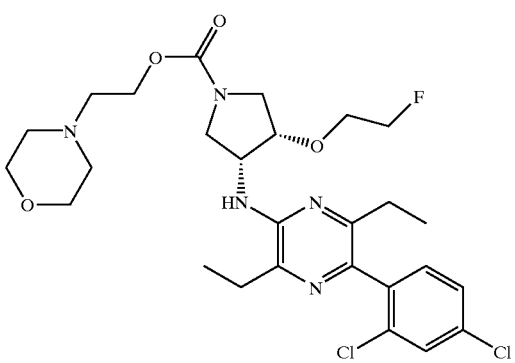

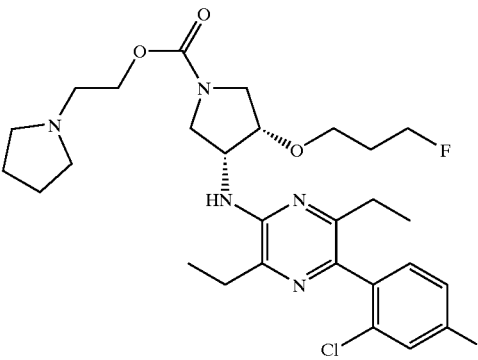

2-morpholin-4-ylethyl (3R,4S)-3-{[5-(2,4-dichlorophenyl)-3,6-diethylpyrazin-2-yl]amino}-4-(propionyloxy)pyrrolidine-1-carboxylate 2-(1H-imidazol-1-yl)ethyl (3R,4S)-3-{[5-(2,4-dichlorophenyl)-3,6-diethylpyrazin-2-yl]amino}-4-(2-fluoroethoxy)pyrrolidine-1-carboxylate

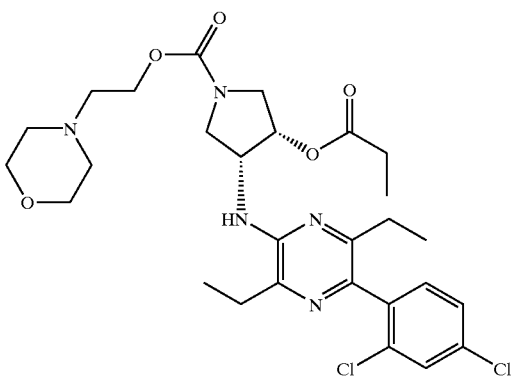

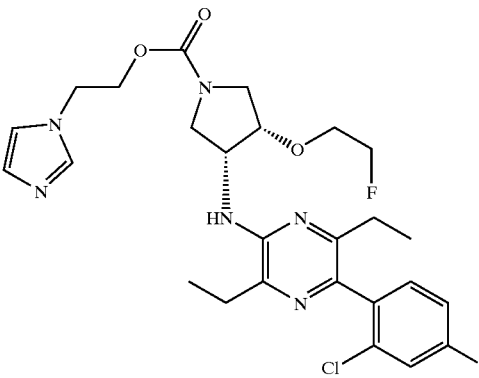

| 55 | 56 |

2-(methylamino)ethyl (3R,4S)-3-{[5-(2,4-dichlorophenyl)-3,6-diethylpyrazin-2-yl]amino}-4-(2-fluoroethoxy)pyrrolidine-1-carboxylate 2-methoxyethyl (3R,4S)-3-{[5-(2,4-dichlorophenyl)-3,6-diethylpyrazin-2-yl]amino}-4-(2-fluoroethoxy)pyrrolidine-1-carboxylate

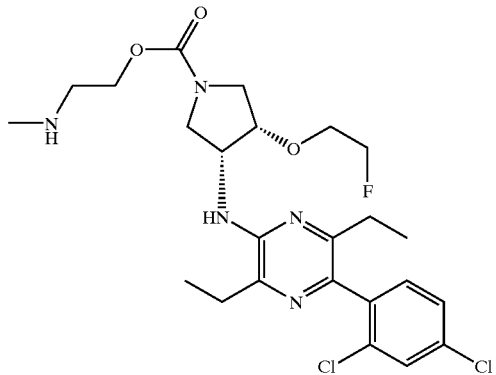
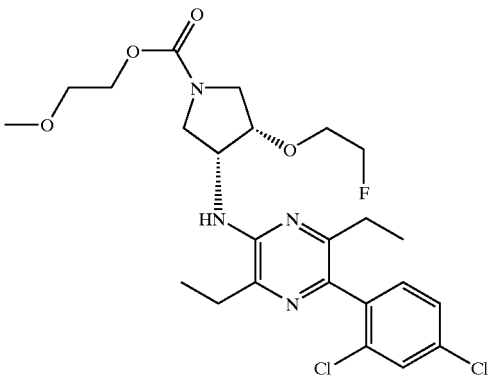

2-aminoethyl (3R,4S)-3-{[5-(2,4-dichlorophenyl)-3,6-diethylpyrazin-2-yl]amino}-4-(2-fluoroethoxy)pyrrolidine-1-carboxylate 2-(2-oxopyrrolidin-1-yl)ethyl (3R,4S)-3-{[5-(2,4-dichlorophenyl)-3,6-diethylpyrazin-2-yl]amino}-4-ethoxypyrrolidine-1-carboxylate

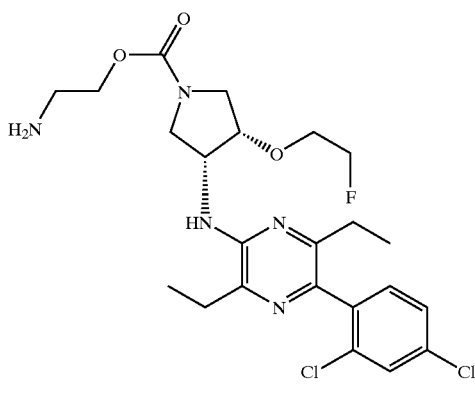
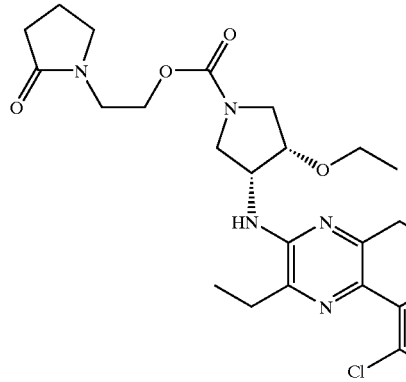

2-hydroxyethyl (3R,4S)-3-{[5-(2,4-dichlorophenyl)-3,6-diethylpyrazin-2-yl]amino}-4-(2-fluoroethoxy)pyrrolidine-1-carboxylate 2-(2-oxopyridin-1(2H)-yl)ethyl (3R,4S)-3-{[5-(2,4-dichlorophenyl)-3,6-diethylpyrazin-2-yl]amino}-4-ethoxypyrrolidine-1-carboxylate

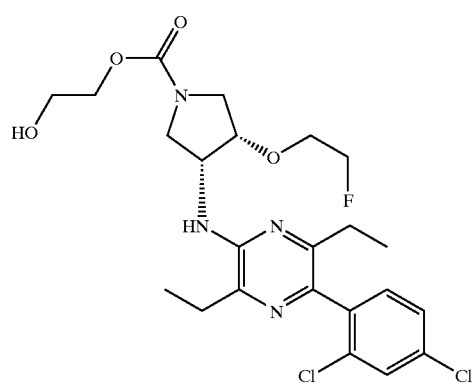
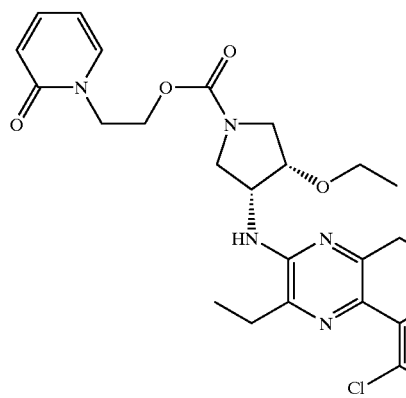

57

(3S,4S)-3-{[5-(2,4-dichlorophenyl)-3,6-diethylpyrazin-2-yl]amino}-4-ethoxypyrrolidin-2-one

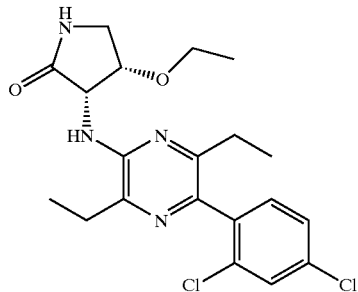

(3S,4S)-3-{[5-(2,4-dichlorophenyl)-3,6-diethylpyrazin-2-yl]amino}-4-ethoxy-1-methylpyrrolidin-2-one

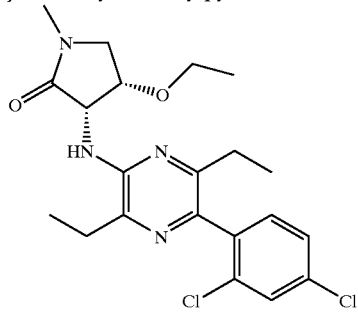

(3S,4S)-1-benzyl-3-{[5-(2,4-dichlorophenyl)-3,6-diethylpyrazin-2-yl]amino}-4-(2-fluoroethoxy)pyrrolidin-2-one

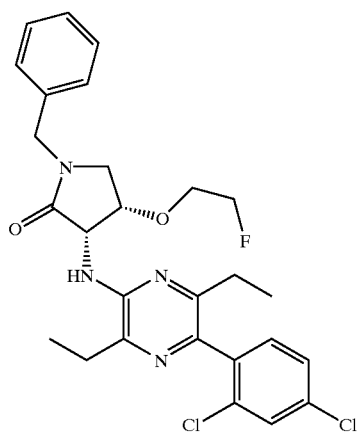

(3R,4R)-4-{[5-(2,4-dichlorophenyl)-3,6-diethylpyrazin-2-yl]amino}-3-(2-fluoroethoxy)pyrrolidin-2-one

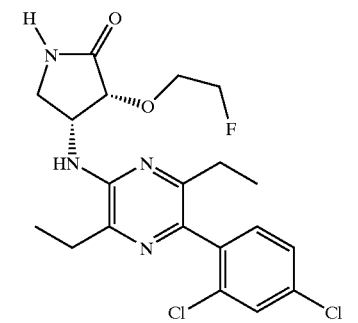

58

(3R,4R)-4-{[5-(2,4-dichlorophenyl)-3,6-diethylpyrazin-2-yl]amino}-3-(2-fluoroethoxy)-1-methylpyrrolidin-2-one

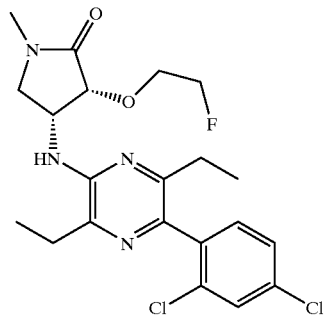

(3R,4R)-1-benzyl-4-{[5-(2,4-dichlorophenyl)-3,6-diethylpyrazin-2-yl]amino}-3-(2-fluoroethoxy)pyrrolidin-2-one

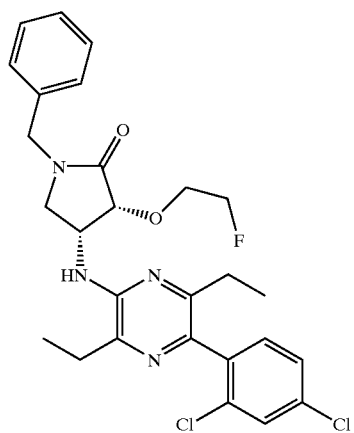

5-(2,4-dichlorophenyl)-3,6-diethyl-N-(1-ethyl-1H-imidazol-2-yl)pyrazin-2-amine

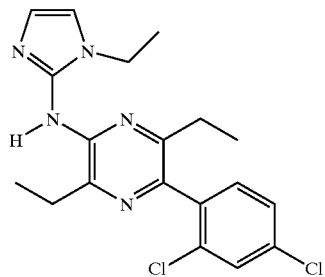

ethyl (2S,3S)-3-{[3,6-diethyl-5-(4-methoxy-2-methylphenyl)pyrazin-2-yl]amino}-2,3-dihydrofuro[2,3-b]pyridine-2-carboxylate

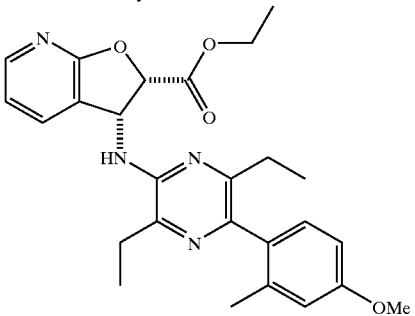

(2S,3S)-N-[3,6-diethyl-5-(4-methoxy-2-methylphenyl)
  pyrazin-2-yl]-2-(ethoxymethyl)-2,3-dihydrofuro[2,3-b]
  pyridin-3-amine

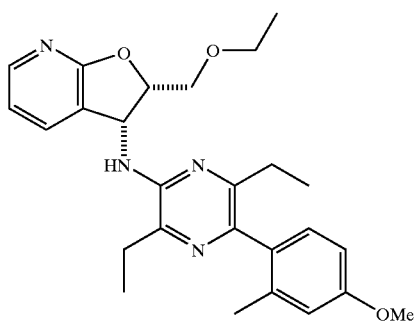

(2R,3S)-N-[3,6-diethyl-5-(4-methoxy-2-methylphenyl)
  pyrazin-2-yl]-2-ethyl-2,3-dihydrofuro[2,3-b]pyridin-3-
  amine

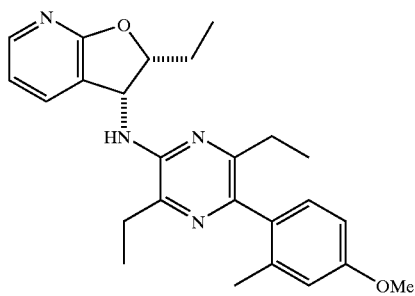

(2R,3S)-N-[3,6-diethyl-5-(4-methoxy-2-methylphenyl)
  pyrazin-2-yl]-2-propyl-2,3-dihydrofuro[2,3-b]pyridin-3-
  amine

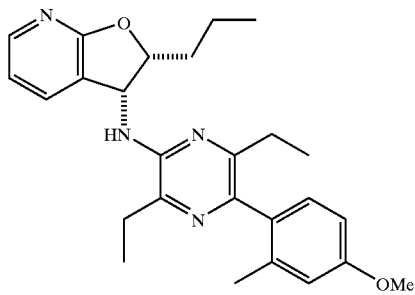

5-(2,4-dichlorophenyl)-3,6-diethyl-N-[(2S)-2-
  (methoxymethyl)pyrrolidin-1-yl]pyrazin-2-amine

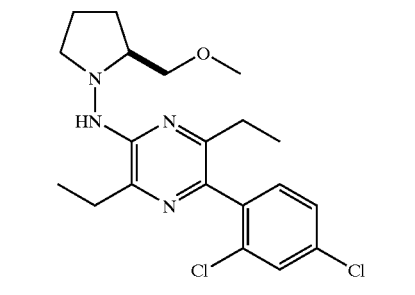

5-(2,4-dichlorophenyl)-3,6-diethyl-N-[(2R)-2-
  (methoxymethyl)pyrrolidin-1-yl]pyrazin-2-amine

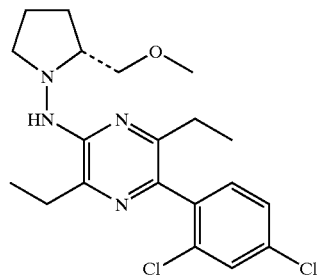

5-(2,4-dichlorophenyl)-N-[(2R)-2-(ethoxymethyl)
  pyrrolidin-1-yl]-3,6-diethylpyrazin-2-amine

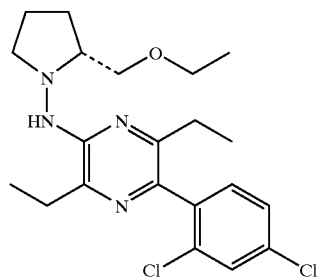

5-(2,4-dichlorophenyl)-3,6-diethyl-N-[(2R)-2-
  (propoxymethyl)pyrrolidin-1-yl]pyrazin-2-amine

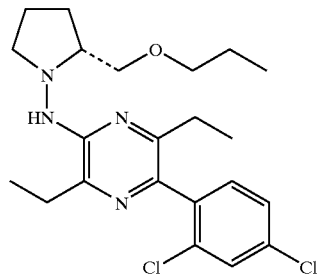

5-(2-chloro-4-methoxyphenyl)-3,6-diethyl-N-{(2R)-2-[(2-
  fluoroethoxy)methyl]pyrrolidin-1-yl}pyrazin-2-amine

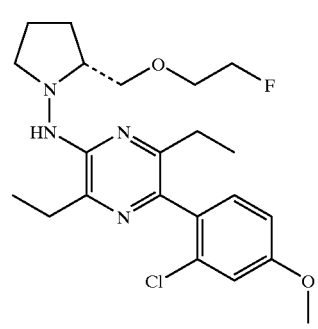

61

5-(2-chloro-4-methoxyphenyl)-N-[(2R)-2-(ethoxymethyl)pyrrolidin-1-yl]-3,6-diethylpyrazin-2-amine

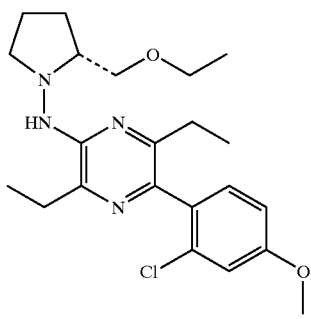

5-(2-chloro-4-methoxyphenyl)-N-[(1R,2S)-2-(2-fluoroethoxy)-2,3-dihydro-1H-inden-1-yl]-3,6-bis(methoxymethyl)pyrazin-2-amine

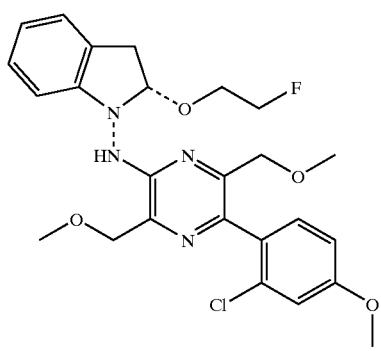

5-(2,4-dichlorophenyl)-N-[(1R,2S)-2-(2-fluoroethoxy)-2,3-dihydro-1H-inden-1-yl]-3,6-bis(methoxymethyl)pyrazin-2-amine

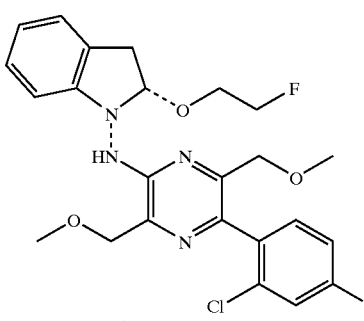

methyl (3R,4S)-3-{[5-(2,4-dichlorophenyl)-3,6-bis(methoxymethyl)pyrazin-2-yl]amino}-4-(2-fluoroethoxy)pyrrolidine-1-carboxylate

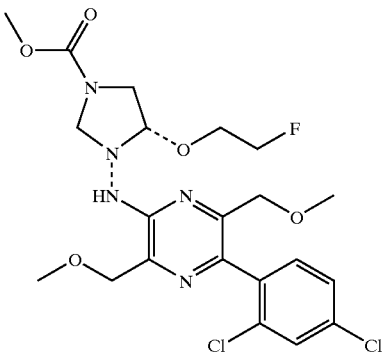

62 methyl (3R,4S)-3-{[5-(2-chloro-4-methoxyphenyl)-3,6-bis(methoxymethyl)pyrazin-2-yl]amino}-4-(2-fluoroethoxy)pyrrolidine-1-carboxylate

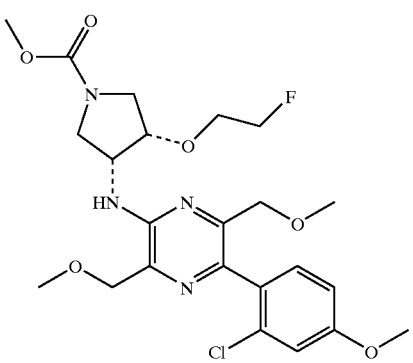

5-(2-chloro-4-methoxyphenyl)-3,6-diethyl-N-[(1R,2S)-2-(3-fluoropropoxy)-2,3-dihydro-1H-inden-1-yl]pyrazin-2-amine

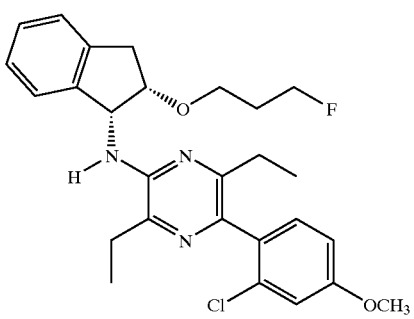

5-(2,4-dichlorophenyl)-3,6-diethyl-N-[(1R,2S)-2-(3-fluoropropoxy)-2,3-dihydro-1H-inden-1-yl]pyrazin-2-amine

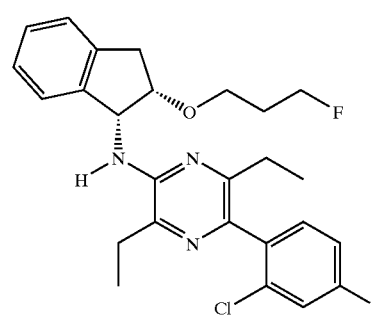

(1R,2S)-1-{[5-(2-chloro-4-methoxyphenyl)-3,6-diethylpyrazin-2-yl]amino}-2,3-dihydro-1H-inden-2-yl hydroxyacetate

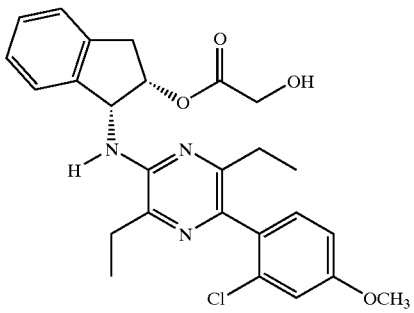

(1R,2S)-1-{[5-(2,4-dichlorophenyl)-3,6-diethylpyrazin-2-yl]amino}-2,3-dihydro-1H-inden-2-yl hydroxyacetate

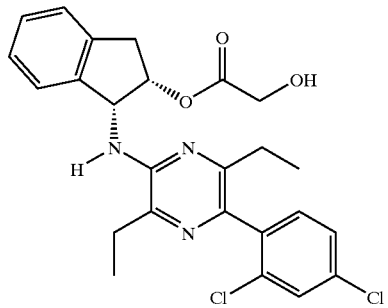

N-[(1R,2S)-2-(2-aminoethoxy)-2,3-dihydro-1H-inden-1-yl]-5-(2,4-dichlorophenyl)-3,6-diethylpyrazin-2-amine

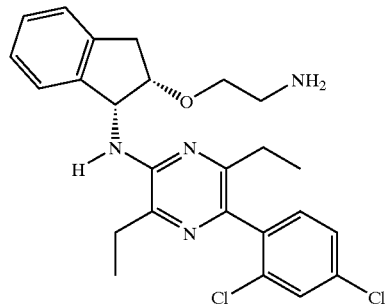

(1R,2S)-1-{[5-(2-chloro-4-methoxyphenyl)-3,6-diethylpyrazin-2-yl]amino}-2,3-dihydro-1H-inden-2-yl methoxyacetate

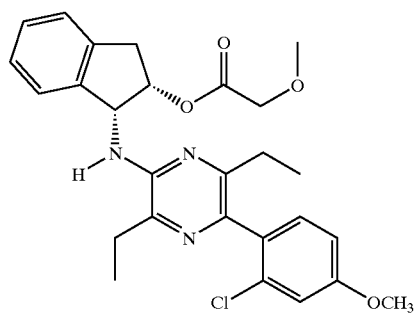

(1R,2S)-1-{[5-(2-chloro-4-methoxyphenyl)-3,6-diethylpyrazin-2-yl]amino}-2,3-dihydro-1H-inden-2-yl glycinate

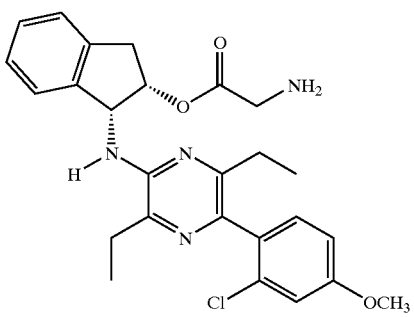

(1R,2S)-1-{[5-(2,4-dichlorophenyl)-3,6-diethylpyrazin-2-yl]amino}-2,3-dihydro-1H-inden-2-yl methoxyacetate

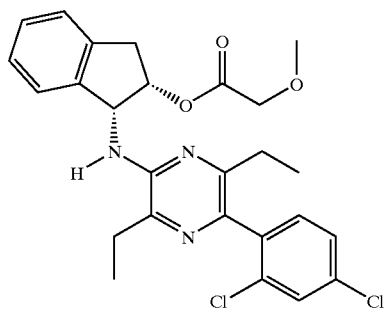

(1R,2S)-1-{[5-(2,4-dichlorophenyl)-3,6-diethylpyrazin-2-yl]amino}-2,3-dihydro-1H-inden-2-yl glycinate

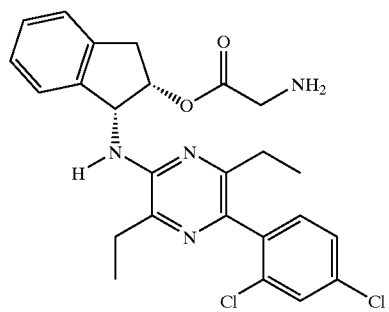

N-[(1R,2S)-2-(2-aminoethoxy)-2,3-dihydro-1H-inden-1-yl]-5-(2-chloro-4-methoxyphenyl)-3,6-diethylpyrazin-2-amine

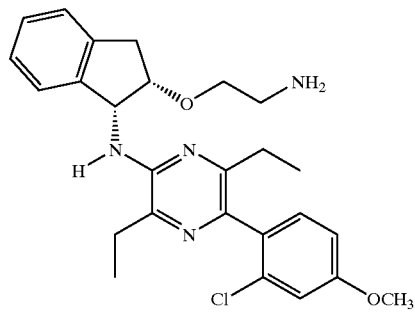

5-(2-chloro-4-methoxyphenyl)-3,6-diethyl-N-{(1R,2S)-2-[2-(methylamino)ethoxy]-2,3-dihydro-1H-inden-1-yl}pyrazin-2-amine

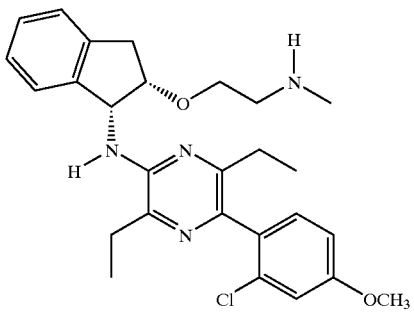

5-(2,4-dichlorophenyl)-3,6-diethyl-N-{(1R,2S)-2-[2-(methylamino)ethoxy]-2,3-dihydro-1H-inden-1-yl}pyrazin-2-amine

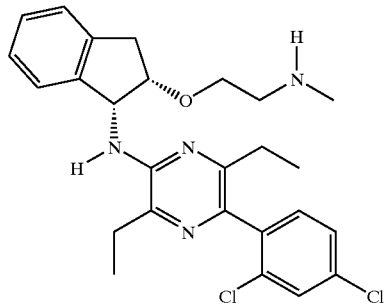

5-(2,4-dichlorophenyl)-N-{(1R,2S)-2-[2-(dimethylamino)ethoxy]-2,3-dihydro-1H-inden-1-yl}-3,6-diethylpyrazin-2-amine

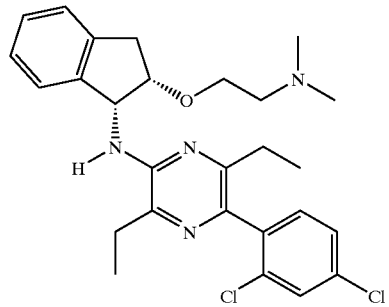

(1R,2S)-1-{[5-(2-chloro-4-methoxyphenyl)-3,6-diethylpyrazin-2-yl]amino}-2,3-dihydro-1H-inden-2-yl N-methylglycinate

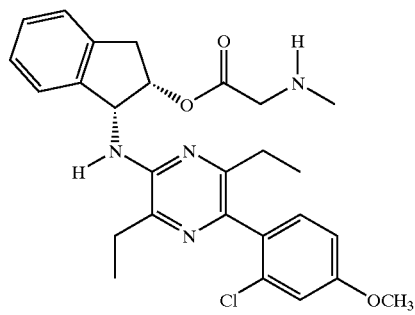

(1R,2S)-1-{[5-(2-chloro-4-methoxyphenyl)-3,6-diethylpyrazin-2-yl]amino}-2,3-dihydro-1H-inden-2-yl N,N-dimethylglycinate

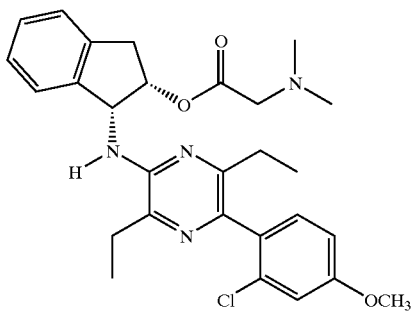

(1R,2S)-1-{[5-(2,4-dichlorophenyl)-3,6-diethylpyrazin-2-yl]amino}-2,3-dihydro-1H-inden-2-yl N-methylglycinate

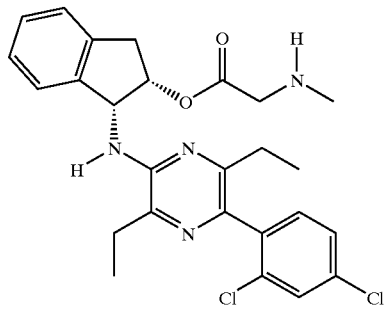

(1R,2S)-1-{[5-(2,4-dichlorophenyl)-3,6-diethylpyrazin-2-yl]amino}-2,3-dihydro-1H-inden-2-yl N,N-dimethylglycinate

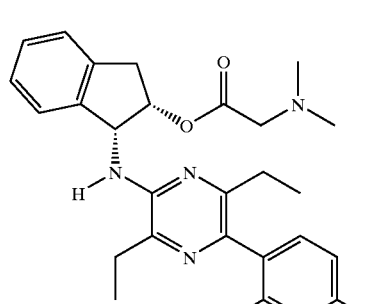

5-(2-chloro-4-methoxyphenyl)-N-{(1R,2S)-2-[2-(dimethylamino)ethoxy]-2,3-dihydro-1H-inden-1-yl}-3,6-diethylpyrazin-2-amine

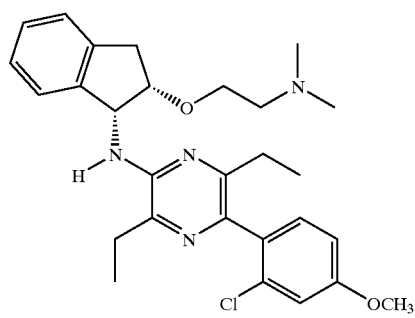

5-(2-chloro-4-methoxyphenyl)-3,6-diethyl-N-{(1R,2S)-2-[2-(methylamino)ethoxy]-2,3-dihydro-1H-inden-1-yl}pyrazin-2-amine

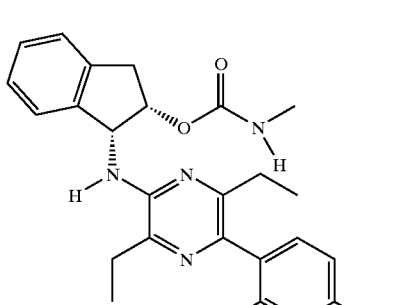

(1R,2S)-1-{[5-(2,4-dichlorophenyl)-3,6-diethylpyrazin-2-yl]amino}-2,3-dihydro-1H-inden-2-yl methylcarbamate

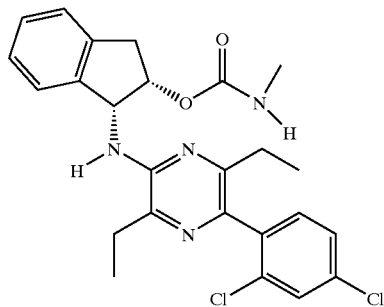

5-(4-chloro-2-methoxyphenyl)-3,6-diethyl-N-[(1R,2S)-2-(2-fluoroethoxy)-2,3-dihydro-1H-inden-1-yl]pyrazin-2-amine

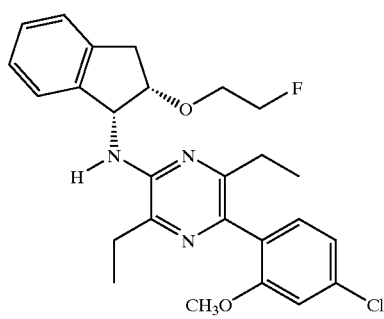

5-(3,5-dichloropyridin-2-yl)-3,6-diethyl-N-[(1R,2S)-2-(2-fluoroethoxy)-2,3-dihydro-1H-inden-1-yl]pyrazin-2-amine

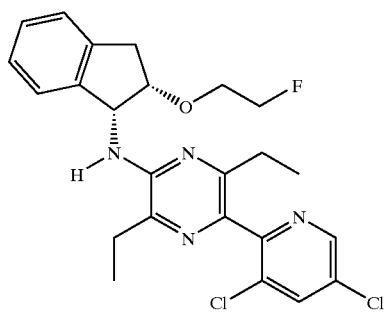

5-(3-chloro-5-methoxypyridin-2-yl)-3,6-diethyl-N-[(1R,2S)-2-(2-fluoroethoxy)-2,3-dihydro-1H-inden-1-yl]pyrazin-2-amine

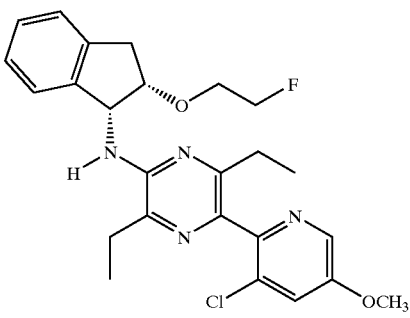

(1R,2S)-1-{[5-(4-chloro-2-methoxyphenyl)-3,6-diethylpyrazin-2-yl]amino}-2,3-dihydro-1H-inden-2-yl acetate

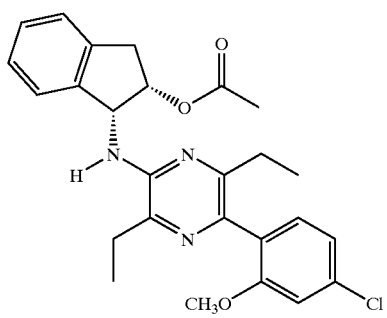

(1R,2S)-1-{[5-(3,5-dichloropyridin-2-yl)-3,6-diethylpyrazin-2-yl]amino}-2,3-dihydro-1H-inden-2-yl acetate

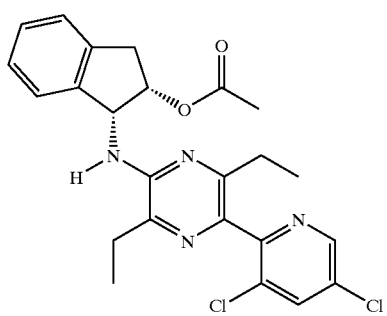

(1R,2S)-1-{[5-(3-chloro-5-methoxypyridin-2-yl)-3,6-diethylpyrazin-2-yl]amino}-2,3-dihydro-1H-inden-2-yl acetate

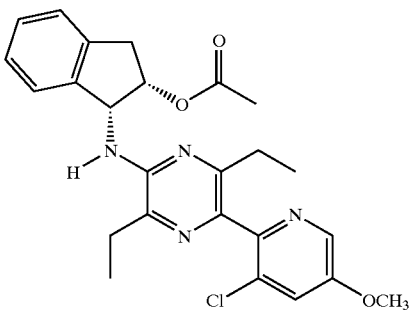

5-(4-chloro-2-methoxyphenyl)-3,6-diethyl-N-[(1R,2S)-2-(3-fluoropropoxy)-2,3-dihydro-1H-inden-1-yl]pyrazin-2-amine

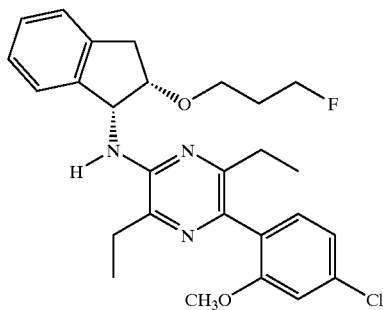

(3R,4R)-4-{[5-(2-chloro-4-methoxyphenyl)-3,6-diethylpyrazin-2-yl]amino}tetrahydrofuran-3-yl acetate

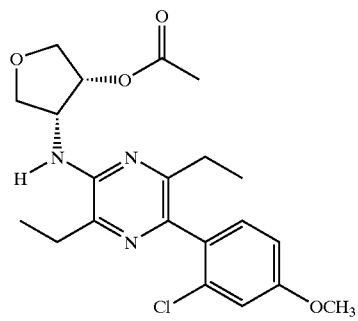

(3R,4R)-4-{[5-(2,4-dichlorophenyl)-3,6-diethylpyrazin-2-yl]amino}tetrahydrofuran-3-yl acetate

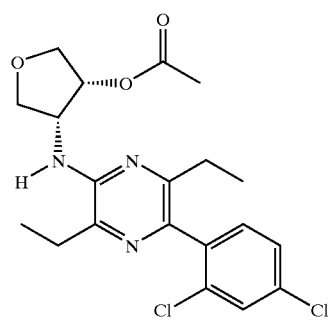

(3R,4R)-4-{[5-(2-chloro-4-methoxyphenyl)-3,6-diethylpyrazin-2-yl]amino}tetrahydrofuran-3-yl propionate

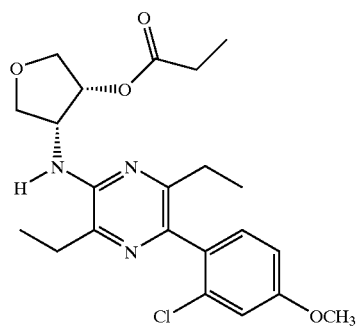

(3R,4R)-4-{[5-(2,4-dichlorophenyl)-3,6-diethylpyrazin-2-yl]amino}tetrahydrofuran-3-yl propionate

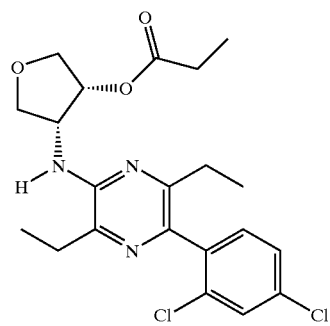

5-(2,4-dichlorophenyl)-3,6-diethyl-N-[(3R,4R)-4-propoxytetrahydrofuran-3-yl]pyrazin-2-amine

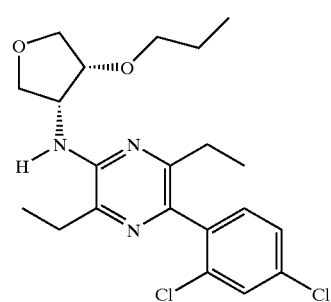

5-(2,4-dichlorophenyl)-3,6-diethyl-N-[(3R,4R)-4-(3-fluoropropoxy)tetrahydrofuran-3-yl]pyrazin-2-amine

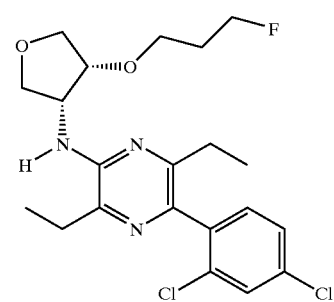

(3S,4R)-3-{[5-(2-chloro-4-methoxyphenyl)-3,6-diethylpyrazin-2-yl]amino}-4-(2-fluoroethoxy)dihydrofuran-2(3H)-one

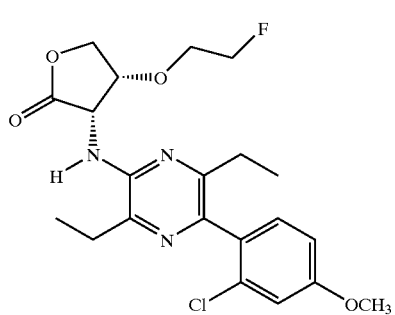

(3S,4R)-3-{[5-(2-chloro-4-methoxyphenyl)-3,6-diethylpyrazin-2-yl]amino}-4-ethoxydihydrofuran-2(3H)-one

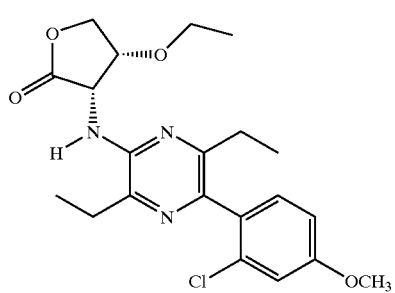

(3R,4S)-4-{[5-(2-chloro-4-methoxyphenyl)-3,6-diethylpyrazin-2-yl]amino}-5-oxotetrahydrofuran-3-yl acetate

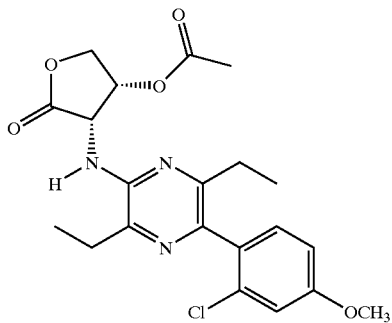

(1R,2S)-N-[5-(2,4-dichlorophenyl)-3,6-diethylpyrazin-2-yl]-N'-ethyl-2,3-dihydro-1H-indene-1,2-diamine

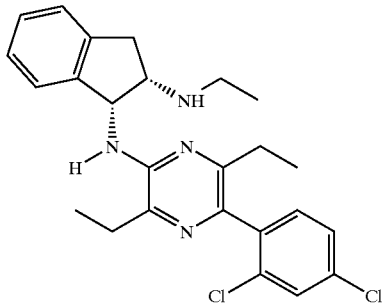

(3R,4S)-4-{[5-(2-chloro-4-methoxyphenyl)-3,6-diethylpyrazin-2-yl]amino}-5-oxotetrahydrofuran-3-yl propionate

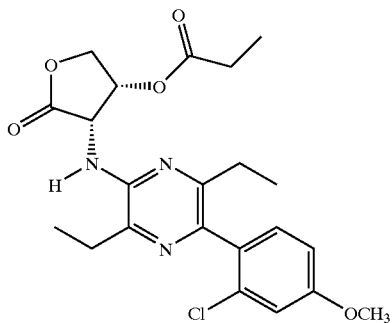

N-((1R,2S)-1-{[5-(2,4-dichlorophenyl)-3,6-diethylpyrazin-2-yl]amino}-2,3-dihydro-1H-inden-2-yl)acetamide

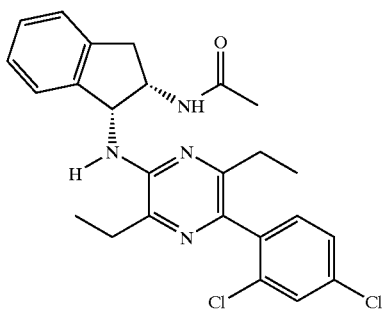

(3S,4R)-3-{[5-(2-chloro-4-methoxyphenyl)-3,6-diethylpyrazin-2-yl]amino}-4-propoxydihydrofuran-2(3H)-one

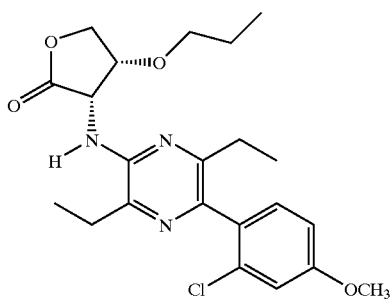

5-(2,4-dichlorophenyl)-N-[(1R,2S)-2-ethoxy-2,3-dihydro-1H-inden-1-yl]-3,6-dimethoxypyrazin-2-amine

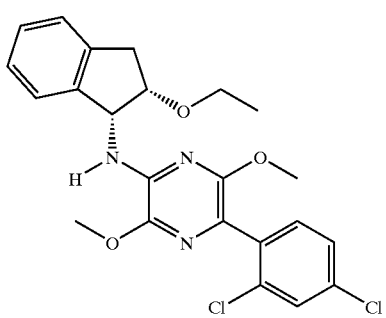

(3S,4R)-3-{[5-(2-chloro-4-methoxyphenyl)-3,6-diethylpyrazin-2-yl]amino}-4-(3-fluoropropoxy)dihydrofuran-2(3H)-one

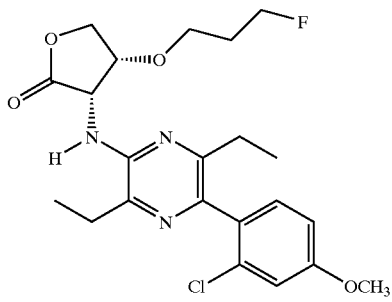

3-cyclopropyl-5-(2,4-dichlorophenyl)-N-[(1R,2S)-2-ethoxy-2,3-dihydro-1H-inden-1-yl]-6-methoxypyrazin-2-amine

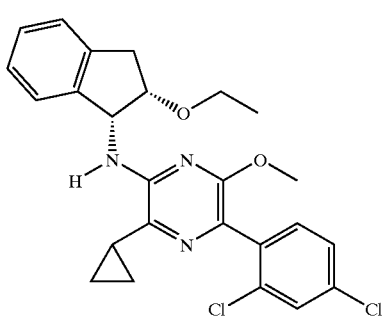

3-(2,4-dichlorophenyl)-6-{[(1R,2S)-2-ethoxy-2,3-dihydro-1H-inden-1-yl]amino}-5-ethylpyrazine-2-carboxamide

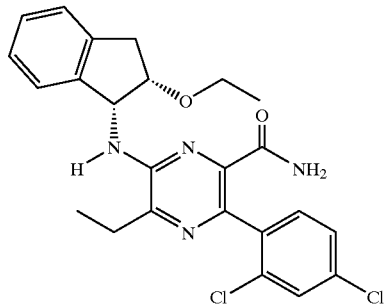

3-(2,4-dichlorophenyl)-6-{[(1R,2S)-2-ethoxy-2,3-dihydro-1H-inden-1-yl]amino}-5-methoxypyrazine-2-carboxamide

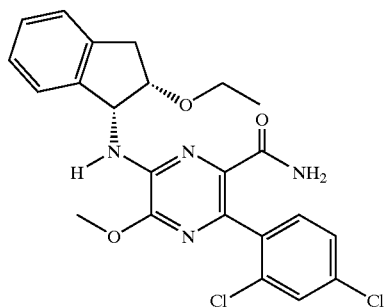

3-(2,4-dichlorophenyl)-6-{[(1R,2S)-2-ethoxy-2,3-dihydro-1H-inden-1-yl]amino}-5-(methylthio)pyrazine-2-carboxamide

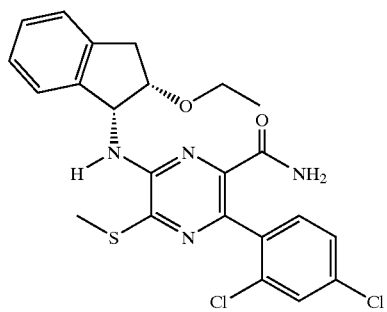

5-(2,4-dichlorophenyl)-N-[(1R,2S)-2-ethoxy-2,3-dihydro-1H-inden-1-yl]-6-ethyl-3-(methylthio)pyrazin-2-amine

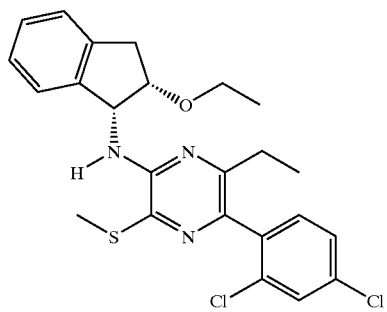

5-(2,4-dichlorophenyl)-N-[(1R,2S)-2-ethoxy-2,3-dihydro-1H-inden-1-yl]-6-ethyl-3-methoxypyrazin-2-amine

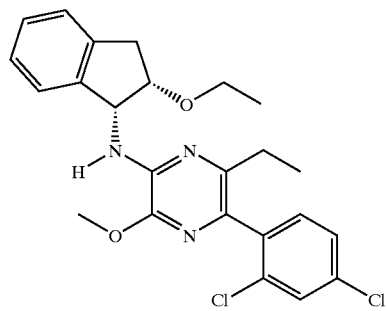

5-(2,4-dichlorophenyl)-N-[(1R,2S)-2-ethoxy-2,3-dihydro-1H-inden-1-yl]-3-ethyl-6-methoxypyrazin-2-amine

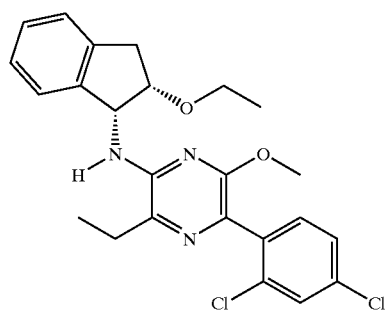

5-(2,4-dichlorophenyl)-N-[(1R,2S)-2-ethoxy-2,3-dihydro-1H-inden-1-yl]-3-ethyl-6-(methylthio)pyrazin-2-amine

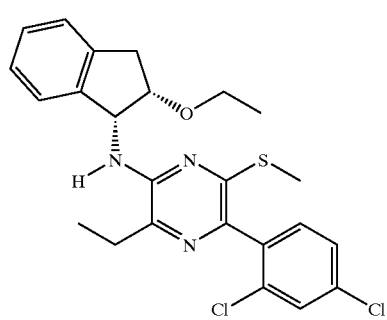

5-(2,4-dichlorophenyl)-N-[(1R,2S)-2-ethoxy-2,3-dihydro-1H-inden-1-yl]-3,6-bis(methylthio)pyrazin-2-amine

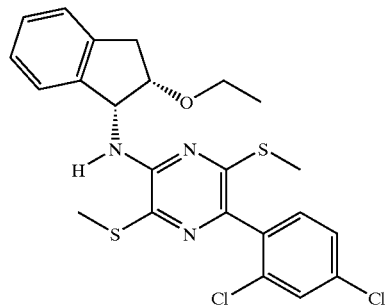

6-(2,4-dichlorophenyl)-3-{[(1R,2S)-2-ethoxy-2,3-dihydro-1H-inden-1-yl]amino}-5-ethylpyrazine-2-carboxamide

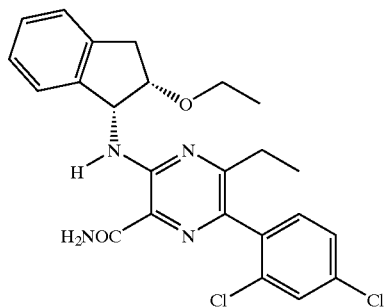

6-(2,4-dichlorophenyl)-3-{[(1R,2S)-2-ethoxy-2,3-dihydro-1H-inden-1-yl]amino}-5-methoxypyrazine-2-carboxamide

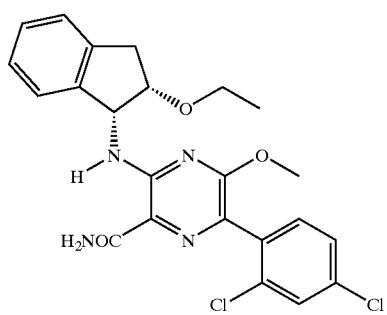

6-(2,4-dichlorophenyl)-3-{[(1R,2S)-2-ethoxy-2,3-dihydro-1H-inden-1-yl]amino}-5-(methylthio)pyrazine-2-carboxamide

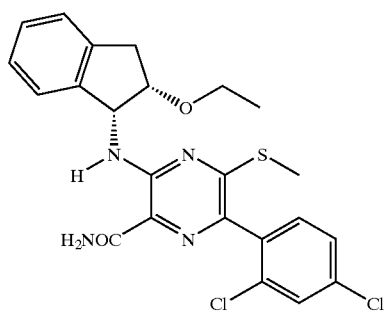

5-(2,4-dichlorophenyl)-N-[(1R,2S)-2-ethoxy-2,3-dihydro-1H-inden-1-yl]-6-ethyl-N'-methylpyrazine-2,3-diamine

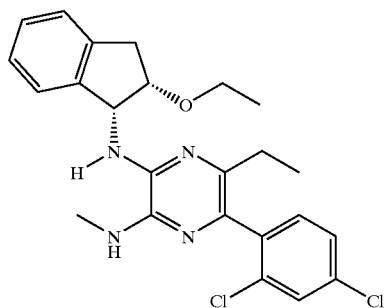

6-(2,4-dichlorophenyl)-N-[(1R,2S)-2-ethoxy-2,3-dihydro-1H-inden-1-yl]-N',N''-dimethylpyrazine-2,3,5-triamine

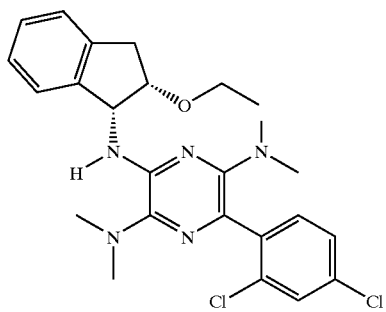

3-(2,4-dichlorophenyl)-N-[(1R,2S)-2-ethoxy-2,3-dihydro-1H-inden-1-yl]-5-ethyl-N'-methylpyrazine-2,6-diamine

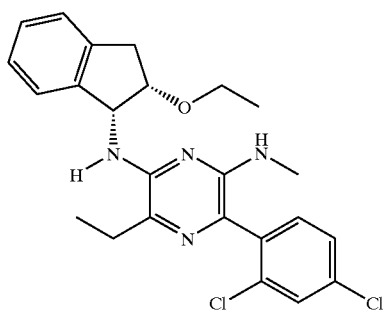

Compounds of the invention can be prepared using the reactions depicted in the following charts or variations thereof known to those skilled in the art. As illustrated in Chart A, the aminopyrazine A-II can be prepared from the suitably functionalized chloropyrazine A-I (see Chart C) by reaction with the appropriate heterocyclic or carbocyclic amine in the presence of a transition metal catalyst (e.g. palladium(II) acetate or tris(dibenzylideneacetone) dipalladium(0)), base (e.g. sodium or potassium tert-butoxide) in solvents such as but not limited to toluene, DMF, or dioxane. (for example see Buchwald, S. L. et al *J. Org. Chem.* 2000, 65, 1158.). A variety of heterocyclic and carbocyclic amines are commercially available or can be synthesized by those skilled in the art. Halogenation of A-II can be accomplished by a number of methods well-known to those skilled in the art utilizing reagents such as N-chlorosuccinimide, N-bromosuccinimide, N-iodosuccinimide, bromine, iodine, pyridinium tribromide in solvents such as dichloromethane, acetic acid, DMF, etc, to give the halopyrazine A-III. Formation of the claimed compounds I is accomplished by a transition metal catalyzed coupling reaction A-III and an appropriate metalloaryl reagent such as aryl boronic acids (see for example Miyaura, N.; et al *Chem. Rev.* 1995, 95, 2457), aryl stannanes (see for example Mitchell, T. N. *Synthesis* 1992, 803), or aryl Grignards (see for example Miller, J. A. *Tetrahedron Lett.* 1998, 39, 7275). Alternatively, A-I can be coupled with a suitable metalloaryl reagent as described above to provide the arylpyrazine A-IV. Oxidation of the sterically less hindered nitrogen can be effected by using a variety of known oxidizing agents (eg, MCPBA, hydrogen peroxide), and the resulting N-oxide can be treated with phosphorous oxybromide to provide the bromopyrazine A-V. Reaction of the halogen with an amine as described above provides I.

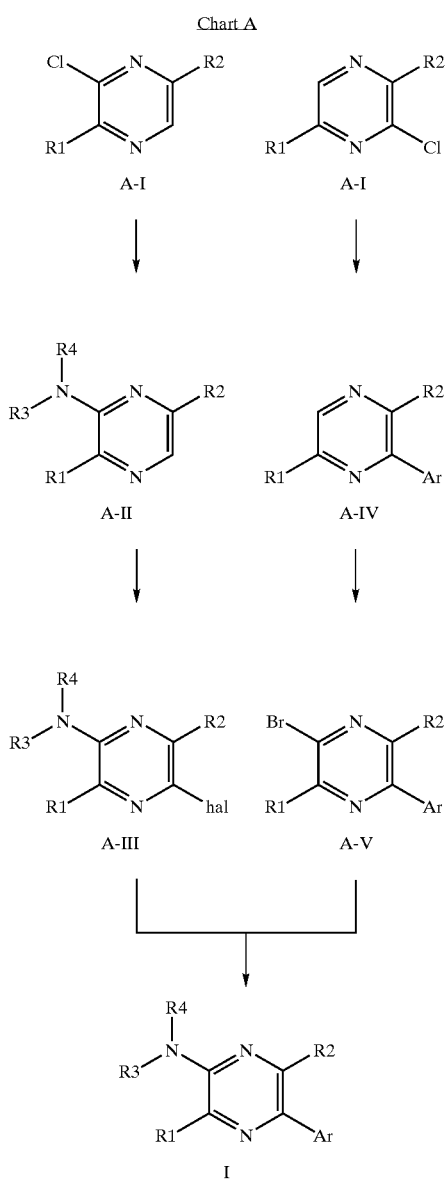

Another way of preparing the compounds of this invention is illustrated in Chart B. Dialkyl-dichloropyrazines B-I (see Chart C) can serve as the starting point for sequential displacement of one chlorine with the appropriate secondary amine (as described in Chart A) followed by biaryl formation with a suitable metalloaryl reagent (as described in Chart A) to afford I. In some instances, this sequence can also be conducted in the opposite order, i.e. biaryl formation followed by nucleophilic displacement by a secondary amine.

Chart C illustrates the preparation of mono- and dichloropyrazine A-I and B-I respectively when R1 and R2 are alkyl and the same. The reaction sequence shown below follows that described in *Chemical and Pharmaceutical Bulletin of Japan*, 1979, 27, 2027.

As illustrated in Chart D, treatment of A-V (depicted in Chart A) with an alkoxide or sodium or potassium salt of a thiol should afford compounds such as D-1. Alternatively, if direct alkoxide addition fails, palladium catalysis (see Buchwald, S. L. et al *J. Am. Chem. Soc.* 2001,123, 10770) or copper catalysis (see Fagan, P. J. et al *J. Am. Chem. Soc.* 2000, 122, 5043) of an alkoxide will provide the desired pyrazinyl aryl ether. Another literature method for forming aryl sulfur bonds is demonstrated by the work of Herradura et al. (see, Herradura, P. S. et al *Org. Lett.* 2000, 2, 2019).

As illustrated in Chart E, treatment of A-V (depicted in Chart A) with a nucleophile such as an alkyl Grignard or alkyl lithium reagent would afford compounds such as E-I.

Alternatively, treatment with an alkyl boronic acid (see Fu, G. C. et al *J. Am. Chem. Soc.* 2000, 122, 4020.) under transition metal catalysis should also provide compounds like E-I.

Chart E

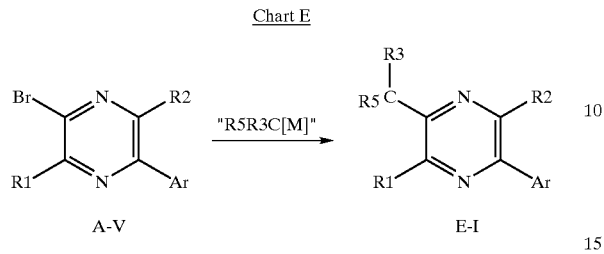

As illustrated in Chart F, reaction of an amine with a pyrazinyl chloride following the protocol of Buchwald et al (*J. Org. Chem.* 2000, 1158.) provides the desired aniline (F-I). Halogenation with NBS (or other suitable reagents as described above) and standard palladium mediated coupling provides the biaryl product (F-III). Alkylation with a base such as NaH and an alkyl halide affords the desired alkyl ethers (F-IV).

Chart F

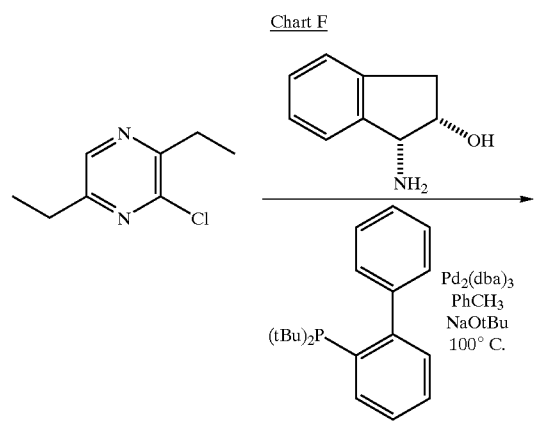

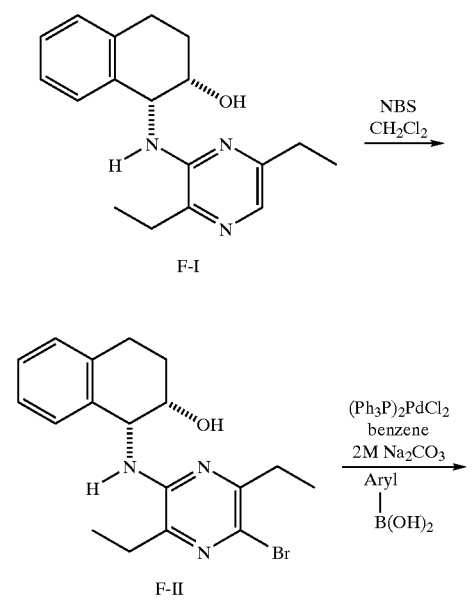

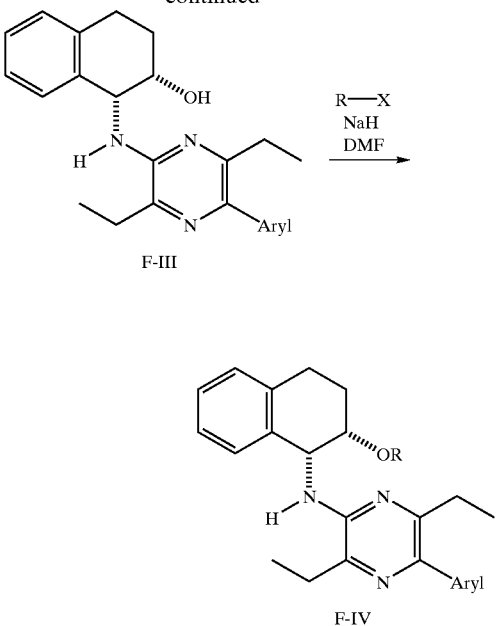

The preparation of unsymmetrically substituted pyrazines ($R_1 \neq R_2$) is shown in Chart G. The synthesis commences with the coupling of a suitably protected amino acid, such as G-I, to an N-protected amino acid, such as G-II, using methods known to those skilled in the art. The N-protecting group is removed from G-III to afford G-IV. Cyclization of G-IV to G-V and the conversion of G-V into the regioisomeric chloro-pyrazines G-VI and G-VII proceed through standard methods (see *Chemical and Pharmaceutical Bulletin of Japan*, 1979, 27, 2027).

Chart G

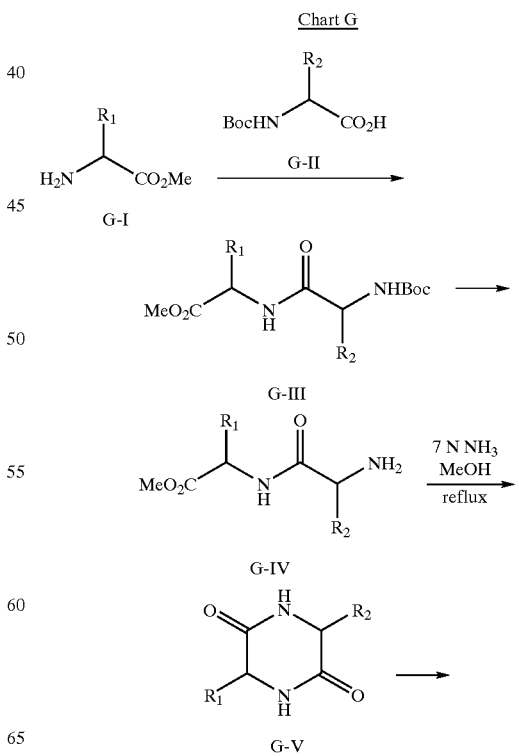

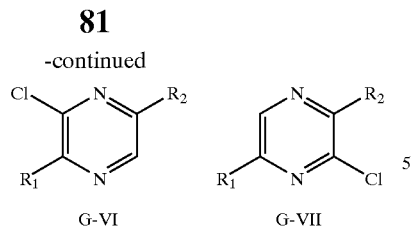

G-VI        G-VII

Yet another method for preparing the compounds of the present invention is detailed in Chart H. Following literature precedence (*J. Heterocyclic Chem.* 1986, 23, 1465), compounds H-I and H-II may be reacted in a suitable solvent (e.g. DME) in the presence of a base, such as NaH, to form H-III. Formation of the triflate compound H-IV from the ketone H-III is achieved by standard methods such as reaction of H-III with 2-[N,N-bis(trifluoromethylsulfonylamino]-5-chloropyridine and triethylamine in methylene chloride. The coupling partner H-V may be prepared from A-V (from Chart A) using the methods described in Buckwald, S. L. et al *Tetrahedron Lett.* 1997, 38, 6367. Palladium-catalyzed coupling (see, for example, *Tetrahedron Lett.* 1997, 38, 6363) of H-IV and H-V gives H-VI, which may be reduced by standard methods, such as catalytic hydrogenation, to give H-VII.

Chart H

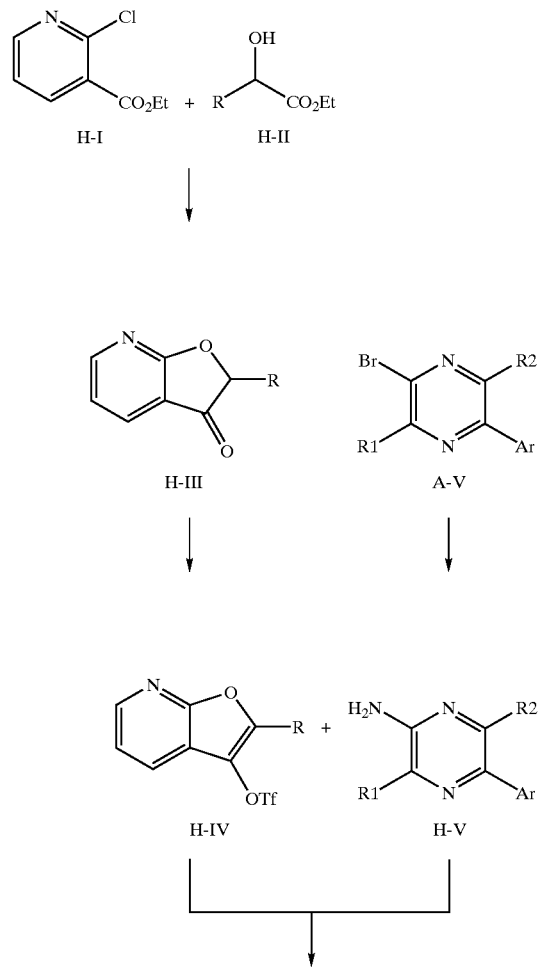

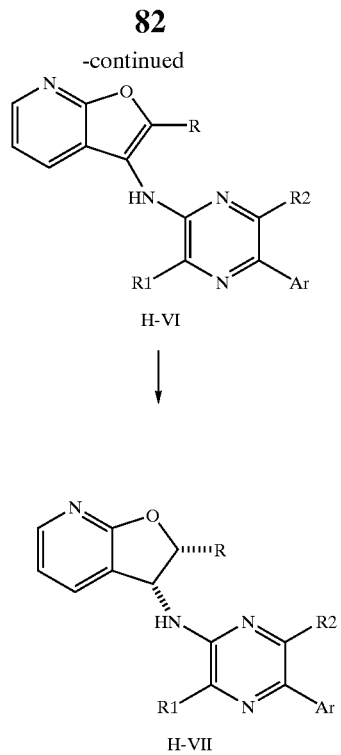

As illustrated in Chart I, the epoxide I-1 is prepared by treatment of the commercially available olefin (benzyl 2,5-dihydro-1H-pyrrole-1-carboxylate) with MCPBA. The resultant epoxide can be opened in an asymmetric fashion with azide following the protocol of Jacobsen et al (*J. Org. Chem.* 1997, 62, 4197) or in a racemic fashion by treatment with ammonium hydroxide. Conversion of the trans amino alcohol to the cis follows the protocol of Jacobsen et al (*J. Org. Chem.* 1997, 62, 4197). Reaction of the pyrrolidine amine with a pyrazinyl chloride following the protocol of Buchwald et al (*J. Org. Chem.* 2000, 1158.) provides the desired aniline. Halogenation with NBS and standard palladium mediated coupling provides the biaryl product. Alkylation with NaH and an alkyl halide or acid chloride affords the desired alkyl ethers or esters. Removal of the CBZ group and treatment of the amine with chloroformates provides carbamates. Alternatively treatment with an acid chloride results in the production of amides. Other functionalization of the amine can be carried out by those skilled in the art.

Chart I

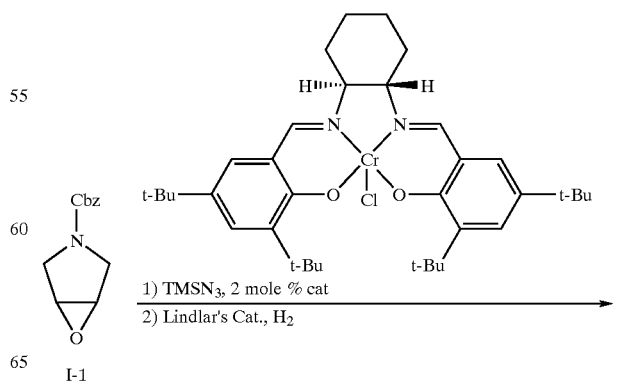

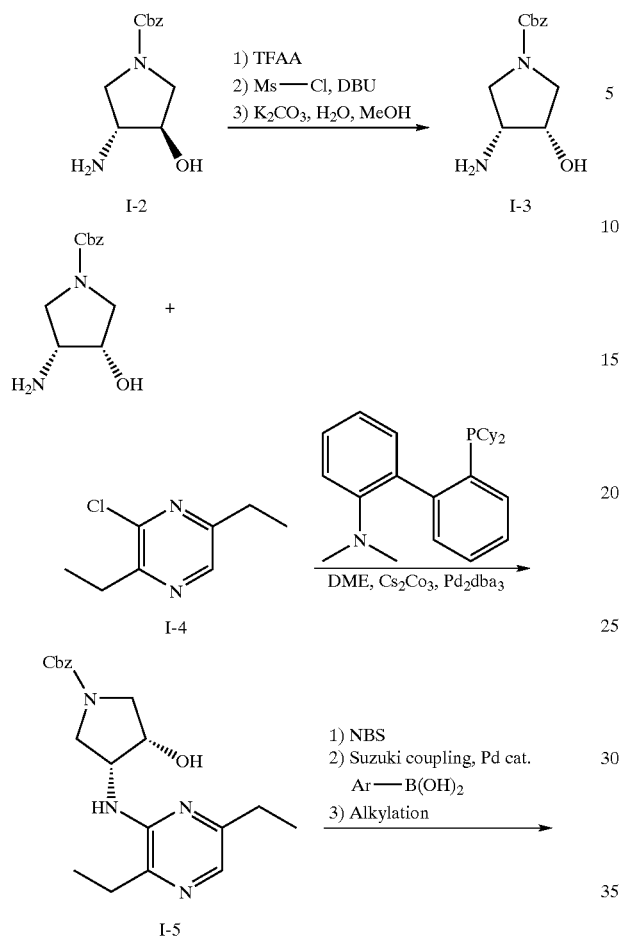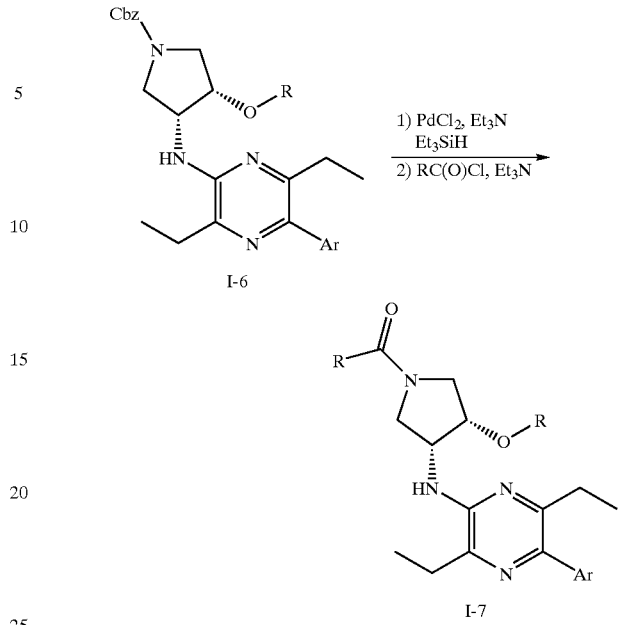

As illustrated in Chart J, the commercially available epoxide J-1 is opened in a racemic fashion by treatment with ammonium hydroxide or in an asymmetric fashion with azide following the protocol of Jacobsen et al (*J. Org. Chem.* 1997, 62, 4197). Conversion of the trans amino alcohol to the cis follows the protocol of Jacobsen et al (*J. Org. Chem.* 1997, 62, 4197). Reaction of the tetrahydrofuran amine J-3 with a pyrazinyl chloride following the protocol of Buchwald et al (*J. Org. Chem.* 2000, 1158.) provides the desired aniline J-4. Halogenation with NBS affords J-5 followed by standard palladium mediated coupling provides the biaryl product J-6. Alkylation with NaH and an alkyl halide or acid chloride affords the desired alkyl ethers or esters J-7.

Chart J

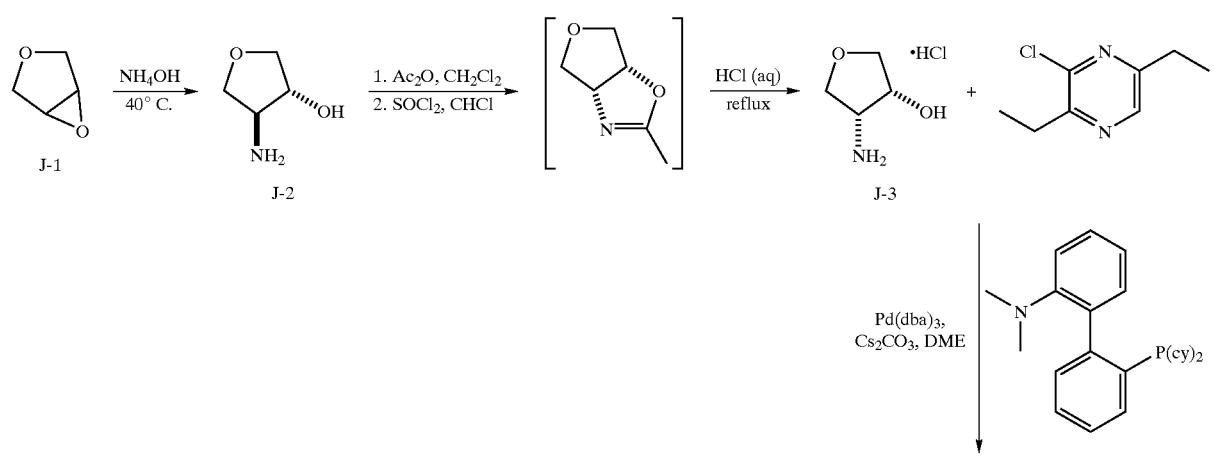

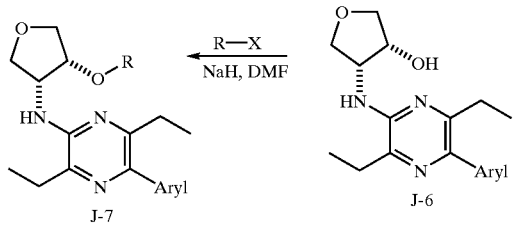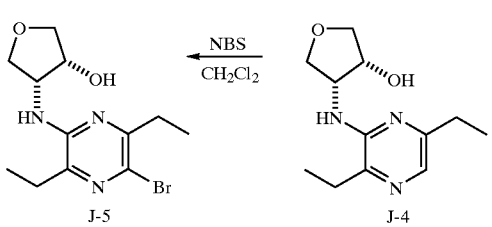

In a second aspect, the present invention provides a pharmaceutical composition comprising a pharmaceutically acceptable carrier and a therapeutically effective amount of a compound of the invention useful for the treatment of a disorder described herein above in a mammal, particularly in a human.

In another aspect, the present invention provides a method of antagonizing a $CRF_1$ receptor in a mammal, comprising administering to the mammal a therapeutically effective amount of a compound of the invention.

In another aspect, the present invention provides a method of treating a disorder manifesting hypersecretion of CRF in a mammal, comprising administering to the animal a therapeutically effective amount of a compound of the invention.

In another aspect, the present invention provides a method for the treatment of a disorder, the treatment of which can be effected or facilitated by antagonizing $CRF_1$ receptor, in a mammal, comprising administering to the mammal a therapeutically effective of a compound of the invention.

In another aspect, the present invention provides a method of treating anxiety or depression in a mammal, particularly in a human, comprising administering to the mammal or human a therapeutically effective amount of a compound of the invention.

In another aspect, the present invention provides a method for screening for ligands for $CRF_1$ receptors, which method comprises: a) carrying out a competitive binding assay with $CRF_1$ receptors, a compound of the invention which is labelled with a detectable label, and a candidate ligand; and b) determining the ability of said candidate ligand to displace said labelled compound.

In another aspect, the present invention provides a method for detecting CRF receptors in tissue comprising: a) contacting a compound of the invention which is labelled with a detectable label, with a tissue, under conditions that permit binding of the compound to the tissue; and b) detecting the labelled compound bound to the tissue.

In another aspect, the present invention provides a method of inhibiting the binding of CRF to a $CRF_1$ receptor, comprising contacting a compound of the invention with a solution comprising cells expressing the $CRF_1$ receptor, wherein the compound is present in the solution at a concentration sufficient to inhibit the binding of CRF to the $CRF_1$ receptor.

In another aspect, the present invention provides an article of manufacture comprising: a) a packaging material; b) a compound of the invention; and c) a label or package insert contained within said packaging material indicating that said compound is effective for treating a pre-selected disorder described herein above.

Compounds of the invention are useful for treating various disorders in a mammal, particularly in a human, such as social anxiety disorder; panic disorder; obsessive-compulsive disorder; anxiety with co-morbid depressive illness; affective disorder; anxiety; depression; irritable bowel syndrome; post-traumatic stress disorder; supranuclear palsy; immune suppression; gastrointestinal disease; anorexia nervosa or other feeding disorder; drug or alcohol withdrawal symptoms; substance abuse disorder (e.g., nicotine, cocaine, ethanol, opiates, or other drugs); inflammatory disorder; fertility problems; disorders the treatment of which can be effected or facilitated by antagonizing CRF, including but not limited to disorders induced or facilitated by CRF; a disorder selected from inflammatory disorders such as rheumatoid arthritis and osteoarthritis, pain, asthma, psoriasis and allergies; generalized anxiety disorder; panic, phobias, obsessive-compulsive disorder; post-traumatic stress disorder; sleep disorders induced by stress; pain perception such as fibromyalgia; mood disorders such as depression, including major depression, single episode depression, recurrent depression, child abuse induced depression, and postpartum depression; dysthemia; bipolar disorders; cyclothymia; fatigue syndrome; stress-induced headache; cancer, human immunodeficiency virus (HIV) infections; neurodegenerative diseases such as Alzheimer's disease, Parkinson's disease and Huntington's disease; gastrointestinal diseases such as ulcers, irritable bowel syndrome, Crohn's disease, spastic colon, diarrhea, and post operative ilius and colonic hypersensitivity associated by psychopathological disturbances or stress; eating disorders such as anorexia and bulimia nervosa; hemorrhagic stress; stress-induced psychotic episodes; euthyroid sick syndrome; syndrome of inappropriate antidiarrhetic hormone (ADH); obesity; infertility; head traumas; spinal cord trauma; ischemic neuronal damage (e.g., cerebral ischemia such as cerebral hippocampal ischemia); excitotoxic neuronal damage; epilepsy; cardiovascular and hear related disorders including hypertension, tachycardia and congestive heart failure; stroke; immune dysfunctions including stress induced immune dysfunctions (e.g., stress induced fevers, porcine stress syndrome, bovine shipping fever, equine paroxysmal fibrillation, and dysfunctions induced by confinement in chickens, sheering stress in sheep or human-animal interaction related stress in dogs); muscular spasms; urinary incontinence; senile dementia of the Alzheimer's type; multiinfarct dementia; amyotrophic lateral sclerosis; chemical dependencies and addictions (e.g., dependences on alcohol, cocaine, heroin, benzodiazepines, or other drugs); osteoporosis; psychosocial dwarfism and hypoglycemia.

Thus, in another aspect, the present invention provides a method of treating a disorder described herein above in a mammal, particularly in a human, comprising administering to the mammal or human a therapeutically effective amount of a compound of the invention.

Particular disorders that can be treated by the method of the invention preferably include the following: affective disorder; anxiety; depression; irritable bowel syndrome; post-traumatic stress disorder; supranuclear palsy; obsessive-compulsive disorder; anxiety with co-morbid depressive illness; Alzheimer's disease; gastrointestinal disease; skin disorders (e.g., acne, psoriasis); anorexia nervosa; social anxiety disorder; bulimia nervosa or other feeding disorder; drug (e.g., dependencies on cocaine, heroin, benzodiazepines, nicotine or other drugs) or alcohol withdrawal symptoms; substance abuse disorder (e.g., nicotine, cocaine, ethanol, opiates, or other drugs); inflammatory disorder; disorders; the treatment of which can be effected or facilitated by antagonizing CRF, including but not limited to disorders induced or facilitated by CRF; or a disorder selected from inflammatory disorders such as rheumatoid arthritis and osteoarthritis, pain, asthma, psoriasis and allergies; generalized anxiety disorder; panic disorder; phobias; obsessive-compulsive disorder; sleep disorders induced by stress; pain perception such as fibromyalgia; mood disorders such as depression, including major depression, single episode depression, recurrent depression, child abuse induced depression, and postpartum depression; dysthymia; bipolar disorders; cyclothymia; fatigue syndrome; stress-induced headache; cancer; neurodegenerative diseases such as, Parkinson's disease and Huntington's disease; gastrointestinal diseases such as ulcers, Crohn's disease, spastic colon, diarrhea, and post operative ilius and colonic hypersensitivity associated by psychopathological disturbances or stress; stress-induced psychotic episodes; syndrome of inappropriate antidiarrhetic hormone (ADH); cardiovascular and hear related disorders including hypertension, tachycardia and congestive heart failure; stroke; senile dementia of the Alzheimer's type; multiinfarct dementia; amyotrophic lateral sclerosis.

Particular disorders that can be treated by the method of the invention more preferably include the following: generalized anxiety disorder; social anxiety disorder; anxiety; obsessive-compulsive disorder; anxiety with co-morbid depressive illness; panic disorder; mood disorders such as depression, including major depression, single episode depression, recurrent depression, child abuse induced depression, and postpartum depression; bipolar disorders; post-traumatic stress disorder; substance abuse disorder (e.g., nicotine, cocaine, ethanol, opiates, or other drugs); inflammatory disorders such as rheumatoid arthritis and osteoarthritis; gastrointestinal diseases such as irritable bowel syndrome, ulcers, Crohn's disease, spastic colon, diarrhea, and post operative ilius and colonic hypersensitivity associated by psychopathological disturbances or stress; inflammatory disorder; and skin disorders such as acne and psoriasis.

Particular disorders that can be treated by the method of the invention even more preferably include the following: generalized anxiety disorder; social anxiety disorder; anxiety; obsessive-compulsive disorder; anxiety with co-morbid depressive illness; panic disorder; mood disorders such as depression, including major depression, single episode depression, recurrent depression, child abuse induced depression, and postpartum depression; bipolar disorders; and post-traumatic stress disorder.

A compound of this invention can be administered to treat these abnormalities in a mammal or human by means that produce contact of the active agent with the agent's site of action in the body of the mammal or human. The compounds can be administered by any conventional means available for use in conjunction with pharmaceuticals either as individual therapeutic agent or in combination of therapeutic agents. It can be administered alone, but will generally be administered with a pharmaceutical carrier selected on the basis of the chosen route of administration and standard pharmaceutical practice.

The dosage administered will vary depending on the use and known factors such as pharmacodynamic character of the particular agent, and its mode and route of administration; the recipient's age, weight, and health; nature and extent of symptoms; kind of concurrent treatment; frequency of treatment; and desired effect.

For use in the treatment of said diseases or conditions, a compound of this invention can be orally administered at a dosage of the active ingredient of 0.002 to 200 mg/kg of body weight. Ordinarily, a dose of 0.01 to 10 mg/kg in divided doses one to four times a day, or in sustained release formulation will be effective in obtaining the desired pharmacological effect.

Dosage forms (compositions) suitable for administration contain from about 1 mg to about 100 mg of active ingredient per unit. In these pharmaceutical compositions, the active ingredient will ordinarily be present in an amount of about 0.5 to 95% by weight based on the total weight of the composition.

The active ingredient can be administered orally in solid dosage forms, such as capsules, tablets and powders; or in liquid forms such as elixirs, syrups, and/or suspensions. The compounds of this invention can also be administered parenterally in sterile liquid dose formulations. Gelatin capsules can be used to contain the active ingredient and a suitable carrier such as but not limited to lactose, starch, magnesium stearate, steric acid, or cellulose derivatives. Similar diluents can be used to make compressed tablets. Both tablets and capsules can be manufactured as sustained release products to provide for continuous release of medication over a period of time. Compressed tablets can be sugar coated or film-coated to mask any unpleasant taste, or used to protect the active ingredients from the atmosphere, or to allow selective disintegration of the tablet in the gastrointestinal tract. Liquid dose forms for oral administration can contain coloring or flavoring agents to increase patient acceptance. In general, water, pharmaceutically acceptable oils, saline, aqueous dextrose (glucose), and related sugar solutions and glycols, such as propylene glycol or polyethylene glycol, are suitable carriers for parenteral solutions. Solutions for parenteral administration preferably contain a water soluble salt of the active ingredient, suitable stabilizing agents, and if necessary, butter substances. Antioxidizing agents, such as sodium bisulfite, sodium sulfite, or ascorbic acid, either alone or in combination, are suitable stabilizing agents. Also used are citric acid and its salts, and EDTA. In addition, parenteral solutions can contain preservatives such as benzalkonium chloride, methyl- or propylparaben, and chlorobutanol. Suitable pharmaceutical carriers are described in "Remington's Pharmaceutical Sciences", A. Osol, a standard reference in the field.

Useful pharmaceutical dosage forms or administration of the compounds of this invention can be illustrated as follows: (1) Capsules. A large number of units capsules are prepared by filling standard two-piece hard gelatin capsules each with 100 mg of powdered active ingredient, 150 mg lactose, 50 mg cellulose, and 6 mg magnesium stearate. (2) Soft Gelatin Capsules. A mixture of active ingredient in a digestible oil such as soybean, cottonseed oil, or olive oil is prepared and injected by means of a positive displacement was pumped into gelatin to form soft gelatin capsules containing 100 mg of the active ingredient. The capsules were washed and dried. (3) Tablets. A large number of tablets are prepared by conventional procedures so that the dosage unit was 100 mg active ingredient, 0.2 mg of colloidal silicon dioxide, 5 mg of magnesium stearate, 275 mg of microcrystalline cellulose, 11 mg of starch, and 98.8 mg lactose. Appropriate coatings may be applied to increase palatability or delayed adsorption.

The compounds of this invention may also be used as reagents or standards in the biochemical study of neurological function, dysfunction, and disease.

Definitions and Conventions

The term "substituted aryl" means an aryl group optionally substituted with 1–5 substituents independently selected from halogen, —NO$_2$, —CN, —R$_a$, —OR$_a$, —S(O)$_m$R$_a$, —NR$_a$R$_a$, —C(O)NR$_a$R$_a$, —C(S)NR$_a$R$_a$—S(O)$_m$NR$_a$R$_a$, —NR$_a$S(O)$_m$R$_a$, —NR$_a$C(O)OR$_a$, —OC(O)NR$_a$R$_a$, —NR$_a$C(O)NR$_a$R$_a$, —NR$_a$C(S)NR$_a$R$_a$, —C(O)OR$_a$, —C(S)OR$_a$, and —OC(O)OR$_a$;

The term "aryl cycloalkyl" means a bicyclic ring system containing 8 to 14 carbon atoms wherein one ring is aryl and the other ring is fused to the aryl ring and may be fully or partially saturated in the portion of the ring fused to the aryl ring, provided that either ring may act as a point of attachment;

The term "substituted aryl cycloalkyl" means an aryl cycloalkyl group having 1–5 substituents independently selected from halogen, —NO$_2$, —CN, —R$_a$, —OR$_a$, —S(O)$_m$ R$_a$, —NR$_a$R$_a$, —C(O)NR$_a$R$_a$, —C(S)NR$_a$R$_a$—S(O)$_m$ NR$_a$R$_a$, —NR$_a$S(O)$_m$R$_a$, —NR$_a$C(O)OR$_a$, —OC(O)NR$_a$R$_a$, —NR$_a$C(O)NR$_a$R$_a$, —NR$_a$C(S)NR$_a$R$_a$, —C(O)OR$_a$, —C(S)OR$_a$, and —OC(O)OR$_a$;

The term "heteroaryl cycloalkyl" means a bicyclic ring system containing 8 to 14 atoms, wherein one ring is heteroaryl and the other ring is fused to the heteroaryl ring and may be fully or partially saturated in the portion of the ring fused to the heteroaryl ring, provided that either ring may act as a point of attachment;

The term "substituted heteroaryl cycloalkyl" means a heteroaryl cycloalkyl group having 1–5 substituents independently selected from halogen, —NO$_2$, —CN, —R$_a$, —OR$_a$, —S(O)$_m$R$_a$, —NR$_a$R$_a$, —C(O)NR$_a$R$_a$, —C(S)NR$_a$R$_a$—S(O)$_m$NR$_a$R$_a$, —NR$_a$S(O)$_m$R$_a$, —NR$_a$C(O)OR$_a$, —OC(O)NR$_a$R$_a$, —NR$_a$C(O)NR$_a$R$_a$, —NR$_a$C(S)NR$_a$R$_a$, —C(O)OR$_a$, —C(S)OR$_a$, and —OC(O)OR$_a$;

The term "aryl heterocycloalkyl" means a bicyclic ring system containing 8 to 14 atoms, wherein one ring is aryl and the other ring is heterocycloalkyl, provided that either ring may act as a point of attachment;

The term "substituted aryl heterocycloalkyl" means an aryl heterocycloalkyl group having 1–5 substituents independently selected from halogen, —NO$_2$, —CN, —R$_a$, —OR$_a$, —S(O)$_m$R$_a$, —NR$_a$R$_a$, —C(O)NR$_a$R$_a$, —C(S)NR$_a$R$_a$—S(O)$_m$NR$_a$R$_a$, —NR$_a$S(O)$_m$R$_a$, —NR$_a$C(O)OR$_a$, —OC(O)NR$_a$R$_a$, —NR$_a$C(O)NR$_a$R$_a$, —NR$_a$C(S)NR$_a$R$_a$, —C(O)OR$_a$, —C(S)OR$_a$, and —OC(O)OR$_a$;

The term "heteroaryl heterocycloalkyl" means a bicyclic ring system containing 8 to 14 atoms, wherein one ring is heteroaryl and the other ring is heterocycloalkyl, provided that either ring may act as a point of attachment;

The term "substituted heteroaryl heterocycloalkyl" means an heteroaryl heterocycloalkyl group having 1–5 substituents independently selected from halogen, —NO$_2$, —CN, —R$_a$, —OR$_a$, —S(O)$_m$R$_a$, —NR$_a$R$_a$, —C(O)NR$_a$R$_a$, —C(S)NR$_a$R$_a$—S(O)$_m$NR$_a$R$_a$, —NR$_a$S(O)$_m$R$_a$, —NR$_a$C(O)OR$_a$, —OC(O)NR$_a$R$_a$, —NR$_a$C(O)NR$_a$R$_a$, —NR$_a$C(S)NR$_a$R$_a$, —C(O)OR$_a$, —C(S)OR$_a$, and —OC(O)OR$_a$;

The term "heteroaryl" means a radical attached via a ring carbon or nitrogen atom of a monocyclic aromatic ring containing five or six ring atoms consisting of carbon and 1, 2, 3, or 4 heteroatoms each selected from the group consisting of non-peroxide O, S, N, with appropriate bonding to satisfy valence requirements as well as a radical (attachment at either carbon or nitrogen) of a fused bicyclic heteroaromatic of about eight to ten ring atoms, and includes radicals such as thienyl, benzothienyl, pyridyl, thiazolyl, quinolyl, pyrazinyl, pyrimidyl, imidazolyl, furanyl, benzofuranyl, benzothiazolyl, isothiazolyl, benzisothiazolyl, benzisoxazolyl, benzimidazolyl, indolyl, and benzoxazolyl, pyrazolyl, triazolyl, tetrazolyl, isoxazolyl, oxazolyl, pyrrolyl, isoquinolinyl, cinnolinyl, indazolyl, indolizinyl, phthalazinyl, pydridazinyl, triazinyl, isoindolyl, purinyl, oxadiazolyl, furazanyl, benzofurazanyl, benzothiophenyl, benzothiazolyl, quinazolinyl, quinoxalinyl, naphthridinyl, and furopyridinyl;

The term "substituted heteroaryl" means a heteroaryl group having 1–5 substituents independently selected from halogen, —NO$_2$, —CN, —R$_a$, —OR$_a$, —S(O)$_m$R$_a$, —NR$_a$R$_a$, —C(O)NR$_a$R$_a$, —C(S)NR$_a$R$_a$—S(O)$_m$NR$_a$R$_a$, —NR$_a$S(O)$_m$R$_a$, —NR$_a$C(O)OR$_a$, —OC(O)NR$_a$R$_a$, —NR$_a$C(O)NR$_a$R$_a$, —NR$_a$C(S)NR$_a$R$_a$, —C(O)OR$_a$, —C(S)OR$_a$, and —OC(O)OR$_a$ The term "heterocycloalkyl", unless otherwise specified, means a 4 to 8 membered monocyclic ring or bicyclic ring, wherein at least one carbon atom is replaced with a heteromember selected from oxygen, nitrogen, —NH—, or —S(O)$_m$— wherein m is zero, 1, or 2, optionally containing from one to three double bonds, provided that the molecule is not aromatic; and provided that ring attachment can occur at either a carbon or nitrogen atom; Heterocycloalkyl includes tetrahydrofuranyl, tetrahydropyranyl, morpholinyl, pyrrolidinyl, piperidinyl, piperazinyl, [2.2.1]-azabicyclic rings, [2.2.2]-azabicyclic rings, [3.3.1]-azabicyclic rings, quinuclidinyl, azetidinyl, azetidinonyl, oxindolyl, dihydroimidazolyl, and pyrrolidinonyl The term "substituted heterocycloalkyl" is a heterocycloalkyl group having 1–5 substituents independently selected from halogen, —NO$_2$, —CN, —R$_a$, —OR$_a$, —S(O)$_m$ R$_a$, —NR$_a$R$_a$, —C(O)NR$_a$R$_a$, —C(S)NR$_a$R$_a$—S(O)$_m$ NR$_a$R$_a$, —NR$_a$S(O)$_m$R$_a$, —NR$_a$C(O)OR$_a$, —OC(O) NR$_a$R$_a$, —NR$_a$C(O)NR$_a$R$_a$, —NR$_a$C(S)NR$_a$R$_a$, —C(O) OR$_a$, —C(S)OR$_a$, and —OC(O)OR$_a$;

Halogen is a group selected from —F, —Cl, —Br, and —I;

The term "alkyl" means both straight and branched chain moieties having from 1–10 carbon atoms optionally containing one or more double or triple bonds;

The term "cycloalkyl" means a monocyclic or bicyclic alkyl moiety, having from 3–10 carbon atoms optionally containing 1 to 2 double bonds provided that the moiety is not aromatic;

The term "haloalkyl" means an alkyl moiety having from 1–10 carbon atoms and having 1 to (2v+1) independently selected halogen substituent(s) where v is the number of carbon atoms in the moiety;

The term "pharmaceutically acceptable salt" refers to a salt prepared from pharmaceutically acceptable non-toxic acids, including inorganic acids and organic acids. Suitable non-toxic acids include inorganic and organic acids of basic residues such as amines, for example, acetic, benzenesulfonic, benzoic, amphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, barbaric acid, p-toluenesulfonic and the like; and alkali or organic salts of acidic residues such as carboxylic acids, for example, alkali and alkaline earth metal salts derived from the following bases: sodium hydride, sodium hydroxide, potassium hydroxide, calcium hydroxide, aluminum hydroxide, lithium hydroxide, magnesium hydroxide, zinc hydroxide, ammonia, trimethylammonia, triethylammonia, ethylenediamine, lysine, arginine, ornithine, choline, N,N'-dibenzylethylenediamine, chloroprocaine, diethanolamine, procaine, n-benzylphenethylamine, diethylamine, piperazine, tris(hydroxymethyl)-aminomethane, tetramethylammonium hydroxide, and the like. Pharmaceutically acceptable salts of the compounds of the invention can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ea., Mack Publishing Company, Easton, Pa., 1985, p. 1418, the disclosure of which is hereby incorporated by reference.

The term "prodrug" as used herein means any covalently bonded carrier which releases the active parent drug of Formula I in vivo when such prodrug is administered to a mammalian subject. Prodrugs of the compounds of Formula I are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" means compounds that are rapidly transformed in viva to yield the parent compound of formula I, for example by hydrolysis in blood. Functional groups which may be rapidly transformed, by metabolic cleavage, in viva form a class of groups reactive with the carboxyl group of the compounds of this invention. They include, but are not limited to such groups as alkanoyl (such as acetyl, propionyl, butyryl, and the like), unsubstituted and substituted aroyl (such as benzoyl and substituted benzoyl), alkoxycarbonyl (such as ethoxycarbonyl), trialkylsilyl (such as trimethyl- and triethysilyl), monoesters formed with dicarboxylic acids (such as succinyl), and the like. Because of the ease with which the metabolically cleavable groups of the compounds useful according to this invention are cleaved in viva, the compounds bearing such groups act as pro-drugs. The compounds bearing the metabolically cleavable groups have the advantage that they may exhibit improved bioavailability as a result of enhanced solubility and/or rate of absorption conferred upon the parent compound by virtue of the presence of the metabolically cleavable group. A thorough discussion of prodrugs is provided in the following: Design of Prodrugs, H. Bundgaard, ea., Elsevier, 1985; Methods in Enzymology, K. Widder et al, Ed., Academic Press, 42, p. 309–396, 25 1985; A Textbook of Drug Design and Development, Krogsgaard-Larsen and H. Bundgaard, ea., Chapter 5; "Design and Applications of Prodrugs" p. 113–191, 1991; Advanced Drug Delivery Reviews, H. Bundgard, 8, p. 1–38, 1992; Journal of Pharmaceutical Sciences, 77, p. 285, 30 1988; Chem. Pharm. Bull., N. Nakeya et al, 32, p. 692, 1984; Pro-drugs as Novel Delivery Systems, T. Higuchi and V. Stella, Vol. 14 of the A.C.S. Symposium Series, and Bioreversible Carriers in Drug Design, Edward B. Roche, ea., American Pharmaceutical Association and Pergamon Press, 1987, which are incorporated herein by reference. "Prodrugs" are considered to be any covalently bonded carriers which release the active parent drug of Formula I in vivo when such prodrug is administered to a mammalian subject. Prodrugs of the compounds of Formula I are prepared by modifying functional groups present in the compounds in such a way that the modifications are cleaved, either in routine manipulation or in vivo, to the parent compounds.

Prodrugs include compounds wherein hydroxy, amine, or sulfhydryl groups are bonded to any group that, when administered to a mammalian subject, cleaves to form a free hydroxyl, amino, or sulfhydryl group, respectively. Examples of Prodrugs include, but are not limited to, acetate, formate and benzoate derivatives of alcohol and amine functional groups in the compounds of Formula I, and the like.

The term "therapeutically effective amount" of a compound of this invention means an amount effective to antagonize abnormal level of CRF or treat the symptoms of affective disorder, anxiety, depression, or other disorders described herein above, in a host.

The term "compound of the invention" means a compound of Formula I, a stereoisomer thereof, a pharmaceutically acceptable salt thereof, or a prodrug thereof.

PREPARATIONS AND EXAMPLES

The invention is illustrated further by the following examples and preparations, which are not to be construed as limiting the invention in scope or spirit to the specific procedures described in them.

Example A

CRF$_1$ Receptor Binding Assay for the Evaluation of Biological Activity

The following is a description of the isolation of rat brain membranes for use in the standard binding assay as well as a description of the binding assay itself. It is based on a modified protocol described by De Souza (De Souza, 1987).

To prepare brain membranes for binding assays, rat frontal cortex is homogenized in 10 mL of ice cold tissue buffer (50 mM HEPES buffer pH 7.0, containing 10 mM MgCl$_2$, 2 mM EGTA, 1 μg/ml aprotinin, 1 μg/ml leupeptin and 1 μg/ml pepstatin). The homogenate is centrifuged at 48,000×g for 10 min. and the resulting pellet rehomogenized in 10 mL of tissue buffer. Following an additional centrifugation at 48,000×g for 10 min., the pellet is resuspended to a protein concentration of 300 μg/mL.

Binding assays are performed in 96 well plates at a final volume of 300 μL. The assays are initiated by the addition of 150 μL membrane suspension to 150 μL of assay buffer containing $^{125}$I-ovine-CRF (final concentration 150 pM) and various concentrations of inhibitors. The assay buffer is the same as described above for membrane preparation with the addition of 0.1% ovalbumin and 0.15 mM bacitracin. Radioligand binding is terminated after 2 hours at room temperature by filtration through Packard GF/C unifilter plates (presoaked with 0.3% polyethyleneimine) using a Packard cell harvester. Filters are washed three times with ice cold phosphate buffered saline pH 7.0 containing 0.01% Triton X-100. Filters are assessed for radioactivity in a Packard TopCount. Nonspecific binding is determined in the presence of excess (10 μM) α-helical CRF.

Alternatively, tissues and cells that naturally express CRF receptors, such as IMR-32 human neuroblastoma cells (ATCC; Hogg et al., 1996), can be employed in binding assays analogous to those described above.

IC$_{50}$ values are calculated using standard methods known in the art, such as with the non-linear curve fitting program RS/1 (BBN Software Products Corp., Cambridge, Mass.). A compound is considered to be active if it has an $IC_{50}$ value of less than about 10 micromolar ($\mu$M) for the inhibition of $CRF_1$ receptors. The binding affinity of the compounds of Formula I expressed as $IC_{50}$ values generally ranges from about 0.5 nanomolar to about 10 micromolar. Preferred compounds of Formula I exhibit $IC_{50}$ of 1 micromolar or less, more preferred compounds of Formula I exhibit $IC_{50}$ of less than 100 nanomolar or less, still more preferred compounds of Formula I exhibit $IC_{50}$ of less than 10 nanomolar or less.

Example B

Inhibition of CRF-Stimulated Adenylate Cyclase Activity

Inhibition of CRF-stimulated adenylate cyclase activity can be performed as previously described [G. Battaglia et al., *Synapse* 1:572 (1987)]. Briefly, assays are carried out at 37° C. for 10 min in 200 mL of buffer containing 100 mM Tris-HCl (pH 7.4 at 37° C.), 10 mM $MgCl_2$, 0.4 mM EGTA, 0.1% BSA, 1 mM isobutylmethylxanthine (IBMX), 250 units/mL phosphocreatine kinase, 5 mM creatine phosphate, 100 mM guanosine 5'-triphosphate, 100 nM o-CRF, antagonist peptides (various concentrations) and 0.8 mg original wet weight tissue (approximately 40–60 mg protein). Reactions are initiated by the addition of 1 mM ATP/[$^{32}$P]ATP (approximately 2–4 mCi/tube) and terminated by the addition of 100 mL of 50 mM Tris-HCl, 45 mM ATP and 2% sodium dodecyl sulfate. In order to monitor the recovery of cAMP, 1 mL of [$^3$H]cAMP (approximately 40,000 dpm) is added to each tube prior to separation. The separation of [$^{32}$P]cAMP from [$^{32}$P]ATP is performed by sequential elution over Dowex and alumina columns.

Alternatively, adenylate cyclase activity can be assessed in a 96-well format utilizing the Adenylyl Cyclase Activation FlashPlate Assay from NEN Life Sciences according to the protocols provided. Briefly, a fixed amount of radiolabeled cAMP is added to 96-well plates that are precoated with anti-cyclic AMP antibody. Cells or tissues are added and stimulated in the presence or absence of inhibitors. Unlabeled cAMP produced by the cells will displace the radiolabeled cAMP from the antibody. The bound radiolabeled cAMP produces a light signal that can be detected using a microplate scintillation counter such as the Packard TopCount. Increasing amounts of unlabeled cAMP results in a decrease of detectable signal over a set incubation time (2–24 hours).

Preparation 1

(1R,2S)-1-[(3,6-diethylpyrazin-2-yl)amino]-2,3-dihydro-1H-inden-2-ol

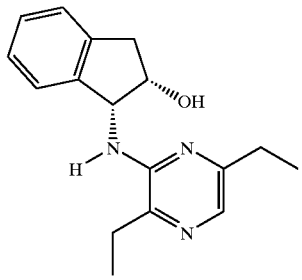

A solution of 3-chloro-2,5-diethylpyrazine (171 mg, 1.0 mmol), (1R,2S)-(+)-cis-1-amino-2-indanol (298 mg, 2.0 mmol), tris(dibenzylideneacetone)dipalladium (0) (28 mg, 0.03 mmol), and 2-(di-tertbutylphosphino)biphenyl (18 mg, 0.06 mmol) in toluene (2.0 mL) was purged with nitrogen and treated with sodium tertbutoxide (135 mg, 1.4 mmol). The resulting brown suspension was heated to 100° C. for 2 hours. At this time, the reaction was quenched with a saturated water solution of $NaHCO_3$ and extracted twice with ethyl acetate (20 mL). The combined organics were washed with brine (15 mL), dried over $MgSO_4$, filtered, and concentrated to give a black solid. This material was purified by biotage MPLC (40 g column, 25% ethyl acetate/heptane) to afford 184 mg (65%) of the title compound as a light purple solid. IR (diffuse reflectance) 3435, 3241, 2962, 2935, 2912, 2873, 1581, 1547, 1500, 1453, 1184, 1163, 1047, 744, 733 $cm^{-1}$; OAMS supporting ions at: ESI+ 384.0; MS (CI) m/z 284 (MH$^+$); HRMS (FAB) calcd for $C_{17}H_{21}N_3O+H_1$ 284.1763, found 284.1754. [$\alpha$]$^{25}_D$=12 (c 0.55, methylene chloride); Anal. Calcd for $C_{17}H_{21}N_3O$: C, 72.06; H, 7.47; N, 14.83. Found: C, 72.15; H, 7.53; N, 14.42.

Preparation 2

(1R,2S)-1-[(5-bromo-3,6-diethylpyrazin-2-yl)amino]-2,3-dihydro-1H-inden-2-ol

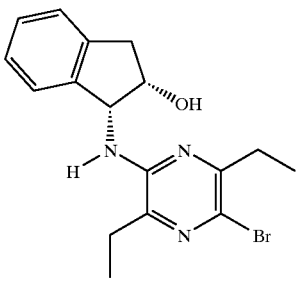

A solution of (1R,2S)-1-[(3,6-diethylpyrazin-2-yl)amino]-2,3-dihydro-1H-inden-2-ol (1.94 g, 6.8 mmol) in dichloromethane (35 mL) was purged with nitrogen and cooled to 0° C. This light purple/grey homogenous solution was treated with a single portion of N-bromosuccinimide (1.34 g, 7.5 mmol) instantly becoming a lighter color. The reaction was warmed to room temperature for 15 minutes, transferred to a separatory funnel, diluted with 100 mL additional dichloromethane, washed twice with water (75 mL), and once with brine (75 mL). The organics were dried over $MgSO_4$, filtered, and concentrated to give a golden oil. This material was purified by biotage MPLC (90 g column, 15% ethyl acetate/heptane) to afford 2.24 g (90%) of the title compound as a pale yellow solid. IR (diffuse reflectance) 3416, 3355, 2969, 2941, 1555, 1538, 1482, 1385, 1378, 1295, 1285, 1200, 1181, 1043, 733 $cm^{-1}$; OAMS supporting ions at: ESI+ 361.9; MS (EI) m/z 361 (M$^+$); [$\alpha$]$^{25}_D$=−35 (c 0.53, methylene chloride); Anal. Calcd for $C_{17}H_{20}BrN_3O$: C, 56.36; H, 5.56; N, 11.60. Found: C, 56.46; H, 5.59; N, 11.50.

Preparation 3

(1R,2S)-1-{[5-(2,4-dichlorophenyl)-3,6-diethylpyrazin-2-yl]amino}-2,3-dihydro-1H-inden-2-ol

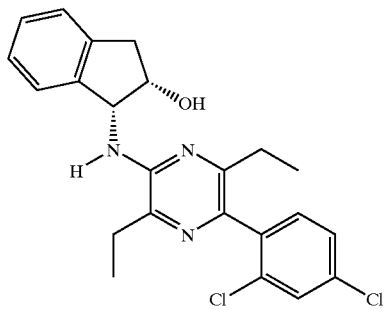

A solution of (1R,2S)-1-[(5-bromo-3,6-diethylpyrazin-2-yl)amino]-2,3-dihydro-1H-inden-2-ol (1.48 g, 4.12 mmol) and 2,4-dichlorophenyl boronic acid (858 mg, 4.5 mmol) in benzene (41 mL) and 2M sodium carbonate (7 mL) was purged with nitrogen and treated with a single portion of bistriphenylphosphinepalladium(II)chloride (287 mg, 0.41 mmol). The resulting golden 2-phase solution was heated to 80° C. gradually darkening in color. After 16 hours, the reaction was cooled to room temperature, transferred to a separatory funnel, and washed with water (50 mL). The aqueous layer was extracted twice with ethyl acetate (75 mL) and the combined organics were washed once with brine (75 mL), dried over MgSO$_4$, filtered, and concentrated to give 2.36 g of a brown syrup. This material was purified by biotage MPLC (90 g column, 20% ethyl acetate/heptane) to afford 1.25 g (71%) of the title compound as a tan solid. OAMS supporting ions at: ESI+ 428.0; HRMS (FAB) calcd for $C_{23}H_{23}CL_2N_3O+H_1$ 428.1296, found 428.1292.

Example 1

The Preparation of 5-(2,4-dichlorophenyl)-N-[(1R,2S)-2-ethoxy-2,3-dihydro-1H-inden-1-yl]-3,6-diethylpyrazin-2-amine

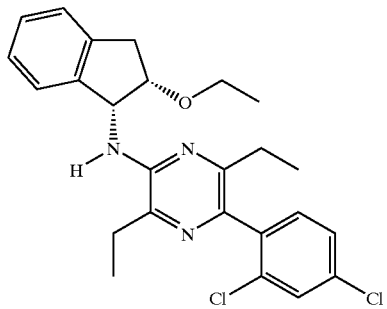

A solution of sodium hydride (60% oil dispersion, 26 mg, 0.65 mmol) was suspended in DMF (1.5 mL), purged with nitrogen, and treated with a single portion of (1R,2S)-1-{[5-(2,4-dichlorophenyl)-3,6-diethylpyrazin-2-yl]amino}-2,3-dihydro-1H-inden-2-ol (214 mg, 0.5 mmol) with copious gas evolution. The resulting green/golden solution was stirred for 5 minutes at room temperature and treated with iodoethane (88 μL, 1.1 mmol). After 3 hours, the reaction was poured into 20 mL 1:1 water/brine and extracted twice with ethyl acetate (20 mL). The combined organics were washed once with brine, dried over MgSO$_4$, filtered, and concentrated to give 389 mg of a golden oil. This material was purified by LC (18 g silica gel, 7% ethyl acetate/heptane) to afford 157 mg (69%) of the title compound as a pale yellow syrup. IR (liq.) 3446, 2972, 2935, 2896, 2874, 1565, 1552, 1498, 1470, 1391, 1206, 1184, 1101, 1091, 1080 cm$^{-1}$; OAMS supporting ions at: ESI+ 456.1; MS (EI) m/z 455 (M$^+$); $[\alpha]^{25}_D$=−94 (c 0.38, methylene chloride); Anal. Calcd for $C_{25}H_{27}Cl_2N_3O$: C, 65.79; H, 5.96; N, 9.21. Found: C, 66.06; H, 6.10; N, 9.17.

Example 2

The Preparation of 5-(2,4-dichlorophenyl)-3,6-diethyl-N-[(1R,2S)-2-methoxy-2,3-dihydro-1H-inden-1-yl]pyrazin-2-amine

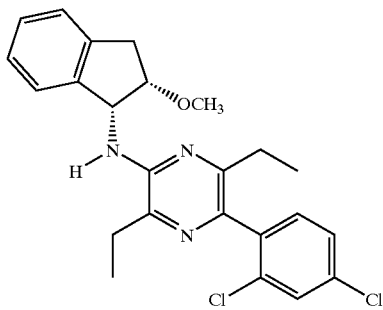

Following the procedure for the preparation of 5-(2,4-dichlorophenyl)-N-[(1R,2S)-2-ethoxy-2,3-dihydro-1H-inden-1-yl]-3,6-diethylpyrazin-2-amine but substituting iodomethane provided the title compound as colorless syrup. OAMS supporting ions at: ESI+ 442.0; MS (EI) m/z 441 (M$^+$); HRMS (FAB) calcd for $C_{24}H_{25}CL_2N_3O+H_1$ 442.14, found 442.1456.

Example 3

The Preparation of 5-(2,4-dichlorophenyl)-3,6-diethyl-N-[(1R,2S)-2-isopropoxy-2,3-dihydro-1H-inden-1-yl]pyrazin-2-amine

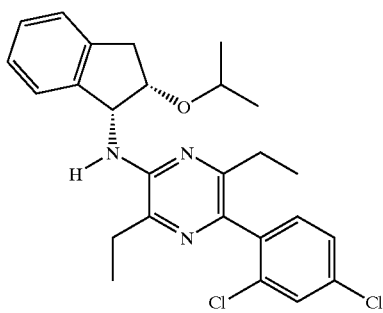

Following the procedure for the preparation of 5-(2,4-dichlorophenyl)-N-[(1R,2S)-2-ethoxy-2,3-dihydro-1H-inden-1-yl]-3,6-diethylpyrazin-2-amine but substituting 2-iodopropane (20 equivalents iodide and sodium hydride with portion-wise addition) provided the title compound as a light yellow syrup. IR (liq.) 2971, 2935, 1564, 1552, 1497, 1471, 1392, 1379, 1368, 1206, 1177, 1140, 1123, 1101, 1061 cm$^{-1}$; OAMS supporting ions at: ESI+ 470.2; MS (EI) m/z 469 (M$^+$); HRMS (FAB) calcd for $C_{26}H_{29}CL_2N_3O+H_1$ 470.1766, found 470.1773. $[\alpha]^{25}_D$=−93 (c 0.33, methylene chloride); Anal. Calcd for $C_{26}H_{29}Cl_2N_3O$: C, 66.38; H, 6.21; N, 8.93. Found: C, 66.53; H, 6.19; N, 8.89.

Preparation 4

Preparation of (1S,2R)-1-[(3,6-diethylpyrazin-2-yl)amino]-2,3-dihydro-1H-inden-2-ol

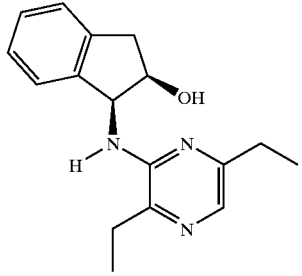

Following the procedure for the preparation of (1R,2S)-1-[(3,6-diethylpyrazin-2-yl)amino]-2,3-dihydro-1H-inden-2-ol but substituting (1S,2R)-(−)-cis-1-amino-2-indanol and making non-critical variations provided the title compound as a light purple solid. MS (ESI+) for $C_{17}H_{21}N_3O$ m/z 284.0 (M+H)+.

Preparation 5

Preparation of (1S,2R)-1-[(5-bromo-3,6-diethylpyrazin-2-yl)amino]-2,3-dihydro-1H-inden-2-ol

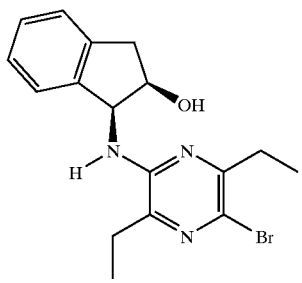

Following the procedure for the preparation of (1R,2S)-1-[(5-bromo-3,6-diethylpyrazin-2-yl)amino]-2,3-dihydro-1H-inden-2-ol but substituting (1S,2R)-1-[(3,6-diethylpyrazin-2-yl)amino]-2,3-dihydro-1H-inden-2-ol and making non-critical variations provided the title compound as a pale yellow solid. MS (ESI+) for $C_{17}H_{20}BrN_3O$ m/z 361.9 (M+H)+.

Preparation 6

Preparation of (1S,2R)-1-{[5-(2,4-dichlorophenyl)-3,6-diethylpyrazin-2-yl]amino}-2,3-dihydro-1H-inden-2-ol

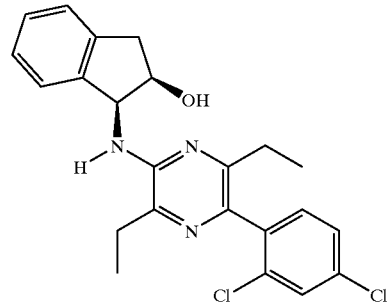

Following the procedure for the preparation of (1R,2S)-1-{[5-(2,4-dichlorophenyl)-3,6-diethylpyrazin-2-yl]amino}-2,3-dihydro-1H-inden-2-ol but substituting (1S,2R)-1-[(5-bromo-3,6-diethylpyrazin-2-yl)amino]-2,3-dihydro-1H-inden-2-ol and making non-critical variations provided the title compound as a tan solid. IR (diffuse reflectance) 3439, 2964, 1568, 1551, 1500, 1469, 1391, 1373, 1204, 1183, 1102, 1048, 819, 748, 741 cm$^{-1}$; OAMS supporting ions at: ESI+ 427.9; MS (EI) m/z 427 (M+); HRMS (FAB) calcd for $C_{23}H_{23}Cl_2N_3O+H_1$ 428.1296, found 428.1286. Anal. Calcd for $C_{23}H_{23}Cl_2N_3O$: C, 64.49; H, 5.41; N, 9.81. Found: C, 64.43; H, 5.54; N, 9.42.

Example 4

Preparation of 5-(2,4-dichlorophenyl)-3,6-diethyl-N-[(1S,2R)-2-methoxy-2,3-dihydro-1H-inden-1-yl]pyrazin-2-amine

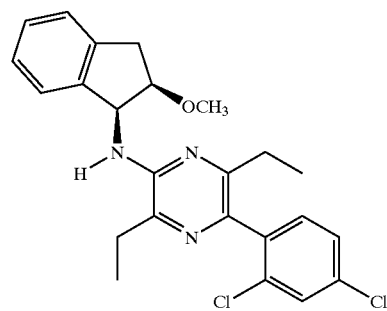

Following the procedure for the preparation of 5-(2,4-dichlorophenyl)-N-[(1R,2S)-2-ethoxy-2,3-dihydro-1H-inden-1-yl]-3,6-diethylpyrazin-2-amine but substituting (1S,2R)-1-{[5-(2,4-dichlorophenyl)-3,6-diethylpyrazin-2-yl]amino}-2,3-dihydro-1H-inden-2-ol and iodomethane and making non-critical variations provided the title compound as a colorless syrup. IR (liq.) 3447, 2972, 2934, 2907, 2877, 1589, 1565, 1552, 1498, 1471, 1391, 1375, 1196, 1177, 1093 cm$^{-1}$; OAMS supporting ions at: ESI+ 442.0; MS (EI) m/z 441 (M+); $[\alpha]^{25}{}_D$=55 (c 0.51, methanol); Anal. Calcd for $C_{24}H_{25}Cl_2N_3O$: C, 65.16; H, 5.70; N, 9.50. Found: C, 65.20; H, 5.63; N, 9.43.

Preparation 7

Preparation of (1S,2S)-1-{[5-(2,4-dichlorophenyl)-3,6-diethylpyrazin-2-yl]amino}-2,3-dihydro-1H-inden-2-yl 4-nitrobenzoate

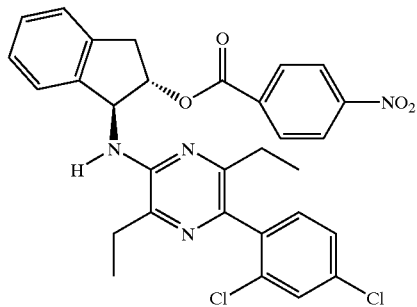

A solution of (1S,2R)-1-{[5-(2,4-dichlorophenyl)-3,6-diethylpyrazin-2-yl]amino}-2,3-dihydro-1H-inden-2-ol (321 mg, 0.75 mmol), 4-nitrobenzoic acid (552 mg, 3.3 mmol), and triphenylphosphine (964 mg, 3.7 mmol) in benzene (19 mL) was purged with nitrogen and cooled to 0° C. The resulting yellow suspension was treated with diethylazodicarboxylate (0.58 mL, 3.7 mmol) becoming lighter in color with gradual warming to RT. After 18 hours, the volatiles were removed under reduced pressure with the resulting crude residue being absorbed on 6 g silica gel and purified by Biotage MPLC (40 g column, 15% ethyl acetate/heptane) to afford the title compound as a light yellow solid. IR (diffuse reflectance) 1725, 1568, 1550, 1527, 1498, 1467, 1392, 1372, 1349, 1320, 1273, 1119, 1103, 836, 719 cm$^{-1}$; OAMS supporting ions at: ESI+ 576.8; MS (CI) m/z 577 (MH$^+$); HRMS (FAB) calcd for $C_{30}H_{26}CL_2N_4O_4$ +H$_1$ 577.1409, found 577.1417.

Preparation 8

Preparation of (1S,2S)-1-{[5-(2,4-dichlorophenyl)-3,6-diethylpyrazin-2-yl]amino}-2,3-dihydro-1H-inden-2-ol

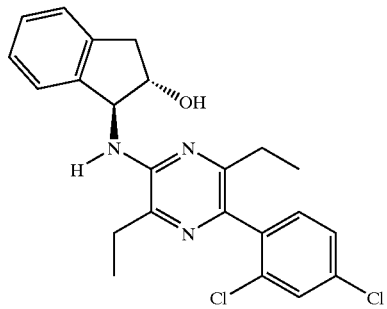

A solution of (1S,2S)-1-{[5-(2,4-dichlorophenyl)-3,6-diethylpyrazin-2-yl]amino}-2,3-dihydro-1H-inden-2-yl 4-nitrobenzoate (369 mg, 0.64 mmol) in methanol (3 mL) and tetrahydrofuran (6 mL) was treated with a 1M solution of lithium hydroxide (5 mL, 5 mmol). After 16 hrs, the volatiles were removed under reduced pressure and the aqueous residue was diluted with 1M sodium hydroxide (10 mL) and extracted twice with ethyl acetate (20 mL). The combined organics were washed once with brine (20 mL), dried over MgSO$_4$, filtered, and concentrated to give 302 mg of a yellow syrup. This material was purified by Biotage MPLC (40 g column, 20% ethyl acetate/heptane) to afford 250 mg (91%) of the title compound as a white solid. IR (diffuse reflectance) 3325, 2976, 2936, 2900, 2876, 1571, 1550, 1503, 1471, 1449, 1435, 1399, 861, 819, 753 cm$^{-1}$; OAMS supporting ions at: ESI+ 427.9; MS (EI) m/z 427 (M$^+$); $[\alpha]^{25}_D$=−108 (c 0.58, methylene chloride); Anal. Calcd for $C_{23}H_{23}Cl_2N_3O$: C, 64.49; H, 5.41; N, 9.81; Cl, 16.55. Found: C, 64.27; H, 5.46; N, 9.58.

Examples 5 and 6

Preparation of 5-(2,4-dichlorophenyl)-3,6-diethyl-N-[(1S,2S)-2-methoxy-2,3-dihydro-1H-inden-1-yl]pyrazin-2-amine and 5-(2,4-dichlorophenyl)-3,6-diethyl-N-[(1S,2S)-2-methoxy-2,3-dihydro-1H-inden-1-yl]-N-methylpyrazin-2-amine Following the procedure for the preparation of 5-(2,4-dichlorophenyl)-N-[(1R,2S)-2-ethoxy-2,3-dihydro-1H-inden-1-yl]-3,6-diethylpyrazin-2-amine but substituting (1S,2S)-1-{[5-(2,4-dichlorophenyl)-3,6-diethylpyrazin-2-yl]amino}-2,3-dihydro-1H-inden-2-ol. and iodomethane and making non-critical variations provided the title compounds. Analytical data for 5-(2,4-dichlorophenyl)-3,6-diethyl-N-[(1S,2S)-2-methoxy-2,3-dihydro-1H-inden-1-yl]pyrazin-2-amine; IR (diffuse reflectance) 2965, 1569, 1551, 1500, 1468, 1397, 1393, 1372, 1203, 1189, 1106, 988, 838, 819, 748 cm$^{-1}$; OAMS supporting ions at: ESI+ 442.1; MS (EI) m/z 441 (M$^+$); Anal. Calcd for $C_{24}H_{25}Cl_2N_3O$: C, 65.16; H, 5.70; N, 9.50; Cl, 16.03. Found: C, 65.14; H, 5.90; N, 9.32. Analytical data for 5-(2,4-dichlorophenyl)-3,6-diethyl-N-[(1S,2S)-2-methoxy-2,3-dihydro-1H-inden-1-yl]-N-methylpyrazin-2-amine; OAMS supporting ions at: ESI+ 455.8; HRMS (FAB) calcd for $C_{25}H_{27}CL_2N_3O+H_1$ 456.1609, found 456.1601.

Preparation 9

Preparation of (1R,2R)-1-{[5-(2,4-dichlorophenyl)-3,6-diethylpyrazin-2-yl]amino}-2,3-dihydro-1H-inden-2-yl 4-nitrobenzoate

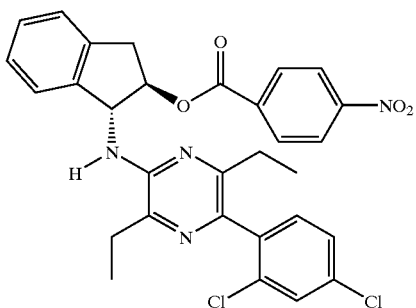

Following the procedure for the preparation of (1S,2S)-1-{[5-(2,4-dichlorophenyl)-3,6-diethylpyrazin-2-yl]amino}-2,3-dihydro-1H-inden-2-yl 4-nitrobenzoate but substituting (1R,2S)-1-[(3,6-diethylpyrazin-2-yl)amino]-2,3-dihydro-1H-inden-2-ol and making non-critical variations provided the title compound as a yellow solid. IR (diffuse reflectance) 1725, 1568, 1550, 1527, 1498, 1467, 1392, 1372, 1349, 1320, 1273, 1119, 1103, 1014, 719 cm$^{-1}$; OAMS supporting ions at: ESI+ 577.1; MS (CI) m/z 577 (MH$^+$); HRMS (FAB) calcd for $C_{30}H_{26}CL_2N_4O_4+H_1$ 577.1409, found 577.1393; $[\alpha]^{25}_D$=−118 (c 0.62, methylene chloride).

Preparation 10

Preparation of (1R,2R)-1-{[5-(2,4-dichlorophenyl)-3,6-diethylpyrazin-2-yl]amino}-2,3-dihydro-1H-inden-2-ol

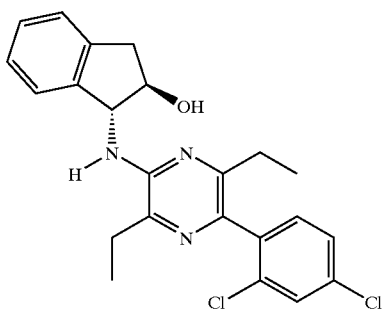

Following the procedure for the preparation of (1S,2S)-1-{[5-(2,4-dichlorophenyl)-3,6-diethylpyrazin-2-yl]amino}-2,3-dihydro-1H-inden-2-ol but substituting (1R, 2R)-1-{[5-(2,4-dichlorophenyl)-3,6-diethylpyrazin-2-yl]amino}-2,3-dihydro-1H-inden-2-yl 4-nitrobenzoate and making non-critical variations provided the title compound as an off-white solid. IR (diffuse reflectance) 3326, 2976, 1572, 1550, 1503, 1472, 1449, 1435, 1399, 1358, 1198, 1074, 862, 819, 753 cm$^{-1}$; OAMS supporting ions at: ESI+ 428.1; MS (EI) m/z 427 (M$^+$); HRMS (FAB) calcd for $C_{23}H_{23}CL_2N_3O+H_1$ 428.1296, found 428.1295. $[\alpha]^{25}_D$=112 (c 0.58, methylene chloride). Anal. Calcd for $C_{23}H_{23}Cl_2N_3O$: C, 64.49; H, 5.41; N, 9.81. Found: C, 64.60; H, 5.34; N, 9.75.

Examples 7 and 8

Preparation of 5-(2,4-dichlorophenyl)-3,6-diethyl-N-[(1R,2R)-2-methoxy-2,3-dihydro-1H-inden-1-yl]pyrazin-2-amine and 5-(2,4-dichlorophenyl)-3,6-diethyl-N-[(1R,2R)-2-methoxy-2,3-dihydro-1H-inden-1-yl]-N-methylpyrazin-2-amine

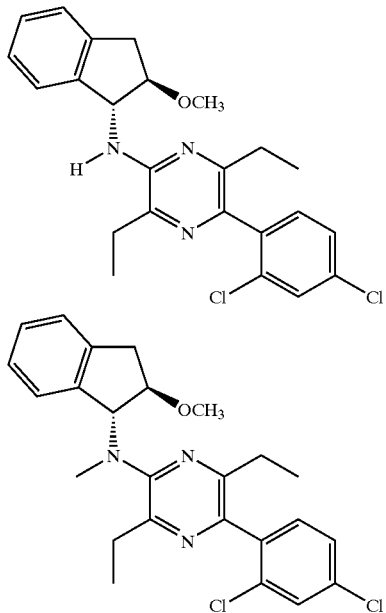

Following the procedure for the preparation of 5-(2,4-dichlorophenyl)-N-[(1R,2S)-2-ethoxy-2,3-dihydro-1H-inden-1-yl]-3,6-diethylpyrazin-2-amine but substituting (1R,2R)-1-{[5-(2,4-dichlorophenyl)-3,6-diethylpyrazin-2-yl]amino}-2,3-dihydro-1H-inden-2-ol and iodomethane and making non-critical variations provided the title compounds. Analytical data for 5-(2,4-dichlorophenyl)-3,6-diethyl-N-[(1R,2R)-2-methoxy-2,3-dihydro-1H-inden-1-yl]pyrazin-2-amine: IR (diffuse reflectance) 3382, 2963, 2933, 1568, 1550, 1500, 1469, 1396, 1371, 1203, 1189, 1105, 988, 838, 748 cm$^{-1}$; OAMS supporting ions at: ESI+ 441.1; MS (EI) m/z 441 (M$^+$); HRMS (FAB) calcd for $C_{24}H_{25}CL_2N_3O+H_1$ 442.1453, found 442.1455. $[\alpha]^{25}_D$=−76 (c 0.64, methylene chloride). Analytical data for 5-(2,4-dichlorophenyl)-3,6-diethyl-N-[(1R,2R)-2-methoxy-2,3-dihydro-1H-inden-1-yl]-N-methylpyrazin-2-amine: OAMS supporting ions at: ESI+ 456.1.

Example 9

Preparation of N-[(1R,2S)-2-(cyclopropylmethoxy)-2,3-dihydro-1H-inden-1-yl]-5-(2,4-dichlorophenyl)-3,6-diethylpyrazin-2-amine

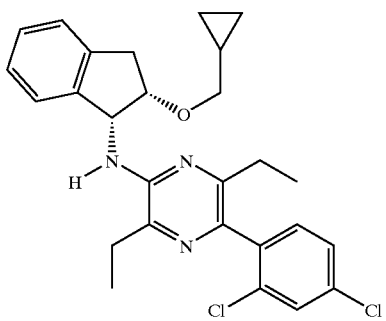

Following the procedure for the preparation of 5-(2,4-dichlorophenyl)-N-[(1R,2S)-2-ethoxy-2,3-dihydro-1H-inden-1-yl]-3,6-diethylpyrazin-2-amine but substituting (bromomethyl)cyclopropane and making non-critical variations provided the title compound as a yellow amorphous solid. IR (liq.) 3442, 2971, 2935, 2874, 1565, 1552, 1498, 1471, 1393, 1206, 1184, 1101, 1077, 1021, 740 cm$^{-1}$; OAMS supporting ions at: ESI+ 481.8; MS (EI) m/z 481 (M$^+$); HRMS (FAB) calcd for $C_{27}H_{29}CL_2N_3O$ +H$_1$ 482.1766, found 482.1775. $[\alpha]^{25}_D$=−65 (c 0.73, methylene chloride); Anal. Calcd for $C_{27}H_{29}Cl_2N_3O$: C, 67.22; H, 6.06; N, 8.71. Found: C, 67.15; H, 6.08; N, 8.66.

Example 10

Preparation of 5-(2,4-dichlorophenyl)-3,6-diethyl-N-[(1R,2S)-2-(prop-2-ynyloxy)-2,3-dihydro-1H-inden-1-yl]pyrazin-2-amine

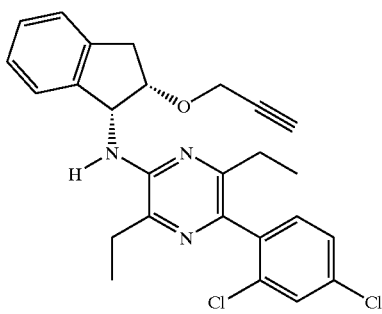

Following the procedure for the preparation of 5-(2,4-dichlorophenyl)-N-[(1R,2S)-2-ethoxy-2,3-dihydro-1H-inden-1-yl]-3,6-diethylpyrazin-2-amine but substituting propargylbromide and making non-critical variations provided the title compound as a white solid. IR (diffuse reflectance) 3451, 3293, 2964, 2932, 1563, 1493, 1469, 1390, 1204, 1184, 1087, 1076, 820, 742, 646 cm$^{-1}$; OAMS supporting ions at: ESI+ 465.8; MS (EI) m/z 465 (M$^+$); HRMS (FAB) calcd for $C_{26}H_{25}CL_2N_3O$+H$_1$ 466.1453, found 466.1455. $[\alpha]^{25}_D$=−56 (c 0.83, methylene chloride). Anal. Calcd for $C_{26}H_{25}Cl_2N_3O$: C, 66.96; H, 5.40; N, 9.01. Found: C, 66.96; H, 5.49 N, 8.93.

Example 11

Preparation of 5-(2,4-dichlorophenyl)-3,6-diethyl-N-[(1R,2S)-2-(2-methoxyethoxy)-2,3-dihydro-1H-inden-1-yl]pyrazin-2-amine

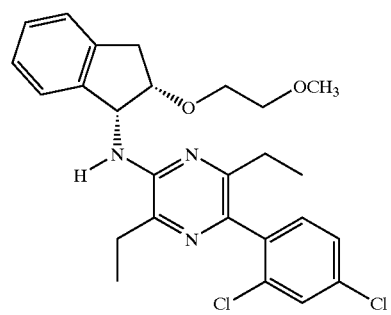

Following the procedure for the preparation of 5-(2,4-dichlorophenyl)-N-[(1R,2S)-2-ethoxy-2,3-dihydro-1H-inden-1-yl]-3,6-diethylpyrazin-2-amine but substituting 2-bromoethylmethylether and making non-critical variations provided the title compound as a light yellow syrup. IR (liq.) 3418, 2971, 2934, 2875, 1565, 1552, 1498, 1471, 1392, 1376, 1201, 1183, 1132, 1100, 748 cm$^{-1}$; OAMS supporting ions at: ESI+ 485.8; MS (CI) m/z 486 (MH$^+$); $[\alpha]^{25}_D$=−102 (c 0.57, methylene chloride); Anal. Calcd for $C_{26}H_{29}Cl_2N_3O_2$: C, 64.20; H, 6.01; N, 8.64. Found: C, 63.92; H, 6.14; N, 8.53.

Example 12

Preparation of N-[(1R,2S)-2-(allyloxy)-2,3-dihydro-1H-inden-1-yl]-5-(2,4-dichlorophenyl)-3,6-diethylpyrazin-2-amine

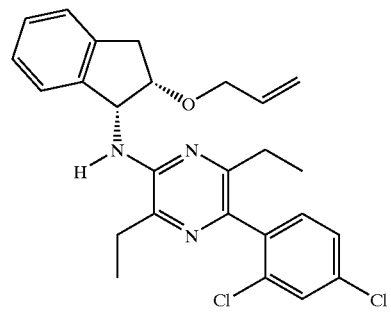

Following the procedure for the preparation of 5-(2,4-dichlorophenyl)-N-[(1R,2S)-2-ethoxy-2,3-dihydro-1H-inden-1-yl]-3,6-diethylpyrazin-2-amine but substituting allybromide and making non-critical variations provided the title compound as a light yellow semi-solid. IR (liq.) 3446, 2972, 2935, 2874, 1565, 1552, 1497, 1471, 1392, 1206, 1181, 1101, 1087, 1078, 744 cm$^{-1}$; OAMS supporting ions at: ESI+ 467.9; MS (EI) m/z 467 (M$^+$); $[\alpha]^{25}_D$=−73 (c 0.79, methylene chloride). Anal. Calcd for $C_{26}H_{27}Cl_2N_3O$: C, 66.67; H, 5.81; N, 8.97. Found: C, 66.49; H, 5.87; N, 8.91.

Example 13

Preparation of 5-(2,4-dichlorophenyl)-3,6-diethyl-N-[(1R,2S)-2-(2-fluoroethoxy)-2,3-dihydro-1H-inden-1-yl]pyrazin-2-amine

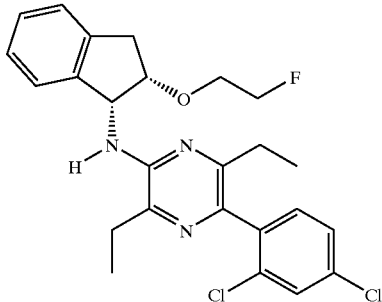

Following the procedure for the preparation of 5-(2,4-dichlorophenyl)-N-[(1R,2S)-2-ethoxy-2,3-dihydro-1H-inden-1-yl]-3,6-diethylpyrazin-2-amine but substituting 1-bromo-2-fluoroethane and making non-critical variations provided the title compound as a light yellow amorphous solid. IR (diffuse reflectance) 2972, 2934, 1564, 1551, 1498, 1468, 1392, 1377, 1206, 1182, 1123, 1102, 1046, 826, 750 cm$^{-1}$; OAMS supporting ions at: ESI+ 473.9; MS (EI) m/z 473 (M$^+$); $[\alpha]^{25}_D$=−87 (c 0.77, methylene chloride); Anal. Calcd for $C_{25}H_{26}Cl_2FN_3O$: C, 63.30; H, 5.52; N, 8.86. Found: C, 63.10; H, 5.60; N, 8.79.

Example 14

Preparation of 5-(2,4-dichlorophenyl)-3,6-diethyl-N-[(1R,2S)-2-propoxy-2,3-dihydro-1H-inden-1-yl]pyrazin-2-amine

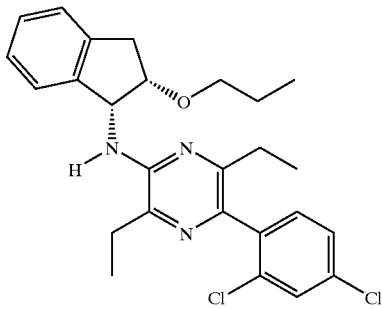

Following the procedure for the preparation of 5-(2,4-dichlorophenyl)-N-[(1R,2S)-2-ethoxy-2,3-dihydro-1H-inden-1-yl]-3,6-diethylpyrazin-2-amine but substituting 1-iodopropane and making non-critical variations provided the title compound as a light yellow syrup. IR (liq.) 3446, 2967, 2935, 2875, 1564, 1552, 1497, 1470, 1392, 1206, 1184, 1101, 1091, 1082, 748 cm$^{-1}$; OAMS supporting ions at: ESI+ 469.9; MS (EI) m/z 469 (M$^+$); $[\alpha]^{25}_D$=−98 (c 0.91, methylene chloride); Anal. Calcd for $C_{26}H_{29}Cl_2N_3O$: C, 66.38; H, 6.21; N, 8.93. Found: C, 66.53; H, 6.15; N, 9.05.

Example 15

Preparation of 2-[((1R,2S)-1-{[5-(2,4-dichlorophenyl)-3,6-diethylpyrazin-2-yl]amino}-2,3-dihydro-1H-inden-2-yl)oxy]ethanol

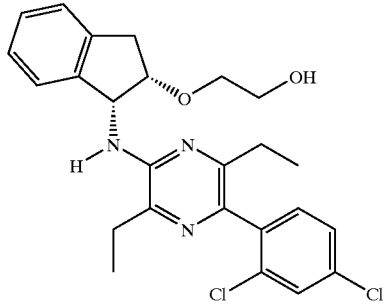

Following the procedure for the preparation of 5-(2,4-dichlorophenyl)-N-[(1R,2S)-2-ethoxy-2,3-dihydro-1H-inden-1-yl]-3,6-diethylpyrazin-2-amine but substituting 2-(bromoethoxy)-tertbutyldimethylsilane and making non-critical variations provided N-[(1R,2S)-2-(2-{[tert-butyl (dimethyl)silyl]oxy}ethoxy)-2,3-dihydro-1H-inden-1-yl]-5-(2,4-dichlorophenyl)-3,6-diethylpyrazin-2-amine. The crude product was treated with 5% hydrochloric acid in ethanol for 18 hrs followed by removal of the volatiles under reduced pressure. The resulting residue was basified with 1N sodium hydroxide and extracted twice with ethyl acetate. The combined organics were washed once with brine, dried over MgSO$_4$, filtered, and concentrated to give a tan syrup. This material was purified by Biotage MPLC (40 g column, 25% ethyl acetate/heptane) to afford 67 mg of the title compound as a white solid. IR (diffuse reflectance) 2969, 2933, 1567, 1551, 1498, 1468, 1392, 1373, 1206, 1182, 1101, 1079, 1061, 1046, 749 cm$^{-1}$; OAMS supporting ions at: ESI+ 472.2; MS (EI) m/z 471 (M$^+$); HRMS (FAB) calcd for $C_{25}H_{27}CL_2N_3O_2+H_1$ 472.1558, found 472.1560. $[\alpha]^{25}_D$=−73 (c 0.50, methylene chloride); Anal. Calcd for $C_{25}H_{27}Cl_2N_3O_2$: C, 63.56; H, 5.76; N, 8.89. Found: C, 63.23; H, 5.91; N, 8.75.

Example 16

Preparation of (1R,2S)-1-{[5-(2,4-dichlorophenyl)-3,6-diethylpyrazin-2-yl]amino}-2,3-dihydro-1H-inden-2-yl dimethylcarbamate

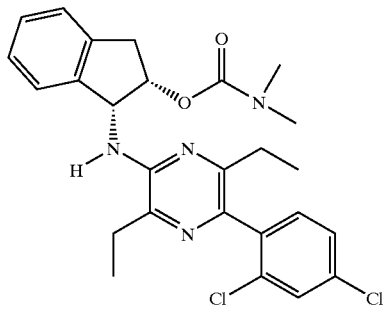

Following the procedure for the preparation of 5-(2,4-dichlorophenyl)-N-[(1R,2S)-2-ethoxy-2,3-dihydro-1H-inden-1-yl]-3,6-diethylpyrazin-2-amine but substituting dimethylcarbamylchloride and making non-critical variations provided the title compound as a white solid. IR (diffuse reflectance) 3374, 2965, 1694, 1568, 1551, 1503, 1469, 1397, 1354, 1218, 1205, 1182, 765, 759, 751 cm$^{-1}$; OAMS supporting ions at: ESI+ 499.1; MS (EI) m/z 498 (M$^+$); HRMS (FAB) calcd for $C_{26}H_{28}CL_2N_4O_2+H_1$ 499.1667, found 499.1684. [α]$^{25}_D$=63 (c 0.71, methylene chloride); Anal. Calcd for $C_{26}H_{28}Cl_2N_4O_2$: C, 62.53; H, 5.65; N, 11.22. Found: C, 62.37; H, 5.74; N, 11.09.

Example 17

Preparation of (1R,2S)-1-{[5-(2,4-dichlorophenyl)-3,6-diethylpyrazin-2-yl]amino}-2,3-dihydro-1H-inden-2-yl acetate

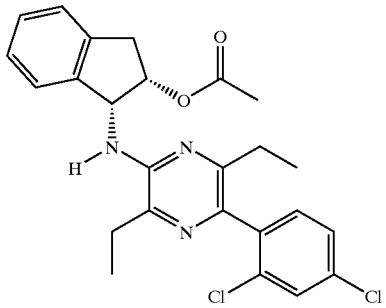

A solution of (1R,2S)-1-{[5-(2,4-dichlorophenyl)-3,6-diethylpyrazin-2-yl]amino}-2,3-dihydro-1H-inden-2-ol (214 mg, 0.5 mmol) and pyridine (44 µL, 0.55 mmol) in dichloromethane (5 mL) was purged with nitrogen and cooled to 0° C. The light yellow homogenous solution was treated with acetyl chloride (34 µL, 0.48 mmol) with no visible change. The reaction mixture was gradually warmed to RT. After 16 hrs, the volatiles were removed under reduced pressure and the resulting residue was absorbed on 4 g silica gel and purified by Biotage MPLC (40 g column, 15% ethyl acetate/heptane) to afford the title compound as an off-white solid. IR (diffuse reflectance) 2971, 2934, 1743, 1568, 1550, 1498, 1467, 1393, 1372, 1238, 1207, 1177, 1101, 1036, 751 cm$^{-1}$; OAMS supporting ions at: ESI+ 470.1; MS (EI) m/z 469 (M$^+$); HRMS (FAB) calcd for $C_{25}H_{25}CL_2N_3O_2+H_1$ 470.1402, found 470.1404. [α]$^{25}_D$=73 (c 0.60, methylene chloride); Anal. Calcd for $C_{25}H_{25}Cl_2N_3O_2$: C, 63.83; H, 5.36; N, 8.93. Found: C, 63.45; H, 5.40; N, 8.79.

Preparation 11

Preparation of (1R,2S)-1-{[5-(2-chloro-4-methoxyphenyl)-3,6-diethylpyrazin-2-yl]amino}-2,3-dihydro-1H-inden-2-ol

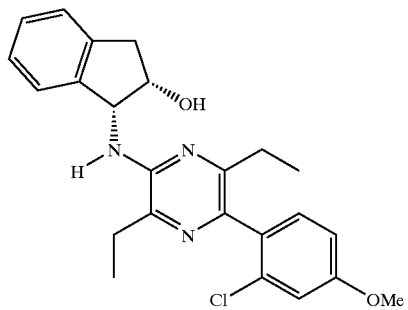

Following the procedure for the preparation of (1R,2S)-1-{[5-(2,4-dichlorophenyl)-3,6-diethylpyrazin-2-yl] amino}-2,3-dihydro-1H-inden-2-ol but substituting 2-chloro-4-methoxyphenylboronic acid and making non-critical variations provided the title compound as an off-white amorphous solid. IR (diffuse reflectance) 2969, 2934, 1604, 1568, 1550, 1482, 1448, 1439, 1392, 1287, 1228, 1203, 1180, 1045, 740 cm$^{-1}$; OAMS supporting ions at: ESI+ 423.9; MS (CI) m/z 424 (MH$^+$); HRMS (FAB) calcd for $C_{24}H_{26}CLN_3O_2+H_1$ 424.1792, found 424.1789. Anal. Calcd for $C_{24}H_{26}ClN_3O_2$: C, 68.00; H, 6.18; N, 9.91. Found: C, 67.86; H, 6.29; N, 9.79.

Example 18

Preparation of 5-(2-chloro-4-methoxyphenyl)-N-[(1R,2S)-2-ethoxy-2,3-dihydro-1H-inden-1-yl]-3,6-diethylpyrazin-2-amine

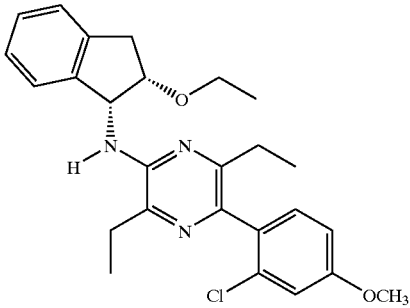

Following the procedure for the preparation of 5-(2,4-dichlorophenyl)-N-[(1R,2S)-2-ethoxy-2,3-dihydro-1H-inden-1-yl]-3,6-diethylpyrazin-2-amine but substituting (1R,2S)-1-{[5-(2-chloro-4-methoxyphenyl)-3,6-diethylpyrazin-2-yl]amino}-2,3-dihydro-1H-inden-2-ol and making non-critical variations provided the title compound as a pale yellow semi-solid. IR (liq.) 2971, 2935, 2875, 1606, 1565, 1480, 1440, 1391, 1287, 1230, 1206, 1183, 1091, 1079, 1044 cm$^{-1}$; OAMS supporting ions at: ESI+ 452.1; MS (EI) m/z 451 (M$^+$); MS (FAB) calcd for $C_{26}H_{30}CLN_3O_2 +H_1$ 452.2104, found 452.2100. [α]$^{25}_D$=-91 (c 0.39, methylene chloride); Anal. Calcd for $C_{26}H_{30}ClN_3O_2$: C, 69.09; H, 6.69; N, 9.30. Found: C, 69.04; H, 6.74; N, 9.30.

Example 19

Preparation of 5-(2-chloro-4-methoxyphenyl)-3,6-diethyl-N-[(1R,2S)-2-(2-fluoroethoxy)-2,3-dihydro-1H-inden-1-yl]pyrazin-2-amine

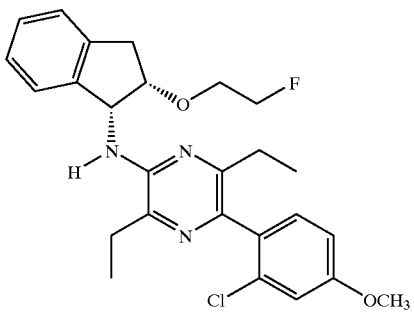

Following the procedure for the preparation of 5-(2,4-dichlorophenyl)-N-[(1R,2S)-2-ethoxy-2,3-dihydro-1H- inden-1-yl]-3,6-diethylpyrazin-2-amine but substituting (1R,2S)-1-{[5-(2-chloro-4-methoxyphenyl)-3,6-diethylpyrazin-2-yl]amino}-2,3-dihydro-1H-inden-2-ol and 1-bromo-2-fluoroethane and making non-critical variations provided the title compound as a pale yellow semi-solid. IR (diffuse reflectance) 2970, 1604, 1564, 1481, 1439, 1391, 1286, 1228, 1204, 1182, 1123, 1109, 1044, 876, 750 cm$^{-1}$; OAMS supporting ions at: ESI+ 470.1; MS (EI) m/z 469 (M$^+$); HRMS (FAB) calcd for $C_{26}H_{29}ClFN_3O_2+H_1$ 470.2010, found 470.2013. $[\alpha]^{25}_D=-82$ (c 0.39, methylene chloride); Anal. Calcd for $C_{26}H_{29}ClFN_3O_2$: C, 66.45; H, 6.22; N, 8.94. Found: C, 66.41; H, 6.37; N, 8.84.

Example 20

Preparation of (1R,2S)-1-{[5-(2-chloro-4-methoxyphenyl)-3,6-diethylpyrazin-2-yl]amino}-2,3-dihydro-1H-inden-2-yl acetate

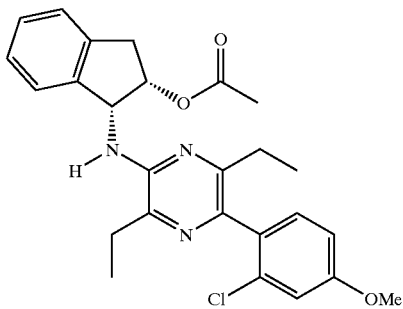

Following the procedure for the preparation of (1R,2S)-1-{[5-(2,4-dichlorophenyl)-3,6-diethylpyrazin-2-yl]amino}-2,3-dihydro-1H-inden-2-yl acetate but substituting (1R,2S)-1-{[5-(2-chloro-4-methoxyphenyl)-3,6-diethylpyrazin-2-yl]amino}-2,3-dihydro-1H-inden-2-ol and making non-critical variations provided the title compound as a light yellow semi-solid. IR (diffuse reflectance) 2969, 2933, 1742, 1604, 1568, 1551, 1482, 1439, 1393, 1372, 1286, 1232, 1204, 1176, 1037 cm$^{-1}$; OAMS supporting ions at: ESI+ 465.2; MS (EI) m/z 465 (M$^+$); $[\alpha]^{25}_D=79$ (c 0.80, methylene chloride); Anal. Calcd for $C_{26}H_{28}ClN_3O_3$: C, 67.02; H, 6.06; N, 9.02. Found: C, 66.99; H, 6.18; N, 8.92.

Preparation 12

Preparation of (1R,2S)-1-{[3,6-diethyl-5-(4-methoxy-2-methylphenyl)pyrazin-2-yl]amino}-2,3-dihydro-1H-inden-2-ol

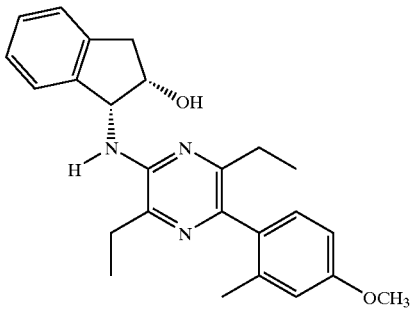

Following the procedure for the preparation of (1R,2S)-1-{[5-(2,4-dichlorophenyl)-3,6-diethylpyrazin-2-yl]amino}-2,3-dihydro-1H-inden-2-ol but substituting 2-methyl-4-methoxyphenylboronic acid and making non-critical variations provided the title compound as a peach colored foam. IR (diffuse reflectance) 3439, 2968, 2933, 2875, 1608, 1564, 1482, 1391, 1294, 1279, 1242, 1204, 1175, 1050, 742 cm$^{-1}$; OAMS supporting ions at: ESI+ 404.0 & ESI– 402.1; MS (EI) m/z 403 (M$^+$); HRMS (FAB) calcd for $C_{25}H_{29}N_3O_2+H_1$ 404.2338, found 404.2324. Anal. Calcd for $C_{25}H_{29}N_3O_2$: C, 74.41; H, 7.24; N, 10.41. Found: C, 74.05; H, 7.44; N, 10.28.

Example 21

Preparation of N-[(1R,2S)-2-ethoxy-2,3-dihydro-1H-inden-1-yl]-3,6-diethyl-5-(4-methoxy-2-methylphenyl)pyrazin-2-amine

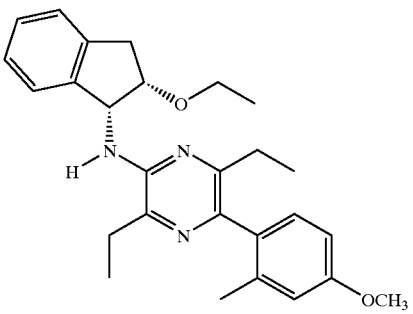

Following the procedure for the preparation of 5-(2,4-dichlorophenyl)-N-[(1R,2S)-2-ethoxy-2,3-dihydro-1H-inden-1-yl]-3,6-diethylpyrazin-2-amine but substituting (1R,2S)-1-{[3,6-diethyl-5-(4-methoxy-2-methylphenyl)pyrazin-2-yl]amino}-2,3-dihydro-1H-inden-2-ol and making non-critical variations provided the title compound as a light yellow semi-solid. IR (liq.) 2971, 2934, 1609, 1562, 1480, 1391, 1294, 1243, 1206, 1184, 1171, 1161, 1119, 1091, 1054 cm$^{-1}$; OAMS supporting ions at: ESI+ 432.1; MS (EI) m/z 431 (M$^+$); HRMS (FAB) calcd for $C_{27}H_{33}N_3O_2+H_1$ 432.2651, found 432.2650. Anal. Calcd for $C_{27}H_{33}N_3O_2$: C, 75.14; H, 7.71; N, 9.74. Found: C, 74.86; H, 7.72; N, 9.67.

Example 22

Preparation of 3,6-diethyl-N-[(1R,2S)-2-(2-fluoroethoxy)-2,3-dihydro-1H-inden-1-yl]-5-(4-methoxy-2-methylphenyl)pyrazin-2-amine

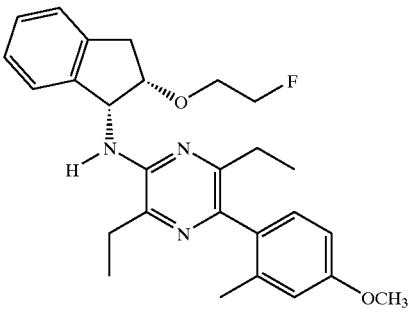

Following the procedure for the preparation of 5-(2,4-dichlorophenyl)-N-[(1R,2S)-2-ethoxy-2,3-dihydro-1H-inden-1-yl]-3,6-diethylpyrazin-2-amine but substituting (1R,2S)-1-{[3,6-diethyl-5-(4-methoxy-2-methylphenyl)

pyrazin-2-yl]amino}-2,3-dihydro-1H-inden-2-ol and 1-bromo-2-fluoroethane and making non-critical variations provided the title compound as a pale yellow semi-solid. IR (liq.) 2969, 2935, 1609, 1563, 1482, 1391, 1294, 1243, 1206, 1182, 1172, 1159, 1124, 1110, 1047 cm$^{-1}$; OAMS supporting ions at: ESI+ 450.0; MS (CI) m/z 450 (MH$^+$); HRMS (FAB) calcd for $C_{27}H_{32}FN_3O_2+H_1$ 450.2556, found 450.2544. Anal. Calcd for $C_{27}H_{32}FN_3O_2$: C, 72.14; H, 7.17; N, 9.35. Found: C, 72.24; H, 7.20; N, 9.33.

Preparation 13

Preparation of (1R,2S)-1-{[5-(2,4-dimethoxyphenyl)-3,6-diethylpyrazin-2-yl]amino}-2,3-dihydro-1H-inden-2-ol

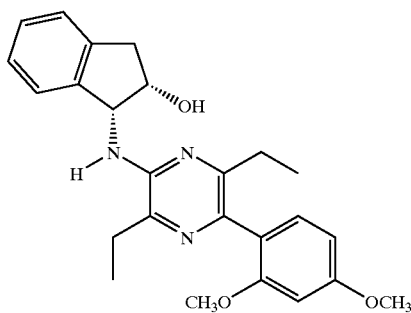

Following the procedure for the preparation of (1R,2S)-1-{[5-(2,4-dichlorophenyl)-3,6-diethylpyrazin-2-yl]amino}-2,3-dihydro-1H-inden-2-ol but substituting 2,4-dimethoxyphenylboronic acid and making non-critical variations provided the title compound as an off-white foam. IR (diffuse reflectance) 2966, 2934, 1610, 1567, 1483, 1391, 1303, 1280, 1253, 1208, 1159, 1128, 1046, 1034, 741 cm$^{-1}$; OAMS supporting ions at: ESI+ 420.1; MS (EI) m/z 419 (M$^+$); HRMS (FAB) calcd for $C_{25}H_{29}N_3O_3+H_1$ 420.2287, found 420.2278.

Example 23

Preparation of 5-(2,4-dimethoxyphenyl)-N-[(1R,2S)-2-ethoxy-2,3-dihydro-1H-inden-1-yl]-3,6-diethylpyrazin-2-amine

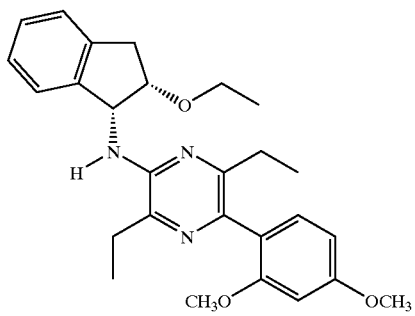

Following the procedure for the preparation of 5-(2,4-dichlorophenyl)-N-[(1R,2S)-2-ethoxy-2,3-dihydro-1H-inden-1-yl]-3,6-diethylpyrazin-2-amine but substituting (1R,2S)-1-{[5-(2,4-dimethoxyphenyl)-3,6-diethylpyrazin-2-yl]amino}-2,3-1H-inden-2-ol and making non-critical variations provided the title compound as a white solid, m.p. 120–121° C. (uncorrected). IR (diffuse reflectance) 2965, 2935, 1615, 1566, 1480, 1390, 1305, 1256, 1215, 1209, 1183, 1165, 1040, 825, 747 cm$^{-1}$; OAMS supporting ions at: ESI+ 448.1; MS (EI) m/z 447 (M$^+$); HRMS (FAB) calcd for $C_{27}H_{33}N_3O_3+H_1$ 448.2600, found 448.2600. Anal. Calcd for $C_{27}H_{33}N_3O_3$: C, 72.46; H, 7.43; N, 9.39. Found: C, 72.46; H, 7.59; N, 9.39.

Example 24

Preparation of 5-(2,4-dimethoxyphenyl)-3,6-diethyl-N-[(1R,2S)-2-(2-fluoroethoxy)-2,3-dihydro-1H-inden-1-yl]pyrazin-2-amine

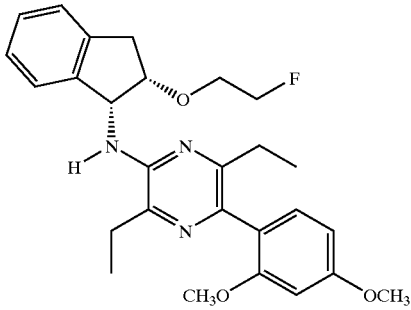

Following the procedure for the preparation of 5-(2,4-dichlorophenyl)-N-[(1R,2S)-2-ethoxy-2,3-dihydro-1H-inden-1-yl]-3,6-diethylpyrazin-2-amine but substituting (1R,2S)-1-{[5-(2,4-dimethoxyphenyl)-3,6-diethylpyrazin-2-yl]amino}-2,3-dihydro-1H-inden-2-ol and 1-bromo-2-fluoroethane and making non-critical variations provided the title compound as a white solid. IR (diffuse reflectance) 2964, 2935, 1614, 1567, 1480, 1392, 1305, 1256, 1215, 1209, 1165, 1158, 1040, 825, 747 cm$^{-1}$; OAMS supporting ions at: ESI+ 466.2; MS (EI) m/z 465 (M$^+$); Anal. Calcd for $C_{27}H_{32}FN_3O_3$: C, 69.66; H, 6.93; N, 9.03. Found: C, 69.61; H, 7.02; N, 8.98.

Preparation 14

Preparation of (1R,2S)-1-({5-[2-chloro-4-(dimethylamino)phenyl]-3,6-diethylpyrazin-2-yl}amino)-2,3-dihydro-1H-inden-2-ol

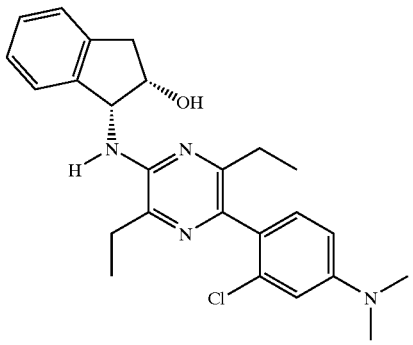

Following the procedure for the preparation of (1R,2S)-1-{[5-(2,4-dichlorophenyl)-3,6-diethylpyrazin-2-yl]amino}-2,3-dihydro-1H-inden-2-ol but substituting 2-chloro-4-dimethylaminophenylboronic acid and making non-critical variations provided the title compound as a pale yellow amorphous solid. IR (diffuse reflectance) 2969, 2932, 1607, 1567, 1550, 1486, 1443, 1391, 1353, 1225, 1207, 1177, 1043, 961, 740 cm$^{-1}$; OAMS ESI+ 437.2; MS (EI) m/z 436 (M$^+$); HRMS (FAB) calcd for $C_{25}H_{29}ClN_4O+H_1$ 437.2108, found 437.2089. $[\alpha]^{25}{}_D=-7$ (c 0.70, methylene chloride); Anal. Calcd for $C_{25}H_{29}ClN_4O$: C, 68.72; H, 6.69; N, 12.82. Found: C, 68.48; H, 6.84; N, 12.66.

Example 25

Preparation of 5-[2-chloro-4-(dimethylamino)phenyl]-N-[(1R,2S)-2-ethoxy-2,3-dihydro-1H-inden-1-yl]-3,6-diethylpyrazin-2-amine

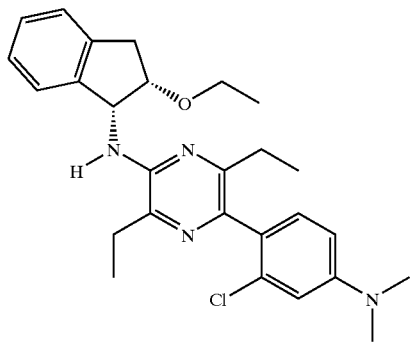

Following the procedure for the preparation of 5-(2,4-dichlorophenyl)-N-[(1R,2S)-2-ethoxy-2,3-dihydro-1H-inden-1-yl]-3,6-diethylpyrazin-2-amine but substituting (1R,2S)-1-({5-[2-chloro-4-(dimethylamino)phenyl]-3,6-diethylpyrazin-2-yl}amino)-2,3-dihydro-1H-inden-2-ol and making non-critical variations provided the title compound as a pale yellow amorphous solid. IR (diffuse reflectance) 2971, 2932, 2890, 2875, 1608, 1563, 1482, 1442, 1389, 1366, 1352, 1207, 1175, 1090, 961 cm$^{-1}$; OAMS supporting ions at: ESI+ 465.2; MS (EI) m/z 464 (M$^+$); HRMS (FAB) calcd for $C_{27}H_{33}ClN_4O+H_1$ 465.2421, found 465.2406. Anal. Calcd for $C_{27}H_{33}ClN_4O$: C, 69.74; H, 7.15; N, 12.05. Found: C, 69.68; H, 7.16; N, 11.99.

Example 26

Preparation of 5-[2-chloro-4-(dimethylamino)phenyl]-3,6-diethyl-N-[(1R,2S)-2-(2-fluoroethoxy)-2,3-dihydro-1H-inden-1-yl]pyrazin-2-amine

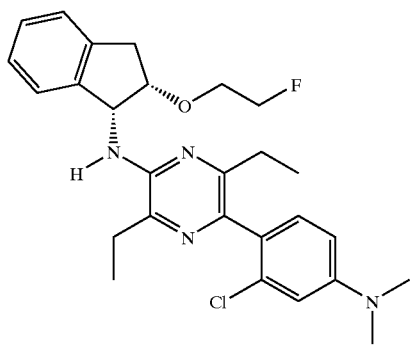

Following the procedure for the preparation of 5-(2,4-dichlorophenyl)-N-[(1R,2S)-2-ethoxy-2,3-dihydro-1H-inden-1-yl]-3,6-diethylpyrazin-2-amine but substituting (1R,2S)-1-({5-[2-chloro-4-(dimethylamino)phenyl]-3,6-diethylpyrazin-2-yl}amino 2,3-dihydro-1H-inden-2-ol and 1-bromo-2-fluoroethane and making non-critical variations provided the title compound as a light yellow amorphous solid. IR (diffuse reflectance) 2969, 2932, 2907, 2877, 1608, 1563, 1545, 1483, 1447, 1392, 1353, 1207, 1177, 1123, 1042 cm$^{-1}$; OAMS supporting ions at: ESI+ 483.2; MS (EI) m/z 482 (M$^+$); HRMS (FAB) calcd for $C_{27}H_{32}ClFN_4O+H_1$ 483.2327, found 483.2324. $[\alpha]^{25}{}_D=-79$ (c 0.52, methylene chloride); Anal. Calcd for $C_{27}H_{32}ClFN_4O$: C, 67.14; H, 6.68; N, 11.60. Found: C, 67.19; H, 6.90; N, 11.63.

Preparation 15

Preparation of (1R,2S)-1-({5-[6-(dimethylamino)-4-methylpyridin-3-yl]-3,6-diethylpyrazin-2-yl}amino)-2,3-dihydro-1H-inden-2-ol

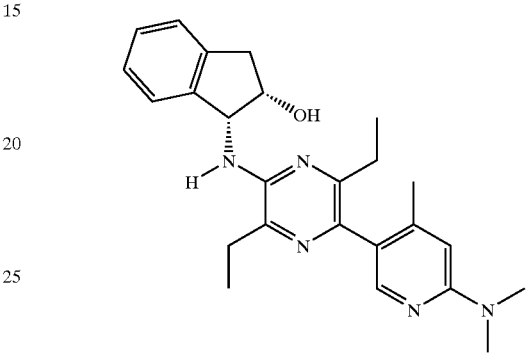

Following the procedure for the preparation of (1R,2S)-1-{[5-(2,4-dichlorophenyl)-3,6-diethylpyrazin-2-yl]amino}-2,3-dihydro-1H-inden-2-ol but substituting 6-(dimethylamino)-4-methylpyridin-3-ylboronic acid and making non-critical variations provided the title compound as a light yellow amorphous solid. IR (diffuse reflectance) 3448, 2962, 2954, 2933, 1611, 1567, 1520, 1482, 1392, 1376, 1174, 1160, 1046, 741, 737 cm$^{-1}$; OAMS supporting ions at: ESI+ 418.3; MS (EI) m/z 417 (M$^+$); HRMS (FAB) calcd for $C_{25}H_{31}N_5O+H_1$ 418.2607, found 418.2611. Anal. Calcd for $C_{25}H_{31}N_5O$: C, 71.91; H, 7.48; N, 16.77. Found: C, 71.59; H, 7.57; N, 16.40.

Example 27

Preparation of 5-[6-(dimethylamino)-4-methylpyridin-3-yl]-N-[(1R,2S)-2-ethoxy-2,3-dihydro-1H-inden-1-yl]-3,6-diethylpyrazin-2-amine

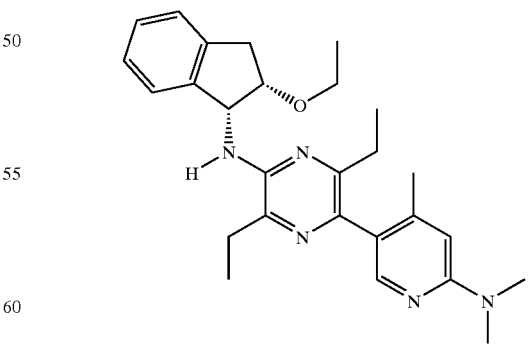

Following the procedure for the preparation of 5-(2,4-dichlorophenyl)-N-[(1R,2S)-2-ethoxy-2,3-dihydro-1H-inden-1-yl]-3,6-diethylpyrazin-2-amine but substituting (1R,2S)-1-({5-[6-(dimethylamino)-4-methylpyridin-3-yl]-

3,6-diethylpyrazin-2-yl}amino)-2,3-dihydro-1H-inden-2-ol and making non-critical variations provided the title compound as a light golden amorphous solid. IR (diffuse reflectance) 3446, 2969, 2931, 2893, 2874, 1604, 1562, 1517, 1487, 1392, 1372, 1208, 1174, 1123, 1089 cm$^{-1}$; OAMS supporting ions at: ESI+ 446.3; MS (EI) m/z 445 (M$^+$); HRMS (FAB) calcd for $C_{27}H_{35}N_5O+H_1$ 446.2920, found 446.2915. $[\alpha]^{25}_D$=−89 (c 0.47, methylene chloride); Anal. Calcd for $C_{27}H_{35}N_5O$: C, 72.78; H, 7.92; N, 15.72. Found: C, 72.58; H, 7.94; N, 15.59.

Preparation 16

Preparation of N-(2,3-dihydro-1H-inden-1-yl)-3,6-dimethylpyrazin-2-amine

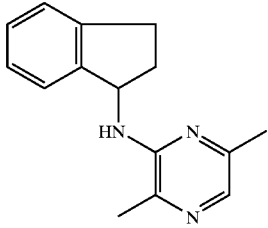

Following the procedure for the preparation of (1R,2S)-1-[(3,6-diethylpyrazin-2-yl)amino]-2,3-dihydro-1H-inden-2-ol but substituting 1-Aminoindane and 3-chloro-2,5-dimethylpyrazine, and making non-critical variations provided the title compound as a oil: $^1$H NMR (CDCl$_3$) δ 1.88, 2.35, 2.41, 2.77, 2.94, 3.03, 4.55, 5.78, 7.3, 7.64; MS (ESI+) for $C_{15}H_{17}N_3$ m/z 240.30 (M+H)$^+$.

Preparation 17

Preparation of 5-bromo-N-(2,3-dihydro-1H-inden-1-yl)-3,6-dimethylpyrazin-2-amine

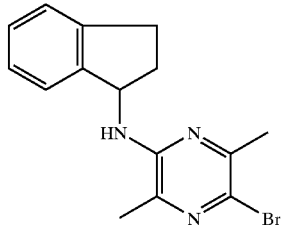

Following the procedure for the preparation of (1R,2S)-1-[(5-bromo-3,6-diethylpyrazin-2-yl)amino]-2,3-dihydro-1H-inden-2-ol but substituting N-(2,3-dihydro-1H-inden-1-yl)-3,6-dimethylpyrazin-2-amine and making non-critical variations provided the title compound as a oil: $^1$H NMR (CDCl$_3$) δ 1.86, 2.26, 2.53, 2.70, 2.93, 3.03, 4.50, 5.72, 7.28; $^{13}$C NMR (CDCl$_3$) δ 19.23, 23.21, 30.25, 34.56, 56.45, 124.05, 124.81, 124.97, 126.78, 128.03, 136.98, 143.71, 144.09, 148.36, 151.15; MS (ESI+) for $C_{15}H_{16}N_3Br_1$ m/z 319.20 (M+H)$^+$.

Example 28

Preparation of 5-(2,4-dichlorophenyl)-N-(2,3-dihydro-1H-inden-1-yl)-3,6-dimethylpyrazin-2-amine

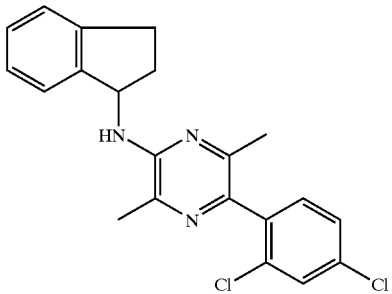

Following the procedure for the preparation of (1R,2S)-1-{[5-(2,4-dichlorophenyl)-3,6-diethylpyrazin-2-yl]amino}-2,3-dihydro-1H-inden-2-ol but substituting 5-bromo-N-(2,3-dihydro-1H-inden-1-yl)-3,6-dimethylpyrazin-2-amine and making non-critical variations provided the title compound as a oil: $^1$H NMR (CDCl$_3$) δ 1.94, 2.29, 2.39, 2.80, 2.96, 3.08, 4.64, 5.83, 7.33, 7.51; MS (ESI+) for $C_{21}H_{19}Cl_2N_3$ m/z 385.30 (M+H)$^+$.

Example 29

Preparation of N-(2,3-dihydro-1H-inden-1-yl)-5-(4-methoxy-2-methylphenyl)-3,6-dimethylpyrazin-2-amine

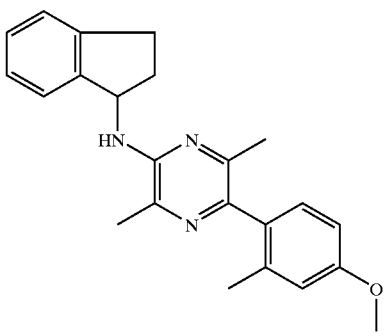

Following the procedure for the preparation of (1R,2S)-1-{[5-(2,4-dichlorophenyl)-3,6-diethylpyrazin-2-yl]amino}-2,3-dihydro-1H-inden-2-ol but substituting 5-bromo-N-(2,3-dihydro-1H-inden-1-yl)-3,6-dimethylpyrazin-2-amine and 2-methyl-4-methoxy phenyl boronic acid, and making non-critical variations provided the title compound as a oil: $^1$H NMR (CDCl$_3$) δ 1.92, 2.17, 2.26, 2.39, 2.80, 2.98, 3.07, 3.85, 4.54, 5.82, 6.84, 7.15, 7.30, 7.41; MS (ESI+) for C$_{23}$H$_{25}$N$_3$O$_1$ m/z 360.4 (M+H)$^+$.

Preparation 18

Preparation of 3,6-dimethyl-N-(1,2,3,4-tetrahydronaphthalen-1-yl)pyrazin-2-amine

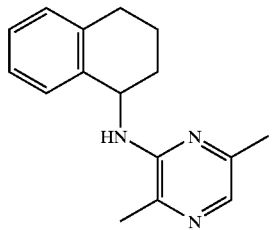

Following the procedure for the preparation of (1R,2S)-1-[(3,6-diethylpyrazin-2-yl)amino]-2,3-dihydro-1H-inden-2-ol but substituting 1,2,3,4-tetrahydronaphthalen-1-amine and 3-chloro-2,5-dimethylpyrazine, and making non-critical variations provided the title compound as a oil: $^1$H NMR (CDCl$_3$) δ 1.91, 2.11, 2.31, 2.40, 2.87, 4.50, 5.16, 7.21, 7.35, 7.62; MS (ESI+) for C$_{16}$H$_{19}$N$_3$ m/z 254.4 (M+H)$^+$.

Preparation 19

Preparation of 5-bromo-3,6-dimethyl-N-(1,2,3,4-tetrahydronaphthalen-1-yl)pyrazin-2-amine

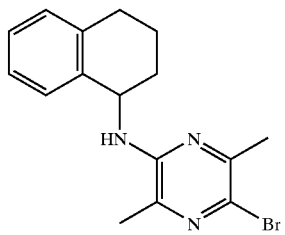

Following the procedure for the preparation of (1R,2S)-1-[(5-bromo-3,6-diethylpyrazin-2-yl)amino]-2,3-dihydro-1H-inden-2-ol but substituting 3,6-dimethyl-N-(1,2,3,4-tetrahydronaphthalen-1-yl)pyrazin-2-amine and making non-critical variations provided the title compound as a oil: $^1$H NMR (CDCl$_3$) δ 1.92, 2.08, 2.29, 2.53, 2.86, 4.48, 5.40, 7.21, 7.33; $^{13}$C NMR (CDCl$_3$) δ 19.63, 20.32, 23.67, 29.81, 30.00, 49.20, 124.85, 126.66, 127.69, 129.23, 129.63, 137.17, 138.12, 138.25, 148.78, 151.23; MS (ESI+) for C$_{16}$H$_{18}$N$_3$Br$_1$ m/z 333.3 (M+H)$^+$.

Example 30

Preparation of 5-(2,4-dichlorophenyl)-3,6-dimethyl-N-(1,2,3,4-tetrahydronaphthalen-1-yl)pyrazin-2-amine

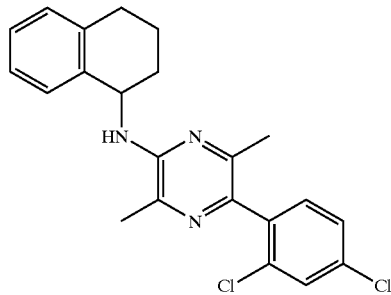

Following the procedure for the preparation of (1R,2S)-1-{[5-(2,4-dichlorophenyl)-3,6-diethylpyrazin-2-yl]amino}-2,3-dihydro-1H-inden-2-ol but substituting Preparation of 5-bromo-3,6-dimethyl-N-(1,2,3,4-tetrahydronaphthalen-1-yl)pyrazin-2-amine and making non-critical variations provided the title compound as a oil: $^1$H NMR (CDCl$_3$) δ 1.95, 2.15, 2.28, 2.35, 2.90, 4.62, 5.52, 7.23, 7.34, 7.41, 7.51; MS (ESI+) for C$_{22}$H$_{21}$Cl$_3$N$_3$ m/z 399.1 (M+H)$^+$.

Example 31

Preparation of 5-(4-methoxy-2-methylphenyl)-3,6-dimethyl-N-(1,2,3,4-tetrahydronaphthalen-1-yl)pyrazin-2-amine

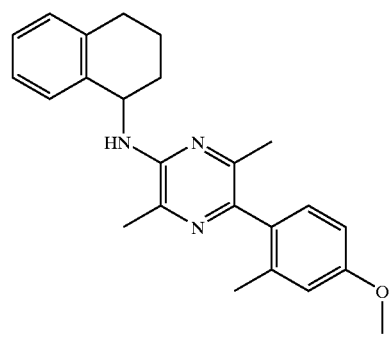

Following the procedure for the preparation of (1R,2S)-1-{[5-(2,4-dichlorophenyl)-3,6-diethylpyrazin-2-yl]amino}-2,3-dihydro-1H-inden-2-ol but substituting 5-(2,4-dichlorophenyl)-3,6-dimethyl-N-(1,2,3,4-tetrahydronaphthalen-1-yl)pyrazin-2-amine and 2-methyl-4-methoxy phenyl boronic acid, and making non-critical variations provided the title compound as a oil: $^1$H NMR (CDCl$_3$) δ 1.81, 2.01, 2.06, 2.13, 2.22, 2.77, 3.71, 4.38, 5.39, 6.70, 7.09, 7.31; $^{13}$C NMR (CDCl$_3$) δ 20.07, 20.47, 20.54, 22.09, 29.96, 30.28, 48.94, 55.68, 111.58, 116.05, 126.64, 127.57, 129.43, 129.60, 131.24, 132.37, 135.83, 138.31, 138.56, 138.74, 140.69, 147.04, 150.92, 159.51; HRMS (ESI+) for $C_{24}H_{27}N_3O_1$ m/z calcd 374.2232 (M+H)$^+$ found 374.2226

Preparation 20

Preparation of 3-(2,4-dichlorophenyl)-2,5-dimethylpyrazine

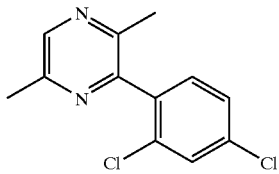

To a solution of 3-chloro-2,5-dimethylpyrazine (2 g, 14 mmol) in DME (35 ml) and 2N sodium bicarbonate (14 ml) was added 2,4-dichloroboranic acid (15.4 mmol, 2.94 g) and tetrakis(triphenylphosphine)palladium (810 mg). The reaction mixture was heated at 85° C. for 12 hr. The reaction mixture was cooled, diluted with $Et_2O$, washed with $NaHCO_3$ (sat'd) and dried ($MgSO_4$). Flash chromatography (Silica gel, Heptane:EtOAc 20:1) gave the title compound (91% yield). $^1$H NMR (CDCl$_3$) δ 2.40, 2.60, 7.29, 7.40, 8.43; $^{13}$C NMR (CDCl$_3$) δ 21.52, 21.72, 127.97, 129.99, 131.80, 134.18, 135.69, 136.77, 143.58, 149.73, 150.66, 150.82; MS (ESI+) for $C_{12}H_{10}Cl_2N_2$ m/z 254.2 (M+H)$^+$.

Preparation 21

Preparation of 2-bromo-5-(2,4-dichlorophenyl)-3,6-dimethylpyrazine

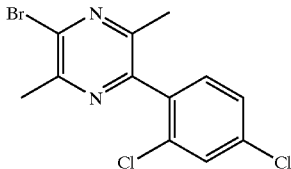

POBr3 (573 mg) was added to the solution of 3-(2,4-dichlorophenyl)-2,5-dimethylpyrazine 1-oxide (270 mg) and proton sponge (197 mg) in $CH_2Cl_2$ at 0° C. The reaction mixture was warmed to r.t. for 10 h. The reaction mixture was washed with 1N HCl, $NaHCO_3$ and brine, dried ($MgSO_4$), filtered and concentrated. Flash chromatography (silica gel Heptane:EtOAC 100:1) gave the title compound (110 mg, 35%) and 3-(2,4-dichlorophenyl)-2,5-dimethylpyrazine (100 mg, 38%). $^1$H NMR (CDCl$_3$) δ 2.40, 2.71, 7.28, 7.40, 7.54; MS (ESI+) for $C_{12}H_9Cl_2N_2Br_1$ m/z 333.0 (M+H)$^+$.

Example 32

Preparation of N-[5-(2,4-dichlorophenyl)-3,6-dimethylpyrazin-2-yl]isoquinolin-1-amine

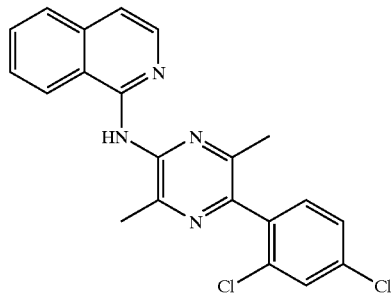

Following the procedure for the preparation of (1R,2S)-1-[(3,6-diethylpyrazin-2-yl)amino]-2,3-dihydro-1H-inden-2-ol but substituting 2-bromo-5-(2,4-dichlorophenyl)-3,6-dimethylpyrazine and isoquinolin-1-amine, and making non-critical variations provided the title compound as a oil: $^1$H NMR (CDCl$_3$) δ 2.36, 2.93, 6.75, 7.38, 7.53, 7.57, 8.96; HRMS (ESI+) calcd for $C_{21}H_{16}Cl_2N_4$ (M+H)$^+$ 395.0830, found 395.0821.

Preparation 22

Preparation of 3-(2,4-dichlorophenyl)-2,5-dimethylpyrazine 1-oxide

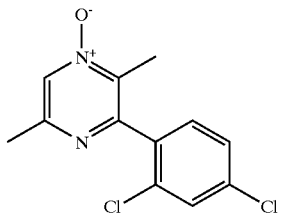

To a solution of 3-(2,4-dichlorophenyl)-2,5-dimethylpyrazine at 0° C. in dioxane was added mCPBA (750 mg). The reaction mixture was heated at 45° C. for 3 h. The reaction was diluted with $CH_2Cl_2$, washed with $NaHCO_3$, dried ($MgSO_4$), filtered, and concentrated. It was used without purification: $^1$H NMR (CDCl$_3$) δ 2.30, 2.54, 7.33, 7.42, 7.54, 8.13; $^{13}$C NMR (CDCl$_3$) δ 14.04, 21.85, 128.10, 130.12, 131.64, 132.14, 134.07, 135.23, 136.44, 141.66, 153.87, 154.24.

Preparation 23

Preparation of 3-(2,4-dichlorophenyl)-2,5-diethylpyrazine

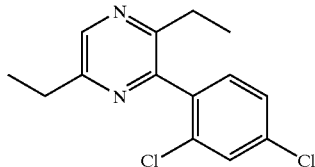

Following the procedure for the preparation of 3-(2,4-dichlorophenyl)-2,5-dimethylpyrazine but 3-chloro-2,5-diethylpyrazine and making non-critical variations provided the title compound as a oil: ¹H NMR (CDCl₃) δ 1.19, 1.35, 2.65, 2.88, 7.29, 7.39, 7.54, 8.47; ¹³C NMR (CDCl₃) δ 13.52, 14.48, 28.03, 28.97, 128.01, 130.22, 132.07, 134.61, 135.77, 137.02, 143.22, 150.44, 154.57, 155.84; MS (ESI+) for $C_{14}H_{14}Cl_2N_2$ m/z 282.2 (M+H)⁺.

Preparation 24

Preparation of 3-(2,4-dichlorophenyl)-2,5-diethylpyrazine 1-oxide

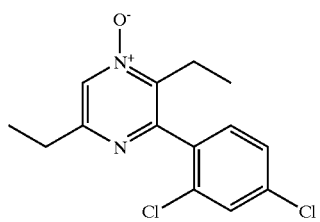

Following the procedure of 3-(2,4-dichlorophenyl)-2,5-dimethylpyrazine 1-oxide but substituting Preparation of 3-(2,4-dichlorophenyl)-2,5-diethylpyrazine and making non-critical variations, the title compound was obtained (quantitative). It was used without preparation. ¹H NMR (CDCl₃) δ 1.12, 1.34, 2.55, 2.81, 2.89, 7.28, 7.40, 7.55, 8.11.

Preparation 25

Preparation of 2-bromo-5-(2,4-dichlorophenyl)-3,6-diethylpyrazine

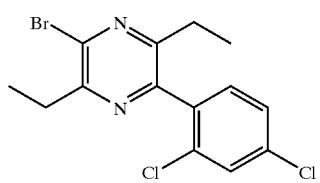

Following the procedure of 2-bromo-5-(2,4-dichlorophenyl)-3,6-dimethylpyrazine but substituting 3-(2,4-dichlorophenyl)-2,5-diethylpyrazine 1-oxide and making non-critical variations provided the title compound as an oil: ¹H NMR (CDCl₃) δ 1.19 7.5, 1.33, 2.63, 3.02, 7.28, 7.39, 7.54; MS (ESI+) for $C_{14}H_{13}Br_1Cl_2N_2$ m/z 361.1 (M+H)⁺.

Example 33

Preparation of 5-(2,4-dichlorophenyl)-3,6-diethyl-N-(3-ethyl-6-methylpyridin-2-yl)pyrazin-2-amine

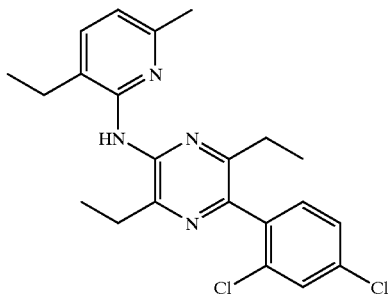

Following the procedure for the preparation of (1R,2S)-1-[(3,6-diethylpyrazin-2-yl)amino]-2,3-dihydro-1H-inden-2-ol but substituting 2-bromo-5-(2,4-dichlorophenyl)-3,6-diethylpyrazine and 3-ethyl-6-methylpyridin-2-amine, and making non-critical variations provided the title compound as a oil: ¹H NMR (DMSO-d₆) δ 0.95, 1.15, 2.33, 2.31, 2.51, 2.70, 6.95, 7.51, 7.75, 8.57; HRMS (ESI+) calcd for $C_{22}H_{24}Cl_2N_4$ (M+H)⁺ 415.1456, found 415.1442.

Example 34

Preparation of 5-(2,4-dichlorophenyl)-N-(4,6-dimethylpyridin-2-yl)-3,6-diethylpyrazin-2-amine

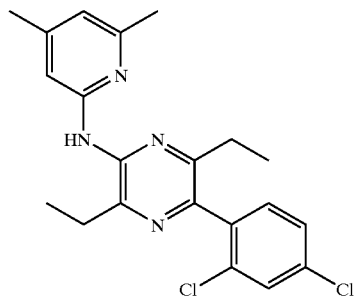

Following the procedure for the preparation of (1R,2S)-1-[(3,6-diethylpyrazin-2-yl)amino]-2,3-dihydro-1H-inden-2-ol but substituting 2-bromo-5-(2,4-dichlorophenyl)-3,6-diethylpyrazine and 4,6-dimethylpyridin-2-amine, and making non-critical variations provided the title compound as a oil: ¹H NMR (CDCl₃) δ 1.31, 1.38, 2.37, 2.46, 2.62, 2.90, 6.68, 7.31, 7.37, 7.52, 8.28; HRMS (ESI+) Calcd for $C_{21}H_{22}Cl_2N_4$ (M+H)⁺ 401.1299, found 401.1317.

Preparation 26

Preparation of 4,5,6,7-tetrahydro-1-benzofuran-4-amine

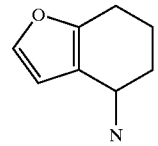

To a solution of 6,7-dihydro-1-benzofuran-4(5H)-one (2.0 g) in methanol (50 ml) was added 3 Å sieves (15 g), ammonium acetate (11.3 g) and sodium cyanoborohydride (1.22 g). After 48 h of stirring, the reaction mixture was filtered through celite, concentrated, dissolved in 1 N HCl (100 ml) and washed with ethyl ether (3×100 ml). The Aqueous layer was basified to pH 10 (NaOH), extracted methylene chloride (3×100 ml), dried MgSO$_4$, filtered and concentrated to yield (760 mg, 38%) of the title compound as an oil:

$^1$H NMR (400 MHz, CDCl$_3$) δ 7.27, 6.39, 3.87, 2.61, 2.00, 1.81, 1.48; $^{13}$C NMR (100 MHz, CDCl$_3$) δ 151.47, 141.11, 122.31, 109.29, 45.93, 34.81, 23.38, 20.63.

Preparation 27

Preparation of 3,6-diethyl-N-(4,5,6,7-tetrahydro-1-benzofuran-4-yl)pyrazin-2-amine

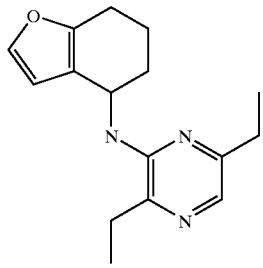

Following the procedure for the preparation of (1R,2S)-1-[(3,6-diethylpyrazin-2-yl)amino]-2,3-dihydro-1H-inden-2-ol but substituting 4,5,6,7-tetrahydro-1-benzofuran-4-amine and making non-critical variations provided the title compound as a oil:

$^1$H NMR (400 MHz, CDCl$_3$) δ 7.66, 7.29, 6.32, 5.25, 4.40, 2.69, 2.57, 2.07, 1.92, 1.36; (MS/CI) calcd for C$_{16}$H$_{21}$N$_3$O+H 272.1, found 272.1.

Preparation 28

Preparation of 5-bromo-3,6-diethyl-N-(4,5,6,7-tetrahydro-1-benzofuran-4-yl)pyrazin-2-amine

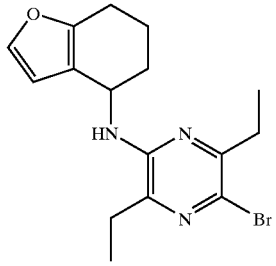

Following the procedure for the preparation of (1R,2S)-1-[(5-bromo-3,6-diethylpyrazin-2-yl)amino]-2,3-dihydro-1H-inden-2-ol but substituting 3,6-diethyl-N-(4,5,6,7-tetrahydro-1-benzofuran-4-yl)pyrazin-2-amine and making non-critical variations provided the title compound as a oil: $^1$H NMR (400 MHz, CDCl$_3$) δ 7.29, 6.03, 5.18, 4.49, 2.81, 2.65, 2.55, 2.03, 1.89, 1.23; (FAB) calcd for C$_{16}$H$_{20}$BrN$_3$O+H 351.0, found 351.0.

Example 35

Preparation of 5-(2,4-dichlorophenyl)-3,6-diethyl-N-(4,5,6,7-tetrahydro-1-benzofuran-4-yl)pyrazin-2-amine

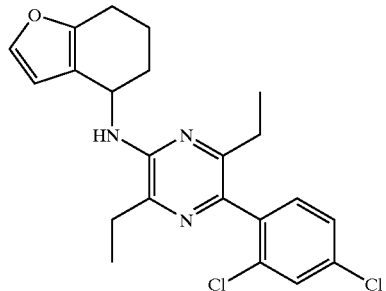

Following the procedure for the preparation of (1R,2S)-1-{[5-(2,4-dichlorophenyl)-3,6-diethylpyrazin-2-yl]amino}-2,3-dihydro-1H-inden-2-ol but substituting 3,6-diethyl-N-(4,5,6,7-tetrahydro-1-benzofuran-4-yl)pyrazin-2-amine and making non-critical variations provided the title compound as a oil: $^1$H NMR (400 MHz, CDCl$_3$) δ 7.50, 7.34, 5.30, 4.53, 2.68, 2.62, 2.51, 2.09, 1.94 1.26, 1.20; HRMS (EI) calcd for C$_{22}$H$_{23}$Cl$_2$N$_3$O 415.1218, found 415.1217.

Preparation 29

Preparation of 5-methyl-6,7-dihydro-1-benzofuran-4 (5H)-one

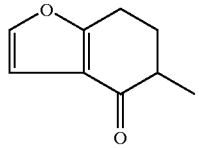

Following the procedure for the preparation of 5-methyl-6,7-dihydro-1-benzothiophen-4(5H)-one but substituting 6,7-dihydro-1-benzofuran-4(5H)-one and making non-critical variations provided the title compound as a oil: $^1$H NMR (CDCl$_3$) δ 1.24, 1.95, 2.25, 2.55, 2.93, 6.68, 7.33; MS (EI) m/z (rel. intensity) 150 (M+, 54), 150 (54), 121 (10), 109 (8), 108 (99), 86 (26), 84 (39), 80 (56), 52 (19), 51 (26), 50 (7). HRMS (FAB) calcd for C$_9$H$_{10}$O$_2$+H 151.0759, found 151.0760. Anal. Calcd for C$_9$H$_{10}$O$_2$: C, 71.98; H, 6.71. Found: C, 71.55; H, 6.74; N, 0.19.

Preparation 30

Preparation of 5-methyl-4,5,6,7-tetrahydro-1-benzofuran-4-amine

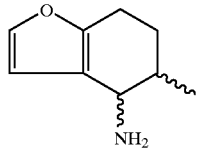

Following the procedure for the preparation of 4,5,6,7-tetrahydro-1-benzofuran-4-amine but substituting 5-methyl- 6,7-dihydro-1-benzofuran-4(5H)-one and making non-critical variations provided the title compound as a oil: MS (EI) m/z (rel. intensity) 151 (M+, 64), 151 (64), 134 (86), 110 (83), 109 (99), 108 (55), 88 (56), 86 (87), 84 (92), 80 (76), 51 (67). HRMS (FAB) calcd for $C_9H_{13}NO+H$ 152.1075, found 152.1066.

Example 36

Preparation of 5-(2,4-dichlorophenyl)-3,6-diethyl-N-(5-methyl-4,5,6,7-tetrahydro-1-benzofuran-4-yl)pyrazin-2-amine

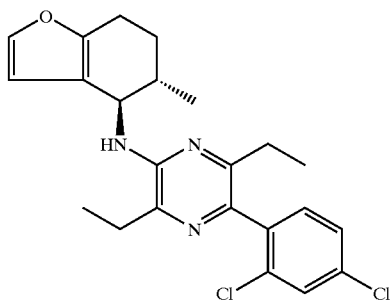

Following the procedure for the preparation of (1R,2S)-1-[(3,6-diethylpyrazin-2-yl)amino]-2,3-dihydro-1H-inden-2-ol but substituting 2-bromo-5-(2,4-dichlorophenyl)-3,6-diethylpyrazine and making non-critical variations provided the title compound as a oil: $^1$H NMR (CDCl$_3$) δ 1.13, 1.19, 1.26, 1.78, 2.04, 2.50, 2.65, 4.50, 5.02, 6., 7.31, 7.50; HRMS (ESI+) calcd for $C_{23}H_{25}Cl_2N_3O_1$ (M+H)$^+$ 480.1453, found 430.1436.

Preparation 31

Preparation of 5-ethyl-6,7-dihydro-1-benzofuran-4(5H)-one

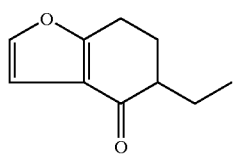

Following the procedure for the preparation of 5-methyl-6,7-dihydro-1-benzothiophen-4(5H)-one but substituting 6,7-dihydro-1-benzofuran-4(5H)-one and ethyl iodide and making non-critical variations provided the title compound as a oil: $^1$H NMR (CDCl$_3$) δ 1.00, 1.54, 1.95, 2.29, 2.91, 6.67, 7.3; MS (EI) m/z (rel. intensity) 164 (M+, 36), 164 (36), 136 (90), 135 (24), 108 (76), 88 (13), 86 (69), 84 (99), 80 (58), 52 (21), 51 (57). HRMS (FAB) calcd for $C_{10}H_{12}O_2+H$ 165.0916, found 165.0919. Anal. Calcd for $C_{10}H_{12}O_2$: C, 73.15; H, 7.37. Found: C, 72.81; H, 7.60.

Preparation 32

Preparation of (4E) and (4Z)-5-ethyl-6,7-dihydro-1-benzofuran-4(5H)-one oxime

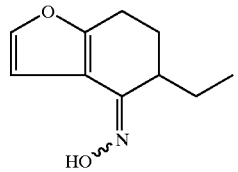

Following the procedure for the preparation of (4E)-2,3-dihydro-4H-chromen-4-one oxime but substituting 5-ethyl-6,7-dihydro-1-benzofuran-4(5H)-one and making non-critical variations provided the title compound as a oil: MS (EI) m/z (rel. intensity) 179 (M+, 21), 162 (50), 151 (43), 135 (99), 134 (99), 107 (86), 106 (83), 84 (34), 79 (35), 52 (47), 51(48). HRMS (FAB) calcd for $C_{10}H_{13}NO_2+H$ 180.1024, found 180.1015.

Preparation 33

Preparation of cis 5-ethyl-4,5,6,7-tetrahydro-1-benzofuran-4-amine

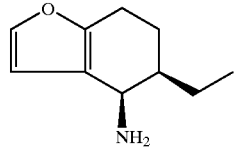

Following the procedure for the preparation of cis-5-propyl-4,5,6,7-tetrahydro-1-benzothiophen-4-amine but substituting (4E) and (4Z)-5-ethyl-6,7-dihydro-1-benzofuran-4(5H)-one oxime and making non-critical variations provided the title compound as a oil: $^1$H NMR (CDCl$_3$) δ 1.02, 1.30–1.73, 2.50–2.67, 3.84, 6.38, 7.27; HRMS (FAB) calcd for $C_{10}H_{15}NO+H$ 166.1232, found 166.1231. Anal. Calcd for $C_{10}H_{15}NO$: C, 72.69; H, 9.15; N, 8.48. Found: C, 72.33; H, 9.14; N, 8.08.

Preparation 34

Preparation of trans 5-ethyl-4,5,6,7-tetrahydro-1-benzofuran-4-amine

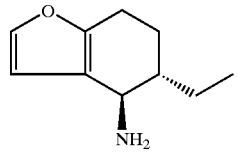

Following the procedure for the preparation of cis-5-propyl-4,5,6,7-tetrahydro-1-benzothiophen-4-amine but substituting (4E) and (4Z)-5-ethyl-6,7-dihydro-1-benzofuran-4(5H)-one oxime and making non-critical variations provided the title compound as a oil: $^1$H NMR (CDCl$_3$) δ 1.02, 1.30–1.73, 2.50–2.67, 4.46, 6.10, 7.24; HRMS (FAB) calcd for $C_{10}H_{15}NO+H$ 166.1232, found 166.1231. Anal. Calcd for $C_{10}H_{15}NO$: C, 72.69; H, 9.15; N, 8.48. Found: C, 72.33; H, 9.14; N, 8.08

Example 37

Preparation of 5-(2,4-dichlorophenyl)-3,6-diethyl-N-[(cis)-5-ethyl-4,5,6,7-tetrahydro-1-benzofuran-4-yl]pyrazin-2-amine

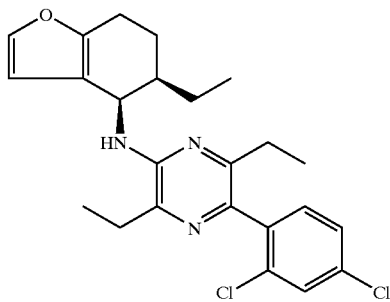

Following the procedure for the preparation of (1R,2S)-1-[(3,6-diethylpyrazin-2-yl)amino]-2,3-dihydro-1H-inden-2-ol but substituting cis 5-ethyl-4,5,6,7-tetrahydro-1-benzofuran-4-amine and making non-critical variations provided the title compound as a oil: $^1$H NMR (CDCl$_3$) δ 0.89, 1.11, 1.16, 1.53–1.65, 1.86, 2.42–2.49, 2.53, 2.65–2.74, 3.66, 3.77, 4.21, 5.48, 6.27, 7.01, 7.10–7.31, 7.40; MS (EI) m/z (rel. intensity) 443 (M+, 29), 443 (29), 296 (22), 295 (23), 207 (39), 149 (99), 148 (57), 119 (39), 107 (23), 91 (45), 55 (22). HRMS (FAB) calcd for C$_{24}$H$_{27}$Cl$_2$N$_3$O+H 444.1609, found 444.1610.

Example 38

Preparation of 5-(2,4-dichlorophenyl)-3,6-diethyl-N-[(cis)-5-ethyl-4,5,6,7-tetrahydro-1-benzofuran-4-yl]pyrazin-2-amine

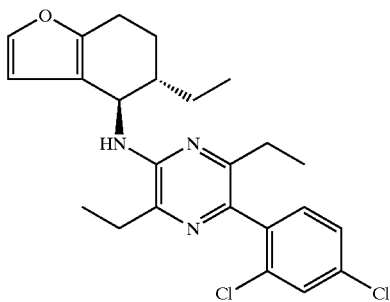

Following the procedure for the preparation of (1R,2S)-1-[(3,6-diethylpyrazin-2-yl)amino]-2,3-dihydro-1H-inden-2-ol but substituting trans-5-ethyl-4,5,6,7-tetrahydro-1-benzofuran-4-amine and making non-critical variations provided the title compound as a oil: $^1$H NMR (CDCl$_3$) δ 1.05, 1.17, 1.29, 1.80, 1.90, 2.04, 2.49, 2.63, 3.49, 3.83, 4.50, 5.11, 6.32, 7.30–7.38, 7.50; HRMS (FAB) calcd for C$_{24}$H$_{27}$Cl$_2$N$_3$O+H 444.1609, found 444.1600.

Preparation 35

Preparation of 3,4-dihydro-2H-thiochromen-4-ylamine

Following the procedure for the preparation of 4,5,6,7-tetrahydro-1-benzofuran-4-amine but substituting 2,3-dihydro-4H-thiochromen-4-one and making non-critical variations provided the title compound as a oil: $^1$H NMR (300 MHz, CDCl$_3$) δ 7.30, 7.07, 4.07, 3.28, 2.96, 2.16, 1.61; (MS/CI) calcd for C$_9$H$_{11}$NS+H 166.3, found 166.3.

Preparation 36

Preparation of N-(3,4-dihydro-2H-thiochromen-4-yl)-3,6-diethylpyrazin-2-amine

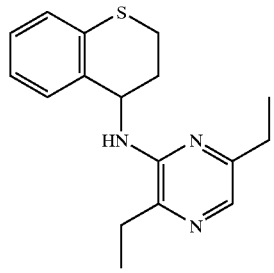

Following the procedure for the preparation of (1R,2S)-1-[(3,6-diethylpyrazin-2-yl)amino]-2,3-dihydro-1H-inden-2-ol but substituting 3,4-dihydro-2H-thiochromen-4-ylamine and making non-critical variations provided the title compound as a oil: $^1$H NMR (400 MHz, CDCl$_3$) δ 7.71, 7.30, 7.15, 7.05, 5.44, 4.51, 3.17, 2.98, 2.68, 2.64, 2.56, 2.14, 1.31; HRMS (FAB) calcd for C$_{17}$H$_{21}$N$_3$S+H 300.1534, found 300.1532.

Preparation 37

Preparation of 5-bromo-N-(3,4-dihydro-2H-thiochromen-4-yl)-3,6-diethylpyrazin-2-amine

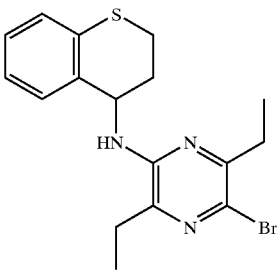

Following the procedure for the preparation of (1R,2S)-1-[(5-bromo-3,6-diethylpyrazin-2-yl)amino]-2,3-dihydro-1H-inden-2-ol but substituting N-(3,4-dihydro-2H-thiochromen-4-yl)-3,6-diethylpyrazin-2-amine and making non-critical variations provided the title compound as a oil: ¹H NMR (400 MHz, CDCl₃) δ 7.28, 7.19, 7.04, 5.38, 4.50, 3.53, 2.99, 2.84, 2.64, 2.55, 2.13, 1.31, 1.24; ¹³C NMR (100 MHz, CDCl₃) δ 152.50, 149.99, 141.71, 134.14, 134.03, 131.10, 128.59, 127.30, 125.65, 124.88, 48.74, 29.40, 27.58, 25.83, 23.05, 12.52, 11.26; HRMS (EI) calcd for $C_{17}H_{20}BrN_3S$ 377.0562, found 377.0565.

Example 39

Preparation of 5-(2,4-dichlorophenyl)-N-(3,4-dihydro-2H-thiochromen-4-yl)-3,6-diethylpyrazin-2-amine

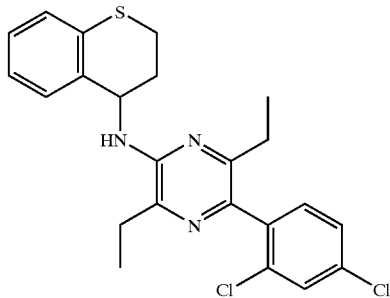

Following the procedure for the preparation of (1R,2S)-1-{[5-(2,4-dichlorophenyl)-3,6-diethylpyrazin-2-yl]amino}-2,3-dihydro-1H-inden-2-ol but substituting 5-bromo-N-(3,4-dihydro-2H-thiochromen-4-yl)-3,6-diethylpyrazin-2-amine and making non-critical variations provided the title compound as a oil: ¹H NMR (400 MHz, CDCl₃) δ 7.51, 7.36, 7.32, 7.29, 7.20, 7.07, 5.49, 4.64, 3.23, 3.02, 2.72, 2.64, 2.53, 2.20, 1.27, 1.22; ¹³C NMR (100 MHz, CDCl₃) δ 151.42, 150.26, 140.63, 137.74, 137.67, 135.29, 134.57, 134.22, 132.88, 131.23, 129.81, 129.11, 128.53, 127.52, 127.28, 124.87, 48.48, 27.58, 26.34, 23.18, 23.11, 13.30, 11.64; HRMS (FAB) calcd for $C_{23}H_{23}Cl_2N_3S$+H 444.1068, found 444.1055.

Preparation 38

Preparation of 3,6-diethyl-N-(1,2,3,4-tetrahydronaphthalen-1-yl)pyrazin-2-amine

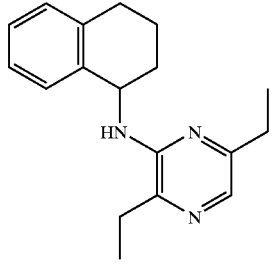

Following the procedure for the preparation of (1R,2S)-1-[(3,6-diethylpyrazin-2-yl)amino]-2,3-dihydro-1H-inden-2-ol but substituting 1,2,3,4-tetrahydronaphthalen-1-amine and making non-critical variations provided the title compound as a oil: ¹H NMR (400 MHz, CDCl₃) δ 7.81, 7.38, 7.19, 5.49, 4.56, 2.87, 2.69, 2.57, 2.12, 1.98, 1.91, 1.32; 13C NMR (100 MHz, CDCl3) δ 153.69, 151.42, 140.81, 138.70, 138.29, 129.85, 129.56, 129.18, 127.49, 126.58, 48.71, 30.07, 29.94, 28.56, 26.07, 20.42, 13.96, 11.16; HRMS (FAB) calcd for $C_{18}H_{23}N_3$+H 282.1970, found 282.1975.

Preparation 39

Preparation of 5-bromo-3,6-diethyl-N-(1,2,3,4-tetrahydronaphthalen-1-yl)pyrazin-2-amine

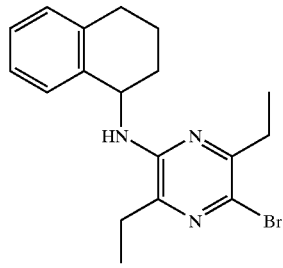

Following the procedure for the preparation of (1R,2S)-1-[(5-bromo-3,6-diethylpyrazin-2-yl)amino]-2,3-dihydro-1H-inden-2-ol but substituting 3,6-diethyl-N-(1,2,3,4-tetrahydronaphthalen-1-yl)pyrazin-2-amine and making non-critical variations provided the title compound as a oil: ¹H NMR (400 MHz, CDCl₃) δ 7.34, 7.21, 5.40, 4.54, 2.55, 2.09, 1.95, 1.28; ¹³C NMR (100 MHz, CDCl₃) δ 152.49, 150.66, 141.49, 138.29, 138.21, 129.63, 129.27, 127.64, 126.65, 124.90, 60.81, 49.31, 29.89, 28.87, 29.39, 21.46, 20.32, 14.61, 11.26. (MS/CI) calcd for $C_{18}H_{22}BrN_3$+H 360.3, found 360.3.

Example 40

Preparation of 5-(2,4-dichlorophenyl)-3,6-diethyl-N-(1,2,3,4-tetrahydronaphthalen-1-yl)pyrazin-2-amine

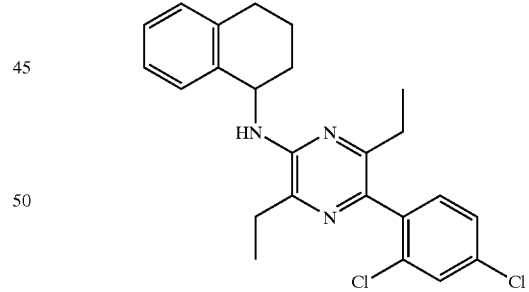

Following the procedure for the preparation of (1R,2S)-1-{[5-(2,4-dichlorophenyl)-3,6-diethylpyrazin-2-yl]amino}-2,3-dihydro-1H-inden-2-ol but substituting 5-bromo-3,6-diethyl-N-(1,2,3,4-tetrahydronaphthalen-1-yl)pyrazin-2-amine and making non-critical variations provided the title compound as a oil: ¹H NMR (400 MHz, CDCl₃) δ 7.40, 7.32, 7.20, 7.08, 5.41, 4.57, 2.80, 2.53, 2.41, 2.06, 1.96, 1.90, 1.18; ¹³C NMR (100 MHz, CDCl₃) δ 151.50, 150.93, 140.37, 138.53, 138.37, 137.87, 137.123, 135.36, 134.43, 132.95, 129.78, 129.62, 129.44, 127.57, 127.51, 125.63, 60.82, 49.01, 29.96, 27.62, 26.93, 14.61, 13.32, 11.67; HRMS (FAB) calcd for $C_{18}H_{22}BrN_3$+H 360.1076, found 360.1065.

Example 41

Preparation of 2-(2,4-dichlorophenyl)-3,6-diethyl-5-(1,2,3,4-tetrahydronaphthalen-1-yloxy)pyrazine

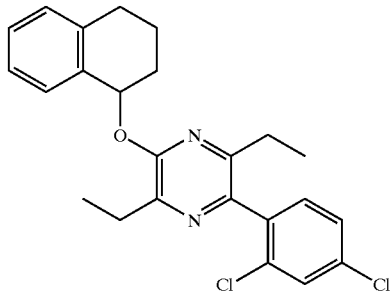

A solution of 1,2,3,4-tetrahydronaphthalen-1-ol (248 mg) in DMSO (3 ml) was added to NaH (100 mg) suspended in DMSO (4 ml). The reaction mixture was stirred at r.t. for 1 hour and heated at 75° C. for 1 hour. 2-bromo-5-(2,4-dichlorophenyl)-3,6-diethylpyrazine in DMSO (3 ml) was added. After 24 h, the rxn mixture was diluted with 30 ml of $H_2O$, extracted with $CH_2Cl_2$, washed with $NaHCO_3$, brine, dried ($MgSO_4$), filtered and concentrated. Flash chromatography (1:50 EtOAC:Heptane) gave the title compound: $^1H$ NMR (CDCl$_3$) δ 1.23, 1.95, 2.13, 2.20, 2.58, 2.83, 2.96, 6.46, 7.36; HRMS (ESI+) calcd for $C_{24}H_{24}Cl_2N_2O_1$ (M+H)$^+$ 427.1344, found 427.1359.

Preparation 40

Preparation of 7-methoxy-1,2,3,4-tetrahydronaphthalen-1-amine

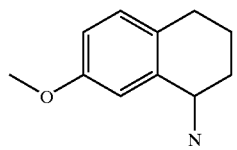

Following the procedure for the preparation of 4,5,6,7-tetrahydro-1-benzofuran-4-amine but substituting 7-methoxy-3,4-dihydronaphthalen-1(2H)-one and making non-critical variations provided the title compound as a oil: $^1H$ NMR (400 MHz, CDCl$_3$) δ 6.99, 6.75, 3.95, 3.82, 2.74, 2.05, 1.96, 1.71, 1.67, 1.56; $^{13}C$ NMR (100 MHz, CDCl$_3$) δ 158.28, 142.62, 130.30, 129.19, 113.44, 112.88, 55.73, 50.12, 34.17, 29.12, 20.26.

Preparation 41

Preparation of 3,6-diethyl-N-(7-methoxy-1,2,3,4-tetrahydronaphthalen-1-yl)pyrazin-2-amine

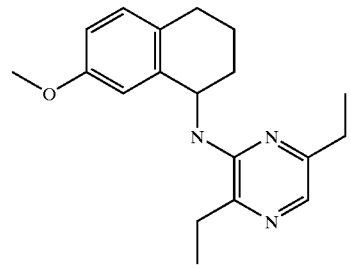

Following the procedure for the preparation of (1R,2S)-1-[(3,6-diethylpyrazin-2-yl)amino]-2,3-dihydro-1H-inden-2-ol but substituting 7-methoxy-1,2,3,4-tetrahydronaphthalen-1-amine and making non-critical variations provided the title compound as a oil: $^1H$ NMR (400 MHz, CDCl$_3$) δ 7.67, 7.08, 6.92, 6.81, 5.42, 4.54, 3.75, 2.84–2.77, 2.68, 2.56, 2.10, 1.88, 1.36–1.27; (MS/CI) calcd for $C_{19}H_{25}N_3O$+H 312.4, found 312.1.

Preparation 42

Preparation of 5-bromo-3,6-diethyl-N-(7-methoxy-1,2,3,4-tetrahydronaphthalen-1-yl)pyrazin-2-amine

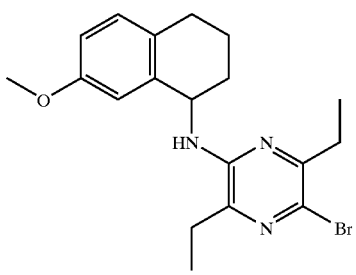

Following the procedure for the preparation of (1R,2S)-1-[(5-bromo-3,6-diethylpyrazin-2-yl)amino]-2,3-dihydro-1H-inden-2-ol but substituting 3,6-diethyl-N-(7-methoxy-1,2,3,4-tetrahydronaphthalen-1-yl)pyrazin-2-amine and making non-critical variations provided the title compound as a oil: $^1H$ NMR (400 MHz, CDCl$_3$) δ 7.08, 6.88, 6.81, 5.36, 4.52, 3.76, 2.79, 2.56, 2.08, 1.91, 1.31; (FAB) calcd for $C_{19}H_{24Br}N_3O$+H 390.0, found 390.0.

Example 42

Preparation of 5-(2,4-dichlorophenyl)-3,6-diethyl-N-(7-methoxy-1,2,3,4-tetrahydronaphthalen-1-yl)pyrazin-2-amine

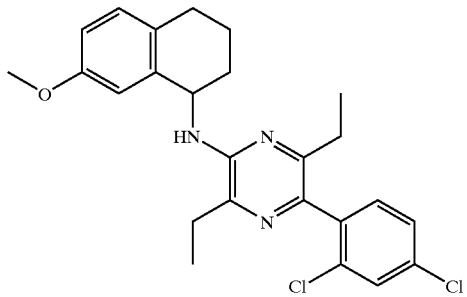

Following the procedure for the preparation of (1R,2S)-1-{[5-(2,4-dichlorophenyl)-3,6-diethylpyrazin-2-yl]amino}-2,3-dihydro-1H-inden-2-ol but substituting 5-bromo-3,6-diethyl-N-(7-methoxy-1,2,3,4-tetrahydronaphthalen-1-yl)pyrazin-2-amine and making non-critical variations provided the title compound as a oil: $^1$H NMR (400 MHz, CDCl$_3$) δ 7.51, 7.34, 7.10, 6.99, 6.83, 5.47, 4.68, 3.78, 2.85, 2.65, 2.53, 2.15, 2.01, 1.27, 1.21; $^{13}$C NMR (100 MHz, CDCl$_3$) δ 173.14, 157.25, 150.37, 149.81, 139.28, 138.42, 136.72, 136.05, 134.21, 133.33, 131.82, 129.41, 129.26, 128.65, 126.39, 112.41, 54.61, 48.17, 28.92, 28.00, 26.49, 25.27, 19.52, 12.19, 10.54; HRMS (FAB) calcd for $C_{25}H_{27}Cl_2N_3O$+H 456.1609, found 456.1601.

Example 43

Preparation of 5-(2-chloro-4-methoxyphenyl)-3,6-diethyl-N-(7-methoxy-1,2,3,4-tetrahydronaphthalen-1-yl)pyrazin-2-amine

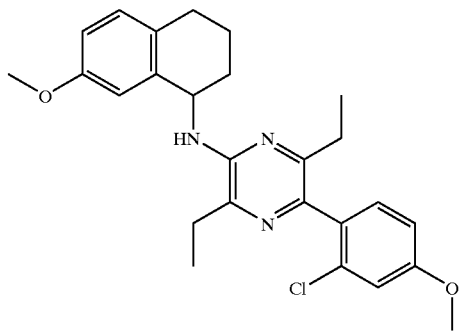

Following the procedure for the preparation of (1R,2S)-1-{[5-(2,4-dichlorophenyl)-3,6-diethylpyrazin-2-yl]amino}-2,3-dihydro-1H-inden-2-ol but substituting 5-bromo-3,6-diethyl-N-(7-methoxy-1,2,3,4-tetrahydronaphthalen-1-yl)pyrazin-2-amine and 2-chloro-4-methoxyphenylboronic acid, and making non-critical variations provided the title compound as a oil: $^1$H NMR (400 MHz, CDCl$_3$) δ 7.29, 7.11, 7.04, 6.99, 6.91, 6.84, 5.47, 4.64, 3.86, 3.78, 2.83, 2.68, 2.55, 2.15, 1.91, 1.74, 1.27, 1.21; $^{13}$C NMR (100 MHz, CDCl$_3$) δ 160.08, 158.37, 151.72, 150.71, 140.19, 139.72, 138.22, 136.12, 135.06, 132.59, 131.63, 130.50, 130.39, 115.13, 114.20, 113.41, 55.99, 55.74, 49.29, 30.08, 29.16, 27.66, 26.50, 20.66, 13.35, 11.82; HRMS (FAB) calcd for $C_{26}H_{30}ClN_3O_2$+H 452.2104, found 452.2097.

Preparation 43

Preparation of 5-methoxy-1,2,3,4-tetrahydronaphthalen-1-amine

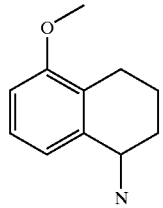

Following the procedure for the preparation of 4,5,6,7-tetrahydro-1-benzofuran-4-amine but substituting 5-methoxy-3,4-dihydronaphthalen-1(2H)-one and making non-critical variations provided the title compound as a oil: $^1$H NMR (400 MHz, CDCl$_3$) δ 7.19, 7.05, 6.75, 4.00, 3.84, 2.76, 2.61, 1.97, 1.70; $^{13}$C NMR (100 MHz, CDCl$_3$) δ 157.44, 142.83, 126.67, 126.02, 120.53, 108.09, 55.72, 49.75, 33.21, 23.57, 19.11; HRMS (FAB) calcd for $C_{11}H_{15}NO$+H 178.1232, found 178.1233.

Preparation 44

Preparation of 3,6-diethyl-N-(5-methoxy-1,2,3,4-tetrahydronaphthalen-1-yl)pyrazin-2-amine

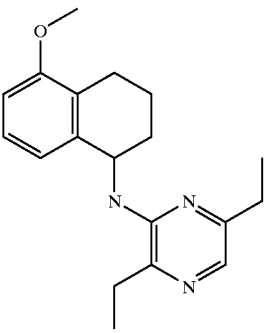

Following the procedure for the preparation of (1R,2S)-1-[(3,6-diethylpyrazin-2-yl)amino]-2,3-dihydro-1H-inden-2-ol but substituting 5-methoxy-1,2,3,4-tetrahydronaphthalen-1-amine and making non-critical variations provided the title compound as a oil: $^1$H NMR (400 MHz, CDCl$_3$) δ 7.66, 7.19, 7.00, 6.78, 5.47, 4.54, 3.87, 2.83, 2.68, 2.54, 2.06, 2.02, 1.97, 1.31; $^{13}$C NMR (100 MHz, CDCl$_3$) δ 157.50, 153.66, 161.36, 140.81, 139.90, 129.80, 127.37, 126.82, 121.33, 108.49, 55.75, 48.72, 29.44, 28.55, 26.08, 23.59, 19.62, 13.93, 11.14; HRMS (FAB) calcd for $C_{19}H_{25}N_3O$+H 312.2076, found 312.2066.

Preparation 45

Preparation of 5-bromo-3,6-diethyl-N-(5-methoxy-1,2,3,4-tetrahydronaphthalen-1-yl)pyrazin-2-amine

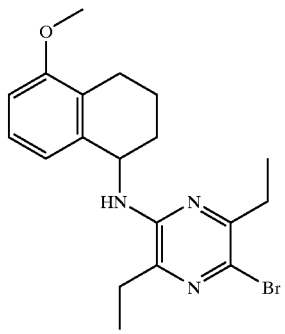

Following the procedure for the preparation of (1R,2S)-1-[(5-bromo-3,6-diethylpyrazin-2-yl)amino]-2,3-dihydro-1H-inden-2-ol but substituting 3,6-diethyl-N-(5-methoxy-1,2,3,4-tetrahydronaphthalen-1-yl)pyrazin-2-amine and making non-critical variations provided the title compound as a oil: 1H NMR (400 MHz, CDCl3) δ) 7.18, 6.97, 6.79, 5.37, 4.53, 2.87–2.76, 2.70–2.64, 2.54, 2.01–1.86, 1.35–1.24; HRMS (FAB) calcd for $C_{19}H_{24}BrN_3O+H$ 390.1181, found 390.1186.

Example 44

Preparation of 5-(2,4-dichlorophenyl)-3,6-diethyl-N-(5-methoxy-1,2,3,4-tetrahydronaphthalen-1-yl)pyrazin-2-amine

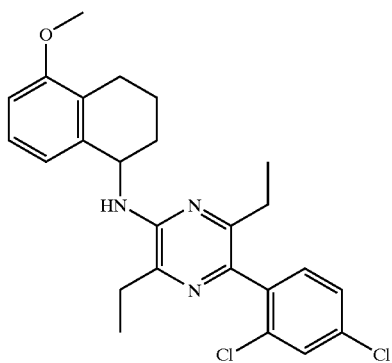

Following the procedure for the preparation of (1R,2S)-1-{[5-(2,4-dichlorophenyl)-3,6-diethylpyrazin-2-yl]amino}-2,3-dihydro-1H-inden-2-ol but substituting 5-bromo-3,6-diethyl-N-(5-methoxy-1,2,3,4-tetrahydronaphthalen-1-yl)pyrazin-2-amine and making non-critical variations provided the title compound as a oil: $^1$H NMR (400 MHz, CDCl$_3$) δ) 7.51, 7.33, 7.23, 7.07, 6.81, 5.50, 4.68, 3.89, 2.87–2.80, 2.72–2.61, 2.12–2.01, 1.91, 1.30–1.19; HRMS (FAB) calcd for $C_{25}H_{27}Cl_2N_3O+H$ 456.1609, found 456.1627.

Preparation 46

Preparation of 6-methoxy-1,2,3,4-tetrahydronaphthalen-1-amine

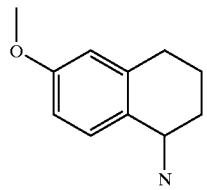

Following the procedure for the preparation of 4,5,6,7-tetrahydro-1-benzofuran-4-amine but substituting 6-methoxy-3,4-dihydronaphthalen-1(2H)-one and making non-critical variations provided the title compound as a oil: $^1$H NMR (400 MHz, CDCl$_3$) δ 7.34, 6.78, 6.63, 3.97, 3.79, 2.74, 1.77, 1.89; $^{13}$C NMR (100 MHz, CDCl$_3$) δ 158.47, 138.45, 133.91, 129.64, 113.71, 112.67, 55.61, 49.23, 34.25, 30.31, 24.6, 23.23, 19.87.

Preparation 47

Preparation of 3,6-diethyl-N-(6-methoxy-1,2,3,4-tetrahydronaphthalen-1-yl)pyrazin-2-amine

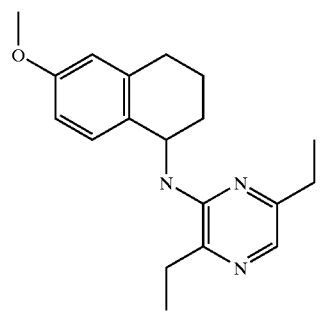

Following the procedure for the preparation of (1R,2S)-1-[(3,6-diethylpyrazin-2-yl)amino]-2,3-dihydro-1H-inden-2-ol but substituting 6-methoxy-1,2,3,4-tetrahydronaphthalen-1-amine and making non-critical variations provided the title compound as a oil: HRMS (FAB) calcd for $C_{19}H_{25}N_3O+H$ 312.2076, found 312.2075; Anal. Calcd for $C_{19}H_{25}N_3O$: C, 73.28; H, 8.09; N, 13.49. Found C, 73.38; H, 8.11; N, 13.32.

Preparation 48

Preparation of 5-bromo-3,6-diethyl-N-(6-methoxy-1,2,3,4-tetrahydronaphthalen-1-yl)pyrazin-2-amine

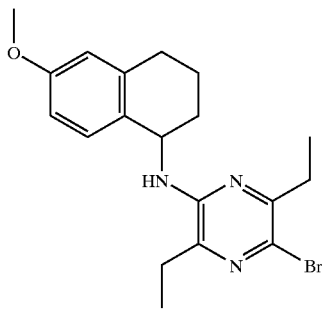

Following the procedure for the preparation of (1R,2S)-1-[(5-bromo-3,6-diethylpyrazin-2-yl)amino]-2,3-dihydro-1H-inden-2-ol but substituting 3,6-diethyl-N-(6-methoxy-1,2,3,4-tetrahydronaphthalen-1-yl)pyrazin-2-amine and making non-critical variations provided the title compound as a oil: $^1$H NMR (400 MHz, CDCl$_3$) δ) 7.26, 6.78, 6.69, 5.33, 4.49, 3.82, 2.89–2.78, 2.55, 2.05–1.84, 1.33–1.26; HRMS (FAB) calcd for C$_{19}$H$_{24}$BrN$_3$O+H 390.1181, found 390.1180.

Example 45

Preparation of 5-(2,4-dichlorophenyl)-3,6-diethyl-N-(6-methoxy-1,2,3,4-tetrahydronaphthalen-1-yl)pyrazin-2-amine

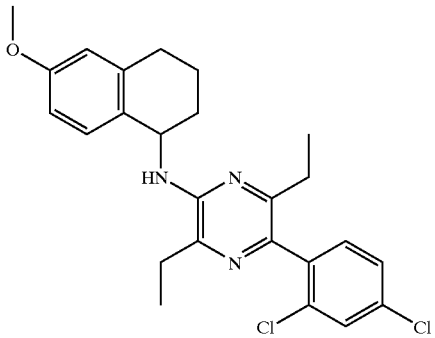

Following the procedure for the preparation of (1R,2S)-1-{[5-(2,4-dichlorophenyl)-3,6-diethylpyrazin-2-yl]amino}-2,3-dihydro-1H-inden-2-ol but substituting 5-bromo-3,6-diethyl-N-(6-methoxy-1,2,3,4-tetrahydronaphthalen-1-yl)pyrazin-2-amine, ethylene glycol dimethyl ether and tetrakis(triphenylphosphine) palladium and making non-critical variations provided the title compound as a oil: $^1$H NMR (400 MHz, CDCl$_3$) δ) 7.51, 7.31, 6.81, 6.71, 5.44, 4.63, 3.83, 2.93–2.76, 2.66–2.51, 2.10, 1.91, 1.32–1.14; HRMS (FAB) calcd for C$_{25}$H$_{27}$Cl$_2$N$_3$O+H 456.1609, found 456.1624; Anal. Calcd for C$_{25}$H$_{27}$Cl$_2$N$_3$O: C, 65.79; H, 5.96; N, 9.21. Found: C, 65.58; H, 5.96; N, 8.99.

Preparation 49

Preparation of racemic mixture of (trans)-1-amino-1,2,3,4-tetrahydronaphthalen-2-ol

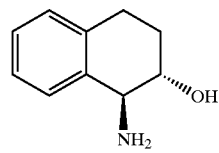

To a mixture of 1,2-dihydronaphthalene (5.12 g) and trifluoroacetone (1.34 g) in acetonitrile (60 ml) and aqueous potassium carbonate (1.5M in 0.4 mM EDTA, 60 ml) was added H$_2$O$_2$ (30%, 18.2 ml) at 0° C. Upon stirring at 0° C. for 4 hours, the rxn mixture was extracted with Et$_2$O, washed with aqueous Na$_2$S$_2$O$_3$ (1M) and brine, dried (MgSO$_4$), filtered and concentrated. The epoxide was used without purification. A mixture of 1a,2,3,7b-tetrahydronaphtho[1,2-b]oxirene and ammonium hydroxide was stirred at 40° C. for 3 days. The excess solvent was removed in vacuo. Flash chromatography (Silica gel, 1:20 MeOH:CH$_2$Cl$_2$, 0.5% NH$_4$OH) gave the title compound. HRMS (FAB) calcd for C$_{10}$H$_{13}$NO+H 164.1075, found 164.1075.

Preparation 50

Preparation of (trans)-1-[(3,6-diethylpyrazin-2-yl)amino]-1,2,3,4-tetrahydronaphthalen-2-ol

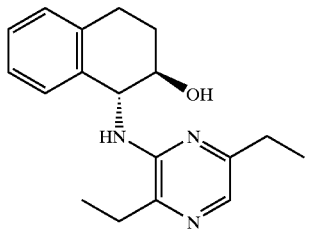

Following the procedure for the preparation of (1R,2S)-1-[(3,6-diethylpyrazin-2-yl)amino]-2,3-dihydro-1H-inden-2-ol but substituting (trans)-1-amino-1,2,3,4-tetrahydronaphthalen-2-ol and making non-critical variations provided the title compound as a oil: $^1$H NMR (CDCl$_3$) δ 1.27–1.34, 2.01, 2.24, 2.64, 2.84, 2.93, 4.03, 4.76, 5.06, 5.17, 7.19–7.21, 7.25–7.27, 7.34–7.37, 7.66;

Preparation 51

Preparation of racemic mixture of trans-1-[(5-bromo-3,6-diethylpyrazin-2-yl)amino]-1,2,3,4-tetrahydronaphthalen-2-ol

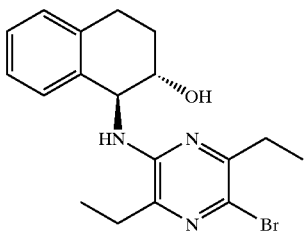

Following the procedure for the preparation of (1R,2S)-1-[(5-bromo-3,6-diethylpyrazin-2-yl)amino]-2,3-dihydro-1H-inden-2-ol but substituting (trans)-1-[(3,6-diethylpyrazin-2-yl)amino]-1,2,3,4-tetrahydronaphthalen-2-ol and making non-critical variations provided the title compound as a oil: $^1$H NMR (CDCl$_3$) δ 1.30 (m, 6H), 1.95 (m, 1H), 2.25 (m, 1H), 2.64 (dd, J=7.5, 15.1 Hz, 2H), 2.84 (dd, J=7.6, 15.2 Hz, 2H), 2.94 (m, 2H), 4.03 (m, 1H), 4.74 (d, J=6.7 Hz, 1H), 5.08 (s, 1H), 5.16 (dd, J=6.7, 7.2 Hz, 1H), 7.2 (m, 1H), 7.28 (m, 2H), 7.35 (m, 1H); MS (EI) m/z (rel. intensity) 375 (M+, 9), 359 (68), 357 (67), 230 (45), 146 (35), 129 (69), 128 (56), 118 (55), 117 (99), 115 (68), 91 (45). HRMS (FAB) calcd for C$_{18}$H$_{22}$BrN$_3$O+H 376.1025, found 376.1029. Anal. Calcd for C$_{18}$H$_{22}$BrN$_3$O: C, 57.45; H, 5.89; N, 11.17; Br, 21.23. Found: C, 57.61; H, 5.88; N, 10.70.

Preparation 52

Preparation of Racemic Mixtures of trans-5-(2,4-dichlorophenyl)-3,6-diethylpyrazin-2-yl]amino}-1,2,3,4-tetrahydronaphthalen-2-ol

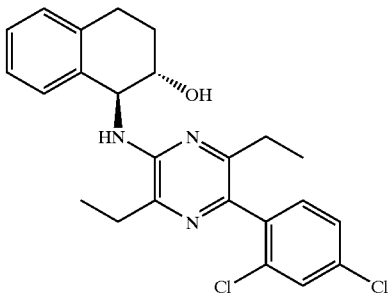

Following the procedure for the preparation of (1R,2S)-1-{[5-(2,4-dichlorophenyl)-3,6-diethylpyrazin-2-yl]amino}-2,3-dihydro-1H-inden-2-ol but substituting trans-1-[(5-bromo-3,6-diethylpyrazin-2-yl)amino]-1,2,3,4-tetrahydronaphthalen-2-ol, ethylene glycol dimethyl ether and tetrakis(triphenylphosphine) palladium and making non-critical variations provided the title compound as a oil: $^1$H NMR (CDCl$_3$) δ 1.10, 1.23, 1.85, 2.20, 2.44, 2.62, 2.87, 3.97, 4.83, 5.14, 5.97, 7.12–7.27, 7.43; HRMS (FAB) calcd for C$_{24}$H$_{25}$Cl$_2$N$_3$O+H 442.1453, found 442.1448.

Example 46

Preparation of racemic mixture of 5-(2,4-dichlorophenyl)-3,6-diethyl-N-[(1R,2R) and (1S,2S)-2-methoxy-1,2,3,4-tetrahydronaphthalen-1-yl]pyrazin-2-amine

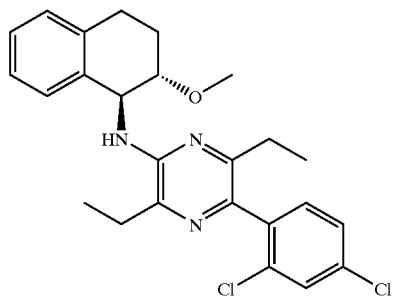

Following the procedure for the preparation of 5-(2,4-dichlorophenyl)-N-[(1R,2S)-2-ethoxy-2,3-dihydro-1H-inden-1-yl]-3,6-diethylpyrazin-2-amine but substituting (1R,2R) and (1S,2S)-1-{[5-(2,4-dichlorophenyl)-3,6-diethylpyrazin-2-yl]amino}-1,2,3,4-tetrahydronaphthalen-2-ol and methyl iodide, and making non-critical variations provided the title compound as a oil: $^1$H NMR (CDCl$_3$) δ 1.28, 2.04, 2.12, 2.53, 2.60, 2.78, 3.05, 3.59, 3.98, 4.55, 5.39, 7.19–7.43, 7.51; HRMS (FAB) calcd for C$_{25}$H$_{27}$Cl$_2$N$_3$O+H 456.1609, found 456.1598. Anal. Calcd for C$_{25}$H$_{27}$Cl$_2$N$_3$O: C, 65.79; H, 5.96; N, 9.21; Cl, 15.54. Found: C, 65.80; H, 6.08; N, 9.09

Example 47

Preparation of racemic mixture of 5-(2,4-dichlorophenyl)-N-[(1R,2R) and (1S,2S)-2-ethoxy-1,2,3,4-tetrahydronaphthalen-1-yl]-3,6-diethylpyrazin-2-amine

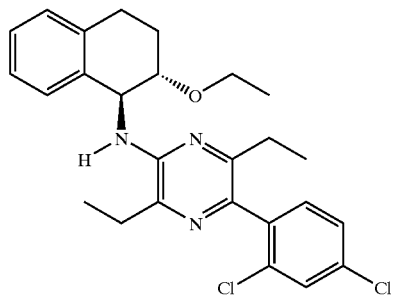

Following the procedure for the preparation of 5-(2,4-dichlorophenyl)-N-[(1R,2S)-2-ethoxy-2,3-dihydro-1H-inden-1-yl]-3,6-diethylpyrazin-2-amine but substituting (1R,2R) and (1S,2S)-1-{[5-(2,4-dichlorophenyl)-3,6-diethylpyrazin-2-yl]amino}-1,2,3,4-tetrahydronaphthalen-2-ol and making non-critical variations provided the title compound as a oil: $^1$H NMR (CDCl$_3$) δ 0.81, 1.10–1.23, 1.91, 1.99, 2.43, 2.51, 2.67, 2.96, 3.70, 3.95, 4.46, 5.25, 7.10–7.28, 7.42; HRMS (FAB) calcd for C$_{28}$H$_{33}$Cl$_2$N$_3$O+H 498.2079, found 498.2079

Preparation 53

Preparation of racemic mixture trans-1-[(5-bromo-3,6-diethylpyrazin-2-yl)amino]-1,2,3,4-tetrahydronaphthalen-2-yl 4-nitrobenzoate

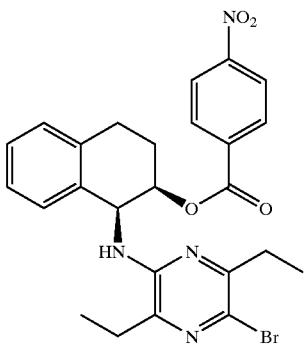

Following the procedure for the preparation of benzyl (cis)-3-{[5-(2,4-dichlorophenyl)-3,6-diethylpyrazin-2-yl]amino}-4-[(4-nitrobenzoyl)oxy]pyrrolidine-1-carboxylate but substituting trans-1-[(5-bromo-3,6-diethylpyrazin-2-yl)amino]-1,2,3,4-tetrahydronaphthalen-2-yl 4-nitrobenzoate and making non-critical variations provided the title compound as a oil: $^1$H NMR (CDCl$_3$) δ 1.15–1.23, 2.23, 2.40, 2.54, 2.68, 3.01, 3.10, 4.62, 5.77, 5.94, 7.23–7.30, 7.40, 7.95, 8.22.

Preparation 54

Preparation of racemic mixture of cis-(5-bromo-3,6-diethylpyrazin-2-yl)amino]-1,2,3,4-tetrahydronaphthalen-2-ol

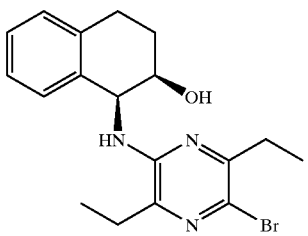

Following the procedure for the preparation of benzyl (cis)-3-{[5-(2,4-dichlorophenyl)-3,6-diethylpyrazin-2-yl]amino}-4-hydroxypyrrolidine-1-carboxylate but substituting trans-1-[(5-bromo-3,6-diethylpyrazin-2-yl)amino]-1,2,3,4-tetrahydronaphthalen-2-yl 4-nitrobenzoate and making non-critical variations provided the title compound as a oil: $^1$H NMR (CDCl$_3$) δ 1.24–1.32, 2.07, 2.62, 2.84, 2.87, 3.02, 4.29, 4.39, 4.63, 5.36, 7.18–7.29; $^{13}$C NMR (CDCl$_3$) δ 11.22, 12.56, 25.94, 26.94, 27.39, 29.33, 32.29, 55.13, 70.92, 125.84, 127.09, 128.44, 129.41, 130.12, 135.89, 137.71, 142.35, 151.62, 151.91.

Example 48

Preparation of racemic mixture of cis-1-{[5-(2,4-dichlorophenyl)-3,6-diethylpyrazin-2-yl]amino}-1,2,3,4-tetrahydronaphthalen-2-ol

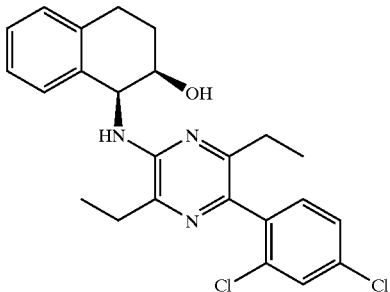

Following the procedure for the preparation of (1R,2S)-1-{[5-(2,4-dichlorophenyl)-3,6-diethylpyrazin-2-yl]amino}-2,3-dihydro-1H-inden-2-ol but substituting cis-(5-bromo-3,6-diethylpyrazin-2-yl)amino]-1,2,3,4-tetrahydronaphthalen-2-ol, ethylene glycol dimethyl ether and tetrakis(triphenylphosphine) palladium and making non-critical variations provided the title compound as a oil: $^1$H NMR (CDCl$_3$) δ 1.18–1.31, 2.09, 2.54, 2.64, 2.95, 2.99, 4.33, 4.69, 5.43, 7.22–7.35, 7.51; HRMS (FAB) calcd for C$_{24}$H$_{25}$Cl$_2$N$_3$O+H 442.1453, found 442.1454.

Example 49

Preparation of racemic mixture of (cis)-2-methoxy-1,2,3,4-tetrahydronaphthalen-1-yl]pyrazin-2-amine

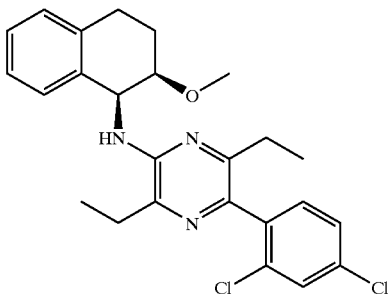

Following the procedure for the preparation of 5-(2,4-dichlorophenyl)-N-[(1R,2S)-2-ethoxy-2,3-dihydro-1H-inden-1-yl]-3,6-diethylpyrazin-2-amine but substituting cis-1-{[5-(2,4-dichlorophenyl)-3,6-diethylpyrazin-2-yl]amino}-1,2,3,4-tetrahydronaphthalen-2-ol and methyl iodide, and making non-critical variations provided the title compound as a oil: ¹H NMR (CDCl₃) δ 1.12, 1.30, 1.99, 2.35, 2.47, 2.74, 3.06, 3.46, 3.89, 5.41, 5.80, 7.18, 7.35, 7.51; HRMS (FAB) calcd for $C_{25}H_{27}Cl_2N_3O+H$ 456.1609, found 456.1617.

Example 50

Preparation of racemic mixture of 5-(2,4-dichlorophenyl)-N-[(cis)-2-ethoxy-1,2,3,4-tetrahydronaphthalen-1-yl]-3,6-diethylpyrazin-2-amine

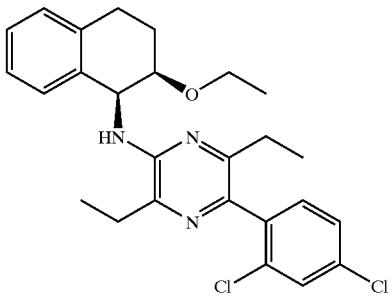

Following the procedure for the preparation of 5-(2,4-dichlorophenyl)-N-[(1R,2S)-2-ethoxy-2,3-dihydro-1H-inden-1-yl]-3,6-diethylpyrazin-2-amine but substituting (cis)-2-methoxy-1,2,3,4-tetrahydronaphthalen-1-yl]pyrazin-2-amine and making non-critical variations provided the title compound as a oil: ¹H NMR (CDCl₃) δ 1.14, 1.20, 1.29, 1.95, 2.31, 2.45, 2.73, 2.82, 3.12, 3.48, 3.74, 3.99, 5.42, 5.75, 7.12–7.21, 7.36, 7.51; HRMS (FAB) calcd for $C_{25}H_{27}Cl_2N_3O+H$ 456.1609, found 456.1617.

Preparation 55

Preparation of 4,5,6,7-tetrahydro-1-benzothiophen-4-amine

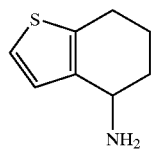

Following the procedure for the preparation of 4,5,6,7-tetrahydro-1-benzofuran-4-amine but substituting 6,7-dihydro-1-benzothiophen-4(5H)-one and making non-critical variations provided the title compound as a oil: ¹H NMR (400 MHz, CDCl₃) δ 7.09, 7.02, 3.95, 2.79, 2.03, 1.85, 1.62; ¹³C NMR (100 MHz, CDCl₃) δ 140.51, 137.18, 126.77, 122.66, 47.96, 34.24, 25.48, 21.48;

Preparation 56

Preparation of 3,6-diethyl-N-(4,5,6,7-tetrahydro-1-benzothien-4-yl)pyrazin-2-amine

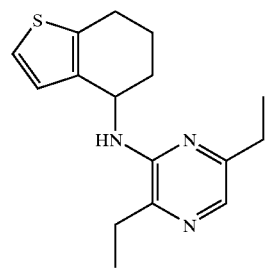

Following the procedure for the preparation of (1R,2S)-1-[(3,6-diethylpyrazin-2-yl)amino]-2,3-dihydro-1H-inden-2-ol but substituting 4,5,6,7-tetrahydro-1-benzothiophen-4-amine and making non-critical variations provided the title compound as a oil: ¹H NMR (400 MHz, CDCl₃) δ 7.67 (s, 1H), 7.10 (d, J=5.2 Hz, 1H), 6.93 (d, J=5.2 Hz, 1H), 5.40 (m, 1H), 4.50 (bs, 1H), 2.83 (m, 2H), 2.66 (q, J=7.5 Hz, 2H), 2.56 (q, J=7.5 Hz, 2H), 2.10 (m, 1H), 1.96 (m, 3H), 1.29 (m, 6H); (MS/CI) calcd for $C_{16}H_{21}N_3S+H$ 287.4, found 287.9.

Preparation 57

Preparation of 5-bromo-3,6-diethyl-N-(4,5,6,7-tetrahydro-1-benzothien-4-yl)pyrazin-2-amine

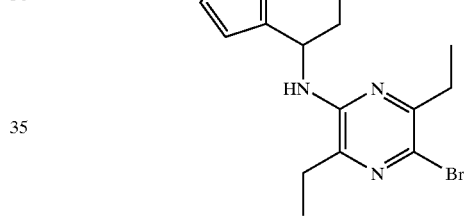

Following the procedure for the preparation of (1R,2S)-1-[(5-bromo-3,6-diethylpyrazin-2-yl)amino]-2,3-dihydro-1H-inden-2-ol but substituting 3,6-diethyl-N-(4,5,6,7-tetrahydro-1-benzothien-4-yl)pyrazin-2-amine and making non-critical variations provided the title compound as a oil: ¹H NMR (300 MHz, CDCl₃) δ 7.10, 6.91, 5.32, 4.47, 2.83, 2.53, 2.10, 1.93, 1.27; (MS/CI) calcd for $C_{16}H_{20}BrN_3S+H$ 369.9, found 369.9.

Example 51

Preparation of 5-(2,4-dichlorophenyl)-3,6-diethyl-N-(4,5,6,7-tetrahydro-1-benzothien-4-yl)pyrazin-2-amine

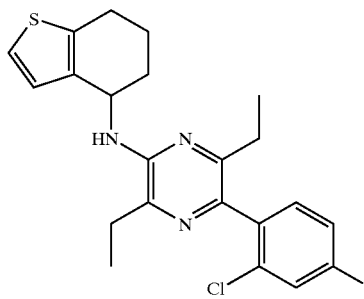

Following the procedure for the preparation of (1R,2S)-1-{[5-(2,4-dichlorophenyl)-3,6-diethylpyrazin-2-yl]

amino}-2,3-dihydro-1H-inden-2-ol but substituting 5-bromo-3,6-diethyl-N-(4,5,6,7-tetrahydro-1-benzothien-4-yl)pyrazin-2-amine and making non-critical variations provided the title compound as a oil: $^1$H NMR (400 MHz, CDCl$_3$) δ 7.51, 7.39, 7.12, 6.99, 5.45, 4.64, 2.90, 2.65, 2.51, 2.20, 1.99, 1.27, 1.20; $^{13}$C NMR (100 MHz, CDCl$_3$) δ 151.51, 150.78, 140.47, 139.15, 137.82, 137.21, 135.35, 134.47, 132.93, 128.78, 127.51, 127.37, 123.01, 117.71, 46.74, 29.97, 27.62, 26.36, 25.53, 21.37,12.32, 11.63; HRMS (FAB) calcd for $C_{22}H_{23}Cl_2N_3S$+H 432.1068, found 432.1073.

Preparation 58

Preparation of 5-methyl-6,7-dihydro-1-benzothiophen-4(5H)-one

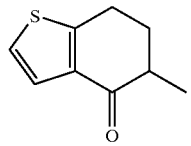

To a solution of 6,7-dihydro-1-benzothiophen-4(5H)-one (1.63 g) in tetrahydrofuran (90 ml) at −78° C. under N$_2$ was added lithium diisopropyl amide (5.89 ml, 2 M). After 30 min, iodomethane (0.732 ml) was added and the reaction was allowed to warm to ambient temperature. After 2 h, the reaction mixture was poured into saturated sodium bicarbonate (100 ml), extracted methylene chloride (3×100 ml), dried MgSO$_4$, filtered and concentrated. MPLC was run on a biotage 40M column with 4–6% ethyl acetate/heptane to provide the title compound as an oil (560 mg, 32%): 1H NMR (300 MHz, CDCl3) δ) 7.41, 7.08, 3.15–2.99, 2.61–2.53, 2.33–2.25, 2.06–1.92, 1.28; HRMS (FAB) calcd for $C_9H_{10}OS$+H 167.0531, found 167.0527.

Preparation 59

Preparation of 5-methyl-4,5,6,7-tetrahydro-1-benzothien-4-ylamine

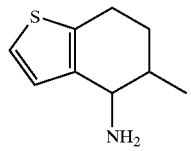

Following the procedure for the preparation of 4,5,6,7-tetrahydro-1-benzofuran-4-amine but substituting 5-methyl-6,7-dihydro-1-benzothiophen-4(5H)-one and making non-critical variations provided the title compound as a oil: $^1$H NMR (400 MHz, CDCl$_3$) δ) 7.12–6.99, 4.13, 3.89, 3.51, 2.86–2.74, 2.13–1.98, 1.75, 1.65, 1.15, 1.07.

Preparation 60

Preparation of 3,6-diethyl-N-(5-methyl-4,5,6,7-tetrahydro-1-benzothien-4-yl)pyrazin-2-amine

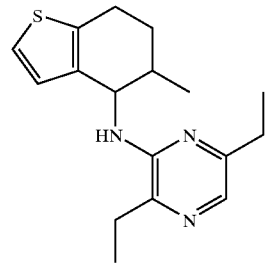

Following the procedure for the preparation of (1R,2S)-1-[(3,6-diethylpyrazin-2-yl)amino]-2,3-dihydro-1H-inden-2-ol but substituting 5-methyl-4,5,6,7-tetrahydro-1-benzothien-4-ylamine and making non-critical variations provided the title compound as a oil: $^1$H NMR (400 MHz, CDCl$_3$) δ) 7.66, 7.07, 6.91, 6.83, 5.62, 5.15, 4.46, 4.35, 3.09, 2.65–2.55, 2.28, 2.06–1.97, 1.80, 1.29, 1.11, 1.01; (MS/CI) calcd for $C_{17}H_{23}N_3S$+H 301.6, found 301.9.

Preparation 61

Preparation of 5-bromo-3,6-diethyl-N-(5-methyl-4,5,6,7-tetrahydro-1-benzothien-4-yl)pyrazin-2-amine

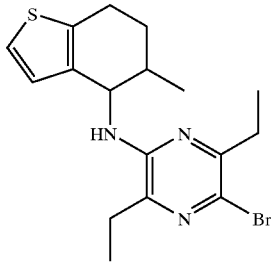

Following the procedure for the preparation of (1R,2S)-1-[(5-bromo-3,6-diethylpyrazin-2-yl)amino]-2,3-dihydro-1H-inden-2-ol but substituting 3,6-diethyl-N-(5-methyl-4,5,6,7-tetrahydro-1-benzothien-4-yl)pyrazin-2-amine and making non-critical variations provided the title compound as a oil: $^1$H NMR (400 MHz, CDCl$_3$) δ) 7.08, 6.87, 6.80, 5.55, 5.08, 4.45, 4.40, 2.91–2.78, 2.58, 2.22, 2.05–1.98, 1.79, 1.28, 1.10, 1.00.

Example 52

Preparation of 5-(2,4-dichlorophenyl)-3,6-diethyl-N-[Cis-5-methyl-4,5,6,7-tetrahydro-1-benzothien-4-yl]pyrazin-2-amine

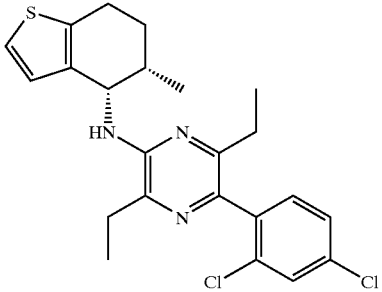

Following the procedure for the preparation of (1R,2S)-1-{[5-(2,4-dichlorophenyl)-3,6-diethylpyrazin-2-yl]

amino}-2,3-dihydro-1H-inden-2-ol but substituting 5-bromo-3,6-diethyl-N-(5-methyl-4,5,6,7-tetrahydro-1-benzothien-4-yl)pyrazin-2-amine, ethylene glycol dimethyl ether and tetrakis(triphenylphosphine) palladium and making non-critical variations provided the title compound as a oil: ¹H NMR (400 MHz, CDCl₃) δ) 7.51, 7.33, 7.11; 6.96, 5.66, 4.52, 2.95–2.62, 2.55, 2.38, 2.05, 1.97, 1.79, 1.26, 1.20, 1.07; HRMS (FAB) calcd for $C_{23}H_{25}Cl_2N_3S+H$ 446.1224, found 446.1224.

Example 53

Preparation of 5-(2,4-dichlorophenyl)-3,6-diethyl-N-[Trans-5-methyl-4,5,6,7-tetrahydro-1-benzothien-4-yl]pyrazin-2-amine

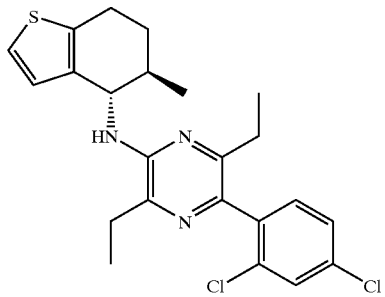

Following the procedure for the preparation of (1R,2S)-1-{[5-(2,4-dichlorophenyl)-3,6-diethylpyrazin-2-yl]amino}-2,3-dihydro-1H-inden-2-ol but substituting 5-bromo-3,6-diethyl-N-(5-methyl-4,5,6,7-tetrahydro-1-benzothien-4-yl)pyrazin-2-amine, ethylene glycol dimethyl ether and tetrakis(triphenylphosphine) palladium and making non-critical variations provided the title compound as a oil: ¹H NMR (400 MHz, CDCl₃) δ) 7.50, 7.35–7.30, 7.10, 6.90, 5.18, 4.60, 2.85, 2.66, 2.49, 2.05, 1.82, 1.29–1.12; HRMS (FAB) calcd for $C_{23}H_{25}Cl_2N_3S+H$ 446.1224, found 446.1230. Anal. Calcd for $C_{23}H_{25}Cl_2N_3S$: C, 61.88; H, 5.64; N, 9.41; Cl, 15.88; S, 7.18. Found: C, 62.04; H, 5.77; N, 9.04.

Preparation 62

Preparation of 5-ethyl-6,7-dihydro-1-benzothiophen-4(5H)-one

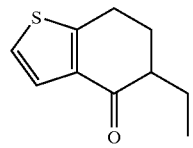

Following the procedure for the preparation of 5-methyl-6,7-dihydro-1-benzothiophen-4(5H)-one but substituting iodoethane and making non-critical variations provided the title compound as a oil: ¹H NMR (300 MHz, CDCl₃) δ) 7.40, 7.07, 3.18–2.96, 2.43–2.27, 2.09–1.94, 1.59, 1.02. HRMS (FAB) calcd for $C_{10}H_{12}OS+H$ 181.0687, found 181.0684. Anal. Calcd for $C_{10}H_{12}OS$: C, 66.63; H, 6.71. Found: C, 66.50; H, 6.75.

Preparation 63

Preparation of 5-ethyl-4,5,6,7-tetrahydro-1-benzothiophen-4-amine

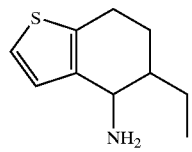

Following the procedure for the preparation of 4,5,6,7-tetrahydro-1-benzofuran-4-amine but substituting 5-ethyl-6,7-dihydro-1-benzothiophen-4(5H)-one and making non-critical variations provided the title compound as a oil: ¹H NMR (400 MHz, CDCl₃) δ) 7.10, 7.05, 6.99, 3.98, 3.65, 2.87–2.73, 2.06–1.90, 1.74–1.19, 1.05–0.97. (MS/CI) calcd for $C_{10}H_{15}NS+H$ 182.3, found 181.9.

Example 54

Preparation of 5-(2,4-dichlorophenyl)-3,6-diethyl-N-[Cis-5-ethyl-4,5,6,7-tetrahydro-1-benzothien-4-yl]pyrazin-2-amine

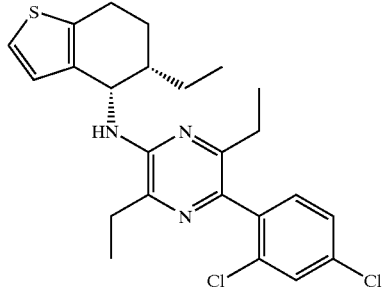

Following the procedure for the preparation of (1R,2S)-1-[(3,6-diethylpyrazin-2-yl)amino]-2,3-dihydro-1H-inden-2-ol but substituting cis-5-ethyl-4,5,6,7-tetrahydro-1-benzothiophen-4-amine and 2-bromo-5-(2,4-dichlorophenyl)-3,6-diethylpyrazine and making non-critical variations provided the title compound as a oil: ¹H NMR (400 MHz, CDCl₃) δ; 7.50, 7.32, 7.08, 6.98, 5.77, 4.42, 2.99, 2.95, 2.62, 2.50, 1.98, 1.73, 1.39–1.18, 1.00; HRMS (FAB) calcd for $C_{24}H_{27}Cl_2N_3S+H$ 460.1381, found 460.1376.

Example 55

Preparation of 5-(2,4-dichlorophenyl)-3,6-diethyl-N-[Trans-5-ethyl-4,5,6,7-tetrahydro-1-benzothien-4-yl]pyrazin-2-amine

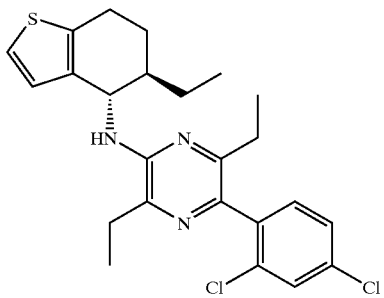

Following the procedure for the preparation of (1R,2S)-1-[(3,6-diethylpyrazin-2-yl)amino]-2,3-dihydro-1H-inden-2-ol but substituting trans-5-ethyl-4,5,6,7-tetrahydro-1-benzothiophen-4-amine and 2-bromo-5-(2,4-dichlorophenyl)-3,6-diethylpyrazine and making non-critical variations provided the title compound as a oil: $^1$H NMR (400 MHz, CDCl$_3$) δ) 7.50, 7.35–7.28, 7.11, 6.91, 5.27, 4.58, 2.85, 2.64, 2.49, 2.08, 1.93, 1.84, 1.66, 1.41, 1.26, 1.18, 1.06; HRMS (FAB) calcd for C$_{24}$H$_{27}$Cl$_2$N$_3$S+H 460.1381, found 460.1398. Anal. Calcd for C$_{24}$H$_{27}$Cl$_2$N$_3$S: C, 62.60; H, 5.91; N, 9.13. Found: C, 62.36; H, 5.94; N, 8.91.

Preparation 64

Preparation of (4E)-2,3-dihydro-4H-chromen-4-one oxime

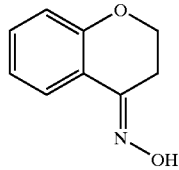

To a solution of 2,3-dihydro-4H-chromen-4-one (3.00 g) in ethanol (15 ml)/water (3 ml) was added sodium acetate (6.64 g) and hydroxyl amine hydrochloride (5.52 g). The reaction mixture was heated at 70° C. for 1 h, poured into saturated sodium bicarbonate (50 ml), extracted methylene chloride (3×50 ml), dried MgSO$_4$, filtered and concentrated to provide the title compound as a solid (3.22 g, 99%): $^1$H NMR (300 MHz, CDCl$_3$) δ) 7.86, 7.28, 7.00–6.91, 4.27, 3.02; HRMS (FAB) calcd for C$_9$H$_9$NO$_2$+H 164.0712, found 164.0703. Anal. Calcd for C$_9$H$_9$NO$_2$: C, 66.25; H, 5.56; N, 8.58. Found: C, 66.21; H, 5.58; N, 8.57.

Preparation 65

Preparation of 3,4-dihydro-2H-chromen-4-ylamine

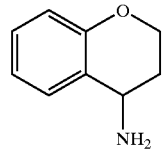

To a solution of (4E)-2,3-dihydro-4H-chromen-4-one oxime (3.20 g) in tetrahydrofuran (50 ml) under N$_2$ atmosphere was added lithium aluminum hydride (1M THF, 50 ml). The reaction mixture stirred at ambient temperature for 16 h and was quenched with 10 ml of water, 10 ml of 2 N NaOH and 20 ml of water. The reaction mixture was filtered through celite, acidified with 1 N HCl (50 ml), washed with ethyl ether (2×50 ml), basified with 2 N NaOH, extracted methylene chloride (3×100 ml), dried MgSO$_4$, filtered and concentrated. MPLC was run on a biotage 40S column with 2–4% methanol/methylene chloride with 0.5% ammonium hydroxide to provide the title compound as an oil (728 mg, 25%): $^1$H NMR (300 MHz, CDCl$_3$) δ) 7.34, 7.17, 6.92, 6.85, 4.31–4.24, 4.09, 2.18, 1.91–1.86; HRMS (FAB) calcd for C$_9$H$_{11}$NO+H 150.0919, found 150.0910.

Preparation 66

Preparation of N-(3,4-dihydro-2H-chromen-4-yl)-3,6-diethylpyrazin-2-amine

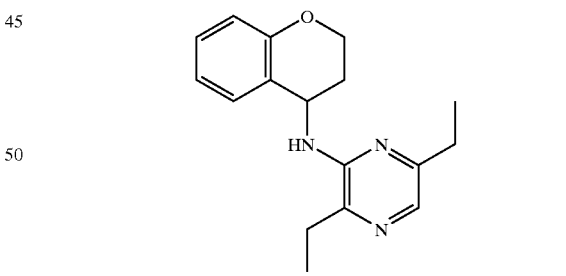

Following the procedure for the preparation of (1R,2S)-1-[(3,6-diethylpyrazin-2-yl)amino]-2,3-dihydro-1H-inden-2-ol but substituting 3,4-dihydro-2H-chromen-4-ylamine and making non-critical variations provided the title compound as a oil: $^1$H NMR (300 MHz, CDCl$_3$) δ) 7.71, 7.31–7.21, 6.95, 6.91, 5.34, 4.54, 4.32–4.24, 2.71, 2.56, 2.25, 1.36–1.26; HRMS (FAB) calcd for C$_{17}$H$_{21}$N$_3$O+H 284.1763, found 284.1768.

Preparation 67

Preparation of 5-bromo-N-(3,4-dihydro-2H-chromen-4-yl)-3,6-diethylpyrazin-2-amine

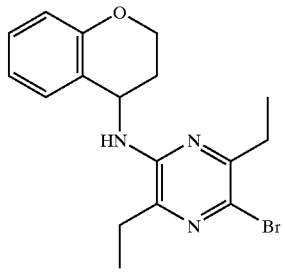

Following the procedure for the preparation of (1R,2S)-1-[(5-bromo-3,6-diethylpyrazin-2-yl)amino]-2,3-dihydro-1H-inden-2-ol but substituting N-(3,4-dihydro-2H-chromen-4-yl)-3,6-diethylpyrazin-2-amine and making non-critical variations provided the title compound as a oil: $^1$H NMR (300 MHz, CDCl$_3$) δ) 7.28–7.21, 6.96–6.89, 5.26, 4.54, 4.29–4.22, 2.84, 2.57, 2.22, 1.32–1.24; HRMS (FAB) calcd for C$_{17}$H$_{20}$BrN$_3$O+H 362.0868, found 362.0861. Anal. Calcd for C$_{17}$H$_{20}$BrN$_3$O: C, 56.36; H, 5.56; N, 11.60. Found: C, 56.10; H, 5.56; N, 11.35.

Example 56

Preparation of 5-(2,4-dichlorophenyl)-N-(3,4-dihydro-2H-chromen-4-yl)-3,6-diethylpyrazin-2-amine

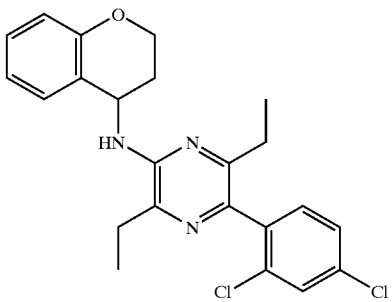

Following the procedure for the preparation of (1R,2S)-1-{[5-(2,4-dichlorophenyl)-3,6-diethylpyrazin-2-yl]amino}-2,3-dihydro-1H-inden-2-ol but substituting 5-bromo-N-(3,4-dihydro-2H-chromen-4-yl)-3,6-diethylpyrazin-2-amine, ethylene glycol dimethyl ether and tetrakis(triphenylphosphine) palladium and making non-critical variations provided the title compound as a oil: $^1$H NMR (300 MHz, CDCl$_3$) δ); 7.51, 7.36–7.23, 6.98–6.90, 5.37, 4.69, 4.32, 2.66, 2.51, 2.31, 1.29–1.17; HRMS (EI) calcd for C$_{23}$H$_{23}$Cl$_2$N$_3$O 427.1218, found 427.1224.

Example 57

Preparation of 5-(2-chloro-4-methylphenyl)-N-(3,4-dihydro-2H-chromen-4-yl)-3,6-diethylpyrazin-2-amine

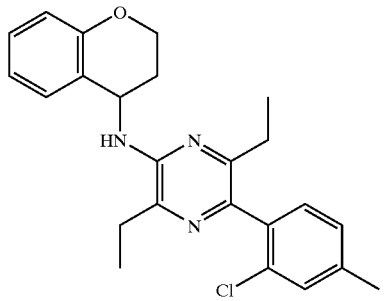

Following the procedure for the preparation of (1R,2S)-1-{[5-(2,4-dichlorophenyl)-3,6-diethylpyrazin-2-yl]amino}-2,3-dihydro-1H-inden-2-ol but substituting 5-bromo-N-(3,4-dihydro-2H-chromen-4-yl)-3,6-diethylpyrazin-2-amine, ethylene glycol dimethyl ether, 2-chloro-4-methyl phenyl boronic acid and tetrakis(triphenylphosphine) palladium and making non-critical variations provided the title compound as a oil: $^1$H NMR (300 MHz, CDCl$_3$) δ) 7.37–7.13, 6.99–6.90, 5.37, 4.64, 4.31, 2.69, 2.54, 2.40, 2.30, 1.29–1.17; HRMS (FAB) calcd for C$_{24}$H$_{26}$ClN$_3$O+H 408.1842, found 408.1848. Anal. Calcd for C$_{24}$H$_{26}$ClN$_3$O: C, 70.66; H, 6.42; N, 10.30. Found: C, 70.93; H, 6.78; N, 10.01.

Example 58

Preparation of N-(3,4-dihydro-2H-chromen-4-yl)-5-(2,4-dimethylphenyl)-3,6-diethylpyrazin-2-amine

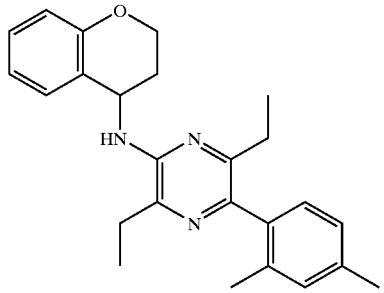

Following the procedure for the preparation of (1R,2S)-1-{[5-(2,4-dichlorophenyl)-3,6-diethylpyrazin-2-yl]amino}-2,3-dihydro-1H-inden-2-ol but substituting 5-bromo-N-(3,4-dihydro-2H-chromen-4-yl)-3,6-diethylpyrazin-2-amine, ethylene glycol dimethyl ether, 2,4-dimethyl phenyl boronic acid and tetrakis(triphenylphosphine) palladium and making non-critical variations provided the title compound as a oil: $^1$H NMR (300 MHz, CDCl$_3$) δ) 7.38, 7.22, 7.11–6.90, 5.38, 4.58, 4.31, 2.68, 2.53, 2.37, 2.26, 2.14, 1.25–1.15; HRMS (FAB) calcd for C$_{25}$H$_{29}$N$_3$O+H 388.2389, found 388.2383.

Preparation 68

Preparation of 5-propyl-6,7-dihydro-1-benzothiophen-4(5H)-one

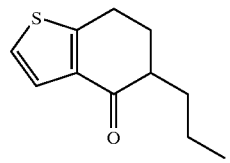

To a solution of KH (30%, 11.44 g) in tetrahydrofuran (160 ml) under N2 was added dropwise 6,7-dihydro-1-benzothiophen-4(5H)-one (8 g) in tetrahydrofuran (40 ml). After 30 min, a triethyl borane (97 ml, 1 M THF) solution was added dropwise over 5 min. After 10 min, iodopropane was and the reaction stirred for 16 h. The reaction mixture was cooled to 0° C. and 1 N NaOH (250 ml) and hydrogen peroxide (12 ml, 30%) was added. The reaction mixture stirred for 1 h and was extracted with 400 ml ethyl acetate. The organic layer was washed with saturated sodium thiosulfate, dried $MgSO_4$, filtered and concentrated. MPLC chromatography on a biotage 40 L with 4% ethyl acetate/heptane provided the title compound as an oil (8.21 g, 80%): $^1$H NMR (300 MHz, $CDCl_3$) δ) 7.40, 7.07, 3.15–3.01, 2.47, 2.32, 2.07–1.88, 1.53–1.30, 1.27, 0.99–0.88; HRMS (FAB) calcd for $C_{11}H_{14}OS+H$ 195.0844, found 195.0835.

Preparation 69

Preparation of (4Z)-5-propyl-6,7-dihydro-1-benzothiophen-4(5H)-one oxime

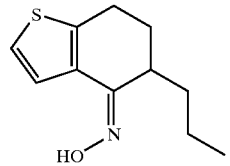

Following the procedure for the preparation of (4E)-2,3-dihydro-4H-chromen-4-one oxime but substituting 5-propyl-6,7-dihydro-1-benzothiophen-4(5H)-one and making non-critical variations provided the title compound as a oil: $^1$H NMR (300 MHz, $CDCl_3$) δ) 7.98, 7.28, 7.15, 7.10, 3.55, 2.99–2.81, 2.21–1.83, 1.59–1.31, 0.95–0.90; (MS/CI) calcd for $C_{10}H_{13}NOS+H$ 195.3, found 195.7.

Preparation 70

Preparation of Cis-5-propyl-4,5,6,7-tetrahydro-1-benzothiophen-4-amine

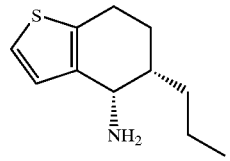

To a solution of sodium borohydride (4.63 g) in ethylene glycol dimethyl ether (150 ml) at 0° C. under $N_2$ was added titanium tetrachloride (6.89 ml). After 5 min, (4Z)-5-propyl-6,7-dihydro-1-benzothiophen-4(5H)-one oxime (6.25 g) in 50 ml of ethylene glycol dimethyl ether was added dropwise to a blue solution. The reaction mixture was stirred at ambient temperate for 24 h and carefully quenched at 0° C. with 2 N NaOH. The aqueous layer was extracted with methylene chloride (3×200 ml), dried $MgSO_4$, filtered and concentrated. MPLC chromatography on a biotage 40 L column with 2–4% methanol/methylene chloride with 0.5% ammonium hydroxide provided Cis-5-propyl-4,5,6,7-tetrahydro-1-benzothiophen-4-amine (2.2 g): $^1$H NMR (300 MHz, $CDCl_3$) δ) 7.10, 6.96, 3.92, 2.90–2.72, 1.72, 1.47–1.36, 0.98; HRMS (FAB) calcd for $C_{11}H_{17}NS+H$ 196.1160, found 196.1164, and trans-5-propyl-4,5,6,7-tetrahydro-1-benzothiophen-4-amine (2.68 g) as an oil: $^1$H NMR (300 MHz, $CDCl_3$) δ) 7.10, 7.02, 3.59, 2.78, 2.07, 1.66–1.48, 1.38–1.24, 0.96; HRMS (FAB) calcd for $C_{11}H_{17}NS+H$ 196.1160, found 196.1157.

Preparation 71

Preparation of 3,6-diethyl-N-[Cis-5-propyl-4,5,6,7-tetrahydro-1-benzothien-4-yl]pyrazin-2-amine

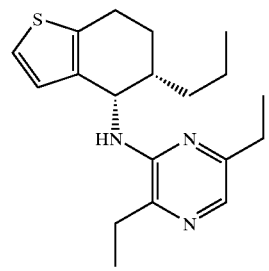

Following the procedure for the preparation of (1R,2S)-1-[(3,6-diethylpyrazin-2-yl)amino]-2,3-dihydro-1H-inden-2-ol but substituting cis-5-propyl-4,5,6,7-tetrahydro-1-benzothiophen-4-amine and making non-critical variations provided the title compound as a oil: $^1$H NMR (300 MHz, $CDCl_3$) δ) 7.65, 7.05, 6.92, 5.68, 4.31, 2.97–2.80, 2.68, 2.53, 2.05, 1.97, 1.71, 1.51–1.25, 0.86; HRMS (FAB) calcd for $C_{19}H_{27}N_3S+H$ 330.2004, found 330.2001. Anal. Calcd for $C_{19}H_{27}N_3S$: C, 69.26; H, 8.26; N, 12.75; S, 9.73. Found: C, 69.21; H, 8.28; N, 12.35.

Preparation 72

Preparation of 3,6-diethyl-N-[Trans-5-propyl-4,5,6,7-tetrahydro-1-benzothien-4-yl]pyrazin-2-amine

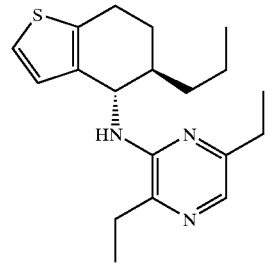

Following the procedure for the preparation of (1R,2S)-1-[(3,6-diethylpyrazin-2-yl)amino]-2,3-dihydro-1H-inden-2-ol but substituting trans-5-propyl-4,5,6,7-tetrahydro-1-benzothiophen-4-amine and making non-critical variations provided the title compound as a oil: $^1$H NMR (300 MHz, CDCl$_3$) δ) 7.66, 7.08, 6.44, 5.19, 4.46, 2.82, 2.68–2.52, 2.03, 1.94, 1.78, 1.53–1.48, 1.26, 0.92; HRMS (FAB) calcd for C$_{19}$H$_{27}$N$_3$S+H 330.2004, found 330.1993.

Preparation 73

Preparation of 5-bromo-3,6-diethyl-N-[Cis-5-propyl-4,5,6,7-tetrahydro-1-benzothien-4-yl]pyrazin-2-amine

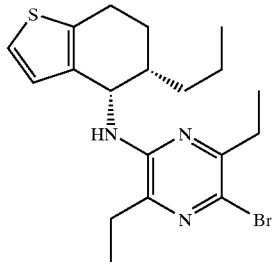

Following the procedure for the preparation of (1R,2S)-1-[(5-bromo-3,6-diethylpyrazin-2-yl)amino]-2,3-dihydro-1H-inden-2-ol but substituting 3,6-diethyl-N-[Cis-5-propyl-4,5,6,7-tetrahydro-1-benzothien-4-yl]pyrazin-2-amine and making non-critical variations provided the title compound as a oil: $^1$H NMR (300 MHz, CDCl$_3$) δ) 7.06, 6.88, 5.61, 4.28, 2.97–2.80, 2.54, 2.05–1.92, 1.74, 1.49–1.21, 0.87; HRMS (FAB) calcd for C$_{19}$H$_{26}$BrN$_3$S+H 408.1109, found 408.1108.

Anal. Calcd for C$_{19}$H$_{26}$BrN$_3$S: C, 55.88; H, 6.42; N, 10.29. Found: C, 55.62; H, 6.45; N, 10.18.

Preparation 74

Preparation of 5-bromo-3,6-diethyl-N-[Trans-5-propyl-4,5,6,7-tetrahydro-1-benzothien-4-yl]pyrazin-2-amine

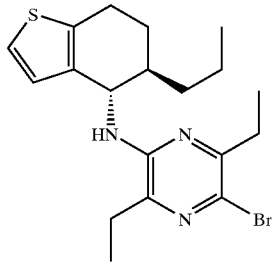

Following the procedure for the preparation of (1R,2S)-1-[(5-bromo-3,6-diethylpyrazin-2-yl)amino]-2,3-dihydro-1H-inden-2-ol but substituting 3,6-diethyl-N-[Trans-5-propyl-4,5,6,7-tetrahydro-1-benzothien-4-yl]pyrazin-2-amine and making non-critical variations provided the title compound as a oil: $^1$H NMR (300 MHz, CDCl$_3$) δ 7.07, 6.82, 5.12, 4.41, 2.82, 2.56, 2.15–1.71, 1.68–1.40, 1.28, 0.92; HRMS (FAB) calcd for C$_{19}$H$_{26}$BrN$_3$S+H 408.1109, found 408.1123.

Example 59

Preparation of 5-(2,4-dichlorophenyl)-3,6-diethyl-N-[Cis-5-propyl-4,5,6,7-tetrahydro-1-benzothien-4-yl]pyrazin-2-amine

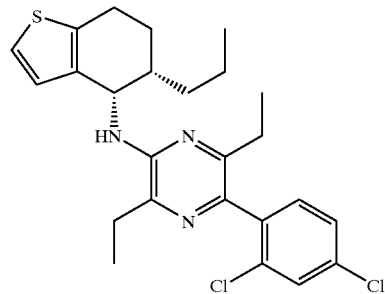

Following the procedure for the preparation of (1R,2S)-1-{[5-(2,4-dichlorophenyl)-3,6-diethylpyrazin-2-yl]amino}-2,3-dihydro-1H-inden-2-ol but substituting 5-bromo-3,6-diethyl-N-[Cis-5-propyl-4,5,6,7-tetrahydro-1-benzothien-4-yl]pyrazin-2-amine, ethylene glycol dimethyl ether and tetrakis(triphenylphosphine) palladium and making non-critical variations provided the title compound as a oil: $^1$H NMR (300 MHz, CDCl$_3$) δ) 7.50, 7.32, 7.08, 6.98, 5.73, 4.43, 2.98, 2.82, 2.62, 2.50, 2.10, 1.95, 1.76, 1.57–1.44, 1.42–1.18, 0.89; HRMS (FAB) calcd for C$_{25}$H$_{29}$Cl$_2$N$_3$S+H 474.1537, found 474.1544. Anal. Calcd for C$_{25}$H$_{29}$Cl$_2$N$_3$S: C, 63.28; H, 6.16; N, 8.86;. Found: C, 63.61; H, 6.33; N, 8.65.

Example 60

Preparation of 5-(2,4-dichlorophenyl)-3,6-diethyl-N-[Trans-5-propyl-4,5,6,7-tetrahydro-1-benzothien-4-yl]pyrazin-2-amine

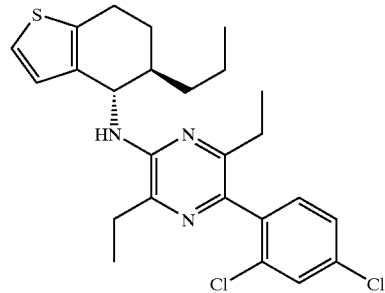

Following the procedure for the preparation of (1R,2S)-1-{[5-(2,4-dichlorophenyl)-3,6-diethylpyrazin-2-yl]amino}-2,3-dihydro-1H-inden-2-ol but substituting 5-bromo-3,6-diethyl-N-[Trans-5-propyl-4,5,6,7-tetrahydro-1-benzothien-4-yl]pyrazin-2-amine, ethylene glycol dimethyl ether and tetrakis(triphenylphosphine) palladium and making non-critical variations provided the title compound as a oil: $^1$H NMR (300 MHz, CDCl$_3$) δ) 7.50, 7.35–7.31, 7.11, 6.91, 5.21, 4.59, 2.82, 2.64, 2.48, 2.05, 1.82, 1.43–1.35, 1.25, 1.18, 0.94; HRMS (FAB) calcd for C$_{25}$H$_{29}$Cl$_2$N$_3$S+H 474.1537, found 474.1526.

Preparation 75

Preparation of (1R,2S)-1-[(3,6-dimethylpyrazin-2-yl)amino]-2,3-dihydro-1H-inden-2-ol

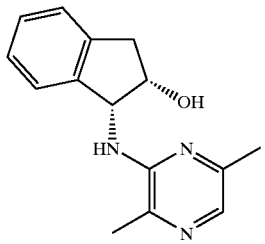

Following the procedure for the preparation of (1R,2S)-1-[(3,6-diethylpyrazin-2-yl)amino]-2,3-dihydro-1H-inden-2-ol but substituting 3-chloro-2,5-dimethylpyrazine and making non-critical variations provided the title compound as a oil: $^1$H NMR (300 MHz, CDCl$_3$) δ) 7.68, 7.32–7.28, 5.59, 4.80, 3.27, 3.09, 2.92, 2.38; HRMS (FAB) calcd for C$_{15}$H$_{17}$N$_3$O+H 256.1450, found 256.1460.

Preparation 76

Preparation of (1R,2S)-1-[(5-bromo-3,6-dimethylpyrazin-2-yl)amino]-2,3-dihydro-1H-inden-2-ol

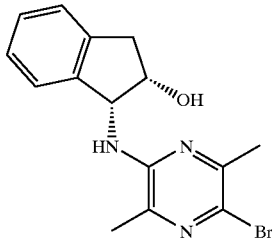

Following the procedure for the preparation of (1R,2S)-1-[(5-bromo-3,6-diethylpyrazin-2-yl)amino]-2,3-dihydro-1H-inden-2-ol but substituting (1R,2S)-1-[(3,6-dimethylpyrazin-2-yl)amino]-2,3-dihydro-1H-inden-2-ol and making non-critical variations provided the title compound as a oil: $^1$H NMR (300 MHz, CDCl$_3$) δ) 7.32–7.28, 5.58, 4.92, 4.77, 3.28, 3.07, 2.51, 2.38, 2.28; HRMS (FAB) calcd for C$_{15}$H$_{16}$BrN$_3$O+H 334.0555, found 334.0557. Anal. Calcd for C$_{15}$H$_{16}$BrN$_3$O: C, 53.91; H, 4.83; N, 12.57. Found: C, 53.55; H, 4.88; N, 12.27.

Preparation 77

Preparation of (1R,2S)-1-{[5-(2,4-dichlorophenyl)-3,6-dimethylpyrazin-2-yl]amino}-2,3-dihydro-1H-inden-2-ol

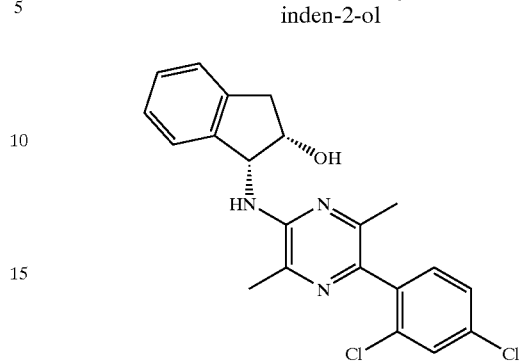

Following the procedure for the preparation of (1R,2S)-1-{[5-(2,4-dichlorophenyl)-3,6-diethylpyrazin-2-yl]amino}-2,3-dihydro-1H-inden-2-ol but substituting (1R,2S)-1-[(5-bromo-3,6-dimethylpyrazin-2-yl)amino]-2,3-dihydro-1H-inden-2-ol and making non-critical variations provided the title compound as a oil: $^1$H NMR (300 MHz, CDCl$_3$) δ) 7.51, 7.36–7.28, 5.66, 4.98, 4.82, 3.25, 3.11, 2.75, 2.42, 2.26; HRMS (FAB) calcd for C$_{21}$H$_{19}$Cl$_2$N$_3$O+H 400.0983, found 400.0995.

Anal. Calcd for C$_{21}$H$_{19}$Cl$_2$N$_3$O: C, 63.01; H, 4.78; N, 10.50. Found: C, 62.86; H, 4.80; N, 10.39.

Example 61

Preparation of 5-(2,4-dichlorophenyl)-N-[(1R,2S)-2-methoxy-2,3-dihydro-1H-inden-1-yl]-3,6-dimethylpyrazin-2-amine

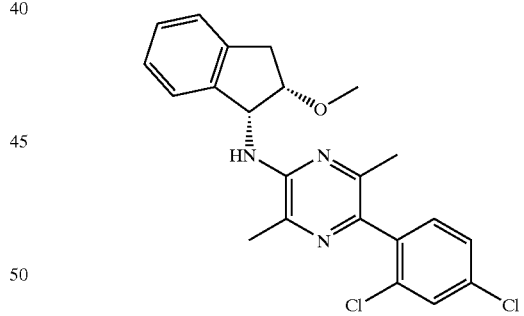

Following the procedure for the preparation of 5-(2,4-dichlorophenyl)-N-[(1R,2S)-2-ethoxy-2,3-dihydro-1H-inden-1-yl]-3,6-diethylpyrazin-2-amine but substituting (1R,2S)-1-{[5-(2,4-dichlorophenyl)-3,6-dimethylpyrazin-2-yl]amino}-2,3-dihydro-1H-inden-2-ol and methyl iodide, and making non-critical variations provided the title compound as a oil: $^1$H NMR (300 MHz, CDCl$_3$) δ) 7.51, 7.43, 7.37–7.25, 5.86, 5.40, 4.28, 3.43, 3.23, 3.06, 2.42, 2.25; HRMS (FAB) calcd for C$_{22}$H$_{21}$Cl$_2$N$_3$O+H 414.1140, found 414.1143.

Anal. Calcd for C$_{22}$H$_{21}$Cl$_2$N$_3$O: C, 63.78; H, 5.11; N, 10.14. Found: C, 63.86; H, 5.21; N, 10.07.

Example 62

Preparation of 5-(2,4-dichlorophenyl)-N-[(1R,2S)-2-ethoxy-2,3-dihydro-1H-inden-1-yl]-3,6-dimethylpyrazin-2-amine

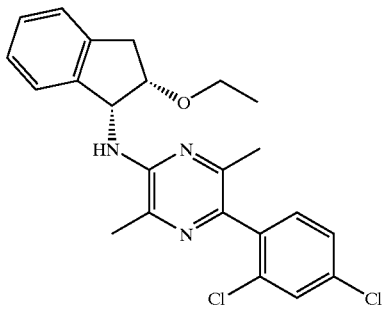

Following the procedure for the preparation of 5-(2,4-dichlorophenyl)-N-[(1R,2S)-2-ethoxy-2,3-dihydro-1H-inden-1-yl]-3,6-diethylpyrazin-2-amine but substituting (1R,2S)-1-{[5-(2,4-dichlorophenyl)-3,6-dimethylpyrazin-2-yl]amino}-2,3-1H-inden-2-ol and making non-critical variations provided the title compound as a oil: $^1$H NMR (300 MHz, CDCl$_3$) δ); 7.50–7.48, 7.32–7.28, 5.81, 5.48, 4.38, 3.70, 3.52, 3.14, 2.41, 2.26, 1.20; HRMS (FAB) calcd for C$_{23}$H$_{23}$Cl$_2$N$_3$O+H 428.1296, found 428.1288.

Anal. Calcd for C$_{23}$H$_{23}$Cl$_2$N$_3$O: C, 64.49; H, 5.41; N, 9.8. Found: C, 64.49; H, 5.48; N, 9.74.

Example 63

Preparation of 5-(2,4-dichlorophenyl)-N-[(1R,2S)-2-isopropoxy-2,3-dihydro-1H-inden-1-yl]-3,6-dimethylpyrazin-2-amine

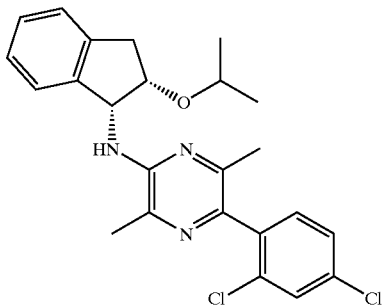

Following the procedure for the preparation of 5-(2,4-dichlorophenyl)-N-[(1R,2S)-2-ethoxy-2,3-dihydro-1H-inden-1-yl]-3,6-diethylpyrazin-2-amine but substituting (1R,2S)-1-{[5-(2,4-dichlorophenyl)-3,6-dimethylpyrazin-2-yl]amino}-2,3-dihydro-1H-inden-2-ol and 2-iodopropane, and making non-critical variations provided the title compound as a oil: $^1$H NMR (300 MHz, CDCl$_3$) δ) 7.50–7.46, 7.34–7.26, 5.76, 5.43, 4.47, 3.72, 3.14–3.11, 2.41, 2.26, 1.20, 1.12; HRMS (FAB) calcd for C$_{24}$H$_{25}$Cl$_2$N$_3$O+H 442.1453, found 442.1441. Anal. Calcd for C$_{24}$H$_{25}$Cl$_2$N$_3$O: C, 65.16; H, 5.70; N, 9.50. Found: C, 65.33; H, 5.83; N, 9.34.

Preparation 78

Preparation of 8-methoxy-1,2,3,4-tetrahydronaphthalen-1-amine

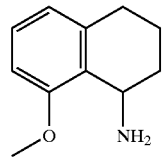

Following the procedure for the preparation of 4,5,6,7-tetrahydro-1-benzofuran-4-amine but substituting 8-methoxy-3,4-dihydronaphthalen-1(2H)-one and making non-critical variations provided the title compound as a oil: $^1$H NMR (300 MHz, CDCl$_3$) δ) 7.13, 6.73, 4.21, 3.87, 2.78–2.72, 1.88; HRMS (FAB) calcd for C$_{11}$H$_{15}$NO+H 178.1232, found 178.1232.

Preparation 79

Preparation of 3,6-diethyl-N-(8-methoxy-1,2,3,4-tetrahydronaphthalen-1-yl)pyrazin-2-amine

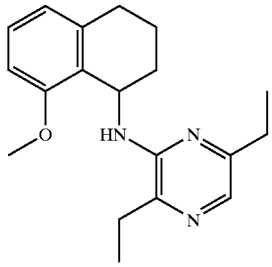

Following the procedure for the preparation of (1R,2S)-1-[(3,6-diethylpyrazin-2-yl)amino]-2,3-dihydro-1H-inden-2-ol but substituting 8-methoxy-1,2,3,4-tetrahydronaphthalen-1-amine and making non-critical variations provided the title compound as a oil: $^1$H NMR (300 MHz, CDCl$_3$) δ) 7.63, 7.22, 6.78, 5.40, 4.31, 3.71, 2.86–2.65, 2.53–2.38, 1.88–1.67, 1.32, 1.21; HRMS (FAB) calcd for C$_{19}$H$_{25}$N$_3$O+H 312.2076, found 312.2077.

Preparation 80

Preparation of 5-bromo-3,6-diethyl-N-(8-methoxy-1,2,3,4-tetrahydronaphthalen-1-yl)pyrazin-2-amine

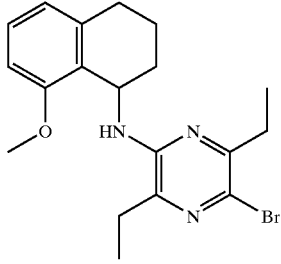

Following the procedure for the preparation of (1R,2S)-1-[(5-bromo-3,6-diethylpyrazin-2-yl)amino]-2,3-dihydro-1H-inden-2-ol but substituting 3,6-diethyl-N-(8-methoxy-1, 2,3,4-tetrahydronaphthalen-1-yl)pyrazin-2-amine and making non-critical variations provided the title compound as a oil: $^1$H NMR (300 MHz, CDCl$_3$) δ) 7.23, 6.78, 5.32, 4.31, 3.71, 2.89–2.77, 2.50–2.35, 1.81–1.65, 1.32, 1.18; HRMS (FAB) calcd for C$_{19}$H$_{24}$BrN$_3$O+H 390.1181, found 390.1172.

Anal. Calcd for C$_{19}$H$_{24}$BrN$_3$O: C, 58.47; H, 6.20; N, 10.77. Found: C, 58.07; H, 6.13; N, 10.51.

Example 64

Preparation of 5-(2,4-dichlorophenyl)-3,6-diethyl-N-(8-methoxy-1,2,3,4-tetrahydronaphthalen-1-yl)pyrazin-2-amine

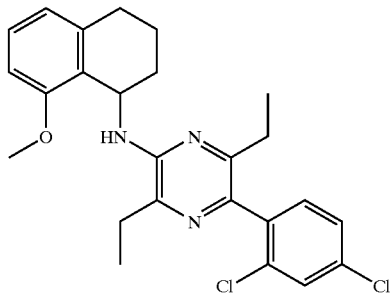

Following the procedure for the preparation of (1R,2S)-1-{[5-(2,4-dichlorophenyl)-3,6-diethylpyrazin-2-yl]amino}-2,3-dihydro-1H-inden-2-ol but substituting 5-bromo-3,6-diethyl-N-(8-methoxy-1,2,3,4-tetrahydronaphthalen-1-yl)pyrazin-2-amine, ethylene glycol dimethyl ether and tetrakis(triphenylphosphine) palladium and making non-critical variations provided the title compound as a oil: $^1$H NMR (300 MHz, CDCl$_3$) δ) 7.50, 7.34–7.22, 6.83, 5.46, 4.45, 3.75, 2.94–2.79, 2.60–2.53, 1.92–1.77, 1.28–1.16; HRMS (FAB) calcd for C$_{25}$H$_{27}$Cl$_2$N$_3$O+H 456.1609, found 456.1602.

Preparation 81

Preparation of 6-methoxyindan-1-amine

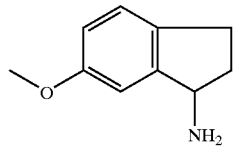

Following the procedure for the preparation of 4,5,6,7-tetrahydro-1-benzofuran-4-amine but substituting 8-methoxy-3,4-dihydronaphthalen-1(2H)-one and making non-critical variations provided the title compound as a oil: $^1$H NMR (CDCl$_3$) δ 1.72, 2.54, 2.74, 2.90, 3.83, 4.34, 6.78, 6.91, 7.13; MS (FAB) m/z (rel. intensity) 164 (MH+, 17), 308 (8), 164 (17), 163 (7), 162 (19), 148 (18), 147 (99), 146 (18), 145 (9), 121 (11), 115 (8). HRMS (FAB) calcd for C$_{10}$H$_{13}$NO+H 164.1075, found 164.1071.

Preparation 82

Preparation of 3,6-diethyl-N-(6-methoxy-2,3-dihydro-1H-inden-1-yl)pyrazin-2-amine

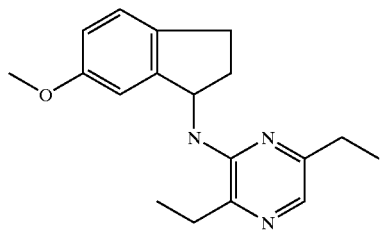

Following the procedure for the preparation of (1R,2S)-1-[(3,6-diethylpyrazin-2-yl)amino]-2,3-dihydro-1H-inden-2-ol but substituting 6-methoxyindan-1-amine and making non-critical variations provided the title compound as a oil: $^1$H NMR (CDCl$_3$) δ 1.31, 1.87, 2.59, 2.67, 2.75, 2.87, 2.95, 3.79, 4.55, 5.75, 6.83, 7.19, 7.70; HRMS (FAB) calcd for C$_{18}$H$_{23}$N$_3$O+H 298.1919, found 298.1909. Anal. Calcd for C$_{18}$H$_{23}$N$_3$O: C, 72.70; H, 7.80; N, 14.13. Found: C, 72.19; H, 7.76; N, 13.84.

Preparation 83

Preparation of 5-bromo-3,6-diethyl-N-(6-methoxy-2,3-dihydro-1H-inden-1-yl)pyrazin-2-amine

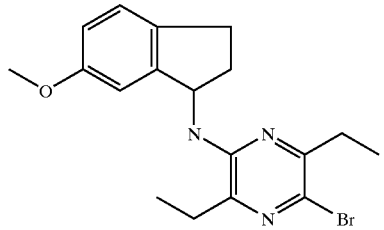

Following the procedure for the preparation of (1R,2S)-1-[(5-bromo-3,6-diethylpyrazin-2-yl)amino]-2,3-dihydro-1H-inden-2-ol but substituting 3,6-diethyl-N-(6-methoxy-2,3-dihydro-1H-inden-1-yl)pyrazin-2-amine and making non-critical variations provided the title compound as a oil: $^1$H NMR (CDCl$_3$) δ 1.27–1.31, 1.86, 2.58, 2.75, 2.83, 2.85, 2.97, 3.80, 4.54, 5.67, 6.83–6.88, 7.20; HRMS (FAB) calcd for C$_{18}$H$_{22}$BrN$_3$O+H 376.1025, found 376.1020. Anal. Calcd for C$_{18}$H$_{22}$BrN$_3$O: C, 57.45; H, 5.89; N, 11.17; Br, 21.23. Found: C, 56.15; H, 5.65; N, 10.83.

Example 65

Preparation of 5-(2,4-dichlorophenyl)-3,6-diethyl-N-(6-methoxy-2,3-dihydro-1H-inden-1-yl)pyrazin-2-amine

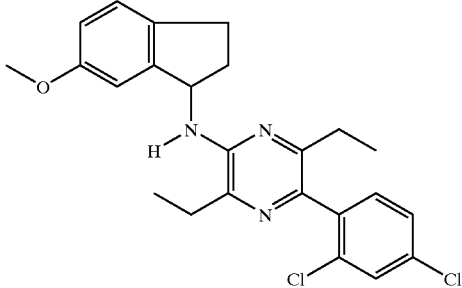

Following the procedure for the preparation of (1R,2S)-1-{[5-(2,4-dichlorophenyl)-3,6-diethylpyrazin-2-yl]amino}-2,3-dihydro-1H-inden-2-ol but substituting 5-bromo-3,6-diethyl-N-(6-methoxy-2,3-dihydro-1H-inden-1-yl)pyrazin-2-amine, ethylene glycol dimethyl ether and tetrakis(triphenylphosphine) palladium and making non-critical variations provided the title compound as a oil: $^1$H NMR (CDCl$_3$) δ 1.21, 1.29, 1.94, 2.51, 2.67, 2.80, 2.92, 3.01, 3.81, 4.69, 5.80, 6.86, 6.95, 7.22, 7.29–7.36, 7.51; HRMS (FAB) calcd for $C_{24}H_{25}Cl_2N_3O+H$ 442.1453, found 442.1443.

Preparation 84

Preparation of 2-ethyl-6-methoxyindan-1-one

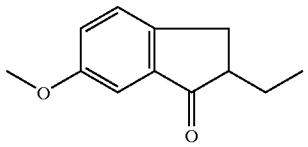

Following the procedure for the preparation of 5-propyl-6,7-dihydro-1-benzothiophen-4(5H)-one but substituting 6-methoxy 1-tetralone and ethyl iodide, and making non-critical variations provided the title compound as a oil: $^1$H NMR (CDCl$_3$) δ 1.02, 1.55, 1.99, 2.68, 2.77, 3.27, 3.86, 7.21, 7.37; HRMS (FAB) calcd for $C_{12}H_{14}O_2+H$ 191.1072, found 191.1075.

Preparation 85

Preparation of 2-ethyl-6-methoxy-2,3-dihydro-1H-inden-1-one oxime

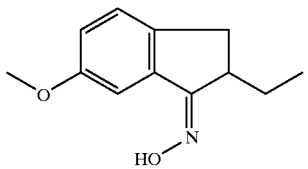

Following the procedure for the preparation of (4E)-2,3-dihydro-4H-chromen-4-one oxime but substituting 2-ethyl-6-methoxyindan-1-one and making non-critical variations provided the title compound as a oil: HRMS (FAB) calcd for $C_{12}H_{15}NO_2+H$ 206.1181, found 206.1175. Anal. Calcd for $C_{12}H_{15}NO_2$: C, 70.22; H, 7.37; N, 6.82. Found: C, 69.90; H, 7.48; N, 6.64.

Preparation 86

Preparation of cis-2-ethyl-6-methoxy-2,3-dihydro-1H-inden-1-amine

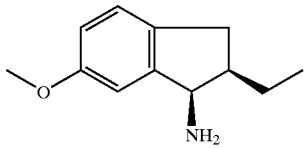

Following the procedure for the preparation of 6,7-dihydro-5H-cyclopenta[b]pyridin-5-amine but substituting 2-ethyl-6-methoxy-2,3-dihydro-1H-inden-1-one oxime and making non-critical variations provided the title compound as a oil: $^1$H NMR (CDCl$_3$) δ 1.03, 1.39, 2.30, 2.63, 2.86, 3.82, 4.26, 6.77, 7.12;

Preparation 87

Preparation of 3,6-diethyl-N-[(cis)-2-ethyl-6-methoxy-2,3-dihydro-1H-inden-1-yl]pyrazin-2-amine

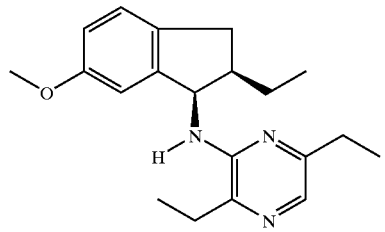

Following the procedure for the preparation of (1R,2S)-1-[(3,6-diethylpyrazin-2-yl)amino]-2,3-dihydro-1H-inden-2-ol but substituting cis-2-ethyl-6-methoxy-2,3-dihydro-1H-inden-1-amine and making non-critical variations provided the title compound as a oil: $^1$H NMR (CDCl$_3$) δ 0.93, 1.27–1.34, 2.58, 2.68, 3.00, 3.79, 4.44, 5.83, 6.80, 6.92, 7.17, 7.68; HRMS (EI) calcd for $C_{20}H_{27}N_3O$ 325.2154, found 325.2157.

Preparation 88

Preparation of 5-bromo-3,6-diethyl-N-[(cis)-2-ethyl-6-methoxy-2,3-dihydro-1H-inden-1-yl]pyrazin-2-amine

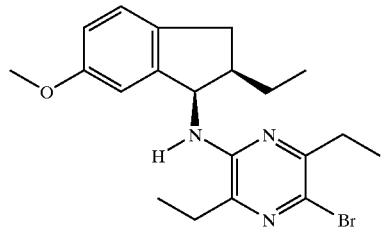

Following the procedure for the preparation of (1R,2S)-1-[(5-bromo-3,6-diethylpyrazin-2-yl)amino]-2,3-dihydro-1H-inden-2-ol but substituting 3,6-diethyl-N-[(cis)-2-ethyl-6-methoxy-2,3-dihydro-1H-inden-1-yl]pyrazin-2-amine and making non-critical variations provided the title compound as a oil: $^1$H NMR (CDCl$_3$) δ 0.93, 1.21–1.34, 2.57, 2.73, 2.82, 3.00, 3.79, 4.41, 5.76, 6.82, 7.17; HRMS (FAB) calcd for $C_{20}H_{26}BrN_3O+H$ 404.1338, found 404.1317. Anal. Calcd for $C_{20}H_{26}BrN_3O$: C, 59.41; H, 6.48; N, 10.39; Br, 19.76. Found: C, 59.05; H, 6.42; N, 10.13.

Example 66

Preparation of 5-(2,4-dichlorophenyl)-3,6-diethyl-N-[(cis)-2-ethyl-6-methoxy-2,3-dihydro-1H-inden-1-yl]pyrazin-2-amine

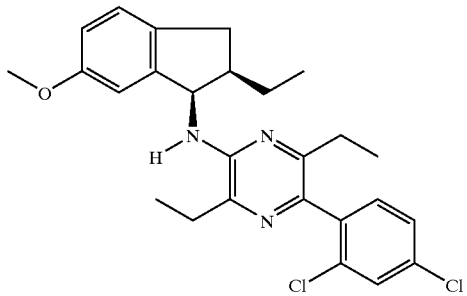

Following the procedure for the preparation of (1R,2S)-1-{[5-(2,4-dichlorophenyl)-3,6-diethylpyrazin-2-yl]amino}-2,3-dihydro-1H-inden-2-ol but substituting 5-bromo-3,6-diethyl-N-[(cis)-2-ethyl-6-methoxy-2,3-dihydro-1H-inden-1-yl]pyrazin-2-amine, ethylene glycol dimethyl ether and tetrakis(triphenylphosphine) palladium and making non-critical variations provided the title compound as a oil: $^1$H NMR (CDCl$_3$) δ 0.97, 1.22, 1.28, 2.52, 2.65, 2.75, 3.04, 3.81, 4.57, 5.87, 6.84, 6.98, 7.18, 7.34, 7.50; HRMS (FAB) calcd for C$_{26}$H$_{29}$Cl$_2$N$_3$O+H 470.1766, found 470.1747

Preparation 89

Preparation of 5-methoxyindan-1-one oxime

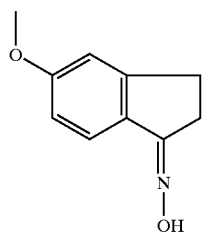

Following the procedure for the preparation of (4E)-2,3-dihydro-4H-chromen-4-one oxime but substituting 5-methoxyindan-1-one and making non-critical variations provided the title compound as a oil: HRMS (EI) calcd for C$_{10}$H$_{11}$O$_2$ 177.0790, found 177.0783. Anal. Calcd for C$_{10}$H$_{11}$NO$_2$: C, 67.78; H, 6.26; N, 7.90. Found: C, 67.73; H, 6.34; N, 7.77.

Preparation 90

Preparation of 5-methoxyindan-1-amine

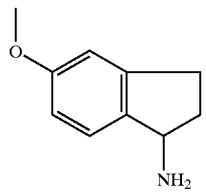

Following the procedure for the preparation of 6,7-dihydro-5H-cyclopenta[b]pyridin-5-amine but substituting 5-methoxyindan-1-one oxime and making non-critical variations provided the title compound as a oil: $^1$H NMR (CDCl$_3$) δ 1.73, 2.75, 2.80, 2.94, 3.82, 4.34, 6.80, 7.25; HRMS (FAB) calcd for C$_{10}$H$_{11}$NO+H 162.0919, found 162.0922.

Preparation 91

Preparation of 3,6-diethyl-N-(5-methoxy-2,3-dihydro-1H-inden-1-yl)pyrazin-2-amine

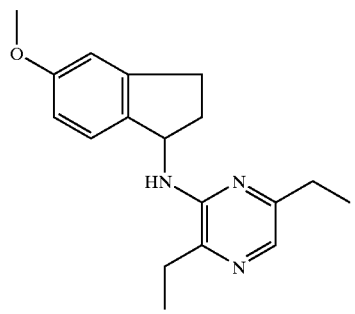

Following the procedure for the preparation of (1R,2S)-1-[(3,6-diethylpyrazin-2-yl)amino]-2,3-dihydro-1H-inden-2-ol but substituting 5-methoxyindan-1-amine and making non-critical variations provided the title compound as a oil: $^1$H NMR (CDCl$_3$) δ 1.31, 1.89, 2.58, 2.67, 2.73, 2.91, 3.00, 3.83, 4.51, 5.69, 6.79, 6.85, 7.26, 7.69; $^{13}$C NMR (CDCl$_3$) δ 11.08, 13.97, 26.04, 28.55, 30.84, 35.35, 55.79, 55.87, 110.39, 113.15, 125.21, 130.10, 137.12, 140.93, 145.91, 151.82, 153.69, 160.25; HRMS (FAB) calcd for C$_{18}$H$_{23}$N$_3$O+H 298.1919, found 298.1900. Anal. Calcd for C$_{18}$H$_{23}$N$_3$O: C, 72.70; H, 7.80; N, 14.13. Found: C, 72.51; H, 8.00; N, 13.82.

Preparation 92

Preparation of 5-bromo-3,6-diethyl-N-(5-methoxy-2,3-dihydro-1H-inden-1-yl)pyrazin-2-amine

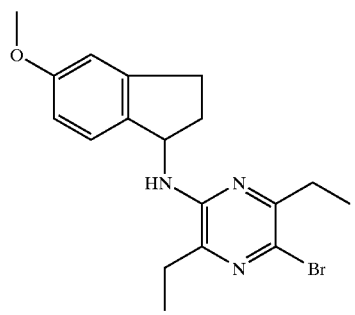

Following the procedure for the preparation of (1R,2S)-1-[(5-bromo-3,6-diethylpyrazin-2-yl)amino]-2,3-dihydro-1H-inden-2-ol but substituting 3,6-diethyl-N-(5-methoxy-2,3-dihydro-1H-inden-1-yl)pyrazin-2-amine and making non-critical variations provided the title compound as a oil: $^1$H NMR (CDCl$_3$) δ 1.29, 1.89, 2.56, 2.70, 2.83, 2.87, 3.00, 3.83, 4.49, 5.61, 6.81, 6.85, 7.23; HRMS (FAB) calcd for C$_{18}$H$_{22}$BrN$_3$O+H 376.1025, found 376.1008.

Example 67

Preparation of 5-(2,4-dichlorophenyl)-3,6-diethyl-N-(5-methoxy-2,3-dihydro-1H-inden-1-yl)pyrazin-2-amine

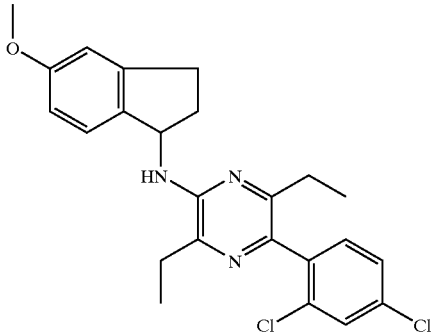

Following the procedure for the preparation of (1R,2S)-1-{[5-(2,4-dichlorophenyl)-3,6-diethylpyrazin-2-yl]amino}-2,3-dihydro-1H-inden-2-ol but substituting 5-bromo-3,6-diethyl-N-(5-methoxy-2,3-dihydro-1H-inden-1-yl)pyrazin-2-amine, ethylene glycol dimethyl ether and tetrakis(triphenylphosphine) palladium and making non-critical variations provided the title compound as a oil: $^1$H NMR (CDCl$_3$) δ) 1.28, 1.95, 2.51, 2.65, 2.80, 2.95, 3.02, 3.85, 4.14, 4.65, 5.73, 6.82, 6.87, 7.28–7.35, 7.5; HRMS (FAB) calcd for $C_{24}H_{25}Cl_2N_3O$+H 442.1453, found 442.1450.

Preparation 93

Preparation of 6,7-dihydro-5H-cyclopenta[b]pyridin-7-amine

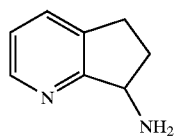

Following the procedure for the preparation of 4,5,6,7-tetrahydro-1-benzofuran-4-amine but 5,6-dihydro-7H-cyclopenta[b]pyridin-7-one and making non-critical variations provided the title compound as a oil: $^1$H NMR (300 MHz, DMSO) δ) 8.49, 7.79, 7.36, 4.65, 3.38, 3.01–2.90, 2.55, 1.93; (MS/CI) calcd for $C_8H_{10}N_2$+H 135.2, found 135.2.

Preparation 94

Preparation of N-(3,6-diethylpyrazin-2-yl)-6,7-dihydro-5H-cyclopenta[b]pyridin-7-amine

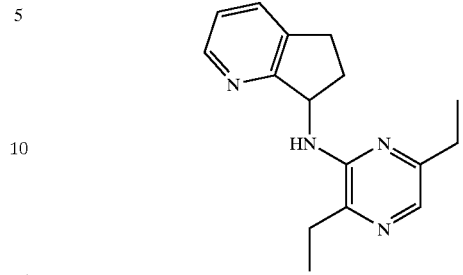

Following the procedure for the preparation of (1R,2S)-1-[(3,6-diethylpyrazin-2-yl)amino]-2,3-dihydro-1H-inden-2-ol but substituting 6,7-dihydro-5H-cyclopenta[b]pyridin-7-amine and making non-critical variations provided the title compound as a oil: $^1$H NMR (300 MHz, CDCl$_3$) δ) 8.46, 7.60, 7.17, 5.37, 5.25, 3.11–2.95, 2.75–2.61, 1.94–1.81, 1.36–1.26; (MS/CI) calcd for $C_{16}H_{20}N_4$+H 269.4, found 269.3.

Preparation 95

Preparation of N-(5-bromo-3,6-diethylpyrazin-2-yl)-6,7-dihydro-5H-cyclopenta[b]pyridin-7-amine

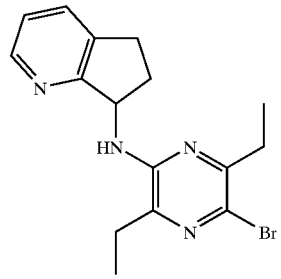

Following the procedure for the preparation of (1R,2S)-1-[(5-bromo-3,6-diethylpyrazin-2-yl)amino]-2,3-dihydro-1H-inden-2-ol but substituting N-(3,6-diethylpyrazin-2-yl)-6,7-dihydro-5H-cyclopenta[b]pyridin-7-amine and making non-critical variations provided the title compound as a oil: $^1$H NMR (300 MHz, CDCl$_3$) δ) 8.47, 7.61, 7.18, 5.30, 3.05, 2.81, 2.78, 1.98, 1.33–1.19; (MS/CI) calcd for $C_{16}H_{19}N_4Br$+H 348.3, found 347.1.

Example 68

Preparation of N-[5-(2,4-dichlorophenyl)-3,6-diethylpyrazin-2-yl]-6,7-dihydro-5H-cyclopenta[b]pyridin-7-amine

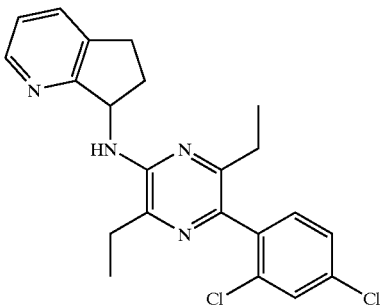

Following the procedure for the preparation of (1R,2S)-1-{[5-(2,4-dichlorophenyl)-3,6-diethylpyrazin-2-yl]amino}-2,3-dihydro-1H-inden-2-ol but substituting N-(5-bromo-3,6-diethylpyrazin-2-yl)-6,7-dihydro-5H-cyclopenta

[b]pyridin-7-amine, ethylene glycol dimethyl ether and tetrakis(triphenylphosphine) palladium and making non-critical variations provided the title compound as a oil: $^1$H NMR (300 MHz, CDCl$_3$) δ) 8.48, 7.62, 7.50, 7.34–7.19, 5.41, 3.07–3.02, 2.75, 2.48, 1.97, 1.33, 1.17; HRMS (FAB) calcd for $C_{22}H_{22}Cl_2N_4$+H 413.1299, found 413.1285.

Anal. Calcd for $C_{22}H_{22}Cl_2N_4$: C, 63.93; H, 5.36; N, 13.555. Found: C, 63.70; H, 5.57; N, 13.15.

Preparation 96

Preparation of (5Z)-6,7-dihydro-5H-cyclopenta[b]pyridin-5-one oxime

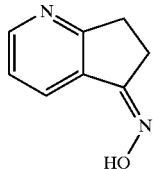

Following the procedure for the preparation of (4E)-2,3-dihydro-4H-chromen-4-one oxime but substituting 6,7-dihydro-5H-cyclopenta[b]pyridin-5-one and making non-critical variations provided the title compound as a oil: $^1$H NMR (400 MHz, DMSO-d$_6$) δ) 11.11, 8.50, 7.89, 7.27, 3.04, 2.81; HRMS (EI) calcd for $C_8H_8N_2O$ 148.0637, found 148.0628.

Preparation 97

Preparation of 6,7-dihydro-5H-cyclopenta[b]pyridin-5-amine

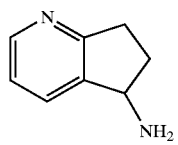

To a solution of (5Z)-6,7-dihydro-5H-cyclopenta[b]pyridin-5-one oxime (320 mg) in methanol (20 ml) under N$_2$ was added nickel chloride hexahydrate. The reaction mixture was cooled to −40° C. and sodium borohydride (817 mg) was slowly added over 30 min. The reaction mixture was warmed to ambient temperature for 1 h and silica gel was added. The reaction mixture was concentrated. MPLC chromatography was run using a biotage 25S column with 5-8% methanol/methylene chloride with 0.5% ammonium hydroxide to provide the title compound as an oil (197 mg, 68%):

$^1$H NMR (400 MHz, CDCl$_3$) δ 8.43, 7.66, 7.28, 7.15, 4.42, 3.13–3.00, 2.97–2.91, 2.63–2.55, 1.81–1.72.

Preparation 98

Preparation of N-(3,6-diethylpyrazin-2-yl)-6,7-dihydro-5H-cyclopenta[b]pyridin-5-amine

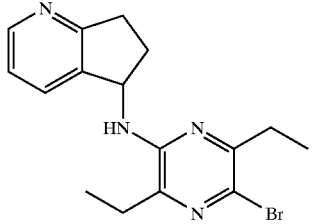

Following the procedure for the preparation of (1R,2S)-1-[(3,6-diethylpyrazin-2-yl)amino]-2,3-dihydro-1H-inden-2-ol but substituting 6,7-dihydro-5H-cyclopenta[b]pyridin-5-amine and making non-critical variations provided the title compound as a oil: $^1$H NMR (400 MHz, CDCl$_3$) δ) 8.48, 7.73, 7.66, 7.14, 5.82, 4.54, 3.22–3.07, 2.79, 2.70–2.57, 1.94 1.36–1.27; HRMS (FAB) calcd for $C_{16}H_{20}N_4$+H 269.1766, found 269.1763.

Preparation 99

Preparation of N-(5-bromo-3,6-diethylpyrazin-2-yl)-6,7-dihydro-5H-cyclopenta[b]pyridin-5-amine

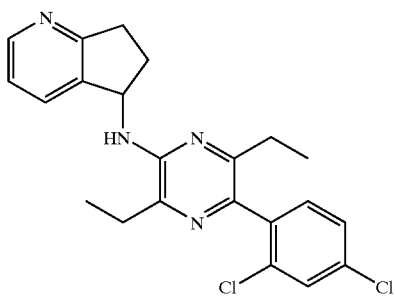

Following the procedure for the preparation of (1R,2S)-1-[(5-bromo-3,6-diethylpyrazin-2-yl)amino]-2,3-dihydro-1H-inden-2-ol but substituting N-(3,6-diethylpyrazin-2-yl)-6,7-dihydro-5H-cyclopenta[b]pyridin-5-amine and making non-critical variations provided the title compound as a oil: $^1$H NMR (400 MHz, CDCl$_3$) δ) 8.49, 7.67, 7.17, 5.77, 4.55, 3.21, 3.09, 2.85–2.75, 2.58, 1.97, 1.31–1.25; HRMS (FAB) calcd for $C_{16}H_{19}BrN_4$+H 347.0872, found 347.0878.

Example 69

Preparation of N-[5-(2,4-dichlorophenyl)-3,6-diethylpyrazin-2-yl]-6,7-dihydro-5H-cyclopenta[b]pyridin-5-amine Following the procedure for the preparation of (1R,2S)-1-{[5-(2,4-dichlorophenyl)-3,6-diethylpyrazin-2-yl]amino}-2,3-dihydro-1H-inden-2-ol but substituting N-(5-bromo-3,6-diethylpyrazin-2-yl)-6,7-dihydro-5H-cyclopenta[b]pyridin-5-amine, ethylene glycol dimethyl ether and tetrakis(triphenylphosphine) palladium and making non-critical variations provided the title compound as a oil: $^1$H NMR (400 MHz, CDCl$_3$) δ) 8.50, 7.73, 7.51, 7.36–7.28, 7.17, 5.88, 4.67, 3.26–3.08, 2.86, 2.70, 2.51, 2.05–1.96, 1.29, 1.12; HRMS (FAB) calcd for C$_{22}$H$_{22}$Cl$_2$N$_4$+H 413.1299, found 413.1286.

Preparation 100

Preparation of 6-ethyl-5,6-dihydro-7H-cyclopenta[b]pyridin-7-one

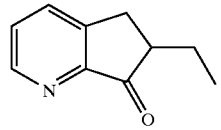

Following the procedure for the preparation of 5-methyl-6,7-dihydro-1-benzothiophen-4(5H)-one but substituting 6,7-dihydro-5H-cyclopenta[b]pyridin-5-one and iodoethane, and making non-critical variations provided the title compound as a oil:

$^1$H NMR (400 MHz, CDCl$_3$) δ) 8.75, 7.86, 7.44, 3.33, 2.81, 2.64, 2.02, 1.58, 1.03; HRMS (FAB) calcd for C$_{10}$H$_{11}$NO+H 162.0919, found 162.0913.

Preparation 101

Preparation of (7Z)-6-ethyl-5,6-dihydro-7H-cyclopenta[b]pyridin-7-one oxime

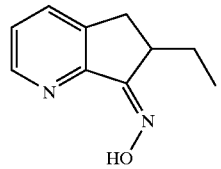

Following the procedure for the preparation of (4E)-2,3-dihydro-4H-chromen-4-one oxime but substituting 6-ethyl-5,6-dihydro-7H-cyclopenta[b]pyridin-7-one and making non-critical variations provided the title compound as a oil: $^1$H NMR (400 MHz, DMSO-d$_6$) δ) 11.21, 8.45, 7.74, 7.29, 3.27, 3.11, 2.65, 1.84, 1.46, 0.85; HRMS (FAB) calcd for C$_{10}$H$_{12}$N$_2$O+H 177.1028, found 177.1029.

Preparation 102

Preparation of 6-ethyl-6,7-dihydro-5H-cyclopenta[b]pyridin-7-amine

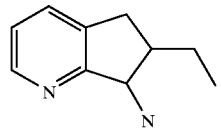

Following the procedure for the preparation of 6,7-dihydro-5H-cyclopenta[b]pyridin-5-amine but substituting (7Z)-6-ethyl-5,6-dihydro-7H-cyclopenta[b]pyridin-7-one oxime and making non-critical variations provided the title compound as a oil: $^1$H NMR (400 MHz, CDCl$_3$) δ) 8.40, 7.51, 7.10, 4.30, 3.95, 3.07, 2.95, 2.74, 2.50, 2.38, 2.03–1.93, 1.75, 1.57, 1.40, 1.09–0.97; HRMS (FAB) calcd for C$_{10}$H$_{14}$N$_2$+H 163.1235, found 163.1229.

Preparation 103

Preparation of N-(3,6-diethylpyrazin-2-yl)-6-ethyl-6,7-dihydro-5H-cyclopenta[b]pyridin-7-amine

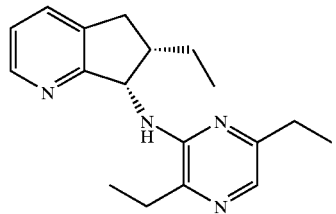

Following the procedure for the preparation of (1R,2S)-1-[(3,6-diethylpyrazin-2-yl)amino]-2,3-dihydro-1H-inden-2-ol but substituting 6-ethyl-6,7-dihydro-5H-cyclopenta[b]pyridin-7-amine and making non-critical variations provided the title compound as a oil: $^1$H NMR (400 MHz, CDCl$_3$) δ) 8.43, 7.68, 7.59, 7.16, 5.44, 5.19, 3.12–3.02, 2.82–2.63, 1.43–1.25, 0.88; HRMS (FAB) calcd for C$_{18}$H$_{24}$N$_4$+H 297.2079, found 297.2080.

Preparation 104

Preparation of N-(3,6-diethylpyrazin-2-yl)-6-ethyl-6,7-dihydro-5H-cyclopenta[b]pyridin-7-amine

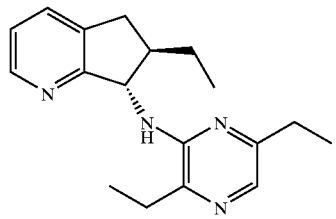

Following the procedure for the preparation of (1R,2S)-1-[(3,6-diethylpyrazin-2-yl)amino]-2,3-dihydro-1H-inden-2-ol but substituting 6-ethyl-6,7-dihydro-5H-cyclopenta[b]pyridin-7-amine and making non-critical variations provided the title compound as a oil: $^1$H NMR (400 MHz, CDCl$_3$) δ) 8.41, 7.66, 7.58, 7.15, 5.53, 4.89, 3.15, 2.71–2.57, 2.31, 2.01, 1.99, 1.65, 1.34, 1.22, 1.04; HRMS (FAB) calcd for C$_{18}$H$_{24}$N$_4$+H 297.2079, found 297.2080.

Preparation 105

Preparation of N-(5-bromo-3,6-diethylpyrazin-2-yl)-6-ethyl-6,7-dihydro-5H-cyclopenta[b]pyridin-7-amine

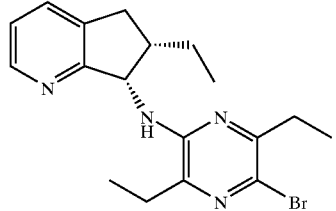

Following the procedure for the preparation of (1R,2S)-1-[(5-bromo-3,6-diethylpyrazin-2-yl)amino]-2,3-dihydro-1H-inden-2-ol but substituting N-(3,6-diethylpyrazin-2-yl)-

6-ethyl-6,7-dihydro-5H-cyclopenta[b]pyridin-7-amine and making non-critical variations provided the title compound as a oil: $^1$H NMR (400 MHz, CDCl$_3$) δ) 8.43, 7.62, 7.19, 5.37, 5.28, 3.11, 3.08, 2.87–2.69, 1.41–1.26, 0.86; HRMS (FAB) calcd for C$_{18}$H$_{23}$BrN$_4$+H 375.1185, found 375.1189.

Preparation 106

Preparation of N-(5-bromo-3,6-diethylpyrazin-2-yl)-6-ethyl-6,7-dihydro-5H-cyclopenta[b]pyridin-7-amine

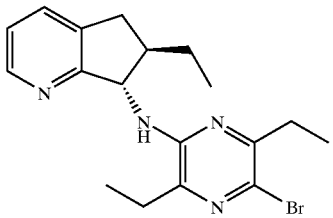

Following the procedure for the preparation of (1R,2S)-1-[(5-bromo-3,6-diethylpyrazin-2-yl)amino]-2,3-dihydro-1H-inden-2-ol but substituting N-(3,6-diethylpyrazin-2-yl)-6-ethyl-6,7-dihydro-5H-cyclopenta[b]pyridin-7-amine and making non-critical variations provided the title compound as a oil: $^1$H NMR (400 MHz, CDCl$_3$) δ) 8.37, 7.78, 7.31, 5.42–5.25, 3.28, 2.75–2.48, 1.96, 1.62, 1.34, 1.05; HRMS (FAB) calcd for C$_{18}$H$_{23}$BrN$_4$+H 375.1185, found 375.1193.

Example 70

Preparation of N-[5-(2-chloro-4-methoxyphenyl)-3,6-diethylpyrazin-2-yl]-6-ethyl-6,7-dihydro-5H-cyclopenta[b]pyridin-7-amine

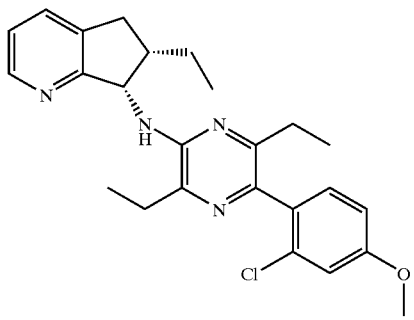

Following the procedure for the preparation of (1R,2S)-1-{[5-(2,4-dichlorophenyl)-3,6-diethylpyrazin-2-yl]amino}-2,3-dihydro-1H-inden-2-ol but substituting N-(5-bromo-3,6-diethylpyrazin-2-yl)-6-ethyl-6,7-dihydro-5H-cyclopenta[b]pyridin-7-amine and, tris(2-chloro-4-methoxyphenyl)boroxin, and making non-critical variations provided the title compound as a oil: $^1$H NMR (400 MHz, CDCl$_3$) δ) 8.45, 7.61, 7.28, 7.19, 7.03, 6.90, 5.50, 5.31, 3.85, 3.14, 3.06, 2.87–2.78, 2.51, 1.52, 1.34, 1.17, 0.97–0.87; HRMS (FAB) calcd for C$_{25}$H$_{29}$ClN$_4$O+H 437.2108, found 437.2103.

Example 71

Preparation of N-[5-(2-chloro-4-methoxyphenyl)-3,6-diethylpyrazin-2-yl]-6-ethyl-6,7-dihydro-5H-cyclopenta[b]pyridin-7-amine

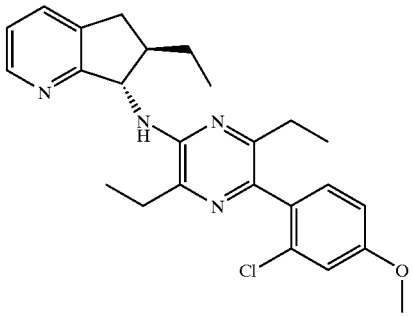

Following the procedure for the preparation of (1R,2S)-1-{[5-(2,4-dichlorophenyl)-3,6-diethylpyrazin-2-yl]amino}-2,3-dihydro-1H-inden-2-ol but substituting N-(5-bromo-3,6-diethylpyrazin-2-yl)-6-ethyl-6,7-dihydro-5H-cyclopenta[b]pyridin-7-amine and, tris(2-chloro-4-methoxyphenyl)boroxin, and making non-critical variations provided the title compound as a oil: $^1$H NMR (400 MHz, CDCl$_3$) δ) 8.43, 7.60, 7.19, 7.01, 6.89, 5.59, 5.08, 3.85, 3.20, 2.77, 2.66, 2.44, 2.06, 1.69, 1.33, 1.07; IR (diffuse reflectance) 2961, 2354 (w), 2063 (w), 1947 (w), 1906 (w), 1577 (s), 1550, 1519, 1491 (s), 1461, 1428 (s), 1397 (s), 1289, 1228, 1196, cm$^{-1}$ HRMS (FAB) calcd for C$_{25}$H$_{29}$ClN$_4$O+H 437.2108, found 437.2109.

Preparation 107

Preparation of (+/−)-2-ethyl-2,3-dihydro-1H-inden-1-one

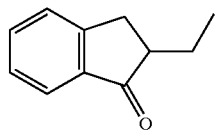

Following the procedure for the preparation of 5-propyl-6,7-dihydro-1-benzothiophen-4(5H)-one but substituting 1-tetralone and ethyl iodide, and making non-critical variations provided the title compound as a colorless mobile oil. IR (liq.) 2963, 2933, 2875, 2860, 1712, 1610, 1588, 1475, 1464, 1327, 1296, 1278, 1205, 749, 718 cm$^{-1}$; MS (EI) m/z 160 (M$^+$); Anal. Calcd for C$_{11}$H$_{12}$O: C, 82.46; H, 7.55. Found: C, 82.16; H, 7.57.

Preparation 108

Preparation of 2-ethyl-2,3-dihydro-1H-inden-1-one oxime

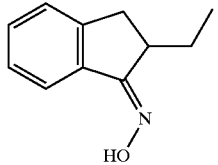

Following the procedure for the preparation of (4E)-2,3-dihydro-4H-chromen-4-one oxime but substituting (+/−)-2-ethyl-2,3-dihydro-1H-inden-1-one and making non-critical variations provided the title compound as a colorless syrup. MS (ESI+) for m/z 176.1 (M+H)$^+$.

Preparation 109

Preparation of 2-ethylindan-1-amine

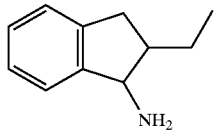

Following the procedure for the preparation of 6,7-dihydro-5H-cyclopenta[b]pyridin-5-amine but substituting 2-ethyl-2,3-dihydro-1H-inden-1-one oxime and making non-critical variations provided the title compound as a colorless oil.

Preparation 110

Preparation of 3,6-diethyl-N-(2-ethyl-2,3-dihydro-1H-inden-1-yl)pyrazin-2-amine

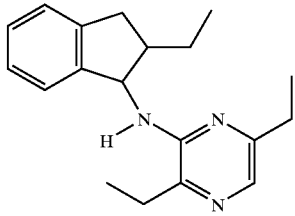

Following the procedure for the preparation of (1R,2S)-1-[(3,6-diethylpyrazin-2-yl)amino]-2,3-dihydro-1H-inden-2-ol but substituting 2-ethylindan-1-amine and making non-critical variations provided the title compound as a yellow oil. MS (ESI+) for m/z 296.2 (M+H)$^+$.

Preparation 111 and 112

Preparation of (+/−)-5-bromo-3,6-diethyl-N-[cis-2-ethyl-2,3-dihydro-1H-inden-1-yl]pyrazin-2-amine and (+/−)-5-bromo-3,6-diethyl-N-[trans-2-ethyl-2,3-dihydro-1H-inden-1-yl]pyrazin-2-amine

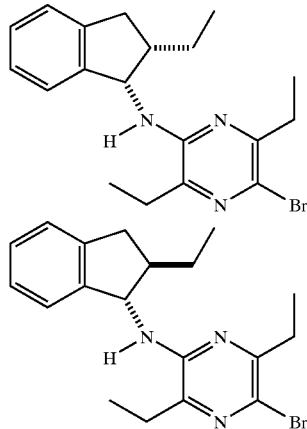

Following the procedure for the preparation of (1R,2S)-1-[(5-bromo-3,6-diethylpyrazin-2-yl)amino]-2,3-dihydro-1H-inden-2-ol but substituting 3,6-diethyl-N-(2-ethyl-2,3-dihydro-1H-inden-1-yl)pyrazin-2-amine and making non-critical variations provided the title compounds. Analytical data for (+/−)-5-bromo-3,6-diethyl-N-[cis-2-ethyl-2,3-dihydro-1H-inden-1-yl]pyrazin-2-amine: IR (liq.) 3435, 2967, 2935, 2874, 1560, 1539, 1479, 1460, 1446, 1416, 1390, 1243, 1177, 751, 731 cm$^{-1}$; MS (EI) m/z 373 (M$^+$); Anal. Calcd for C$_{19}$H$_{24}$BrN$_3$: C, 60.97; H, 6.46; N, 11.23. Found: C, 61.01; H, 6.53; N, 11.22. Analytical data for (+/−)-5-bromo-3,6-diethyl-N-[trans-2-ethyl-2,3-dihydro-1H-inden-1-yl]pyrazin-2-amine: IR (liq.) 2967, 2935, 2874, 2856, 1561, 1537, 1478, 1460, 1447, 1416, 1388, 1186, 1176, 1164, 746 cm$^{-1}$; OAMS supporting ions at: ESI+ 373.8; MS (EI) m/z 373 (M$^+$); Anal. Calcd for C$_{19}$H$_{24}$BrN$_3$: C, 60.97; H, 6.46; N, 11.23. Found: C, 60.97; H, 6.51; N, 11.16.

Example 72

Preparation of (+/−)-5-(2,4-dichlorophenyl)-3,6-diethyl-N-[cis-2-ethyl-2,3-dihydro-1H-inden-1-yl]pyrazin-2-amine

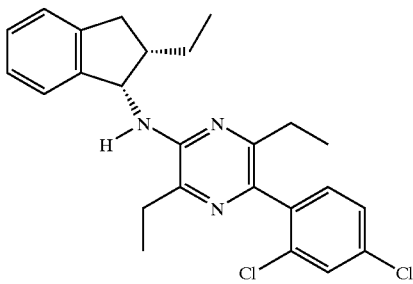

Following the procedure for the preparation of (1R,2S)-1-{[5-(2,4-dichlorophenyl)-3,6-diethylpyrazin-2-yl]amino}-2,3-dihydro-1H-inden-2-ol but substituting (+/−)-5-bromo-3,6-diethyl-N-[cis-2-ethyl-2,3-dihydro-1H-inden-1-yl]pyrazin-2-amine and making non-critical variations provided the title compound as a light yellow semi-solid. IR (liq.) 3452, 2965, 2934, 2874, 1589, 1566, 1551, 1495, 1470, 1392, 1377, 1203, 1175, 1101, 752 cm⁻¹; OAMS supporting ions at: ESI+ 439.8; HRMS (FAB) calcd for $C_{25}H_{27}CL_2N_3+H_1$ 440.1660, found 440.1648. Anal. Calcd for $C_{25}H_{27}Cl_2N_3$: C, 68.18; H, 6.18; N, 9.54. Found: C, 68.33; H, 6.36; N, 9.30.

Example 73

Preparation of (+/−)-5-(2,4-dichlorophenyl)-3,6-diethyl-N-[trans-2-ethyl-2,3-dihydro-1H-inden-1-yl]pyrazin-2-amine

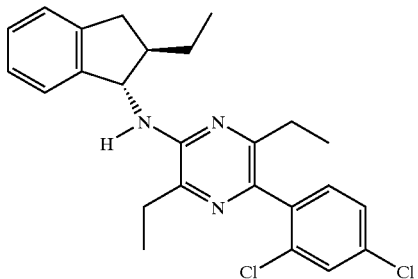

Following the procedure for the preparation of (1R,2S)-1-{[5-(2,4-dichlorophenyl)-3,6-diethylpyrazin-2-yl]amino}-2,3-dihydro-1H-inden-2-ol but substituting (+/−)-5-bromo-3,6-diethyl-N-[trans-2-ethyl-2,3-dihydro-1H-inden-1-yl]pyrazin-2-amine and making non-critical variations provided the title compound as a light yellow semi-solid. IR (liq.) 3443, 2965, 2934, 2874, 1588, 1566, 1551, 1497, 1470, 1390, 1203, 1186, 1173, 1101, 747 cm⁻¹; OAMS supporting ions at: ESI+ 440.0; MS (EI) m/z 439 (M⁺); Anal. Calcd for $C_{25}H_{27}Cl_2N_3$: C, 68.18; H, 6.18; N, 9.54. Found: C, 68.11; H, 6.17; N, 9.29.

Preparation 113

Preparation of benzyl 6-oxa-3-azabicyclo[3.1.0]hexane-3-carboxylate

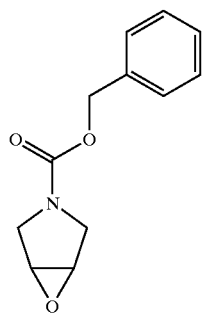

To a solution of the olefin (10.0 g, 49 mmol) in CH₂Cl₂ (250 ml, 0.2M) was added MCPBA (22 g, 2.0 eq.). The reaction was stirred for 48 h and 200 ml of saturated sodium thiosulfate was added. After 20 min, the layers were separated and the organic layer was washed with 2N NaOH (2×100 ml). The organic layer was dried MgSO₄, filtered and concentrated to provide the title compound as an oil (10.79 g, 99%): 1H NMR (300 MHz, CDCl3) δ 7.35, 5.13, 3.93–3.84, 3.71, 3.43–3.38; IR (liq.) 2209 (w), 2068 (w), 1958 (w), 1706 (s), 1455, 1448, 1428 (s), 1397 (s), 1364, 1327 (s), 1214, 1206, 1107 (s), 848 (s), 699, cm⁻¹ Anal. Calcd for $C_{12}H_{13}NO_3$: C, 65.74; H, 5.98; N, 6.39. Found: C, 65.45; H, 6.07; N, 5.99.

Preparation 114

Preparation of benzyl (trans)-3-amino-4-hydroxypyrrolidine-1-carboxylate

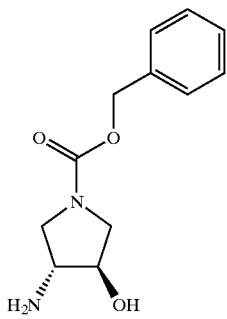

benzyl 6-oxa-3-azabicyclo[3.1.0]hexane-3-carboxylate (10.5 g) was stirred in 200 ml of saturated ammonium hydroxide at 35° C. for 40 h. The reaction mixture was poured into 100 ml of 2 N NaOH, extracted methylene chloride (4×200 ml), dried MgSO₄, filtered and concentrated to provide the title compound as an oil (10.15 g, 95%): ¹H NMR (300 MHz, CDCl₃) δ 7.34, 5.14, 3.99, 3.78, 3.37, 3.19, 1.77; HRMS (FAB) calcd for $C_{12}H_{16}N_2O_3$+H 237.1239, found 237.1244.

Preparation 115

Preparation of benzyl (trans)-3-[(3,6-diethylpyrazin-2-yl)amino]-4-hydroxypyrrolidine-1-carboxylate

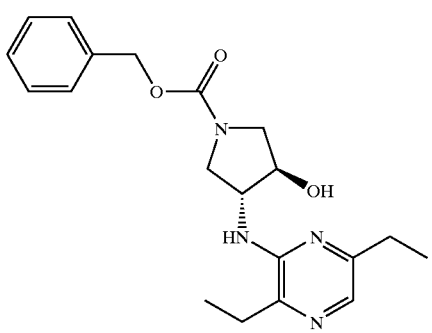

Following the procedure for the preparation of benzyl (3R,4S)-3-[(3,6-diethylpyrazin-2-yl)amino]-4-hydroxypyrrolidine-1-carboxylate but substituting benzyl (trans)-3-amino-4-hydroxypyrrolidine-1-carboxylate and making non-critical variations provided the title compound as a oil: ¹H NMR (300 MHz, CDCl₃) δ) 7.78, 7.39, 6.41, 6.22, 5.18, 4.51–3.95, 3.40, 2.65, 1.31–1.26; (MS/CI) calcd for $C_{20}H_{26}N_4O_3$+H 371.4, found 370.9.

Preparation 116

Preparation of benzyl (trans)-3-[(5-bromo-3,6-diethylpyrazin-2-yl)amino]-4-hydroxypyrrolidine-1-carboxylate

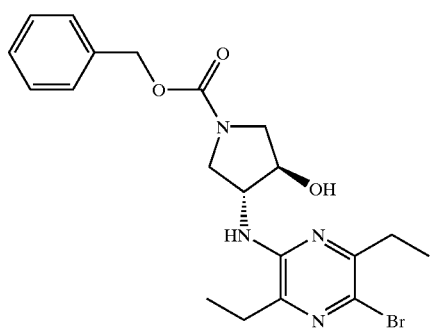

Following the procedure for the preparation of (1R,2S)-1-[(5-bromo-3,6-diethylpyrazin-2-yl)amino]-2,3-dihydro-1H-inden-2-ol but substituting benzyl (trans)-3-[(3,6-diethylpyrazin-2-yl)amino]-4-hydroxypyrrolidine-1-carboxylate and making non-critical variations provided the title compound as a oil: 1H NMR (300 MHz, CDCl3) δ) 7.38, 5.17, 4.48. 4.38, 4.28, 4.12, 3.91, 3.42, 2.86–2.78, 2.58, 1.32–1.24; HRMS (FAB) calcd for $C_{20}H_{25}BrN_4O_3+H$ 449.1189, found 449.1175.

Preparation 117

Preparation of benzyl (trans)-3-{[5-(2,4-dichlorophenyl)-3,6-diethylpyrazin-2-yl]amino}-4-hydroxypyrrolidine-1-carboxylate

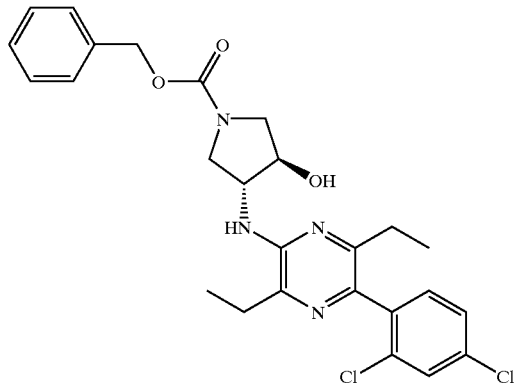

Following the procedure for the preparation of (1R,2S)-1-{[5-(2,4-dichlorophenyl)-3,6-diethylpyrazin-2-yl]amino}-2,3-dihydro-1H-inden-2-ol but substituting benzyl (trans)-3-[(5-bromo-3,6-diethylpyrazin-2-yl)amino]-4-hydroxypyrrolidine-1-carboxylate and making non-critical variations provided the title compound as a oil: $^1$H NMR (300 MHz, CDCl$_3$) δ) 7.49–7.11, 5.97, 5.17, 4.78, 4.67, 4.33–4.26, 4.16–3.96, 3.46, 2.69, 2.49, 1.46–1.24, 1.14; HRMS (FAB) calcd for $C_{26}H_{28}Cl_2N_4O_3+H$ 515.1616, found 515.1606.

Preparation 118

Preparation of benzyl (cis)-3-{[5-(2,4-dichlorophenyl)-3,6-diethylpyrazin-2-yl]amino}-4-[(4-nitrobenzoyl)oxy]pyrrolidine-1-carboxylate

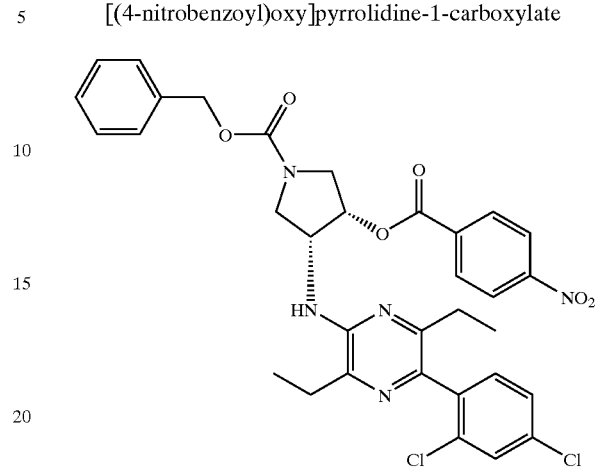

To a solution of benzyl (trans)-3-{[5-(2,4-dichlorophenyl)-3,6-diethylpyrazin-2-yl]amino}-4-hydroxypyrrolidine-1-carboxylate (2.93 g) in tetrahydrofuran (100 ml) was added p-nitrobenzoic acid (1.89 g), triphenyl phosphine (2.23 g) and di-tert-butyl azodicarboxylate (1.95 g). The reaction mixture was heated at 40° C. for 18 h and was poured into saturated sodium bicarbonate (200 ml). The aqueous layer was extracted with ethyl acetate (2×200 ml), dried MgSO$_4$, filtered and concentrated. MPLC chromatography on a biotage 40 M column with 15–20% ethyl acetate/heptane provided the title compound as an oil (3.19 g, 84%): $^1$H NMR (400 MHz, CDCl$_3$) δ) 8.35, 8.20, 7.49–7.22, 6.23, 5.81, 5.32, 5.20, 5.05, 4.83, 4.27, 3.95–3.85, 3.51, 2.58–2.41, 1.63, 1.32–1.14; (MS/CI) calcd for $C_{33}H_{31}Cl_2N_5O_3+H$ 664.5, found 664.1.

Preparation 119 benzyl (cis)-3-{[5-(2,4-dichlorophenyl)-3,6-diethylpyrazin-2-yl]amino}-4-hydroxypyrrolidine-1-carboxylate

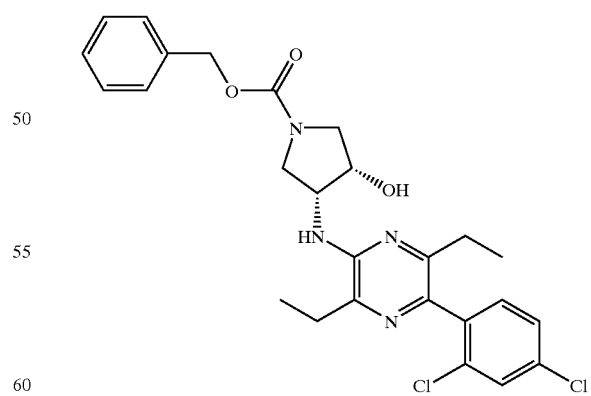

To a solution of benzyl (cis)-3-{[5-(2,4-dichlorophenyl)-3,6-diethylpyrazin-2-yl]amino}-4-[(4-nitrobenzoyl)oxy]pyrrolidine-1-carboxylate (3.17 g) in tetrahydofuran (38 ml) and methanol (3 ml) was added LiOH (1M$_{(aq)}$, 38 ml). The reaction mixture stirred 45 min and was poured into saturated sodium bicarbonate (100 ml). The aqueous layer was extracted ethyl acetate (2×200 ml), dried MgSO$_4$, filtered and concentrated. MPLC chromatography on a biotage 40M column with 20–60% ethyl acetate/heptane provided the title compound as an oil (1.225 g, 50%): $^1$H NMR (400 MHz, CDCl$_3$) δ) 7.50, 7.46–7.25, 5.18, 4.99, 4.89, 4.70, 4.51, 4.04, 3.75–3.59, 3.42–3.35, 2.70, 2.47, 2.19, 1.14; HRMS (FAB) calcd for C$_{26}$H$_{28}$Cl$_2$N$_4$O$_3$+H 515.1616, found 515.1641. Anal. Calcd for C$_{26}$H$_{28}$Cl$_2$N$_4$O$_3$: C, 60.59; H, 5.48; N, 10.87. Found: C, 60.32; H, 5.79; N, 10.54.

Example 74 benzyl (cis)-3-{[5-(2,4-dichlorophenyl)-3,6-diethylpyrazin-2-yl]amino}-4-ethoxypyrrolidine-1-carboxylate

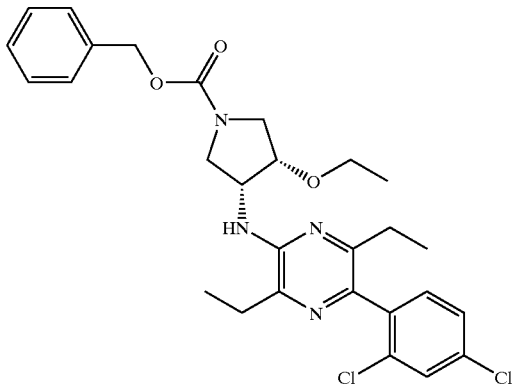

Following the procedure for the preparation of 5-(2,4-dichlorophenyl)-N-[(1R,2S)-2-ethoxy-2,3-dihydro-1H-inden-1-yl]-3,6-diethylpyrazin-2-amine but substituting benzyl (cis)-3-{[5-(2,4-dichlorophenyl)-3,6-diethylpyrazin-2-yl]amino}-4-hydroxypyrrolidine-1-carboxylate and making non-critical variations provided the title compound as an oil: $^1$H NMR (400 MHz, CDCl$_3$) δ) 7.49, 7.40–7.25, 5.20–5.13, 4.73, 4.10, 3.98, 3.77–3.59, 3.53–3.30, 2.70, 2.46, 1.27, 1.15; HRMS (FAB) calcd for C$_{28}$H$_{32}$Cl$_2$N$_4$O$_3$+H 543.1929, found 543.1913. Anal. Calcd for C$_{28}$H$_{32}$Cl$_2$N$_4$O$_3$: C, 61.88; H, 5.93; N, 10.31. Found: C, 62.07; H, 6.14; N, 10.16.

Example 75

5-(2,4-dichlorophenyl)-N-[(cis)-4-ethoxypyrrolidin-3-yl]-3,6-diethylpyrazin-2-amine

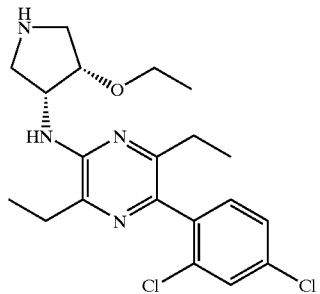

To a solution of benzyl (cis)-3-{[5-(2,4-dichlorophenyl)-3,6-diethylpyrazin-2-yl]amino}-4-ethoxypyrrolidine-1-carboxylate (900 mg) in methylene chloride (16.5 ml) was added palladium dichloride (30 mg) and triethylamine (0.229 ml). Triethyl silane was added (2×0.395 ml) over 2 h. The reaction mixture stirred 1 h and 2 ml of trifluoroacetic acid was added. After 30 min the reaction was basified with 2 N NaOH, extracted methylene chloride (3×100 ml), dried MgSO$_4$, filtered and concentrated. MPLC chromatography was run on a biotage 40S column with 3–5% methanol/methylene chloride with 0.5% ammonium hydroxide to provide the title compound as an oil (501 mg, 74%): $^1$H NMR (400 MHz, CDCl$_3$) δ) 7.49, 7.33–7.26, 5.38, 4.54, 4.07, 3.68, 3.52, 3.22, 2.95, 2.71, 2.46, 1.29, 1.15; HRMS (FAB) calcd for C$_{20}$H$_{26}$Cl$_2$N$_4$O+H 409.1562, found 409.1567. Anal. Calcd for C$_{20}$H$_{26}$Cl$_2$N$_4$O: C, 58.68; H, 6.40; N, 13.69. Found: C, 58.42; H, 6.43; N, 13.50.

Example 76

N-[(cis)-1-acetyl-4-ethoxypyrrolidin-3-yl]-5-(2,4-dichlorophenyl)-3,6-diethylpyrazin-2-amine

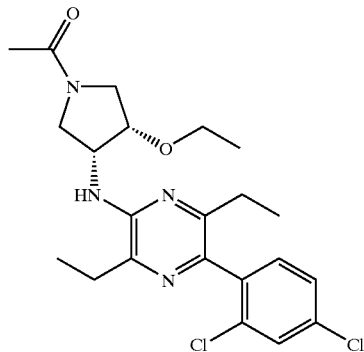

To a solution of 5-(2,4-dichlorophenyl)-N-[(cis)-4-ethoxypyrrolidin-3-yl]-3,6-diethylpyrazin-2-amine (105 mg) in methylene chloride (5 ml) under N$_2$ was added acetyl chloride (0.027 ml). The reaction mixture stirred for 30 min and was poured into saturated sodium bicarbonate (20 ml), extracted methylene chloride (2×20 ml), dried MgSO$_4$, filtered and concentrated. MPLC chromatography was run on a biotage 25 S column with 60% ethyl acetate/heptane to provide the title compound as an oil (79 mg, 69%): $^1$H NMR (400 MHz, CDCl$_3$) δ) 7.50, 7.34–7.26, 5.30, 5.12, 4.81, 4.19, 4.01, 3.87–3.67, 3.61–3.37, 2.72, 2.48, 1.33–1.26, 1.14; HRMS (FAB) calcd for C$_{22}$H$_{28}$Cl$_2$N$_4$O$_2$+H 451.1667, found 451.1667.

Example 77

5-(2,4-dichlorophenyl)-N-[(cis)-4-ethoxy-1-propionylpyrrolidin-3-yl]-3,6-diethylpyrazin-2-amine

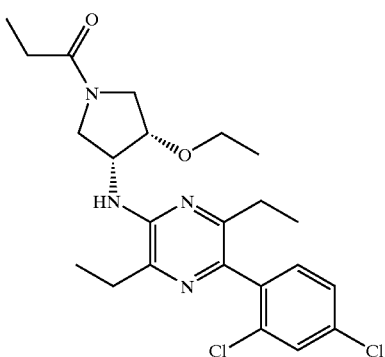

Following the procedure for the preparation of N-[(cis)-1-acetyl-4-ethoxypyrrolidin-3-yl]-5-(2,4-dichlorophenyl)-3, 6-diethylpyrazin-2-amine but substituting propionyl chloride and making non-critical variations provided the title compound as an oil: $^1$H NMR (400 MHz, DMSO) δ) 7.71, 7.50, 7.41, 6.00, 5.98, 4.68, 4.52, 4.22, 4.11, 3.85–3.39, 2.68, 2.37, 2.25, 1.24–0.85; HRMS (FAB) calcd for $C_{23}H_{30}Cl_2N_4O_2$+H 465.1824, found 465.1825.

Example 78

Preparation of methyl (cis)-3-{[5-(2,4-dichlorophenyl)-3,6-diethylpyrazin-2-yl]amino}-4-ethoxypyrrolidine-1-carboxylate

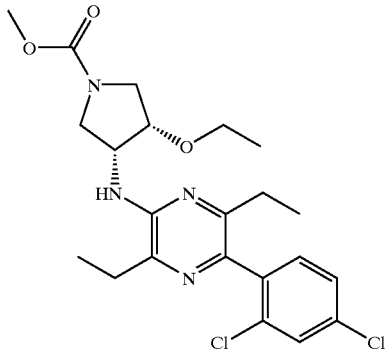

Following the procedure for the preparation of N-[(cis)-1-acetyl-4-ethoxypyrrolidin-3-yl]-5-(2,4-dichlorophenyl)-3,6-diethylpyrazin-2-amine but substituting methyl chloroformate and making non-critical variations provided the title compound as an oil:

$^1$H NMR (400 MHz, DMSO-d$_6$) δ) 7.72, 7.50, 7.41, 6.03, 4.59, 4.17, 3.69, 3.56–3.50, 3.39, 2.67, 2.37, 1.16, 1.09–1.02; HRMS (FAB) calcd for $C_{22}H_{28}Cl_2N_4O_3$+H 467.1617, found 467.1621.

Example 79

Preparation of 5-(2,4-dichlorophenyl)-N-[(cis)-4-ethoxy-1-(methylsulfonyl)pyrrolidin-3-yl]-3,6-diethylpyrazin-2-amine

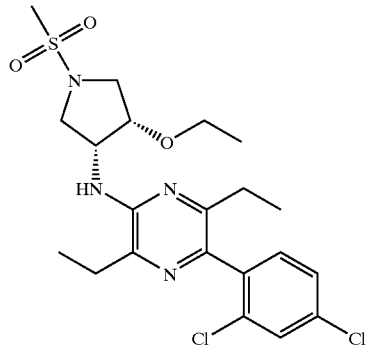

Following the procedure for the preparation of N-[(cis)-1-acetyl-4-ethoxypyrrolidin-3-yl]-5-(2,4-dichlorophenyl)-3,6-diethylpyrazin-2-amine but substituting methanesulfonyl chloride and making non-critical variations provided the title compound as an oil:

$^1$H NMR (400 MHz, DMSO-d$_6$) δ) 7.72, 7.51, 7.42, 6.05, 4.62, 4.18, 3.66–3.57, 3.49, 3.38, 2.92, 2.69, 2.38, 1.18, 1.10–1.05; HRMS (FAB) calcd for $C_{21}H_{28}Cl_2N_4O_3S$+H 487.1337, found 487.1328.

Example 80

Preparation of ethyl (cis)-3-{[5-(2,4-dichlorophenyl)-3,6-diethylpyrazin-2-yl]amino}-4-ethoxypyrrolidine-1-carboxylate

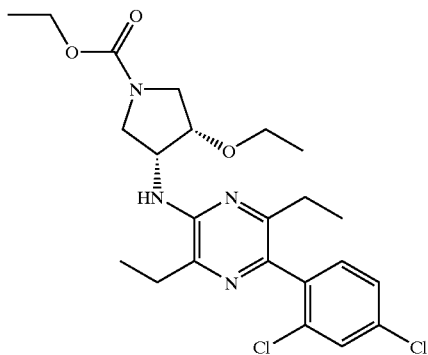

Following the procedure for the preparation of N-[(cis)-1-acetyl-4-ethoxypyrrolidin-3-yl]-5-(2,4-dichlorophenyl)-3,6-diethylpyrazin-2-amine but substituting ethyl chloroformate and making non-critical variations provided the title compound as an oil:

$^1$H NMR (400 MHz, DMSO-d$_6$) δ) 7.72, 7.50, 7.41, 6.04, 4.59, 4.16, 4.04, 3.70, 3.56–3.39, 2.67, 2.35, 1.21–1.02; HRMS (FAB) calcd for $C_{23}H_{30}Cl_2N_4O_3$+H 481.1773, found 481.1772. Anal. Calcd for $C_{23}H_{30}Cl_2N_4O_3$: C, 57.38; H, 6.28; N, 11.64. Found: C, 57.71; H, 6.55; N, 11.44.

Example 81

Preparation of (cis)-3-{[5-(2,4-dichlorophenyl)-3,6-diethylpyrazin-2-yl]amino}-4-ethoxy-N,N-dimethylpyrrolidine-1-carboxamide

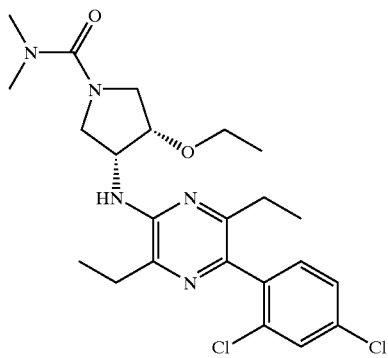

Following the procedure for the preparation of N-[(cis)-1-acetyl-4-ethoxypyrrolidin-3-yl]-5-(2,4-dichlorophenyl)-3,6-diethylpyrazin-2-amine but substituting dimethylcarbamyl chloride and making non-critical variations provided the title compound as an oil:

$^1$H NMR (400 MHz, DMSO-d$_6$) δ) 7.72, 7.50, 7.41, 5.98, 4.52, 4.12, 4.00, 3.61–3.39, 2.74, 2.68, 2.37, 1.23–1.05; HRMS (FAB) calcd for $C_{23}H_{31}Cl_2N_5O_2$+H 480.1933, found 480.1927.

Example 82

Preparation of (cis)-3-{[5-(2,4-dichlorophenyl)-3,6-diethylpyrazin-2-yl]amino}-4-ethoxy-N,N-dimethylpyrrolidine-1-carbothioamide

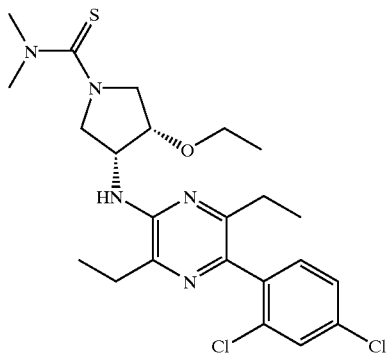

Following the procedure for the preparation of N-[(cis)-1-acetyl-4-ethoxypyrrolidin-3-yl]-5-(2,4-dichlorophenyl)-3,6-diethylpyrazin-2-amine but substituting dimethylthiocarbamyl chloride and making non-critical variations provided the title compound as an oil: $^1$H NMR (400 MHz, CDCl$_3$) δ) 7.50, 7.34–7.25, 5.23, 4.78, 4.11, 3.97, 3.83, 3.74, 3.56–3.45, 2.71, 2.46, 1.33–1.25, 1.14; HRMS (FAB) calcd for C$_{23}$H$_{31}$Cl$_2$N$_5$OS+H 496.1704, found 496.1691.

Example 83

Preparation of isopropyl (cis)-3-{[5-(2,4-dichlorophenyl)-3,6-diethylpyrazin-2-yl]amino}-4-ethoxypyrrolidine-1-carboxylate

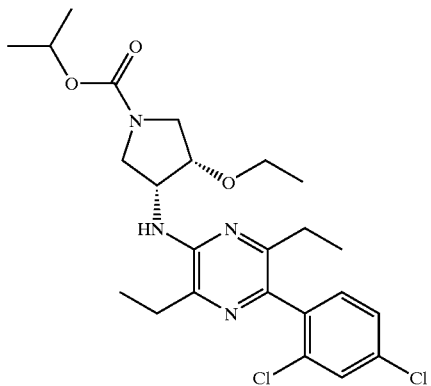

Following the procedure for the preparation of N-[(cis)-1-acetyl-4-ethoxypyrrolidin-3-yl]-5-(2,4-dichlorophenyl)-3,6-diethylpyrazin-2-amine but substituting isopropyl chloroformate and making non-critical variations provided the title compound as an oil: $^1$H NMR (400 MHz, CDCl$_3$) δ) 7.49, 7.34–7.26, 5.22, 4.95, 4.75, 4.08, 3.96, 3.73, 3.60, 3.50, 3.38, 3.25, 2.71, 2.47, 1.32–1.25, 1.16; HRMS (FAB) calcd for C$_{24}$H$_{32}$Cl$_2$N$_4$O$_3$+H 495.1929, found 495.1909. Anal. Calcd for C$_{24}$H$_{32}$Cl$_2$N$_4$O$_3$: C, 58.18; H, 6.51; N, 11.31. Found: C, 58.43; H, 6.64; N, 11.25.

Example 84

Preparation of (cis)-3-{[5-(2,4-dichlorophenyl)-3,6-diethylpyrazin-2-yl]amino}-4-ethoxy-N-methylpyrrolidine-1-carbothioamide

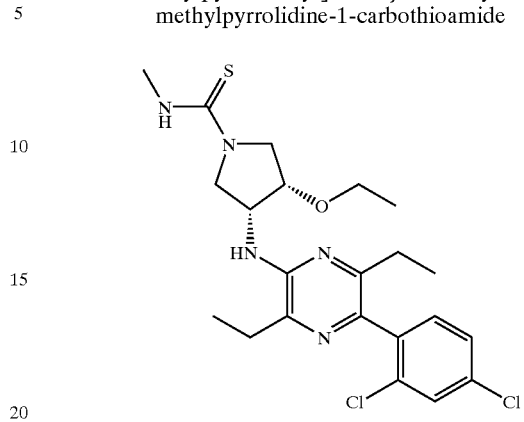

Following the procedure for the preparation of N-[(cis)-1-acetyl-4-ethoxypyrrolidin-3-yl]-5-(2,4-dichlorophenyl)-3,6-diethylpyrazin-2-amine but substituting methyl thiocyanate and making non-critical variations provided the title compound as an oil: $^1$H NMR (400 MHz, CDCl$_3$) δ) 7.50, 7.35–7.25, 5.31, 4.87, 4.15–4.05, 3.88, 3.76, 3.51, 3.40, 2.70, 2.47, 1.32–1.25, 1.15; IR (diffuse reflectance) 2970, 2933, 2351 (w), 2338 (w), 1549 (s), 1536 (s), 1498 (s), 1467 (s), 1392 (s), 1353 (s), 1200, 1122, 1101, 1058, 1048, cm$^{-1}$HRMS (FAB) calcd for C$_{22}$H$_{29}$Cl$_2$N$_5$OS+H 482.1548, found 482.1559.

Example 85

Preparation of 5-(2,4-dichlorophenyl)-N-[(cis)-4-ethoxy-1-(morpholin-4-ylcarbonyl)pyrrolidin-3-yl]-3,6-diethylpyrazin-2-amine

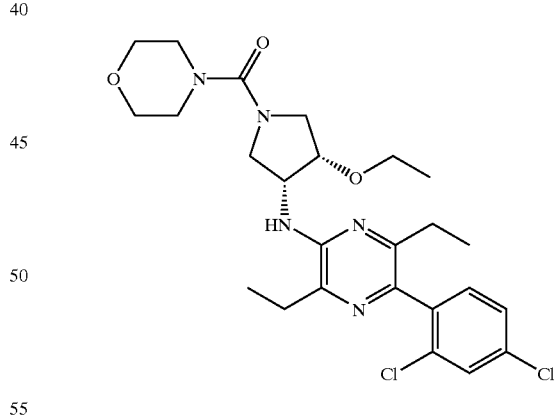

Following the procedure for the preparation of N-[(cis)-1-acetyl-4-ethoxypyrrolidin-3-yl]-5-(2,4-dichlorophenyl)-3,6-diethylpyrazin-2-amine but substituting 4-morpholinecarbonyl chloride and making non-critical variations provided the title compound as an oil: $^1$H NMR (400 MHz, CDCl$_3$) δ) 7.50, 7.34, 7.28, 5.23, 4.69, 4.10, 3.90, 3.80–3.68, 3.58–3.28, 2.70, 2.49, 1.33–1.26, 1.16; IR (liq.) 2970 (s), 2934 (s), 2874 (s), 2353 (w), 1996 (w), 1956 (w), 1642 (s), 1567 (s), 1552 (s), 1500 (s), 1469 (s), 1414 (s,b), 1397 (s), 1118 (s), 1102 (s), cm$^{-1}$HRMS (FAB) calcd for C$_{25}$H$_{33}$Cl$_2$N$_5$O$_3$+H 522.2039, found 522.2038.

Example 86

Preparation of 2-fluoroethyl (cis)-3-{[5-(2,4-dichlorophenyl)-3,6-diethylpyrazin-2-yl]amino}-4-ethoxypyrrolidine-1-carboxylate

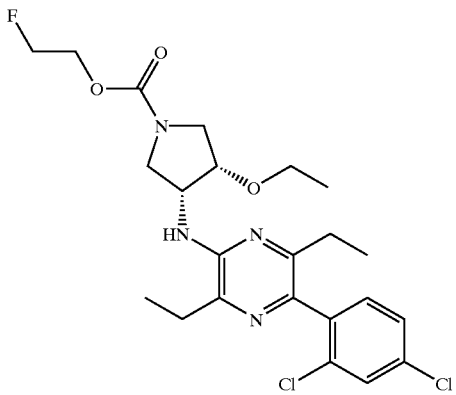

Following the procedure for the preparation of N-[(cis)-1-acetyl-4-ethoxypyrrolidin-3-yl]-5-(2,4-dichlorophenyl)-3,6-diethylpyrazin-2-amine but substituting 2-fluoroethyl chloroformate and making non-critical variations provided the title compound as an oil: $^1$H NMR (400 MHz, CDCl$_3$) δ) 7.49, 7.34–7.26, 5.21, 4.70–4.58, 4.56, 4.42, 4.34, 4.10, 3.99, 3.75–3.30, 2.71, 2.47, 1.32–1.26, 1.15; IR (liq.) 2973 (s), 2347 (b), 2181 (w), 1709 (s), 1567 (s), 1553 (s), 1500 (s), 1470 (s), 1445 (s), 1426 (s), 1396 (s), 1347 (s), 1140 (s), 1103 (s), 1060 (s), cm$^{-1}$HRMS (FAB) calcd for C$_{23}$H$_{29}$Cl$_2$FN$_4$O$_3$+H 499.1679, found 499.1673. Anal. Calcd for C$_{23}$H$_{29}$Cl$_2$FN$_4$O$_3$: C, 55.32; H, 5.85; N, 11.22. Found: C, 55.20; H, 5.91; N, 10.95.

Preparation 120

Preparation of benzyl (3R,4R)-3-(2lambda~5~-triaza-1,2-dienyl)-4-[(trimethylsilyl)oxy]pyrrolidine-1-carboxylate

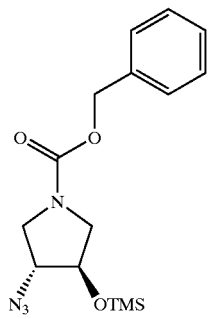

To benzyl 6-oxa-3-azabicyclo[3.1.0]hexane-3-carboxylate (10.4 g, 48 mmole) was added TMSN$_3$ (6.65 ml, 1.05 eq.) and 1S,2S-(−)-[1,2-cyclohexanediamino-N,N'-bis(3,5-di-t-butylsalicylidene)]chromium(III) chloride (STREM 24-0851) (904 mg, 0.03 eq.). The reaction was stirred for 18 h under N$_2$. The red oil was used as is in the next step. $^1$H NMR (400 MHz, CDCl$_3$) δ 7.18 (m, 5H), 4.98 (s, 2H), 3.99 (m, 1H), 3.69 (m, 1H), 3.61–3.51 (m, 2H), 3.31–3.05 (m, 2H).

Preparation 121

Preparation of benzyl (3R,4R)-3-amino-4-hydroxypyrrolidine-1-carboxylate

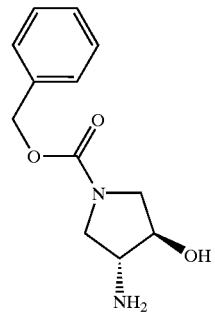

Benzyl (3R,4R)-3-(2lambda~5~-triaza-1,2-dienyl)-4-[(trimethylsilyl)oxy]pyrrolidine-1-carboxylate (23.6 g) in MeOH (250 ml, 0.3M) was treated with TFA (15 ul) for 1.5 hr. Lindlar's catalyst (10 g) was added under 1 atmosphere of H$_2$. It was stirred for 6 days. (Another batch of Lindlar's catalyst 5 g was added on the 4$^{th}$ day). The Pd catalyst was filtered through celite. The filtrate was concentrated, diluted with Et$_2$O (250 ml) and 1N HCl (250 ml). The separated 1 N HCl phase was basified with NaOH (solid) to pH 12. It was extracted with CH$_3$Cl:iPrOH (9:1 mixture 4×300 ml) and EtOAC (3×300 ml). It was dried (MgSO$_4$) and used as is. $^1$H NMR (CDCl$_3$) δ 3.22 (m, 1H), 3.38 (m, 2H), 3.78 (m, 2H), 4.02 (m, 1H), 5.15 (s, 2H), 7.37 (m, 5H);

Preparation 122

Preparation of benzyl (3 R,4S)-3-amino-4-hydroxypyrrolidine-1-carboxylate

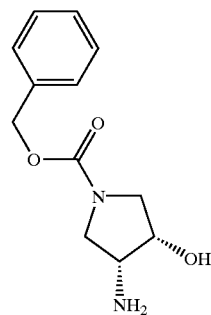

A 50 ml oven-dried r.b. flask was charged with benzyl (3R,4R)-3-amino-4-hydroxypyrrolidine-1-carboxylate (4.235 g, 17.93 mmol) and dissolved in 60 ml of THF. Trifluoroacetic anhydride (2.54 ml, 17.93 mmol) and TEA (3 ml, 21.52 mmol) were added sequentially at 0° C. The rxn was allowed to warm to r.t., and stirred for O/N. The reaction was diluted with H$_2$O (250 ml), extracted with 250 ml (CHCl$_3$:iPrOH 9:1 mixture, ×4), dried (MgSO$_4$), filtered, concentrated in vacuo.

This crude trifluoroamide product (confirmed by LC-MS) was dissolved in 90 ml of CH$_2$Cl$_2$ (0.2M) and cooled to 0° C. under N$_2$ followed by addition of TEA (21.52 mmol, 3 ml) and MsCl (1.63 ml, 19.72 mmol). The reaction was stirred for 15 min at 0° C. and 1 hr at r.t followed by addition of DBU (5.39 ml, 53.79 mmol) with subsequent stirring overnight. The reaction mixture was filtered through silica and washed with (80% EtOAc in Heptane,) 800 ml. The filtrate was collected and concentrated.

The oxazoline was hydrolyzed by addition of $K_2CO_3$ (14.87 g) in 80 ml MeOH/40 ml $H_2O$ for 18 hr. It was reduced in volume and extracted with (9:1 $CHCl_3$:iPrOH) 200 ml×5. The combined organic solvent was dried ($K_2CO_3$), filtered, concentrated, purified by biotage chromatography (1% to 5% MeOH in $CH_2Cl_2$, 0.5% $NH_4OH$) to give the title compound as a solid. $^1$H NMR ($CDCl_3$) δ 3.22 (m, 1H), 3.38 (m, 2H), 3.79 (m, 2H), 4.02 (m, 1H), 5.15 (s, 2H), 7.40 (m, 5H); IR (diffuse reflectance) 3374, 2949, 2316 (w), 1966 (w), 1947 (w), 1686 (s), 1450 (s), 1423 (s), 1354, 1321, 1144, 1096, 1084, 765, 695, $cm^{-1}$ HRMS (FAB) calcd for $C_{12}H_{16}N_2O_3$+H 237.1239, found 237.1236. Specific Rotation (25 C D)=−17 (c 0.97, chloroform).

Preparation 123

Preparation of benzyl (3R,4S)-3-[(3,6-diethylpyrazin-2-yl)amino]-4-hydroxypyrrolidine-1-carboxylate

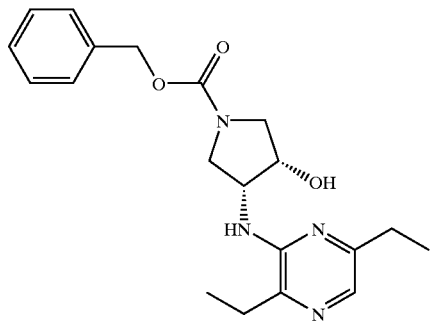

To an 250 ml r.b-flask was sequentially added benzyl (3R,4S)-3-amino-4-hydroxypyrrolidine-1-carboxylate (4.9714 g, 21.04 mmol), chloride (3.949 g, 23.15 mmol), $Pd_2(dba)_3$ (10 mol %, 1.926 g), 2-dicyclohexylphosphino-2'-(N,N-dimethyl amino)biphenyl (20 mol %, 1.656 g), and DME (110 ml). $Cs_2CO_3$ (9.57 g) was then added and the reaction mixture was stirred at 80° C. for 20 hr. It was cooled, diluted with $Et_2O$ (100 ml), poured into $NaHCO_3$ (80 ml), extracted with $CH_2Cl_2$ (150 ml×3), dried ($MgSO_4$), and concentrated. Purification via biotage chromatography (35% EtOAc in heptane) provided the title compound. $^1$H NMR ($CDCl_3$) δ 1.28 (m, 6H), 2.65 (m, 4H), 3.36 (m, 1H), 3.63 (m, 1H), 3.73 (m, 1H), 4.00 (m, 1H), 4.51 (m, 1H), 4.64 (m, 1H), 4.80 (m, 1H), 5.18 (s, 2H), 7.38 (m, 6H), 7.74 (d, 1H); IR (liq.) 2969, 2344 (w), 1996 (w), 1952 (w), 1703 (s), 1691 (s), 1546, 1499 (s), 1449 (s), 1426 (s), 1395, 1359 (s), 1175, 1133, 1095, $cm^{-1}$ HRMS (FAB) calcd for $C_{20}H_{26}N_4O_3$+H 371.2083, found 371.2089.

Preparation 124

Preparation of benzyl (3R,4S)-3-[(5-bromo-3,6-diethylpyrazin-2-yl)amino]-4-hydroxypyrrolidine-1-carboxylate

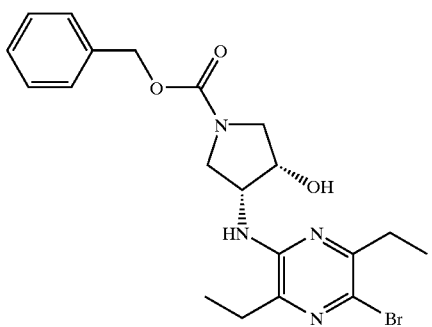

Following the procedure for the preparation of (1R,2S)-1-[(5-bromo-3,6-diethylpyrazin-2-yl)amino]-2,3-dihydro-1H-inden-2-ol but substituting benzyl (3R,4S)-3-[(3,6-diethylpyrazin-2-yl)amino]-4-hydroxypyrrolidine-1-carboxylate and making non-critical variations provided the title compound as a oil: $^1$H NMR (400 MHz, $CDCl_3$) δ) 7.38, 5.16, 4.91, 4.82, 4.59, 4.48, 4.59, 4.48, 4.01, 3.72–3.58, 3.36–3.25, 2.81, 2.69, 2.54, 2.46, 1.31–1.23.

Preparation 125

Preparation of benzyl (3R,4S)-3-{[5-(2,4-dichlorophenyl)-3,6-diethylpyrazin-2-yl]amino}-4-hydroxypyrrolidine-1-carboxylate

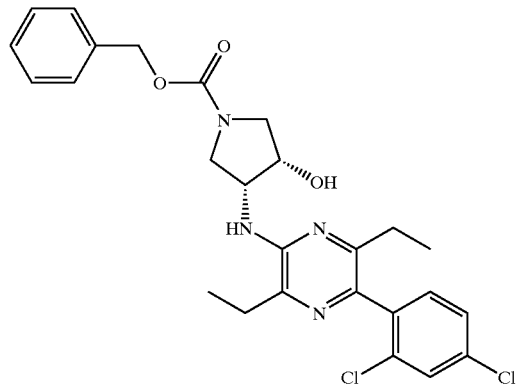

Following the procedure for the preparation of (1R,2S)-1-{[5-(2,4-dichlorophenyl)-3,6-diethylpyrazin-2-yl]amino}-2,3-dihydro-1H-inden-2-ol but substituting benzyl (3R,4S)-3-[(5-bromo-3,6-diethylpyrazin-2-yl)amino]-4-hydroxypyrrolidine-1-carboxylate and making non-critical variations provided the title compound as a oil: $^1$H NMR (400 MHz, $CDCl_3$) δ) 7.49, 7.39–7.25, 5.18, 4.99, 4.89, 4.71, 4.55, 4.04, 3.75–3.58, 3.36, 2.69, 2.49, 1.30, 1.15; HRMS (FAB) calcd for $C_{26}H_{28}Cl_2N_4O_3$+H 515.1616, found 515.1641.

Example 87

Preparation of benzyl (3R,4S)-3-{[5-(2,4-dichlorophenyl)-3,6-diethylpyrazin-2-yl]amino}-4-ethoxypyrrolidine-1-carboxylate

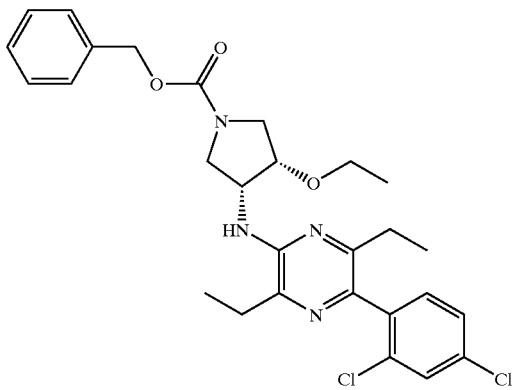

Following the procedure for the preparation of 5-(2,4-dichlorophenyl)-N-[(1R,2S)-2-ethoxy-2,3-dihydro-1H-inden-1-yl]-3,6-diethylpyrazin-2-amine but substituting benzyl (3R,4S)-3-{[5-(2,4-dichlorophenyl)-3,6-diethylpyrazin-2-yl]amino}-4-hydroxypyrrolidine-1-carboxylate and making non-critical variations provided the title compound as a oil: $^1$H NMR (400 MHz, CDCl$_3$) δ) 7.49, 7.40–7.25, 5.20–5.13, 4.76, 4.11, 3.98, 3.73–3.60, 3.51–3.31, 2.70, 2.47, 1.31–1.24, 1.15; IR (liq.) 2972, 2342 (w), 1948 (w), 1709 (s), 1567, 1552, 1498 (s), 1470 (s), 1449 (s), 1420 (s), 1397 (s), 1350, 1126, 1100 (s), 1080, cm$^{-1}$ HRMS (FAB) calcd for C$_{28}$H$_{32}$Cl$_2$N$_4$O$_3$+H 543.1929, found 543.1929. Anal. Calcd for C$_{28}$H$_{32}$Cl$_2$N$_4$O$_3$: C, 61.88; H, 5.93; N, 10.31. Found: C, 61.73; H, 6.08; N, 10.04.

Example 88

Preparation of 5-(2,4-dichlorophenyl)-N-[(3R,4S)-4-ethoxypyrrolidin-3-yl]-3,6-diethylpyrazin-2-amine

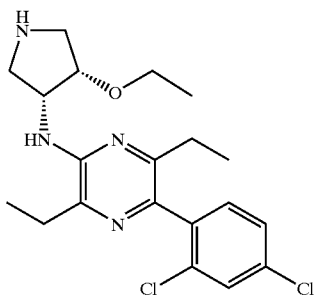

Following the procedure for the preparation of 5-(2,4-dichlorophenyl)-N-[(cis)-4-ethoxypyrrolidin-3-yl]-3,6-diethylpyrazin-2-amine but substituting benzyl (3R,4S)-3-{[5-(2,4-dichlorophenyl)-3,6-diethylpyrazin-2-yl]amino}-4-ethoxypyrrolidine-1-carboxylate and making non-critical variations provided the title compound as an oil: $^1$H NMR (400 MHz, CDCl$_3$) δ) 7.49, 7.33–7.26, 5.38, 4.54, 4.07, 3.68, 3.52, 3.22, 2.95, 2.71, 2.46, 1.29, 1.15; HRMS (FAB) calcd for C$_{20}$H$_{26}$Cl$_2$N$_4$O+H 409.1562, found 409.1567. Anal. Calcd for C$_{20}$H$_{26}$Cl$_2$N$_4$O: C, 58.68; H, 6.40; N, 13.69. Found: C, 58.42; H, 6.43; N, 13.50.

Example 89

Preparation of methyl (3R,4S)-3-{[5-(2,4-dichlorophenyl)-3,6-diethylpyrazin-2-yl]amino}-4-ethoxypyrrolidine-1-carboxylate

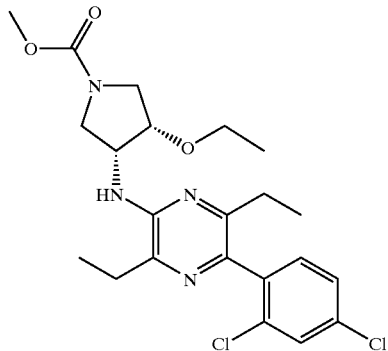

Following the procedure for the preparation of N-[(cis)-1-acetyl-4-ethoxypyrrolidin-3-yl]-5-(2,4-dichlorophenyl)-3,6-diethylpyrazin-2-amine but substituting 5-(2,4-dichlorophenyl)-N-[(3R,4S)-4-ethoxypyrrolidin-3-yl]-3,6-diethylpyrazin-2-amine and methyl chloroformate, and making non-critical variations provided the title compound as an oil: $^1$H NMR (400 MHz, CDCl$_3$) δ) 7.49, 7.34–7.26, 5.20, 4.73, 4.09, 3.95, 3.74, 3.60, 3.50, 3.39, 3.31, 3.26, 2.69, 2.47, 1.32–1.25, 1.15; IR (diffuse reflectance) 2971 (s), 2350 (w), 2341 (w), 2063 (w), 1940 (w), 1921 (w), 1710 (s), 1568, 1551, 1499, 1466 (s), 1452 (s), 1392 (s), 1373, 1102, cm$^{-1}$; HRMS (FAB) calcd for C$_{22}$H$_{28}$Cl$_2$N$_4$O$_3$+H 467.1617, found 467.1619. Anal. Calcd for C$_{22}$H$_{28}$Cl$_2$N$_4$O$_3$: C, 56.54; H, 6.04; N, 11.99. Found: C, 56.64; H, 6.27; N, 11.92.

Example 90

Preparation of benzyl (3R,4S)-3-{[5-(2,4-dichlorophenyl)-3,6-diethylpyrazin-2-yl]amino}-4-(2-fluoroethoxy)pyrrolidine-1-carboxylate

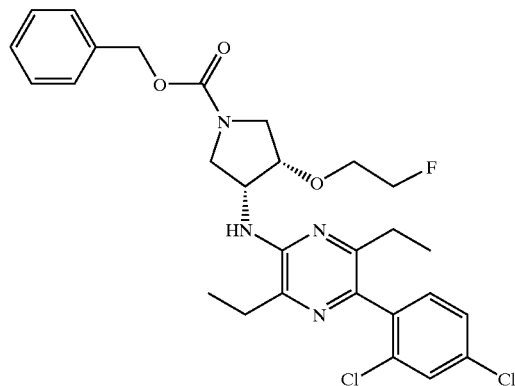

Following the procedure for the preparation of 5-(2,4-dichlorophenyl)-N-[(1R,2S)-2-ethoxy-2,3-dihydro-1H-inden-1-yl]-3,6-diethylpyrazin-2-amine but substituting benzyl (3R,4S)-3-{[5-(2,4-dichlorophenyl)-3,6-diethylpyrazin-2-yl]amino}-4-hydroxypyrrolidine-1-carboxylate and 2-fluoro-1-bromo ethane, and making non-critical variations provided the title compound as a oil: $^1$H NMR (400 MHz, CDCl$_3$) δ) 7.49, 7.41–7.25, 5.18, 4.81, 4.67, 4.55, 4.17, 4.06, 3.80–3.62, 3.39–3.29, 2.69, 2.47, 1.28, 1.15; IR (diffuse reflectance) 2971, 2386 (w), 2350 (w), 2338 (w), 2039 (w), 2014 (w), 1710 (s), 1699 (s,b), 1569, 1499, 1467 (s), 1450, 1428, 1420, 1397, cm$^{-1}$; HRMS (FAB) calcd for $C_{28}H_{31}Cl_2FN_4O_3$+H 561.1835, found 561.1808.

Example 91

Preparation of 5-(2,4-dichlorophenyl)-3,6-diethyl-N-[(3R,4S)-4-(2-fluoroethoxy)pyrrolidin-3-yl]pyrazin-2-amine

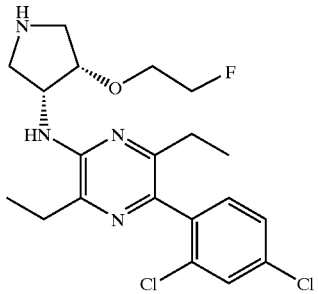

Following the procedure for the preparation of 5-(2,4-dichlorophenyl)-N-[(cis)-4-ethoxypyrrolidin-3-yl]-3,6-diethylpyrazin-2-amine but substituting benzyl (3R,4S)-3-{[5-(2,4-dichlorophenyl)-3,6-diethylpyrazin-2-yl]amino}-4-(2-fluoroethoxy)pyrrolidine-1-carboxylate and making non-critical variations provided the title compound as an oil: $^1$H NMR (400 MHz, CDCl$_3$) δ) 7.49, 7.35–7.26, 5.38, 4.68–4.53, 4.11, 3.88, 3.80, 3.74, 3.46, 3.24–3.16, 2.93, 2.70, 2.62, 2.29, 2.00, 1.33–1.24, 1.15; IR (liq.) 2971 (s), 2936 (s), 2874, 2359 (w), 2342 (w), 1566 (s), 1552 (s), 1500 (s), 1470 (s), 1396 (s), 1200 (s), 1129 (s), 1102 (s), 1046 (s), 868, cm$^{-1}$; HRMS (FAB) calcd for $C_{20}H_{25}Cl_2FN_4O$+H 427.1468, found 427.1474.

Example 92

Preparation of methyl (3R,4S)-3-{[5-(2,4-dichlorophenyl)-3,6-diethylpyrazin-2-yl]amino}-4-(2-fluoroethoxy)pyrrolidine-1-carboxylate

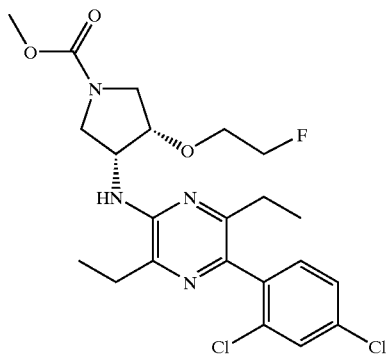

Following the procedure for the preparation of N-[(cis)-1-acetyl-4-ethoxypyrrolidin-3-yl]-5-(2,4-dichlorophenyl)-3,6-diethylpyrazin-2-amine but substituting 5-(2,4-dichlorophenyl)-3,6-diethyl-N-[(3R,4S)-4-(2-fluoroethoxy)pyrrolidin-3-yl]pyrazin-2-amine and methyl chloroformate, and making non-critical variations provided the title compound as an oil: $^1$H NMR (400 MHz, DMSO-d$_6$) δ) 7.71, 7.50, 7.41, 6.04, 4.61, 4.54, 4.42, 4.25, 3.78–3.70, 3.60, 3.54, 3.37, 2.65, 2.37, 1.15, 1.08; IR (diffuse reflectance) 2970, 2934, 2350 (w), 2341 (w), 2039 (w), 1940 (w), 1921 (w), 1710 (s), 1569, 1551, 1499, 1466 (s), 1452 (s), 1393 (s), 1373, cm$^{-1}$; HRMS (FAB) calcd for $C_{22}H_{27}Cl_2FN_4O_3$+H 485.1522, found 485.1541. Anal. Calcd for $C_{22}H_{27}Cl_2FN_4O_3$: C, 54.44; H, 5.61; N, 11.54. Found: C, 54.73; H, 5.76; N, 11.46.

Preparation 126

Preparation of benzyl (3R,4S)-3-[(3,6-diethylpyrazin-2-yl)amino]-4-(2-fluoroethoxy)pyrrolidine-1-carboxylate

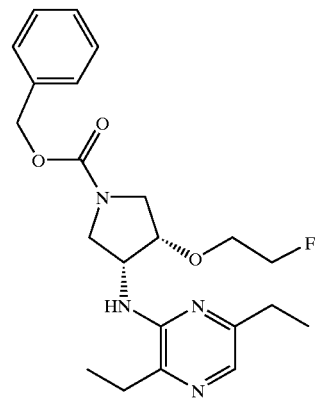

Following the procedure for the preparation of 5-(2,4-dichlorophenyl)-N-[(1R,2S)-2-ethoxy-2,3-dihydro-1H-inden-1-yl]-3,6-diethylpyrazin-2-amine but substituting benzyl (3R,4S)-3-[(3,6-diethylpyrazin-2-yl)amino]-4-hydroxypyrrolidine-1-carboxylate and 2-fluoro-1-bromo ethane, and making non-critical variations provided the title compound as a oil: $^1$H NMR (400 MHz, DMSO-d$_6$) δ) 7.61, 7.38–7.36, 5.85, 5.08, 4.52, 4.50, 4.38, 4.22, 3.75–3.40, 2.60, 2.53, 1.19–1.13; IR (liq.) 2970 (s), 2937 (s), 2340 (w), 2068 (w), 1996 (w), 1954 (w), 1705 (s), 1546 (s), 1499 (s), 1448 (s), 1422 (s), 1395 (s), 1351 (s), 1136 (s), 1107 (s), cm$^{-1}$; HRMS (FAB) calcd for $C_{22}H_{29}FN_4O_3$+H 417.2302, found 417.2299.

Preparation 127

Preparation of 3,6-diethyl-N-[(3R,4S)-4-(2-fluoroethoxy)pyrrolidin-3-yl]pyrazin-2-amine

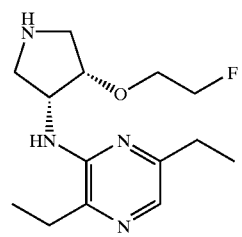

Following the procedure for the preparation of 5-(2,4-dichlorophenyl)-N-[(cis)-4-ethoxypyrrolidin-3-yl]-3,6-diethylpyrazin-2-amine but substituting benzyl (3R,4S)-3-[(3,6-diethylpyrazin-2-yl)amino]-4-(2-fluoroethoxy)pyrrolidine-1-carboxylate and making non-critical variations provided the title compound as an oil: $^1$H NMR (400 MHz, CDCl₃) δ) 7.65, 5.21, 4.64, 4.53, 4.07, 3.81–3.61, 3.40, 3.22, 3.14, 2.82, 2.62, 1.33–1.25; IR (liq.) 3437, 2969 (s), 2936 (s), 2874, 2348 (w), 1580 (s), 1546 (s), 1498 (s), 1464, 1449 (s), 1395, 1162, 1129, 1043 (s), 870, cm⁻¹; HRMS (FAB) calcd for $C_{14}H_{23}FN_4O+H$ 283.1934, found 283.1928.

Preparation 128

Preparation of methyl (3R,4S)-3-[(3,6-diethylpyrazin-2-yl)amino]-4-(2-fluoroethoxy)pyrrolidine-1-carboxylate

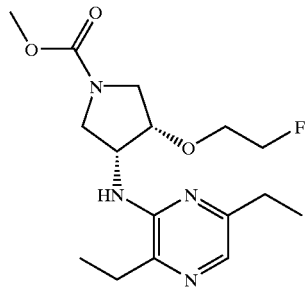

Following the procedure for the preparation of N-[(cis)-1-acetyl-4-ethoxypyrrolidin-3-yl]-5-(2,4-dichlorophenyl)-3,6-diethylpyrazin-2-amine but substituting 3,6-diethyl-N-[(3R,4S)-4-(2-fluoroethoxy)pyrrolidin-3-yl]pyrazin-2-amine and methyl chloroformate, and making non-critical variations provided the title compound as an oil: ¹H NMR (400 MHz, DMSO-d₆) δ) 7.61, 5.82, 4.55, 4.51, 4.39, 4.19, 3.73–3.48, 2.64–2.49, 1.20–1.14; IR (diffuse reflectance) 2967, 2934, 2873, 2450 (w), 2407 (w), 2350 (w), 2334 (w), 2226 (w), 1699 (s), 1499, 1457 (s), 1392 (s), 1158, 1142, 768, cm⁻¹; HRMS (FAB) calcd for $C_{16}H_{25}FN_4O_3+H$ 341.1989, found 341.1988.

Preparation 129

Preparation of methyl (3R,4S)-3-[(5-bromo-3,6-diethylpyrazin-2-yl)amino]-4-(2-fluoroethoxy)pyrrolidine-1-carboxylate

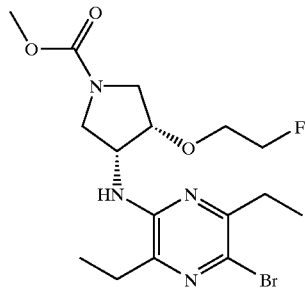

Following the procedure for the preparation of (1R,2S)-1-[(5-bromo-3,6-diethylpyrazin-2-yl)amino]-2,3-dihydro-1H-inden-2-ol but substituting methyl (3R,4S)-3-[(3,6-diethylpyrazin-2-yl)amino]-4-(2-fluoroethoxy)pyrrolidine-1-carboxylate and making non-critical variations provided the title compound as a oil: ¹H NMR (400 MHz, DMSO-d₆) δ) 6.12, 4.49, 4.37, 4.21, 3.69–3.39, 2.71–2.55, 1.20–1.12; IR (liq.) 2973 (s), 2957, 2068 (b), 1996, 1705 (s), 1561 (s), 1541 (s), 1481 (s), 1454 (s), 1392 (s), 1191 (s), 1175, 1140 (s), 1114 (s), 1048, cm⁻¹, HRMS (FAB) calcd for $C_{16}H_{24}BrFN_4O_3+H$ 419.1094, found 419.1112. Anal. Calcd for $C_{16}H_{24}BrFN_4O_3$: C, 45.83; H, 5.77; N, 13.36. Found: C, 45.49; H, 5.81; N, 13.03.

Example 93

Preparation of methyl(3R,4S)-3-{[3,6-diethyl-5-(4-methoxy-2-methylphenyl)pyrazin-2-yl]amino}-4-(2-fluoroethoxy)pyrrolidine-1-carboxylate

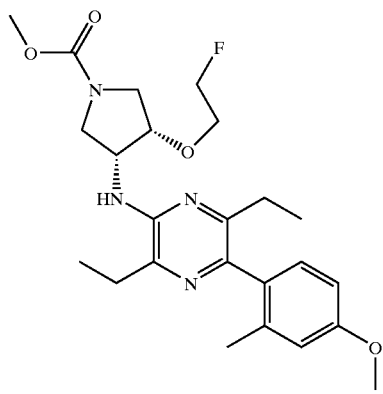

Following the procedure for the preparation of (1R,2S)-1-{[5-(2,4-dichlorophenyl)-3,6-diethylpyrazin-2-yl]amino}-2,3-dihydro-1H-inden-2-ol but substituting methyl (3R,4S)-3-[(5-bromo-3,6-diethylpyrazin-2-yl)amino]-4-(2-fluoroethoxy)pyrrolidine-1-carboxylate and tris(4-methoxy-2-methylphenyl)boroxin, and making non-critical variations provided the title compound as a oil: ¹H NMR (400 MHz, DMSO-d₆) δ) 7.12, 6.80, 5.12, 5.08, 4.80, 4.66, 4.54, 4.16, 3.99–3.60, 3.36, 3.27, 2.70, 2.48, 2.12, 1.28; HRMS (FAB) calcd for $C_{24}H_{33}FN_4O_4+H$ 461.2564, found 461.2570.

Example 94

Preparation of methyl (3R,4S)-3-({5-[2-chloro-4-(dimethylamino)phenyl]-3,6-diethylpyrazin-2-yl}amino)-4-(2-fluoroethoxy)pyrrolidine-1-carboxylate

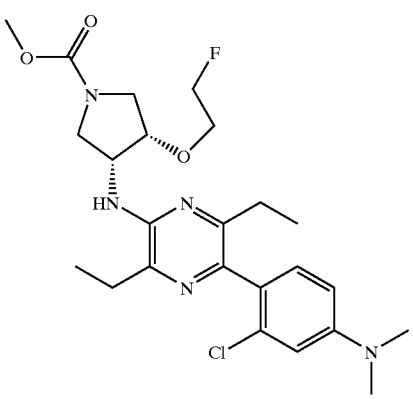

Following the procedure for the preparation of (1R,2S)-1-{[5-(2,4-dichlorophenyl)-3,6-diethylpyrazin-2-yl]amino}-2,3-dihydro-1H-inden-2-ol but substituting methyl (3R,4S)-3-[(5-bromo-3,6-diethylpyrazin-2-yl)amino]-4-(2-fluoroethoxy)pyrrolidine-1-carboxylate and N-(4-{4,6-bis[2-chloro-4-(dimethylamino)phenyl]boroxin-2-yl}-3- chlorophenyl)-N,N-dimethylamine, and making non-critical variations provided the title compound as a oil: $^1$H NMR (400 MHz, DMSO-d$_6$) δ) 7.30, 7.13, 6.76, 5.85, 4.60–4.54, 4.42, 4.28, 3.72–3.53, 2.94, 2.63, 2.38, 1.19–1.13, 1.06; IR (diffuse reflectance) 2963 (b), 2351 (w), 2338 (w), 2054 (w), 1927 (w), 1921 (w), 1710 (s), 1706 (s), 1608, 1568, 1551, 1486 (s), 1451 (s), 1392 (s), 1353, cm$^{-1}$; HRMS (FAB) calcd for $C_{24}H_{33}ClFN_5O_3$+H 494.2334, found 494.2340.

Example 95

Preparation of benzyl (3R,4S)-3-{[5-(2-chloro-4-methoxyphenyl)-3,6-diethylpyrazin-2-yl]amino}-4-hydroxypyrrolidine-1-carboxylate

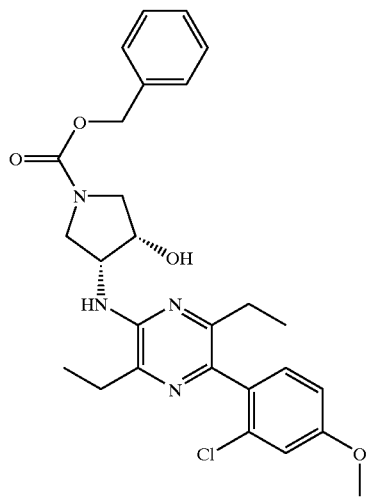

Following the procedure for the preparation of (1R,2S)-1-{[5-(2,4-dichlorophenyl)-3,6-diethylpyrazin-2-yl]amino}-2,3-dihydro-1H-inden-2-ol but substituting benzyl (3R,4S)-3-[(5-bromo-3,6-diethylpyrazin-2-yl)amino]-4-hydroxypyrrolidine-1-carboxylate and 2-chloro-4-methoxy phenyl boronic acid, and making non-critical variations provided the title compound as a oil: $^1$H NMR (DMSO-d$_6$) δ) 1.06, 2.35, 2.67, 3.51, 3.57, 3.62, 3.82, 4.35, 4.46, 5.08, 5.42, 5.95, 6.98, 7.11, 7.24, 7.38; IR (diffuse reflectance) 2968, 2351 (w), 2339 (w), 2063 (w), 1951 (w), 1700 (s,b), 1681 (s), 1568 (s), 1482 (s), 1428 (s,b), 1422 (s), 1397, 1359 (s), 1287, 1229, cm$^{-1}$ HRMS (FAB) calcd for $C_{27}H_{31}ClN_4O_4$+H 511.2112, found 511.2115.

Example 96

Preparation of benzyl (3R,4S)-3-{[5-(2-chloro-4-methoxyphenyl)-3,6-diethylpyrazin-2-yl]amino}-4-ethoxypyrrolidine-1-carboxylate

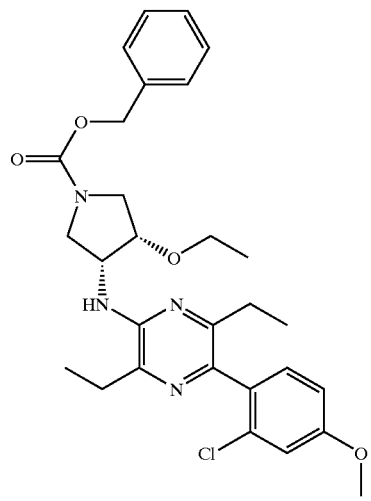

Following the procedure for the preparation of 5-(2,4-dichlorophenyl)-N-[(1R,2S)-2-ethoxy-2,3-dihydro-1H-inden-1-yl]-3,6-diethylpyrazin-2-amine but benzyl (3R,4S)-3-{[5-(2-chloro-4-methoxyphenyl)-3,6-diethylpyrazin-2-yl]amino}-4-hydroxypyrrolidine-1-carboxylate and making non-critical variations provided the title compound as a oil: $^1$H NMR (DMSO-d$_6$) δ) 1.04, 1.16, 2.38, 2.68, 3.34, 3.40, 3.54, 3.70, 3.82, 4.18, 4.62, 5.10, 5.95, 6.98, 7.10, 7.26, 7.38; IR (diffuse reflectance) 2971, 2934, 2350 (w), 2338 (w), 2063 (w), 1949 (w), 1710 (s), 1568, 1482 (s), 1419 (s), 1397 (s), 1348, 1287, 1228, 1096, cm$^{-1}$ HRMS (FAB) calcd for $C_{29}H_{35}ClN_4O_4$+H 539.2425, found 539.2436.

Anal. Calcd for $C_{29}H_{35}ClN_4O_4$: C, 64.61; H, 6.54; N, 10.39; Cl, 6.58. Found: C, 64.30; H, 6.56; N, 10.26.

Example 97

Preparation of benzyl (3R,4S)-3-{[5-(2-chloro-4-methoxyphenyl)-3,6-diethylpyrazin-2-yl]amino}-4-(2-fluoroethoxy)pyrrolidine-1-carboxylate

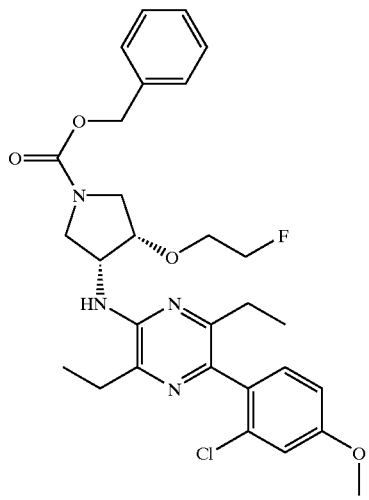

Following the procedure for the preparation of 5-(2,4-dichlorophenyl)-N-[(1R,2S)-2-ethoxy-2,3-dihydro-1H-inden-1-yl]-3,6-diethylpyrazin-2-amine but benzyl (3R,4S)-3-{[5-(2-chloro-4-methoxyphenyl)-3,6-diethylpyrazin-2-yl]

amino}-4-hydroxypyrrolidine-1-carboxylate and 1-bromo-2-fluoro ethane, and making non-critical variations provided the title compound as a oil: $^1$H NMR (DMSO-d6) δ) 1.07, 1.14, 2.36, 2.65, 3.60, 3.72, 3.79, 3.82, 4.27, 4.42, 4254, 4.62, 5.09, 5.95, 6.98, 7.11, 7.25, 7.38; IR (diffuse reflectance) 2350 (w), 2337 (w), 2058 (w), 1952 (w), 1940 (w), 1710 (s), 1569, 1552, 1483 (s), 1459, 1419 (s), 1397, 1353, 1287, 1228, cm$^{-1}$ HRMS (FAB) calcd for $C_{29}H_{34}ClFN_4O_4$+H 557.2330, found 557.2338.

Anal. Calcd for $C_{29}H_{34}ClFN_4O_4$: C, 62.53; H, 6.15; N, 10.06; Cl, 6.36; F, 3.41. Found: C, 62.33; H, 6.32; N, 10.07.

Example 98

Preparation of 5-(2-chloro-4-methoxyphenyl)-N-[(3R,4S)-4-ethoxypyrrolidin-3-yl]-3,6-diethylpyrazin-2-amine

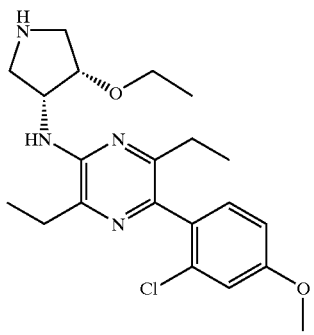

Following the procedure for the preparation of 5-(2,4-dichlorophenyl)-N-[(cis)-4-ethoxypyrrolidin-3-yl]-3,6-diethylpyrazin-2-amine but substituting (3R,4S)-3-{[5-(2-chloro-4-methoxyphenyl)-3,6-diethylpyrazin-2-yl]amino}-4-ethoxypyrrolidine-1-carboxylate and making non-critical variations provided the title compound as an oil: $^1$H NMR (CDCl$_3$) δ 1.15, 1.22–1.34, 2.45, 2.71, 2.89, 3.06, 3.22, 3.41, 3.51, 3.65, 3.85, 4.51, 5.32, 6.88, 7.02, 7.24.

Example 99

Preparation of methyl (3R,4S)-3-{[5-(2-chloro-4-methoxyphenyl)-3,6-diethylpyrazin-2-yl]amino}3-4-ethoxypyrrolidine-1-carboxylate

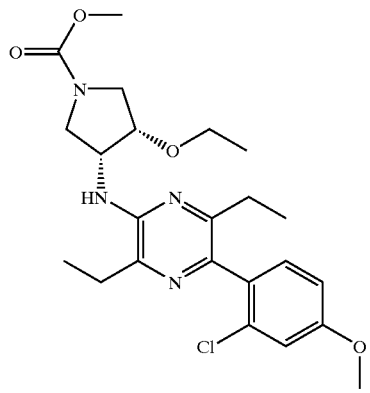

Following the procedure for the preparation of N-[(cis)-1-acetyl-4-ethoxypyrrolidin-3-yl]-5-(2,4-dichlorophenyl)-3,6-diethylpyrazin-2-amine but substituting 5-(2-chloro-4-methoxyphenyl)-N-[(3R,4S)-4-ethoxypyrrolidin-3-yl]-3,6-diethylpyrazin-2-amine and methyl chloroformate, and making non-critical variations provided the title compound as an oil: $^1$H NMR (DMSO-d6) δ 1.03–1.09, 1.16, 2.36, 2.67, 3.78, 3.51, 3.60, 3.69, 3.82, 4.15, 4.62, 5.95, 6.98, 7.11, 7.26; IR (diffuse reflectance) 2965 (s,b), 2937, 2351 (w), 2338 (w), 2213 (w), 2158 (w), 2059 (w), 1710 (s), 1568 (s), 1552, 1483 (s), 1456 (s), 1393 (s), 1287 (s), 1228, cm$^{-1}$ HRMS (FAB) calcd for $C_{23}H_{30}ClFN_4O_4$+H 481.2018, found 481.2026. Anal. Calcd for $C_{23}H_{30}ClFN_4O_4$: C, 57.44; H, 6.29; N, 11.65; Cl, 7.37; F, 3.95. Found: C, 57.14; H, 6.46; N, 11.37.

Example 100

Preparation of 5-(2-chloro-4-methoxyphenyl)-3,6-diethyl-N-[(3R,4S)-4-(2-fluoroethoxy)pyrrolidin-3-yl]pyrazin-2-amine

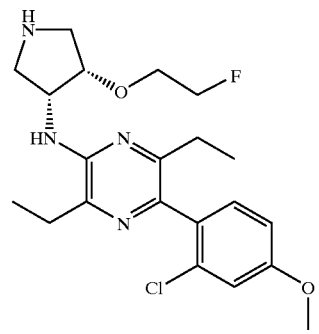

Following the procedure for the preparation of 5-(2,4-dichlorophenyl)-N-[(cis)-4-ethoxypyrrolidin-3-yl]-3,6-diethylpyrazin-2-amine but substituting benzyl (3R,4S)-3-{[5-(2-chloro-4-methoxyphenyl)-3,6-diethylpyrazin-2-yl]amino}-4-(2-fluoroethoxy)pyrrolidine-1-carboxylate and making non-critical variations provided the title compound as an oil: $^1$H NMR (CDCl$_3$) δ 1.15, 1.29, 2.48, 2.70, 2.90, 2.90, 3.15, 3.23, 3.44, 3.85, 4.11, 4.55, 4.66, 5.32, 6.88, 7.02, 7.24.

Example 101

Preparation of methyl (3R,4S)-3-{[5-(2-chloro-4-methoxyphenyl)-3,6-diethylpyrazin-2-yl]amino}-4-(2-fluoroethoxy)pyrrolidine-1-carboxylate

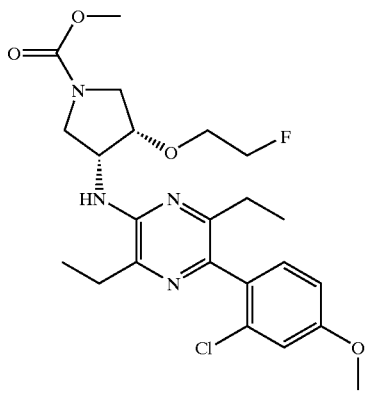

Following the procedure for the preparation of N-[(cis)-1-acetyl-4-ethoxypyrrolidin-3-yl]-5-(2,4-dichlorophenyl)-3, 6-diethylpyrazin-2-amine but substituting 5-(2-chloro-4-methoxyphenyl)-3,6-diethyl-N-[(3R,4S)-4-(2-fluoroethoxy)pyrrolidin-3-yl]pyrazin-2-amine and methyl chloroformate, and making non-critical variations provided the title compound as an oil: $^1$H NMR (DMSO-d6) δ) 1.08, 1.15, 2.37, 2.65, 3.54, 3.60, 3.71, 3.82, 4.25, 4.43, 4.54, 5.93, 6.98, 7.10, 7.26; IR (liq.) 2972, 2068 (w), 1996 (w), 1707 (s), 1607, 1566, 1484 (s), 1454 (s), 1393 (s), 1287, 1230, 1197, 1175, 1128, 1104, cm$^{-1}$ HRMS (FAB) calcd for $C_{23}H_{31}ClN_4O_4$+H 463.2112, found 463.2104.

Preparation 130

Preparation of trans-(+/−)-4-[(3,6-diethylpyrazin-2-yl)amino]tetrahydrofuran-3-ol

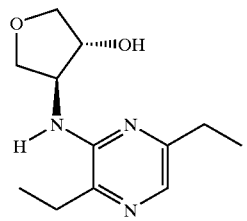

Following the procedure for the preparation of benzyl (3R,4S)-3-[(3,6-diethylpyrazin-2-yl)amino]-4-hydroxypyrrolidine-1-carboxylate but substituting trans-(+/−)-4-aminotetrahydrofuran-3-ol and making non-critical variations provided the title compound as an orange oil. IR (diffuse reflectance) 3356, 3255, 2972, 2938, 1587, 1511, 1464, 1453, 1396, 1337, 1185, 1099, 1064, 965, 888 cm$^{-1}$; OAMS supporting ions at: ESI+ 238.1; MS (EI) m/z 237 (M$^+$); HRMS (FAB) calcd for $C_{12}H_{19}N_3O_2$+H$_1$ 238.1555, found 238.1551.

Preparation 131

Preparation of trans-(+/−)-4-[(5-bromo-3,6-diethylpyrazin-2-yl)amino]tetrahydrofuran-3-ol

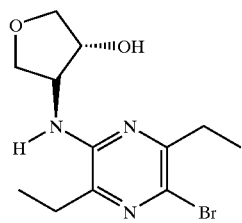

Following the procedure for the preparation of (1R,2S)-1-[(5-bromo-3,6-diethylpyrazin-2-yl)amino]-2,3-dihydro-1H-inden-2-ol but substituting trans-(+/−)-4-[(3,6-diethylpyrazin-2-yl)amino]tetrahydrofuran-3-ol and making non-critical variations provided the title compound as a light yellow solid. IR (diffuse reflectance) 3398, 2971, 2938, 1569, 1539, 1490, 1466, 1447, 1413, 1397, 1251, 1232, 1054, 969, 891 cm$^{-1}$; OAMS supporting ions at: ESI+ 315.9 & ESI− 313.9; MS (EI) m/z 315 (M$^+$); HRMS (FAB) calcd for $C_{12}H_{18}BrN_3O_2$+H$_1$ 316.0661, found 316.0656; Anal. Calcd for $C_{12}H_{18}BrN_3O_2$: C, 45.58; H, 5.74; N, 13.29. Found: C, 45.49; H, 5.84; N, 13.14.

Preparation 132

Preparation of trans-(+/−)-4-{[3,6-diethyl-5-(4-methoxy-2-methylphenyl)pyrazin-2-yl]amino}tetrahydrofuran-3-ol

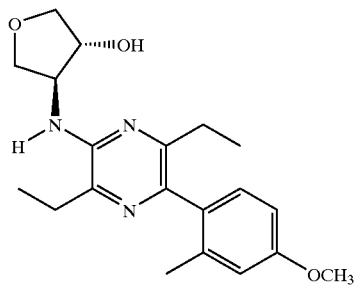

Following the procedure for the preparation of (1R,2S)-1-{[5-(2,4-dichlorophenyl)-3,6-diethylpyrazin-2-yl]amino}-2,3-dihydro-1H-inden-2-ol but substituting trans-(+/−)-4-[(5-bromo-3,6-diethylpyrazin-2-yl)amino]tetrahydrofuran-3-ol and 2-methyl-4-methoxyphenylboronic acid and making non-critical variations provided the title compound as a light yellow solid. IR (diffuse reflectance) 3363, 1603, 1571, 1490, 1447, 1393, 1303, 1233, 1208, 1177, 1170, 1103, 1059, 887, 849 cm$^{-1}$; OAMS supporting ions at: ESI+ 358.1; MS (EI) m/z 357 (M$^+$); HRMS (FAB) calcd for $C_{20}H_{27}N_3O_3$+H$_1$ 358.2130, found 358.2142.

Example 102

Preparation of trans-(+/−)-N-[4-ethoxytetrahydrofuran-3-yl]-3,6-diethyl-5-(4-methoxy-2-methylphenyl)pyrazin-2-amine

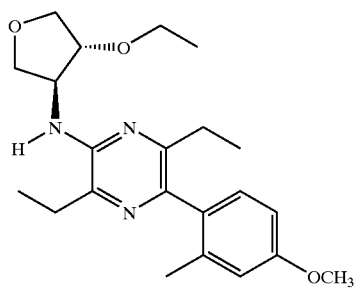

Following the procedure for the preparation of 5-(2,4-dichlorophenyl)-N-[(1R,2S)-2-ethoxy-2,3-dihydro-1H-inden-1-yl]-3,6-diethylpyrazin-2-amine but substituting trans-(+/−)-4-{[3,6-diethyl-5-(4-methoxy-2-methylphenyl)pyrazin-2-yl]amino}tetrahydrofuran-3-ol and making non-critical variations provided the title compound as a light yellow solid. IR (diffuse reflectance) 3354, 2973, 2958, 2938, 1484, 1462, 1446, 1396, 1300, 1239, 1172, 1072, 1050, 1043, 885 cm$^{-1}$; OAMS supporting ions at: ESI+ 386.1; MS (EI) m/z 385 (M$^+$); HRMS (FAB) calcd for $C_{22}H_{31}N_3O_3$ +H$_1$ 386.2443, found 386.2438. Anal. Calcd for $C_{22}H_{31}N_3O_3$: C, 68.54; H, 8.11; N, 10.90. Found: C, 68.38; H, 7.99; N, 10.85.

Preparation 133

Preparation of cis-(+/−)-4-{[3,6-diethyl-5-(4-methoxy-2-methylphenyl)pyrazin-2-yl]amino}tetrahydrofuran-3-yl 4-nitrobenzoate

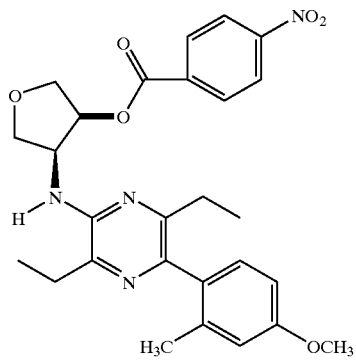

Following the procedure for the preparation of (1S,2S)-1-{[5-(2,4-dichlorophenyl)-3,6-diethylpyrazin-2-yl]amino}-2,3-dihydro-1H-inden-2-yl 4-nitrobenzoate but substituting trans-(+/−)-4-{[3,6-diethyl-5-(4-methoxy-2-methylphenyl)pyrazin-2-yl]amino}tetrahydrofuran-3-ol and making non-critical variations provided the title compound as a light yellow semi-solid. MS (ESI+) for m/z 507.1 (M+H)$^+$.

Preparation 134

Preparation of cis-(+/−)-4-{[3,6-diethyl-5-(4-methoxy-2-methylphenyl)pyrazin-2-yl]amino}tetrahydrofuran-3-ol

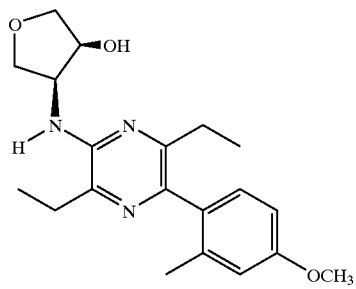

Following the procedure for the preparation of (1S,2S)-1-{[5-(2,4-dichlorophenyl)-3,6-diethylpyrazin-2-yl]amino}-2,3-dihydro-1H-inden-2-ol. but substituting cis-(+/−)-4-{[3,6-diethyl-5-(4-methoxy-2-methylphenyl)pyrazin-2-yl]amino}tetrahydrofuran-3-yl 4-nitrobenzoate and making non-critical variations provided the title compound as a colorless semi-solid. OAMS supporting ions at: ESI+ 358.2; MS (EI) m/z 357 (M$^+$); HRMS (FAB) calcd for $C_{20}H_{27}N_3O_3+H_1$ 358.2130, found 358.2125.

Example 103

Preparation of cis-(+/−)-N-[4-ethoxytetrahydrofuran-3-yl]-3,6-diethyl-5-(4-methoxy-2-methylphenyl)pyrazin-2-amine

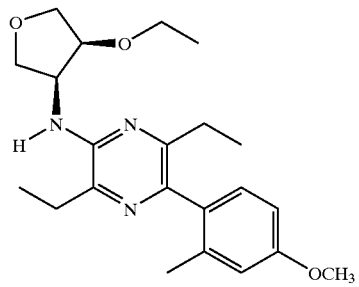

Following the procedure for the preparation of 5-(2,4-dichlorophenyl)-N-[(1R,2S)-2-ethoxy-2,3-dihydro-1H-inden-1-yl]-3,6-diethylpyrazin-2-amine but substituting of cis-(+/−)-4-{[3,6-diethyl-5-(4-methoxy-2-methylphenyl)pyrazin-2-yl]amino}tetrahydrofuran-3-ol and making non-critical variations provided the title compound as a light yellow solid. IR (liq.) 2972, 2935, 2874, 1609, 1564, 1481, 1395, 1294, 1243, 1204, 1160, 1123, 1077, 1069, 1058 cm$^{-1}$; OAMS supporting ions at: ESI+ 386.2; MS (EI) m/z 385 (M$^+$); HRMS (FAB) calcd for $C_{22}H_{31}N_3O_3+H_1$ 386.2443, found 386.2457. Anal. Calcd for $C_{22}H_{31}N_3O_3$: C, 68.54; H, 8.11; N, 10.90. Found: C, 68.22; H, 8.05; N, 10.76.

Preparation 135

Preparation of cis-(+/−)-4-[(3,6-diethylpyrazin-2-yl)amino]tetrahydrofuran-3-ol

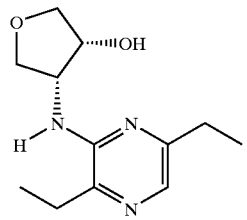

Following the procedure for the preparation of benzyl (3R,4S)-3-[(3,6-diethylpyrazin-2-yl)amino]-4-hydroxypyrrolidine-1-carboxylate but substituting cis-(+/−)-4-aminotetrahydrofuran-3-ol and making non-critical variations provided the title compound as a light yellow amorphous solid. IR (diffuse reflectance) 3399, 3259, 3223, 3218, 3212, 2969, 2867, 2847, 1582, 1546, 1493, 1465, 1160, 1066, 920 cm$^{-1}$; MS (EI) m/z 237 (M$^+$); HRMS (FAB) calcd for $C_{12}H_{19}N_3O_2+H_1$ 238.1555, found 238.1558.

Preparation 136

Preparation of cis-(+/−)-4-[(5-bromo-3,6-diethylpyrazin-2-yl)amino]tetrahydrofuran-3-ol

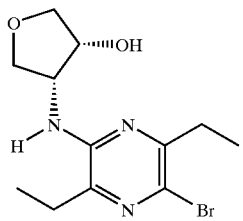

Following the procedure for the preparation of (1R,2S)-1-[(5-bromo-3,6-diethylpyrazin-2-yl)amino]-2,3-dihydro-1H-inden-2-ol but substituting trans-(+/−)-4-[(3,6-diethylpyrazin-2-yl)amino]tetrahydrofuran-3-ol and making non-critical variations provided the title compound as a light yellow solid. IR (diffuse reflectance) 3398, 2971, 2938, 1569, 1539, 1490, 1466, 1447, 1413, 1397, 1251, 1232, 1054, 969, 891 cm$^{-1}$; OAMS supporting ions at: ESI+ 315.9 & ESI− 313.9; MS (EI) m/z 315 (M$^+$); HRMS (FAB) calcd for $C_{12}H_{18}BRN_3O_2+H_1$ 316.0661, found 316.0656; Anal. Calcd for $C_{12}H_{18}BrN_3O_2$: C, 45.58; H, 5.74; N, 13.29. Found: C, 45.49; H, 5.84; N, 13.14.

Preparation 137

Preparation of cis-(+/−)-4-{[5-(2-chloro-4-methoxyphenyl)-3,6-diethylpyrazin-2-yl]amino}tetrahydrofuran-3-ol

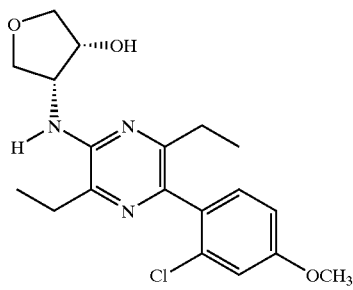

Following the procedure for the preparation of (1R,2S)-1-{[5-(2,4-dichlorophenyl)-3,6-diethylpyrazin-2-yl]amino}-2,3-dihydro-1H-inden-2-ol but substituting cis-(+/−)-4-[(5-bromo-3,6-diethylpyrazin-2-yl)amino]tetrahydrofuran-3-ol and 2-chloro-4-methoxyphenylboronic acid and making non-critical variations provided the title compound as a light yellow amorphous solid. IR (diffuse reflectance) 3420, 2969, 2935, 2873, 1604, 1568, 1482, 1439, 1397, 1393, 1287, 1229, 1204, 1181, 1044 cm$^{-1}$; OAMS supporting ions at: ESI+ 378.1; MS (EI) m/z 377 (M$^+$); HRMS (FAB) calcd for $C_{19}H_{24}ClN_3O_3+H_1$ 378.1584, found 378.1566. Anal. Calcd for $C_{19}H_{24}ClN_3O_3$: C, 60.39; H, 6.40; N, 11.12. Found: C, 59.97; H, 6.46; N, 10.99.

Example 104

Preparation of cis-(+/−)-5-(2-chloro-4-methoxyphenyl)-3,6-diethyl-N-[4-methoxytetrahydrofuran-3-yl]pyrazin-2-amine

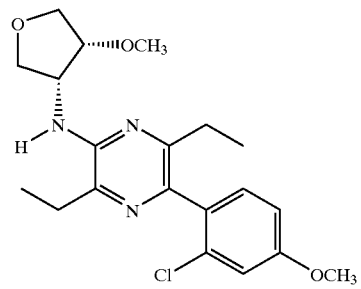

Following the procedure for the preparation of 5-(2,4-dichlorophenyl)-N-[(1R,2S)-2-ethoxy-2,3-dihydro-1H-inden-1-yl]-3,6-diethylpyrazin-2-amine but substituting of cis-(+/−)-4-{[5-(2-chloro-4-methoxyphenyl)-3,6-diethylpyrazin-2-yl]amino}tetrahydrofuran-3-ol and iodomethane and making non-critical variations provided the title compound as a colorless semi-solid. IR (liq.) 2970, 2936, 2874, 1606, 1566, 1483, 1441, 1397, 1287, 1230, 1203, 1182, 1126, 1076, 1049 cm$^{-1}$; OAMS supporting ions at: ESI+ 392.1; MS (EI) m/z 391 (M$^+$); HRMS (FAB) calcd for $C_{20}H_{26}ClN_3O_3+H_1$ 392.1741, found 392.1758. Anal. Calcd for $C_{20}H_{26}ClN_3O_3$: C, 61.30; H, 6.69; N, 10.72. Found: C, 61.16; H, 6.47; N, 10.65.

Example 105

Preparation of cis-(+/−)-5-(2-chloro-4-methoxyphenyl)-N-[4-ethoxytetrahydrofuran-3-yl]-3,6-diethylpyrazin-2-amine

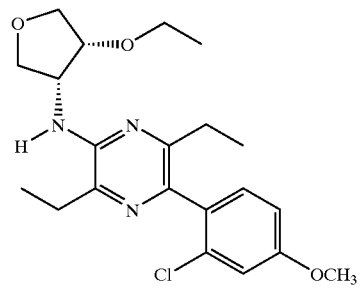

Following the procedure for the preparation of 5-(2,4-dichlorophenyl)-N-[(1R,2S)-2-ethoxy-2,3-dihydro-1H-inden-1-yl]-3,6-diethylpyrazin-2-amine but substituting of cis-(+/−)-4-{[5-(2-chloro-4-methoxyphenyl)-3,6-diethylpyrazin-2-yl]amino}tetrahydrofuran-3-ol and making non-critical variations provided the title compound as a light yellow oil. IR (liq.) 2973, 2936, 2874, 1606, 1566, 1481, 1441, 1396, 1287, 1230, 1203, 1181, 1124, 1078, 1046 cm$^{-1}$; OAMS supporting ions at: ESI+ 406.2; MS (EI) m/z 405 (M$^+$); HRMS (FAB) calcd for $C_{21}H_{28}ClN_3O_3+H_1$ 406.1897, found 406.1889.

Example 106

Preparation of cis-(+/−)-5-(2-chloro-4-methoxyphenyl)-3,6-diethyl-N-[4-propoxytetrahydrofuran-3-yl]pyrazin-2-amine

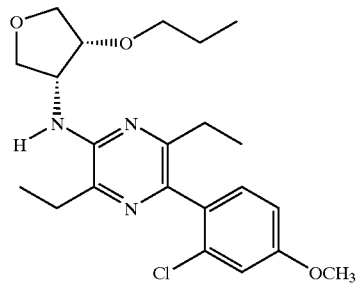

Following the procedure for the preparation of 5-(2,4-dichlorophenyl)-N-[(1R,2S)-2-ethoxy-2,3-dihydro-1H-inden-1-yl]-3,6-diethylpyrazin-2-amine but substituting of cis-(+/−)-4-{[5-(2-chloro-4-methoxyphenyl)-3,6-diethylpyrazin-2-yl]amino}tetrahydrofuran-3-ol and 1-iodopropane and making non-critical variations provided the title compound as a light yellow oil. IR (liq.) 2967, 2936, 2875, 1606, 1566, 1483, 1441, 1396, 1287, 1230, 1203, 1124, 1078, 1058, 1046 cm$^{-1}$; OAMS supporting ions at: ESI+ 420.2; MS (EI) m/z 419 (M$^+$); HRMS (FAB) calcd for $C_{22}H_{30}ClN_3O_3+H_1$ 420.2054, found 420.2052. Anal. Calcd for $C_{22}H_{30}ClN_3O_3$: C, 62.92; H, 7.20; N, 10.01. Found: C, 62.78; H, 7.28; N, 10.01.

Example 107 and 108

Preparation of 5-(2-chloro-4-methoxyphenyl)-3,6-diethyl-N-[(3R,4R)-4-propoxytetrahydrofuran-3-yl]pyrazin-2-amine and 5-(2-chloro-4-methoxyphenyl)-3,6-diethyl-N-[(3S,4S)-4-propoxytetrahydrofuran-3-yl]pyrazin-2-amine

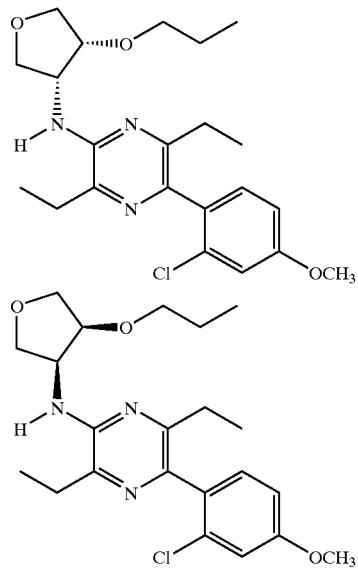

Chiral HPLC separation of a racemic sample of cis-(+/−)-5-(2-chloro-4-methoxyphenyl)-3,6-diethyl-N-[4-propoxytetrahydrofuran-3-yl]pyrazin-2-amine employing an Chiralcel OJ column eluting with 5% isopropyl alcohol/heptane (containing 0.1% diethylamine) provided the title compounds. Analytical data for 5-(2-chloro-4-methoxyphenyl)-3,6-diethyl-N-[(3R,4R)-4-propoxytetrahydrofuran-3-yl]pyrazin-2-amine: OAMS supporting ions at: ESI+ 420.2; MS (EI) m/z 419 (M$^{30}$); $[\alpha]^{25}_D$=23 (c 1.0, methylene chloride); HRMS (FAB) calcd for $C_{22}H_{30}ClN_3O_3+H_1$ 420.2054, found 420.2049. Analytical data for 5-(2-chloro-4-methoxyphenyl)-3,6-diethyl-N-[(3S,4S)-4-propoxytetrahydrofuran-3-yl]pyrazin-2-amine: OAMS supporting ions at: ESI+ 420.2; MS (EI) m/z 419 (M$^+$); $[\alpha]^{25}_D$=−24 (c 1.0, methylene chloride); HRMS (FAB) calcd for $C_{22}H_{30}ClN_3O_3+H_1$ 420.2054, found 420.2064. Anal. Calcd for $C_{22}H_{30}ClN_3O_3$: C, 62.92; H, 7.20; N, 10.01. Found: C, 63.00; H, 7.11; N, 9.67.

Example 109

Preparation of (+/−)-5-(2-chloro-4-methoxyphenyl)-3,6-diethyl-N-[cis-4-(3-fluoropropoxy)tetrahydrofuran-3-yl]pyrazin-2-amine

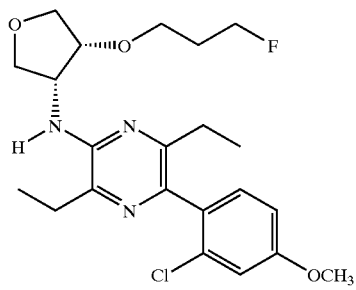

Following the procedure for the preparation of 5-(2,4-dichlorophenyl)-N-[(1R,2S)-2-ethoxy-2,3-dihydro-1H-inden-1-yl]-3,6-diethylpyrazin-2-amine but substituting of cis-(+/−)-4-{[5-(2-chloro-4-methoxyphenyl)-3,6-diethylpyrazin-2-yl]amino}tetrahydrofuran-3-ol and 1-bromo-3-fluoropropane and making non-critical variations provided the title compound as a colorless semi-solid. IR (liq.) 2969, 2936, 2875, 1606, 1565, 1481, 1441, 1397, 1287, 1230, 1203, 1127, 1075, 1059, 1046 cm$^{-1}$; OAMS supporting ions at: ESI+ 438.2; MS (EI) m/z 437 (M$^+$); HRMS (FAB) calcd for $C_{22}H_{29}ClFN_3O_3+H_1$ 438.1960, found 438.1965. Anal. Calcd for $C_{22}H_{29}ClFN_3O_3$: C, 60.34; H, 6.67; N, 9.59. Found: C, 60.31; H, 6.78; N, 9.65.

Preparation 138

N-[(1E)-phenylmethylidene]-1H-imidazol-2-amine

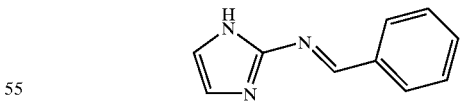

In order to obtain the free base, 2-aminoimidazole sulfate (5.00 g, 37.8 mmol) was dissolved in water (35 mL) and $Na_2CO_3$ (6.25 g, 59.0 mmol) was added. After 20 minutes, the water was removed under reduced pressure. After the addition of ethanol (100 mL), the salts were removed via filtration. Concentration of the filtrate gave a light brown oil that was dissolved in ethanol (15 mL). Benzaldehyde (4.0 mL, 39.4 mmol) was added and the mixture was heated at reflux. After 2 h, the reaction was cooled to rt and concentrated. The crude product was purified by column chromatography (Biotage, 40M) with heptanes/EtOAc (1:1) to give impure product. Crystallization of this material from EtOAc/heptanes gave 2.37 g (first crop, 37%) and 0.78 g (second crop, 12%) of yellow solid: $^1$H NMR (400 MHz, CDCl$_3$) δ 10.33, 9.34, 7.90, 7.48, 7.09, 7.01; IR (diffuse reflectance) 3148, 3134, 3112, 3081, 3063, 3029, 2908, 2895, 2881, 1606, 1449, 1108, 753, 738, 687 cm$^{-1}$; HRMS (FAB) calcd for C$_{10}$H$_9$N$_3$+H 172.0875, found 172.0872; Anal. Calcd for C$_{10}$H$_9$N$_3$: C, 70.16; H, 5.30; N, 24.54, found: C, 70.02; H, 5.32; N, 24.39.

Preparation 139

N-[(1E)-phenylmethylidene]-1-propyl-1H-imidazol-2-amine

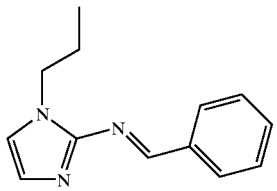

To a solution of N-[(1E)-phenylmethylidene]-1H-imidazol-2-amine (1.00 g, 5.84 mmol) in DMF (20 mL) was added KOt-Bu (0.80 g, 7.13 mmol) and 1-iodopropane (0.63 mL, 6.46 mmol). After 3.5 h, the reaction was diluted with water (50 mL) and extracted with EtOAc (3×50 mL). The combined organic layers were washed with brine, dried over Na$_2$SO$_4$, decanted, and concentrated. The crude product was purified by column chromatography (Biotage, 40M) with heptanes/EtOAc (2:1) to give 1.12 g (90%) of yellow liquid: $^1$H NMR (400 MHz, CDCl$_3$) δ 9.23, 7.94, 7.47, 7.02, 6.94, 4.14, 1.83, 0.95; IR (liq.) 2966, 2935, 2876, 1612, 1576, 1509, 1477, 1450, 1313, 1282, 1150, 761, 738, 716, 690 cm$^{-1}$; HRMS (FAB) calcd for C$_{13}$H$_{15}$N$_3$+H 214.1344, found 214.1336.

Preparation 140

1-propyl-1H-imidazol-2-amine

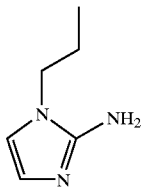

A mixture of N-[(1E)-phenylmethylidene]-1-propyl-1H-imidazol-2-amine (0.92 g, 4.31 mmol) and 6N HCl (25 mL) was heated at reflux for 2 h. After cooling to rt, the reaction was concentrated to a residue then taken up in 2M aqueous Na$_2$CO$_3$ and extracted with CH$_2$Cl$_2$. The combined organic layers were washed with brine, dried over Na$_2$SO$_4$, decanted, and concentrated. The crude product was purified by column chromatography (Biotage, 40M) with CH$_2$Cl$_2$/MeOH/NH$_4$OH (gradient, 950:47:3 to 900:90:10) to give 0.30 g (56%) of brown oil: $^1$H NMR (400 MHz, CDCl$_3$) δ 6.63, 6.52, 4.00, 3.65, 1.75, 0.95; MS (ESI+) 126.7.

Example 110

5-(2,4-dichlorophenyl)-3,6-diethyl-N-(1-propyl-1H-imidazol-2-yl)pyrazin-2-amine

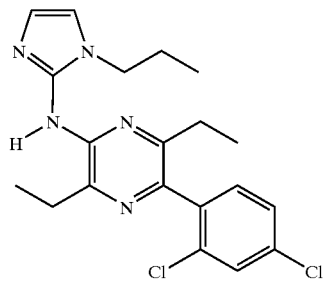

A mixture of 2-bromo-5-(2,4-dichlorophenyl)-3,6-diethylpyrazine (0.25 g, 0.69 mmol), 1-propyl-1H-imidazol-2-amine (0.15 g, 1.2 mmol), tris(dibenzylideneacetone)dipalladium (0.032 g, 0.032 mmol), 2-dicyclohexylphosphino)biphenyl (0.037 g, 0.12 mmol), and sodium tert-butoxide (0.093 g, 0.97 mmol) in dioxane (2.0 mL) was heated at 110° C. for 21 h. After cooling to rt, the reaction was diluted with saturated aqueous NaHCO$_3$ and extracted with CH$_2$Cl$_2$. The combined organic layers were washed with brine, dried over Na$_2$SO$_4$, decanted, and concentrated. The crude product was purified by column chromatography (Biotage, 40M) with (Biotage, 40S) with heptanes/EtOAc (3:1) to give 0.076 g (27%) of dark yellow oil: $^1$H NMR (400 MHz, CDCl$_3$) δ 12.86, 7.47, 7.31, 6.70, 6.55, 3.94, 2.97, 2.48, 2.97, 2.48, 1.84, 1.30, 1.21, 0.98; IR (liq.) 2968, 2934, 1599, 1556, 1549, 1509, 1460, 1422, 1402, 1384, 1373, 1302, 1174, 1102, 712 cm$^{-1}$; HRMS (FAB) calcd for C$_{20}$H$_{23}$Cl$_2$N$_5$+H 404.1408, found 404.1416.

Preparation 141 methyl amino(cyclopropyl)acetate hydrochloride

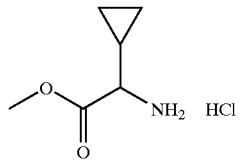

To a solution of cyclopropyl glycine (0.50 g, 4.3 mmol) in ice cold MeOH (4.3 mL) was added dropwise SOCl$_2$ (1.3 g, 0.8 mL, 11 mmol). The ensuing mixture was stirred at 0° C. for 10 min then allowed to warm to rt. Stir at rt overnight, concentrate and dry at rt/0.5 mmHg to provide 0.60 g (85%) of methyl amino(cyclopropyl)acetate hydrochloride as a solid: $^1$H NMR (DMSO-d6) δ 0.51–0.69, 1.05–1.17, 3.36–3.39, 3.75, 8.69.

Preparation 142 methyl 2-aminobutanoate hydrochloride

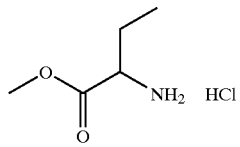

Following the procedure for the preparation of methyl amino(cyclopropyl)acetate hydrochloride but substituting alpha-aminobutyric acid and making non-critical variations provided the title compound as a solid: MS (ESI+) for $C_5H_{11}NO_2$ m/z 235 (2M+H)$^+$.

Preparation 143 methyl {[N-(tert-butoxycarbonyl)-L-alanyl]amino}(cyclopropyl)acetate

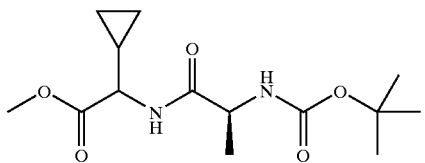

To an ice cold solution of methyl amino(cyclopropyl)acetate hydrochloride (0.25 g, 1.5 mmol), N-Boc-L-alanine-OH (0.34 g, 1.5 mmol) in DMF (7.5 mL) containing diisopropylphenyl amine (0.58 g, 0.8 mL, 4.5 mmol) was added O-(7-azabenzotriazol-1-yl)-N,N,N,N-tetramethyluronium hexafluorophosphate (HATU) (0.57 g, 1.5 mmol). After stirring at rt for 2 days, the mixture was diluted with EtOAc and sequentially washed with sat. aq. NaHCO$_3$ and sat. aq. NaCl. The organic extracts were dried over MgSO$_4$, filtered and concentrated. Purify by biotage MPLC (90 g column, 25–30% ethyl acetate/hexanes) to afford 0.39 g (78%) methyl {[N-(tert-butoxycarbonyl)-L-alanyl]amino}(cyclopropyl)acetate as a solid: $^1$H NMR (CDCl$_3$) δ 0.39–0.62, 1.28–1.39, 1.47, 3.77, 4.03–4.19, 4.99, 6.66; MS (ESI+) for $C_{14}H_{24}N_2O_5$ m/z 301 (M+H)$^+$.

Preparation 144 methyl ({2-[(tert-butoxycarbonyl)amino]butanoyl}amino)(cyclopropyl)acetate

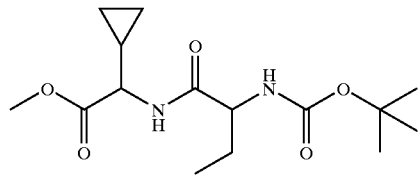

Following the procedure for the preparation of methyl {[N-(tert-butoxycarbonyl)-L-alanyl]amino}(cyclopropyl)acetate but substituting N-Boc-alpha-aminobutyric acid and making non-critical variations provided the title compound as a solid: $^1$H NMR (CDCl$_3$) δ 0.40–0.62, 0.94–0.99, 1.09–1.12, 1.46, 1.63–2.06, 3.77, 4.04, 5.02, 6.54.

Preparation 145 methyl N-{2-[(tert-butoxycarbonyl)amino]butanoyl}alaninate

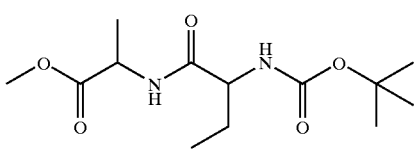

Following the procedure for the preparation of methyl {[N-(tert-butoxycarbonyl)-L-alanyl]amino}(cyclopropyl)acetate but substituting N-Boc-alpha-aminobutyric acid and methyl 2-aminobutanoate hydrochloride and making non-critical variations provided the title compound as a solid: $^1$H NMR (CDCl$_3$) δ 0.82–0.91, 1.24–1.38, 1.52, 1.68–2.05, 3.75, 4.20, 4.52–4.59, 5.05, 6.69.

Preparation 146 methyl (L-alanylamino)(cyclopropyl)acetate hydrochloride

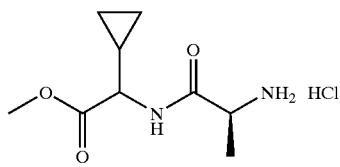

A solution of methyl {[N-(tert-butoxycarbonyl)-L-alanyl]amino}(cyclopropyl)-acetate (72 mg, 0.24 mmol) in 4 N HCl in dioxane (1 mL) was stirred at rt for 45 min. Concentrate to afford 57 mg (100%) of methyl (L-alanylamino)(cyclopropyl)acetate hydrochloride as a solid: $^1$H NMR (DMSO-d6) δ 0.42–0.60, 1.21–1.26, 1.68, 3.65–3.91, 4.60, 8.17; MS (ESI+) for $C_8H_{12}N_2O_2$ m/z 201 (M+H)$^+$.

Preparation 147 methyl [(2-aminobutanoyl)amino](cyclopropyl)acetate hydrochloride

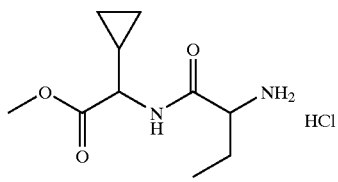

Following the procedure for the preparation of methyl (L-alanylamino)(cyclopropyl)acetate hydrochloride but substituting methyl ({2-[(tert-butoxycarbonyl)amino]butanoyl}amino)(cyclopropyl)acetate and making non-critical variations provided the title compound as a solid: $^1$H NMR (DMSO-d6) δ 0.29–0.40, 0.88–0.94, 1.12, 1.37, 1.75–1.82, 3.57, 3.62–3.79, 8.29.

Preparation 148 methyl N-(2-aminobutanoyl)alaninate hydrochloride

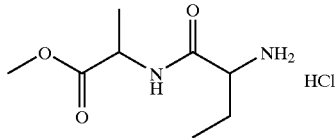

Following the procedure for the preparation of methyl (L-alanylamino)(cyclopropyl)acetate hydrochloride but substituting methyl N-{2-[(tert-butoxycarbonyl)amino]butanoyl}alaninate and making non-critical variations provided the title compound as a solid: $^1$H NMR (DMSO-d6) δ 0.86–0.92, 1.39–1.41, 1.62–1.82, 3.64, 3.92, 4.18–4.23, 8.36. 8.92.

Preparation 149

3,6-dicyclopropylpiperazine-2,5-dione

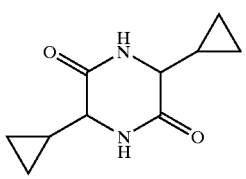

Following the procedure for the preparation of 3,6-diethylpiperazine-2,5-dione but substituting cyclopropyl glycine (prepared as described in patent U.S. Pat. No. 6,191,306) and making non-critical variations provided the title compound as a solid. $^1$H NMR (DMSO-d6) δ 0.26–0.52, 1.04–1.12, 3.15–3.18, 3.24–3.27, 3.33, 8.06, 8.19.

Preparation 150

3-cyclopropyl-6-methylpiperazine-2,5-dione

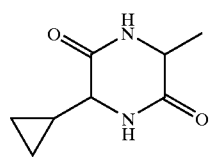

A solution of methyl (L-alanylamino)(cyclopropyl)acetate hydrochloride (230 mg, 0.97 mmol) in 7 N NH$_3$ in MeOH (6 mL) was heated at reflux for 5 hr. Cool to rt and concentrate. The resulting material was dried at rt/0.5 mm Hg to provide 0.21 g of 3-cyclopropyl-6-methylpiperazine-2,5-dione as a solid: $^1$H NMR (CDCl$_3$) δ 0.26–0.51, 1.06–1.37, 3.16–3.25, 3.50, 3.80, 4.00, 8.13.

Preparation 151

3-cyclopropyl-6-ethylpiperazine-2,5-dione

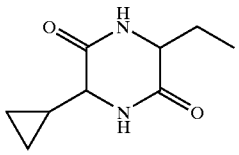

Following the procedure for the preparation of 3-cyclopropyl-6-methylpiperazine-2,5-dione but substituting methyl [(2-aminobutanoyl)amino](cyclopropyl)acetate hydrochloride and making non-critical variations provided the title compound as a solid: $^1$H NMR (DMSO-d6) δ 0.29–0.48, 0.79–1.20, 1.69, 3.20, 3.93, 8.05.

Preparation 152

3-ethyl-6-methylpiperazine-2,5-dione

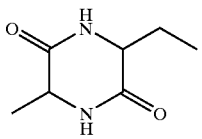

Following the procedure for the preparation of 3-cyclopropyl-6-methylpiperazine-2,5-dione but substituting methyl N-(2-aminobutanoyl)alaninate hydrochloride and making non-critical variations provided the title compound as a solid: $^1$H NMR (DMSO-d6) δ 0.81–0.86, 1.25–1.27, 1.64–1.76, 3.73–3.91, 7.37, 8.07–8.15.

Preparation 153

3-chloro-2,5-dicyclopropylpyrazine

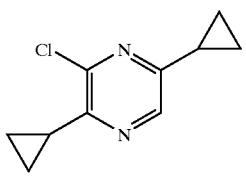

Following the procedure for the preparation of 3-chloro-2,5-diethylpyrazine but substituting 3,6-dicyclopropylpiperazine-2,5-dione and making non-critical variations provided the title compound as an oil: $^1$H NMR (CDCl$_3$) δ 0.99–1.13, 1.94–2.03, 2.38–2.47; MS (ESI+) for C$_{10}$H$_{11}$N$_2$ m/z 195 (M+H)$^+$.

Preparation 154A and 154B 3-chloro-2-cyclopropyl-5-methylpyrazine (A) and
3-chloro-5-cyclopropyl-2-methylpyrazine (B)

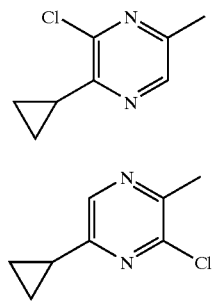

Following the procedure for the preparation of 3-chloro-2,5-diethylpyrazine but substituting 3-cyclopropyl-6-methylpiperazine-2,5-dione and making non-critical variations provided 3-chloro-2-cyclopropyl-5-methylpyrazine (A) and 3-chloro-5-cyclopropyl-2-methylpyrazine (B) as oils. Analytical data for 3-chloro-2-cyclopropyl-5-methylpyrazine (A): $^1$H NMR (CDCl$_3$) δ 1.44, 2.35, 2.90, 3.07, 8.10; MS (ESI+) for C$_8$H$_9$N$_2$Cl m/z 169 (M+H)$^+$; Analytical data for 3-chloro-5-cyclopropyl-2-methylpyrazine (B): $^1$H NMR (CDCl$_3$) δ 1.04, 2.00, 2.57, 8.10; MS (ESI+) for C$_8$H$_9$N$_2$Cl m/z 169 (M+H)$^+$.

Preparation 155A and 155B 3-chloro-2-cyclopropyl-5-ethylpyrazine (A) and 3-chloro-5-cyclopropyl-2-ethylpyrazine (B)

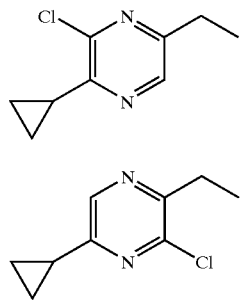

Following the procedure for the preparation of 3-chloro-2,5-diethylpyrazine but substituting 3-cyclopropyl-6-ethylpiperazine-2,5-dione and making non-critical variations provided 3-chloro-2-cyclopropyl-5-methylpyrazine (A) and 3-chloro-5-cyclopropyl-2-methylpyrazine (B) as oils. Analytical data for 3-chloro-2-cyclopropyl-5-ethylpyrazine (A): $^1$H NMR (CDCl$_3$) δ 1.06–1.10, 1.28–1.33, 2.42–2.51, 2.73–2.81, 8.18; Analytical data for 3-chloro-5-cyclopropyl-2-ethylpyrazine (B): $^1$H NMR (CDCl$_3$) δ 1.04–1.08, 1.24–1.39, 1.97–2.06, 2.88–2.95, 8.31.

Preparation 156A and 156B 3-chloro-5-ethyl-2-methylpyrazine (A) and 3-chloro-2-ethyl-5-methylpyrazine (B)

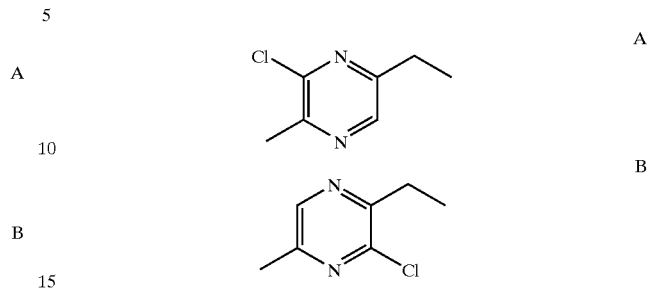

Following the procedure for the preparation of 3-chloro-2,5-diethylpyrazine but substituting 3-ethyl-6-methylpiperazine-2,5-dione and making non-critical variations provided a mixture of 3-chloro-5-ethyl-2-methylpyrazine (A) and 3-chloro-2-ethyl-5-methylpyrazine (B) as an oil: $^1$H NMR (CDCl$_3$) δ 1.29–1.39, 2.53, 2.63, 2.77–2.99, 8.27, 8.30.

Preparation 157

(1R,2S)-1-[(3,6-dicyclopropylpyrazin-2-yl)amino]-2,3-dihydro-1H-inden-2-ol

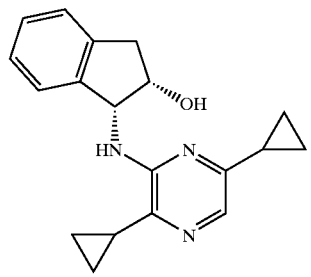

Following the procedure for the preparation of (1R,2S)-1-[(3,6-diethylpyrazin-2-yl)amino]-2,3-dihydro-1H-inden-2-ol but substituting 3-chloro-2,5-dicyclopropylpyrazine and making non-critical variations provided the title compound as a solid: $^1$H NMR (CDCl$_3$) δ 0.86–0.89, 2.00, 2.89, 3.11, 4.54, 5.17, 5.42, 6.22–6.24, 7.17–7.25, 7.64; MS (ESI+) for C$_{19}$H$_{21}$N$_3$O m/z 308 (M+H)$^+$.

Preparation 158

(1R,2S)-1-[(6-cyclopropyl-3-methylpyrazin-2-yl)amino]-2,3-dihydro-1H-inden-2-ol

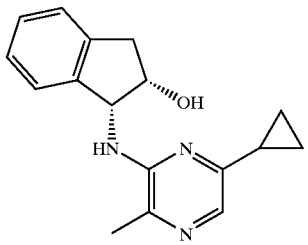

Following the procedure for the preparation of (1R,2S)-1-[(3,6-diethylpyrazin-2-yl)amino]-2,3-dihydro-1H-inden- 2-ol but substituting 3-chloro-5-cyclopropyl-2-methylpyrazine and making non-critical variations provided the title compound as a solid: ¹H NMR (CDCl₃) δ 0.95, 1.93, 2.38, 2.61, 3.09, 3.22, 4.75, 5.50, 7.30, 7.77; MS (ESI+) for C₁₇H₁₉N₃O m/z 282 (M+H)⁺.

Preparation 159

(1R,2S)-1-[(3-cyclopropyl-6-methylpyrazin-2-yl)amino]-2,3-dihydro-1H-inden-2-ol

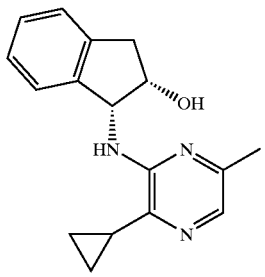

Following the procedure for the preparation of (1R,2S)-1-[(3,6-diethylpyrazin-2-yl)amino]-2,3-dihydro-1H-inden-2-ol but substituting 3-chloro-2-cyclopropyl-5-methylpyrazine and making non-critical variations provided the title compound as a solid: ¹H NMR (CDCl₃) δ 0.92–1.01, 1.25, 1.76, 2.36, 3.08, 3.24, 4.80, 5.38, 5.59, 7.22–7.49, 7.64; MS (ESI+) for C₁₇H₁₉N₃O m/z 282 (M+H)⁺.

Preparation 160

(1R,2S)-1-[(6-cyclopropyl-3-ethylpyrazin-2-yl)amino]-2,3-dihydro-1H-inden-2-ol

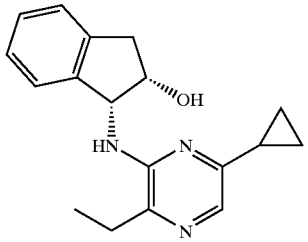

Following the procedure for the preparation of (1R,2S)-1-[(3,6-diethylpyrazin-2-yl)amino]-2,3-dihydro-1H-inden-2-ol but substituting 3-chloro-5-cyclopropyl-2-ethylpyrazine and making non-critical variations provided the title compound as a solid: ¹H NMR (CDCl₃) δ 0.92–0.95, 1.31–1.35, 1.93, 2.59–2.70, 3.03–3.10, 3.22–3.30, 4.74, 4.91, 5.49–5.52, 7.28–7.32, 7.82; MS (ESI+) for C₁₈H₂₁N₃O m/z 296 (M+H)⁺.

Preparation 161

(1R,2S)-1-[(3-cyclopropyl-6-ethylpyrazin-2-yl)amino]-2,3-dihydro-1H-inden-2-ol

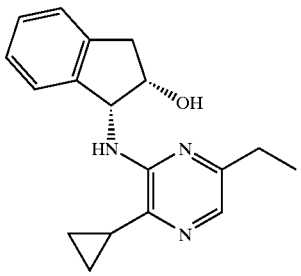

Following the procedure for the preparation of (1R,2S)-1-[(3,6-diethylpyrazin-2-yl)amino]-2,3-dihydro-1H-inden-2-ol but substituting 3-chloro-2-cyclopropyl-5-ethylpyrazine and making non-critical variations provided the title compound as a solid: ¹H NMR (CDCl₃) δ 0.93–1.02, 1.24–1.30, 1.72–1.81, 2.61–2.68, 3.06–3.30, 4.79–4.84, 5.36, 5.58, 7.24–7.35, 7.66; MS (ESI+) for C₁₈H₂₁N₃O m/z 296 (M+H)⁺.

Preparation 162A and 162B (1R,2S)-1-[(6-ethyl-3-methylpyrazin-2-yl)amino]-2,3-dihydro-1H-inden-2-ol (A) and (1R,2S)-1-[(3-ethyl-6-methylpyrazin-2-yl)amino]-2,3-dihydro-1H-inden-2-ol (B)

A

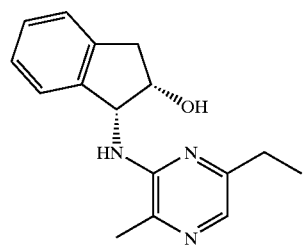

B

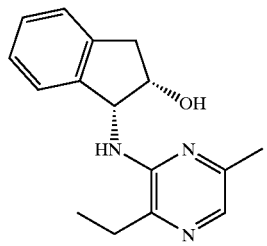

Following the procedure for the preparation of (1R,2S)-1-[(3,6-diethylpyrazin-2-yl)amino]-2,3-dihydro-1H-inden-2-ol but substituting a mixture of 3-chloro-5-ethyl-2-methylpyrazine (A) and 3-chloro-2-ethyl-5-methylpyrazine (B) and making non-critical variations provided a mixture of the title compounds as a solid: ¹H NMR (CDCl₃) δ 1.24–1.34, 2.38, 2.63–2.69, 3.04–3.10, 3.23–3.29, 4.78–4.92, 5.58–5.63, 7.24–7.32, 7.68, 7.73.

Preparation 163

(1S,2S)-1-[(5-bromo-3,6-dicyclopropylpyrazin-2-yl)amino]-2,3-dihydro-1H-inden-2-ol

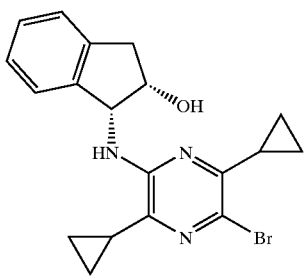

Following the procedure for the preparation of (1R,2S)-1-[(5-bromo-3,6-diethylpyrazin-2-yl)amino]-2,3-dihydro-1H-inden-2-ol but substituting (1R,2S)-1-[(3,6-dicyclopropylpyrazin-2-yl)amino]-2,3-dihydro-1H-inden-2-ol and making non-critical variations provided the title compound as a solid: $^1$H NMR (CDCl$_3$) δ 0.89–1.03, 1.27–1.30, 1.71–1.75, 2.36–2.39, 3.05–3.09, 3.25–3.30, 4.72–4.75, 5.45–5.46, 7.26–7.33; MS (ESI+) for C$_{19}$H$_{20}$BrN$_3$O m/z 386 (M+H)$^+$.

Preparation 164

(1R,2S)-1-[(5-bromo-6-cyclopropyl-3-methylpyrazin-2-yl)amino]-2,3-dihydro-1H-inden-2-ol

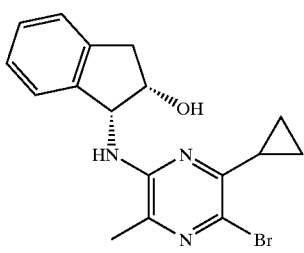

Following the procedure for the preparation of (1R,2S)-1-[(5-bromo-3,6-diethylpyrazin-2-yl)amino]-2,3-dihydro-1H-inden-2-ol but substituting (1R,2S)-1-[(6-cyclopropyl-3-methylpyrazin-2-yl)amino]-2,3-dihydro-1H-inden-2-ol and making non-critical variations provided the title compound as a solid: $^1$H NMR (CDCl$_3$) δ 0.99, 2.08, 2.38, 3.04, 3.25, 4.72, 4.97, 5.45, 7.24–7.31; MS (ESI+) for C$_{17}$H$_{18}$BrN$_3$O m/z 362 (M+H)$^+$.

Preparation 165

(1R,2S)-1-[(5-bromo-3-cyclopropyl-6-methylpyrazin-2-yl)amino]-2,3-dihydro-1H-inden-2-ol

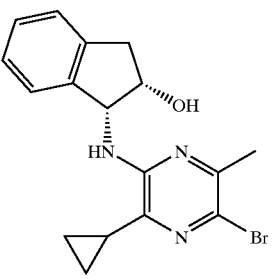

Following the procedure for the preparation of (1R,2S)-1-[(5-bromo-3,6-diethylpyrazin-2-yl)amino]-2,3-dihydro-1H-inden-2-ol but substituting (1R,2S)-1-[(3-cyclopropyl-6-methylpyrazin-2-yl)amino]-2,3-dihydro-1H-inden-2-ol and making non-critical variations provided the title compound as a solid: $^1$H NMR (CDCl$_3$) δ 0.95–1.08, 1.69–1.78, 2.49, 3.04, 3.24, 4.78, 5.39, 5.58, 7.24–7.33; MS (ESI+) for C$_{17}$H$_{18}$BrN$_3$O m/z 360 (M+H)$^+$.

Preparation 166

(1R,2S)-1-[(5-bromo-6-cyclopropyl-3-ethylpyrazin-2-yl)amino]-2,3-dihydro-1H-inden-2-ol

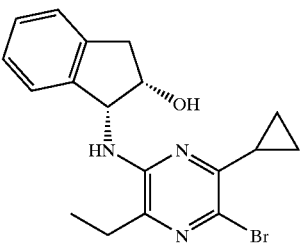

Following the procedure for the preparation of (1R,2S)-1-[(5-bromo-3,6-diethylpyrazin-2-yl)amino]-2,3-dihydro-1H-inden-2-ol but substituting (1R,2S)-1-[(6-cyclopropyl-3-ethylpyrazin-2-yl)amino]-2,3-dihydro-1H-inden-2-ol and making non-critical variations provided the title compound as a solid: $^1$H NMR (CDCl$_3$) δ 0.93–1.09, 1.28–1.39, 2.35–2.43, 2.60–2.67, 2.99–3.05, 3.22–3.29, 4.70, 5.04, 5.44–5.49, 7.23–7.32; MS (ESI+) for C$_{18}$H$_{20}$BrN$_3$O m/z 374 (M+H)$^+$.

Preparation 167

(1R,2S)-1-[(5-bromo-3-cyclopropyl-6-ethylpyrazin-2-yl)amino]-2,3-dihydro-1H-inden-2-ol

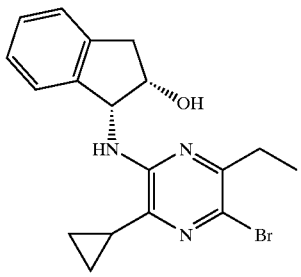

Following the procedure for the preparation of (1R,2S)-1-[(5-bromo-3,6-diethylpyrazin-2-yl)amino]-2,3-dihydro-1H-inden-2-ol but substituting (1R,2S)-1-[(3-cyclopropyl-6-ethylpyrazin-2-yl)amino]-2,3-dihydro-1H-inden-2-ol and making non-critical variations provided the title compound as a solid: $^1$H NMR (CDCl$_3$) δ 0.86–1.08, 1.23–1.30, 1.70–1.79, 2.77–2.84, 3.03–3.09, 3.23–3.30, 4.77–4.81, 5.44, 5.56, 7.23–7.32; MS (ESI+) for C$_{18}$H$_{20}$BrN$_3$O m/z 374 (M+H)$^+$.

Preparation 168

(1R,2S)-1-[(5-bromo-6-ethyl-3-methylpyrazin-2-yl)amino]-2,3-dihydro-1H-inden-2-ol (A) and (1R,2S)-1-[(5-bromo-3-ethyl-6-methylpyrazin-2-yl)amino]-2,3-dihydro-1H-inden-2-ol (B)

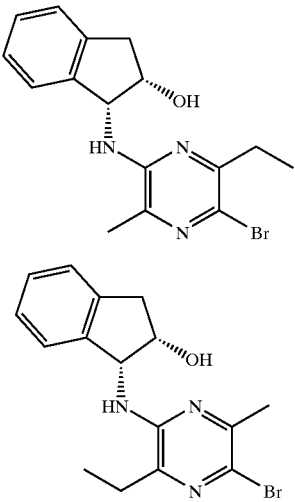

Following the procedure for the preparation of (1R,2S)-1-[(3,6-diethylpyrazin-2-yl)amino]-2,3-dihydro-1H-inden-2-ol but substituting a mixture of (1R,2S)-1-[(6-ethyl-3-methylpyrazin-2-yl)amino]-2,3-dihydro-1H-inden-2-ol (A) and (1R,2S)-1-[(3-ethyl-6-methylpyrazin-2-yl)amino]-2,3-dihydro-1H-inden-2-ol (B) and making non-critical variations provided a mixture of the title compound as a solid: $^1$H NMR (CDCl$_3$) δ 1.11–1.24, 2.26–3.16, 4.63–4.67, 4.94–4.98, 5.20, 5.46–5.50, 7.12–7.30; MS (ESI+) for C$_{16}$H$_{18}$BrN$_3$O m/z 348 (M+H)$^+$.

Preparation 169

(1R,2S)-1-{[3,6-dicyclopropyl-5-(2,4-dichlorophenyl)pyrazin-2-yl]amino}-2,3-dihydro-1H-inden-2-ol

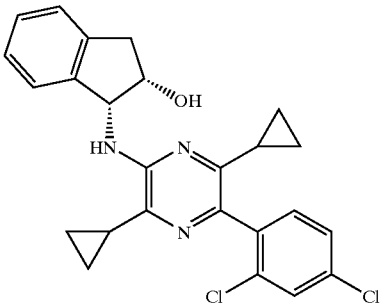

Following the procedure for the preparation of (1R,2S)-1-{[5-(2,4-dichlorophenyl)-3,6-diethylpyrazin-2-yl]amino}-2,3-dihydro-1H-inden-2-ol but substituting (1S,2S)-1-[(5-bromo-3,6-dicyclopropylpyrazin-2-yl)amino]-2,3-dihydro-1H-inden-2-ol and making non-critical variations provided the title compound as a solid: $^1$H NMR (CDCl$_3$) δ 0.85–0.99, 1.67, 1.82, 2.48, 3.10–3.13, 3.27–3.28, 4.79, 5.40, 5.42, 7.30–7.51; MS (ESI+) for C$_{25}$H$_{23}$Cl$_2$N$_3$O m/z 452 (M+H)$^+$.

Preparation 170

(1R,2S)-1-{[6-cyclopropyl-5-(2,4-dichlorophenyl)-3-methylpyrazin-2-yl]amino}-2,3-dihydro-1H-inden-2-ol

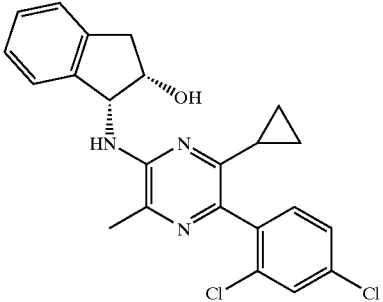

Following the procedure for the preparation of 5-(2,4-dichlorophenyl)-N-[(1R,2S)-2-ethoxy-2,3-dihydro-1H-inden-1-yl]-3,6-diethylpyrazin-2-amine but substituting (1R,2S)-1-[(5-bromo-6-cyclopropyl-3-methylpyrazin-2-yl)amino]-2,3-dihydro-1H-inden-2-ol and making non-critical variations provided the title compound as a solid: $^1$H NMR (CDCl$_3$) δ 0.87–1.03, 1.60–1.69, 2.42, 2.71, 3.03, 3.25, 4.73, 4.99, 5.53, 7.12–7.66; MS (ESI+) for C$_{23}$H$_{21}$Cl$_2$N$_3$O m/z 426 (M+H)$^+$.

Preparation 171

(1R,2S)-1-{[3-cyclopropyl-5-(2,4-dichlorophenyl)-6-methylpyrazin-2-yl]amino}-2,3-dihydro-1H-inden-2-ol

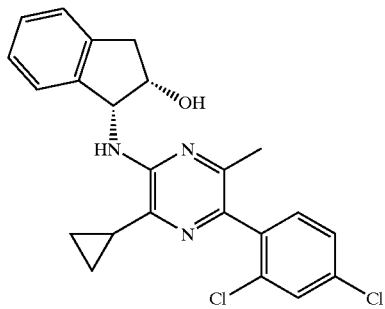

Following the procedure for the preparation of 5-(2,4-dichlorophenyl)-N-[(1R,2S)-2-ethoxy-2,3-dihydro-1H-inden-1-yl]-3,6-diethylpyrazin-2-amine but substituting (1R,2S)-1-[(5-bromo-3-cyclopropyl-6-methylpyrazin-2-yl)amino]-2,3-dihydro-1H-inden-2-ol and making non-critical variations provided the title compound as a solid: $^1$H NMR (CDCl$_3$) δ 0.96–0.99, ,1.58, 1.81, 2.26, 2.85, 3.14, 3.26, 4.86, 5.44, 5.63, 7.26–7.50; MS (ESI+) for C$_{23}$H$_{21}$Cl$_2$N$_3$O m/z 426 (M+H)$^+$.

Preparation 172

(1R,2S)-1-{[6-cyclopropyl-5-(2,4-dichlorophenyl)-3-ethylpyrazin-2-yl]amino}-2,3-dihydro-1H-inden-2-ol

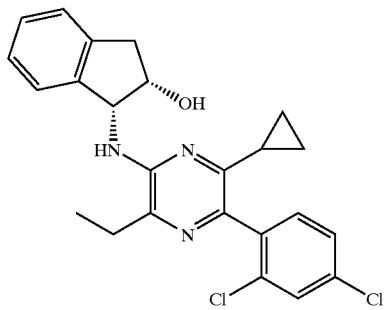

Following the procedure for the preparation of 5-(2,4-dichlorophenyl)-N-[(1R,2S)-2-ethoxy-2,3-dihydro-1H-inden-1-yl]-3,6-diethylpyrazin-2-amine but substituting (1R,2S)-1-[(5-bromo-6-cyclopropyl-3-ethylpyrazin-2-yl)amino]-2,3-dihydro-1H-inden-2-ol and making non-critical variations provided the title compound as a solid: $^1$H NMR (CDCl$_3$) δ 0.96–1.00, 1.26–1.32, 2.04, 2.35–2.40, 2.61–2.66, 3.0–3.04, 3.22–3.27, 4.09–4.14, 4.68–4.70, 5.08, 5.45–5.48, 7.23–7.31; MS (ESI+) for C$_{24}$H$_{23}$Cl$_2$N$_3$O m/z 440 (M+H)$^+$.

Preparation 173

(1R,2S)-1-{[5-(2-chloro-4-methoxyphenyl)-6-cyclopropyl-3-ethylpyrazin-2-yl]amino}-2,3-dihydro-1H-inden-2-ol

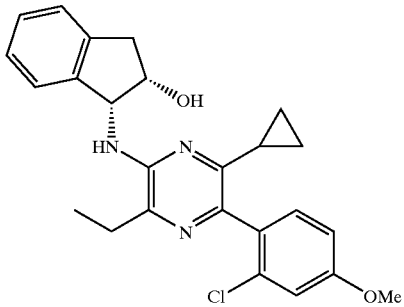

Following the procedure for the preparation of 5-(2,4-dichlorophenyl)-N-[(1R,2S)-2-ethoxy-2,3-dihydro-1H-inden-1-yl]-3,6-diethylpyrazin-2-amine but substituting (1R,2S)-1-[(5-bromo-6-cyclopropyl-3-ethylpyrazin-2-yl)amino]-2,3-dihydro-1H-inden-2-ol and making non-critical variations provided the title compound as a solid: $^1$H NMR (CDCl$_3$) δ; MS (ESI+) for C$_{23}$H$_{21}$Cl$_2$N$_3$O m/z (M+H)$^+$.

Preparation 174

(1R,2S)-1-({6-cyclopropyl-5-[6-(dimethylamino)-4-methylpyridin-3-yl]-3-ethylpyrazin-2-yl}amino)-2,3-dihydro-1H-inden-2-ol

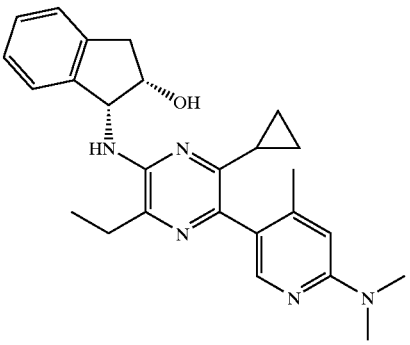

Following the procedure for the preparation of 5-(2,4-dichlorophenyl)-N-[(1R,2S)-2-ethoxy-2,3-dihydro-1H-inden-1-yl]-3,6-diethylpyrazin-2-amine but substituting (1R,2S)-1-[(5-bromo-6-cyclopropyl-3-ethylpyrazin-2-yl)amino]-2,3-dihydro-1H-inden-2-ol and making non-critical variations provided the title compound as a solid: $^1$H NMR (CDCl$_3$) δ; MS (ESI+) for C$_{23}$H$_{21}$Cl$_2$N$_3$O m/z (M+H)$^+$.

Preparation 175

(1R,2S)-1-{[3-cyclopropyl-5-(2,4-dichlorophenyl)-6-ethylpyrazin-2-yl]amino}-2,3-dihydro-1H-inden-2-ol

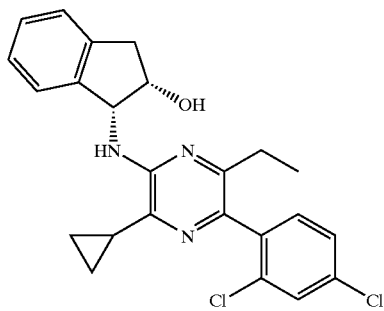

Following the procedure for the preparation of 5-(2,4-dichlorophenyl)-N-[(1R,2S)-2-ethoxy-2,3-dihydro-1H-inden-1-yl]-3,6-diethylpyrazin-2-amine but substituting (1R,2S)-1-[(5-bromo-3-cyclopropyl-6-ethylpyrazin-2-yl)amino]-2,3-dihydro-1H-inden-2-ol and making non-critical variations provided the title compound as a solid: $^1$H NMR (CDCl$_3$) δ 0.94–1.02, 1.14–1.19, 1.26–1.30, 1.68–1.86, 2.06, 2.28–2.49, 3.08–3.32, 4.06–4.18, 4.83–4.87, 5.49, 5.62–5.66, 7.27–7.50; MS (ESI+) for $C_{24}H_{23}Cl_2N_3O$ m/z 440(MH)$^+$.

Preparation 176

(1R,2S)-1-({3-cyclopropyl-5-[6-(dimethylamino)-4-methylpyridin-3-yl]-6-ethylpyrazin-2-yl}amino)-2,3-dihydro-1H-inden-2-ol

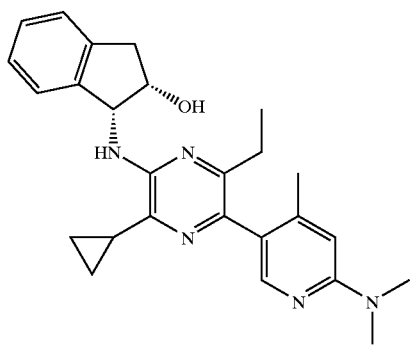

Following the procedure for the preparation of 5-(2,4-dichlorophenyl)-N-[(1R,2S)-2-ethoxy-2,3-dihydro-1H-inden-1-yl]-3,6-diethylpyrazin-2-amine but substituting (1R,2S)-1-[(5-bromo-3-cyclopropyl-6-ethylpyrazin-2-yl)amino]-2,3-dihydro-1H-inden-2-ol and making non-critical variations provided the title compound as a solid: $^1$H NMR (CDCl$_3$) δ 0.88–1.00, 1.13–1.17, 1.25–1.34, 1.77–1.82, 2.11, 2.52–2.58, 3.08–3.12, 3.23–3.28, 4.82–4.85, 5.41, 5.60–5.62, 7.26–7.70, 7.97; MS (ESI+) for $C_{26}H_{31}N_5O$ m/z 430(MH)$^+$.

Preparation 177

(1R,2S)-1-{[5-(2-chloro-4-methoxyphenyl)-3-cyclopropyl-6-ethylpyrazin-2-yl]amino}-2,3-dihydro-1H-inden-2-ol

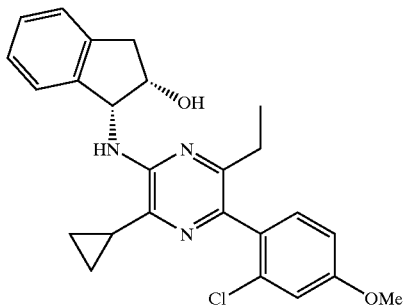

Following the procedure for the preparation of 5-(2,4-dichlorophenyl)-N-[(1R,2S)-2-ethoxy-2,3-dihydro-1H-inden-1-yl]-3,6-diethylpyrazin-2-amine but substituting (1R,2S)-1-[(5-bromo-3-cyclopropyl-6-ethylpyrazin-2-yl)amino]-2,3-dihydro-1H-inden-2-ol and making non-critical variations provided the title compound as a solid: $^1$H NMR (CDCl$_3$) δ 0.95–1.01, 1.14–1.30, 1.80–1.84, 2.52, 2.76–2.84, 3.11–3.16, 3.26–3.31, 3.80–3.88, 4.12–4.17, 4.85–4.88, 5.36, 5.61–5.63, 6.88–7.03, 7.21–7.46; MS (ESI+) for $C_{25}H_{26}ClN_3O_2$ m/z 436(MH)$^+$.

Preparation 178

(1R,2S)-1-{[5-(2,4-dichlorophenyl)-6-ethyl-3-methylpyrazin-2-yl]amino}-2,3-dihydro-1H-inden-2-ol

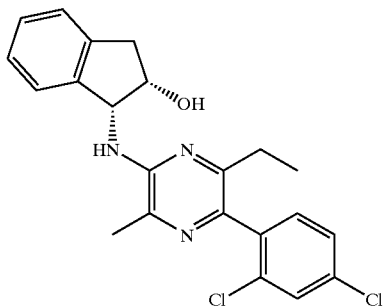

Following the procedure for the preparation of (1R,2S)-1-[(3,6-diethylpyrazin-2-yl)amino]-2,3-dihydro-1H-inden-2-ol but substituting (1R,2S)-1-[(5-bromo-6-ethyl-3-methylpyrazin-2-yl)amino]-2,3-dihydro-1H-inden-2-ol (A) and (1R,2S)-1-[(5-bromo-3-ethyl-6-methylpyrazin-2-yl)amino]-2,3-dihydro-1H-inden-2-ol (B) and making non-critical variations provided the title compound as a solid: $^1$H NMR (CDCl$_3$) δ 1.06–1.09, 1.13–1.20, 2.36–2.38, 3.00–3.22, 4.76, 5.57, 7.19–7.42.

Preparation 179

(1R,2S)-1-{[5-(2,4-dichlorophenyl)-3-ethyl-6-methylpyrazin-2-yl]amino}-2,3-dihydro-1H-inden-2-ol

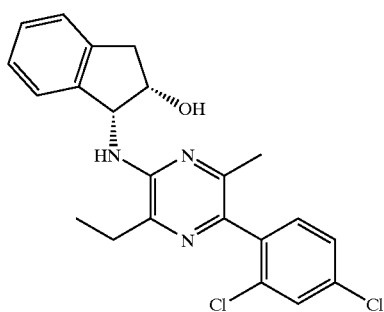

Following the procedure for the preparation of (1R,2S)-1-[(3,6-diethylpyrazin-2-yl)amino]-2,3-dihydro-1H-inden-2-ol but substituting (1R,2S)-1-[(5-bromo-6-ethyl-3-methylpyrazin-2-yl)amino]-2,3-dihydro-1H-inden-2-ol (A) and (1R,2S)-1-[(5-bromo-3-ethyl-6-methylpyrazin-2-yl)amino]-2,3-dihydro-1H-inden-2-ol (B) and making non-critical variations provided the title compound as a solid: $^1$H NMR (CDCl$_3$) δ 1.15–1.28, 2.36–2.52, 2.74, 3.09–3.30, 4.85, 5.68, 7.28–7.68.

Example 111

3,6-dicyclopropyl-5-(2,4-dichlorophenyl)-N-[(1R,2S)-2-ethoxy-2,3-dihydro-1H-inden-1-yl]pyrazin-2-amine

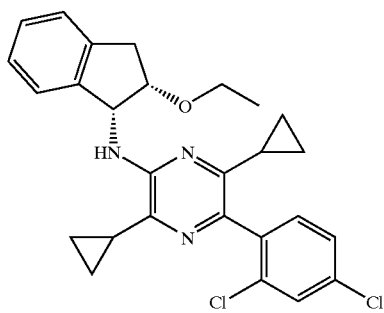

Following the procedure for the preparation of 5-(2,4-dichlorophenyl)-N-[(1R,2S)-2-ethoxy-2,3-dihydro-1H-inden-1-yl]-3,6-diethylpyrazin-2-amine but substituting (1R,2S)-1-{[3,6-dicyclopropyl-5-(2,4-dichlorophenyl)pyrazin-2-yl]amino}-2,3-dihydro-1H-inden-2-ol and making non-critical variations provided the title compound as a solid: $^1$H NMR (CDCl$_3$) δ 0.80–1.07, 1.17–1.20, 1.67, 1.79, 3.14–3.20, 3.46–3.50, 3.70–3.72, 4.35, 5.72, 5.97, 7.24–7.50; MS (ESI+) for C$_{27}$H$_{27}$Cl$_2$N$_3$O m/z 480 (M+H)$^+$.

Example 112

6-cyclopropyl-5-(2,4-dichlorophenyl)-N-[(1R,2S)-2-ethoxy-2,3-dihydro-1H-inden-1-yl]-3-methylpyrazin-2-amine

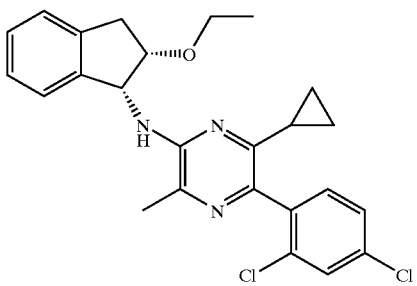

Following the procedure for the preparation of 5-(2,4-dichlorophenyl)-N-[(1R,2S)-2-ethoxy-2,3-dihydro-1H-inden-1-yl]-3,6-diethylpyrazin-2-amine but substituting (1R,2S)-1-{[6-cyclopropyl-5-(2,4-dichlorophenyl)-3-methylpyrazin-2-yl]amino}-2,3-dihydro-1H-inden-2-ol and making non-critical variations provided the title compound as a solid: $^1$H NMR (CDCl$_3$) δ 0.75–1.13, 1.53–1.59, 2.31, 2.98–3.09, 3.35–3.40, 3.57–3.65, 4.23–4.25, 5.37, 5.62, 7.12–7.42; MS (ESI+) for C$_{25}$H$_{25}$Cl$_2$N$_3$O m/z 454 (M+H)$^+$.

Example 113

3-cyclopropyl-5-(2,4-dichlorophenyl)-N-[(1R,2S)-2-ethoxy-2,3-dihydro-1H-inden-1-yl]-6-methylpyrazin-2-amine

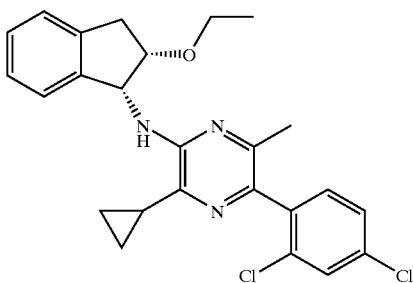

Following the procedure for the preparation of 5-(2,4-dichlorophenyl)-N-[(1R,2S)-2-ethoxy-2,3-dihydro-1H-inden-1-yl]-3,6-diethylpyrazin-2-amine but substituting (1R,2S)-1-{[3-cyclopropyl-5-(2,4-dichlorophenyl)-6-methylpyrazin-2-yl]amino}-2,3-dihydro-1H-inden-2-ol and making non-critical variations provided the title compound as a solid: $^1$H NMR (CDCl$_3$) δ 0.87–1.07, 1.18–1.23, 1.82, 2.27, 3.10–3.16, 3.47–3.57, 3.66–3.76, 4.40, 5.83, 5.98, 7.25–7.50; MS (ESI+) for C$_{25}$H$_{25}$Cl$_2$N$_3$O m/z 454 (M+H)$^+$.

Example 114

6-cyclopropyl-5-(2,4-dichlorophenyl)-N-[(1R,2S)-2-ethoxy-2,3-dihydro-1H-inden-1-yl]-3-ethylpyrazin-2-amine

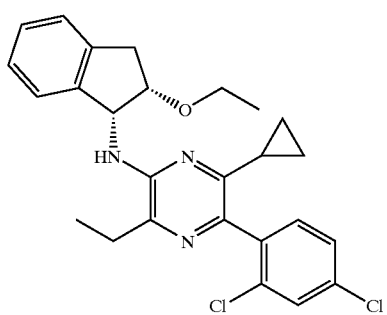

Following the procedure for the preparation of 5-(2,4-dichlorophenyl)-N-[(1R,2S)-2-ethoxy-2,3-dihydro-1H-inden-1-yl]-3,6-diethylpyrazin-2-amine but substituting (1R,2S)-1-{[6-cyclopropyl-5-(2,4-dichlorophenyl)-3-ethylpyrazin-2-yl]amino}-2,3-dihydro-1H-inden-2-ol and making non-critical variations provided the title compound as a solid: $^1$H NMR (CDCl$_3$) δ 0.82–1.33, 1.58–1.71, 2.68–2.76, 3.06–3.19, 3.41–3.51, 3.65–3.75, 4.32–4.36, 5.52–5.54, 5.71–5.76, 7.23–7.52; MS (ESI+) for $C_{26}H_{27}Cl_2N_3O$ m/z 469 (M+H)$^+$.

Example 115

5-(2-chloro-4-methoxyphenyl)-6-cyclopropyl-N-[(1R,2S)-2-ethoxy-2,3-dihydro-1H-inden-1-yl]-3-ethylpyrazin-2-amine

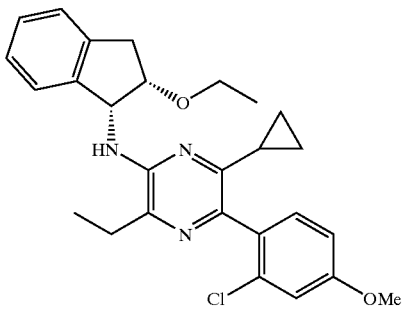

Following the procedure for the preparation of 5-(2,4-dichlorophenyl)-N-[(1R,2S)-2-ethoxy-2,3-dihydro-1H-inden-1-yl]-3,6-diethylpyrazin-2-amine but substituting (1R,2S)-1-{[5-(2-chloro-4-methoxyphenyl)-6-cyclopropyl-3-ethylpyrazin-2-yl]amino}-2,3-dihydro-1H-inden-2-ol and making non-critical variations provided the title compound as a solid: MS (ESI+) for $C_{27}H_{30}ClN_3O_2$ m/z 465 (M+H)$^+$.

Example 116

6-cyclopropyl-5-[6-(dimethylamino)-4-methylpyridin-3-yl]-N-[(1R,2S)-2-ethoxy-2,3-dihydro-1H-inden-1-yl]-3-ethylpyrazin-2-amine

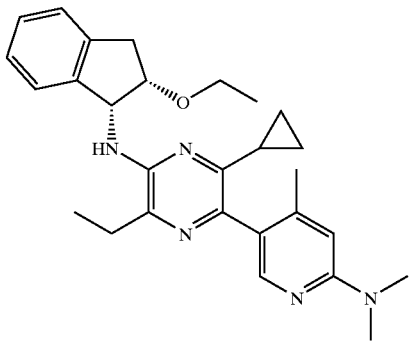

Following the procedure for the preparation of 5-(2,4-dichlorophenyl)-N-[(1R,2S)-2-ethoxy-2,3-dihydro-1H-inden-1-yl]-3,6-diethylpyrazin-2-amine but substituting (1R,2S)-1-({6-cyclopropyl-5-[6-(dimethylamino)-4-methylpyridin-3-yl]-3-ethylpyrazin-2-yl}amino)-2,3-dihydro-1H-inden-2-ol and making non-critical variations provided the title compound as a solid: $^1$H NMR (CDCl$_3$) δ 0.81–1.19, 1.28–1.33, 2.67–2.73, 3.11–3.14, 3.42–3.51, 3.65–3.73, 4.32–4.35, 5.40–5.42, 5.72–5.75, 6.497.22–7.39, 8.19; MS (ESI+) for $C_{28}H_{35}N_5O$ m/z 458 (M+H)$^+$.

Example 117

3-cyclopropyl-5-(2,4-dichlorophenyl)-N-[(1R,2S)-2-ethoxy-2,3-dihydro-1H-inden-1-yl]-6-ethylpyrazin-2-amine

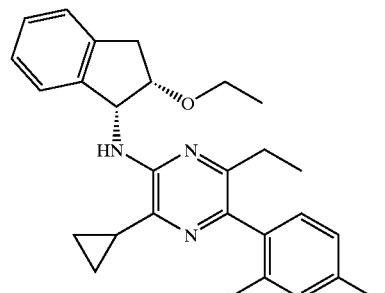

Following the procedure for the preparation of 5-(2,4-dichlorophenyl)-N-[(1R,2S)-2-ethoxy-2,3-dihydro-1H-inden-1-yl]-3,6-diethylpyrazin-2-amine but substituting (1R,2S)-1-{[3-cyclopropyl-5-(2,4-dichlorophenyl)-6-ethylpyrazin-2-yl]amino}-2,3-dihydro-1H-inden-2-ol and making non-critical variations provided the title compound as a solid: $^1$H NMR (CDCl$_3$) δ 0.87–1.21, 1.58, 1.80–1.85, 2.51, 3.15–3.17, 3.46–3.56, 3.66–3.76, 4.40–4.45, 5.88, 6.04, 7.21–7.34, 7.47–7.50; MS (ESI+) for $C_{26}H_{27}Cl_2N_3O$ m/z 469 (M+H)$^+$.

Example 118

3-cyclopropyl-5-[6-(dimethylamino)-4-methylpyridin-3-yl]-N-[(1R,2S)-2-ethoxy-2,3-dihydro-1H-inden-1-yl]-6-ethylpyrazin-2-amine

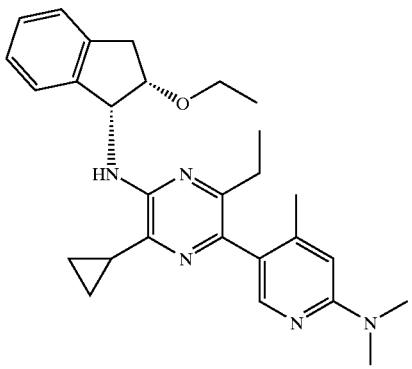

Following the procedure for the preparation of 5-(2,4-dichlorophenyl)-N-[(1R,2S)-2-ethoxy-2,3-dihydro-1H-inden-1-yl]-3,6-diethylpyrazin-2-amine but substituting (1R,2S)-1-{[3-cyclopropyl-5-(2,4-dichlorophenyl)-6-ethylpyrazin-2-yl]amino}-2,3-dihydro-1H-inden-2-ol and making non-critical variations provided the title compound as a solid: $^1$H NMR (CDCl$_3$) δ 0.85–0.95, 1.16–1.34, 1.80–1.83, 2.53–2.58, 3.49–3.55, 3.68–3.72, 4.39–4.42, 5.32, 5.81–5.88, 6.46, 7.24–7.28, 7.51–7.53, 8.01; MS (ESI+) for $C_{28}H_{35}N_5O$ m/z 458 (M+H)$^+$.

Example 119

5-(2-chloro-4-methoxyphenyl)-3-cyclopropyl-N-[(1R,2S)-2-ethoxy-2,3-dihydro-1H-inden-1-yl]-6-ethylpyrazin-2-amine

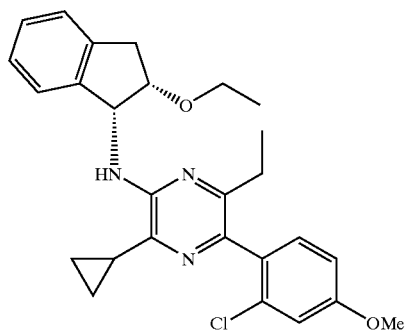

Following the procedure for the preparation of 5-(2,4-dichlorophenyl)-N-[(1R,2S)-2-ethoxy-2,3-dihydro-1H-inden-1-yl]-3,6-diethylpyrazin-2-amine but substituting (1R,2S)-1-{[3-cyclopropyl-5-(2,4-dichlorophenyl)-6-ethylpyrazin-2-yl]amino}-2,3-dihydro-1H-inden-2-ol and making non-critical variations provided the title compound as a solid: $^1$H NMR (CDCl$_3$) δ 0.77–0.86, 0.97–1.23, 1.70–1.76, 2.42, 2.67–2.69, 3.00–3.11, 3.38–3.45, 3.57–3.64, 3.76–3.78, 4.30–4.34, 5.73–5.84, 6.78–6.92, 7.13–7.19, 7.37–7.42; MS (ESI+) for $C_{27}H_{30}ClN_3O_2$ m/z 465 (M+H)$^+$.

Example 120

5-(2-chloro-4-methoxyphenyl)-3-cyclopropyl-N-[(1R,2S)-2-ethoxy-2,3-dihydro-1H-inden-1-yl]-6-ethylpyrazin-2-amine

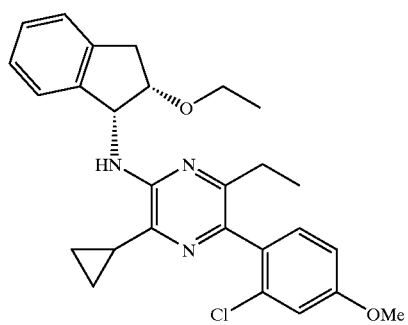

Following the procedure for the preparation of 5-(2,4-dichlorophenyl)-N-[(1R,2S)-2-ethoxy-2,3-dihydro-1H-inden-1-yl]-3,6-diethylpyrazin-2-amine but substituting (1R,2S)-1-{[3-cyclopropyl-5-(2,4-dichlorophenyl)-6-ethylpyrazin-2-yl]amino}-2,3-dihydro-1H-inden-2-ol and making non-critical variations provided the title compound as a solid: $^1$H NMR (CDCl$_3$) δ 0.77–0.86, 0.97–1.23, 1.70–1.78, 2.42, 2.63–2.75, 3.00–3.11, 3.58–3.64, 3.76–3.78, 4.30–4.34, 5.73–5.84, 6.76–6.93, 7.13–7.19, 7.37–7.42; MS (ESI+) for $C_{27}H_{30}ClN_3O_2$ m/z 465 (M+H)$^+$.

Example 121

5-(2,4-dichlorophenyl)-N-[(1R,2S)-2-ethoxy-2,3-dihydro-1H-inden-1-yl]-6-ethyl-3-methylpyrazin-2-amine

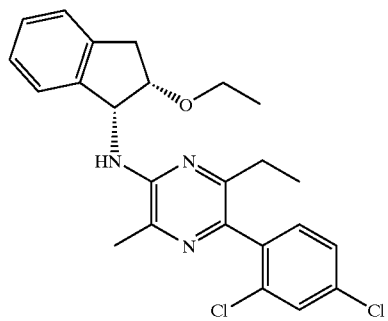

Following the procedure for the preparation of 5-(2,4-dichlorophenyl)-N-[(1R,2S)-2-ethoxy-2,3-dihydro-1H-inden-1-yl]-3,6-diethylpyrazin-2-amine but substituting (1R,2S)-1-{[5-(2,4-dichlorophenyl)-6-ethyl-3-methylpyrazin-2-yl]amino}-2,3-dihydro-1H-inden-2-ol and making non-critical variations provided the title compound as a solid: $^1$H NMR (CDCl$_3$) δ 0.76–0.82, 1.02–1.34, 1.56–1.58, 2.24, 2.62, 3.38–3.55, 3.90–3.95, 5.22, 5.50–5.54, 6.14–6.16, 6.70–6.72, 7.04–7.62; MS (ESI+) for $C_{24}H_{25}Cl_2N_3O$ m/z 443 (M+H)$^+$.

Example 122

5-(2,4-dichlorophenyl)-N-[(1R,2S)-2-ethoxy-2,3-dihydro-1H-inden-1-yl]-3-ethyl-6-methylpyrazin-2-amine

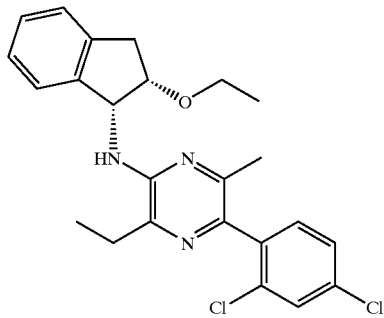

Following the procedure for the preparation of 5-(2,4-dichlorophenyl)-N-[(1R,2S)-2-ethoxy-2,3-dihydro-1H-inden-1-yl]-3,6-diethylpyrazin-2-amine but substituting (1R,2S)-1-{[5-(2,4-dichlorophenyl)-3-ethyl-6-methylpyrazin-2-yl]amino}-2,3-dihydro-1H-inden-2-ol and making non-critical variations provided the title compound as a solid: MS (ESI+) for $C_{24}H_{25}Cl_2N_3O$ m/z 443 (M+H)$^+$.

Preparation 180

N-[(1R,2R)-2-azido-2,3-dihydro-1H-inden-1-yl]-3,6-dicyclopropyl-5-(2,4-dichlorophenyl)pyrazin-2-amine

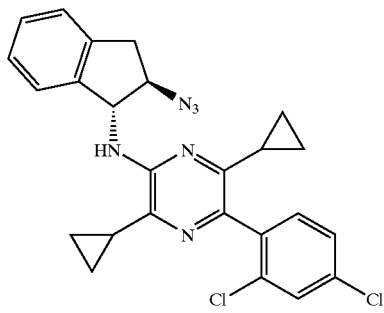

To a solution of (1R,2S)-1-{[3,6-dicyclopropyl-5-(2,4-dichlorophenyl)pyrazin-2-yl]amino}-2,3-dihydro-1H-inden-2-ol (0.76 g, 1.7 mmol) in toluene (10 mL) and THF (10 mL) was added PPh$_3$ (1.14 g, 4.57 mmol). The solution was cooled to 0° C. and HN3 (5.6 mL, 6.38 mmol) and a solution of diethylazodicarboxylate (0.69 mL, 4.37 mmol) in toluene (10 mL) were added. The reaction was stirred at rt overnight. The precipitates were removed by filtration and the filtrate was concentrated. Dissolve residue in 1 N HCl and EtOAc. Extract with EtOAc (3×30 mL). The aqueous phase was neutralized with sat. aq. NaHCO$_3$ to pH 7.5 followed by a small amount of 6 N NaOH to pH 9. The aqueous phase was extracted with CH$_2$Cl$_2$ (3×30 mL). The combined organic extracts were dried over MgSO$_4$, filtered and concentrated. Purify by biotage MPLC (90 g column, 29–39% ethyl acetate/hexanes) to afford 0.8 g (78%) of N-[(1R,2R)-2-azido-2,3-dihydro-1H-inden-1-yl]-3,6-dicyclopropyl-5-(2,4-dichlorophenyl)pyrazin-2-amine as a solid: $^1$H NMR (CDCl$_3$) δ 0.74–1.10, 1.63–1.71, 2.97–3.03, 3.36–3.42, 4.09–4.13, 4.26–4.29, 5.05, 5.57, 7.25–7.53; MS (ESI+) for $C_{25}H_{22}Cl_2N_6$ m/z 477 (M+H)$^+$.

Preparation 181

(1R,2R)-N$^1$-[3,6-dicyclopropyl-5-(2,4-dichlorophenyl)pyrazin-2-yl]-2,3-dihydro-1H-indene-1,2-diamine

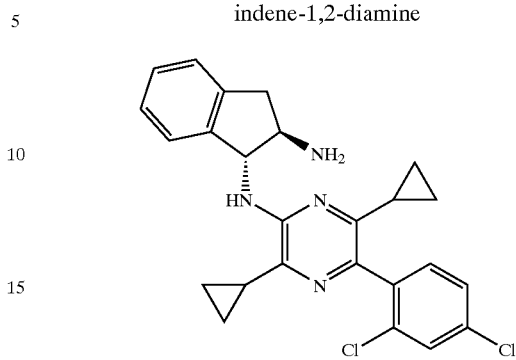

To a solution of N-[(1R,2R)-2-azido-2,3-dihydro-1H-inden-1-yl]-3,6-dicyclopropyl-5-(2,4-dichlorophenyl)pyrazin-2-amine (0.55 g, 1.15 mmol) in anhydrous THF (30 mL) was added PPh$_3$ (0.396 g, 1.51 mmol). The resulting mixture was stirred at rt for 3 hr. To the solution was added water (0.25 mL, 13.9 mmol). The reaction is then allowed to stir overnight at rt. The mixture is concentrated, and the resulting solid is dissolved in MeOH. Purify by passage over Biorad acidic resin by applying the MeOH solution onto the resin and rinsing the resin with MeOH. The resin was then rinsed with 5% triethylamine/MeOH solution to afford 0.52 g (75%) of (1R,2R)-N$^1$-[3,6-dicyclopropyl-5-(2,4-dichlorophenyl)pyrazin-2-yl]-2,3-dihydro-1H-indene-1,2-diamine as a solid: $^1$H NMR (CDCl$_3$) δ 0.85–1.12, 1.64–1.76, 1.89, 2.68–2.82, 3.31–3.39, 3.66–3.72, 5.16, 5.33, 7.28–7.53; MS (ESI+) for $C_{25}H_{24}Cl_2N_4$ m/z 451 (M+H)$^+$.

Example 123

(1R,2R)-N$^1$-[3,6-dicyclopropyl-5-(2,4-dichlorophenyl)pyrazin-2-yl]-N$^2$-ethyl-2,3-dihydro-1H-indene-1,2-diamine

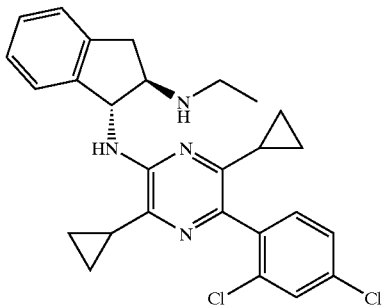

To a solution of (1R,2R)-N$^1$-[3,6-dicyclopropyl-5-(2,4-dichlorophenyl)pyrazin-2-yl]-2,3-dihydro-1H-indene-1,2-diamine (0.15 g, 0.33 mmol) in MeOH (3.3 mL) was sequentially added acetaldehyde (22 mg, 0.5 mmol) and AcOH (5 drops). This mixture was stirred for 30 min before addition of NaBH$_3$CN (1 M solution in THF, 0.6 mL, 0.6 mmol). Stir at rt overnight. Add additional acetic acid (2 drops), acetaldehyde (29 μL, 0.5 mmol) and NaBH$_3$CN (1 M solution in THF, 0.6 mL, 0.6 mmol). After 2 hr, add additional acetic acid (2 drops), acetaldehyde (29 μL, 0.5 mmol) and NaBH$_3$CN (1 M solution in THF, 0.6 mL, 0.6 mmol). After 3 hr, dilute mixture with EtOAc and wash with sat. aq. NaHCO₃ and extract with EtOAc (3×40 mL). The combined organic extracts were dried over MgSO₄, filtered and concentrated. Purify by biotage MPLC (90 g column, 100% ethyl acetate) to afford 0.16 g (44%) of (1R,2R)-N$^1$-[3,6-dicyclopropyl-5-(2,4-dichlorophenyl)pyrazin-2-yl]-N$^2$-ethyl-2,3-dihydro-1H-indene-1,2-diamine as a solid: $^1$H NMR (CDCl₃) δ 0.84–1.05, 1.62–1.75, 2.78–2.86, 3.31–3.37, 3.52, 5.22, 5.52, 7.28–7.51; MS (ESI+) for C₂₇H₂₈Cl₂N₄ m/z 479 (M+H)⁺.

Example 124

N-((1R,2R)-1-{[3,6-dicyclopropyl-5-(2,4-dichlorophenyl)pyrazin-2-yl]amino}-2,3-dihydro-1H-inden-2-yl)acetamide

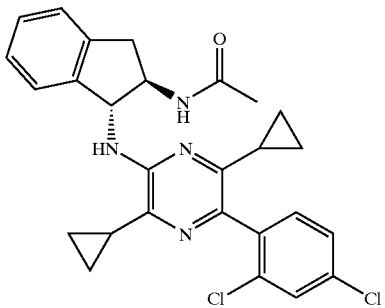

To a solution of (1R,2R)-N$^1$-[3,6-dicyclopropyl-5-(2,4-dichlorophenyl)pyrazin-2-yl]-2,3-dihydro-1H-indene-1,2-diamine (0.10 g, 0.22 mmol) in CHCl₃ (1 mL) at 0° C. under N₂ was added trichloroacetone (30 μL, 0.26 mmol). The mixture was allowed to slowly warn to rt for 1.5 hr. The reaction was then heated at 60° C. for 1.5 h. Cool to rt, add additional trichloroacetone (10 μL) and continue heating at 60° C. for 2 hr. The reaction was concentrated and purified by biotage MPLC (90 g column, 80% ethyl acetate/hexanes) to afford 0.11 g (55%) of N-((1R,2R)-1-{[3,6-dicyclopropyl-5-(2,4-dichlorophenyl)pyrazin-2-yl]amino}-2,3-dihydro-1H-inden-2-yl)acetamide as a solid: $^1$H NMR (CDCl₃) δ 0.84–1.01, 1.61–1.81, 2.04, 2.80–2.86, 3.58–3.64, 4.07–4.13, 4.46, 5.56, 6.56, 7.28–7.51; MS (ESI+) for C₂₇H₂₆Cl₂N₄O m/z 493 (M+H)⁺.

Example 125

(1R,2R)-N$^1$-[3,6-dicyclopropyl-5-(2,4-dichlorophenyl)pyrazin-2-yl]-N$^2$-(2-methoxyethyl)-2,3-dihydro-1H-indene-1,2-diamine

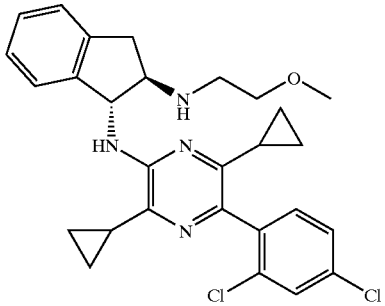

To a solution of (1R,2R)-N$^1$-[3,6-dicyclopropyl-5-(2,4-dichlorophenyl)pyrazin-2-yl]-2,3-dihydro-1H-indene-1,2-diamine (0.10 g, 0.22 mmol) in MeOH (2 mL) containing acetic acid (2 drops) and methoxyacetaldehye (49 mg, 0.66 mmol) was added NaBH₃CN (1 M solution in THF, 0.8 mL, 0.8 mmol). The mixture was stirred at rt overnight. Dilute with sat. aq. NaHCO₃ and extract ED with EtOAc (3×30 mL). The combined organic extracts were dried over MgSO₄, filtered and concentrated to afford an oil that was purified by biotage MPLC (90 g column, 10% ethyl acetate/hexanes) to afford 0.11 g (20%) of (1R,2R)-N$^1$-[3,6-dicyclopropyl-5-(2,4-dichlorophenyl)pyrazin-2-yl]-N$^2$-(2-methoxyethyl)-2,3-dihydro-1H-indene-1,2-diamine as a solid: $^1$H NMR (CDCl₃) δ 0.60–1.01, 1.45–1.70, 2.83–2.99, 3.22–3.33, 3.47–3.56, 5.19, 5.53, 7.11–7.42; MS (ESI+) for C₂₈H₃₀Cl₂N₄O m/z 509 (M+H)⁺.

Example 126

5-(2,4-dichlorophenyl)-N-[(1S,2R)-2-ethoxy-2,3-dihydro-1H-inden-1-yl]-3,6-diethylpyrazin-2-amine

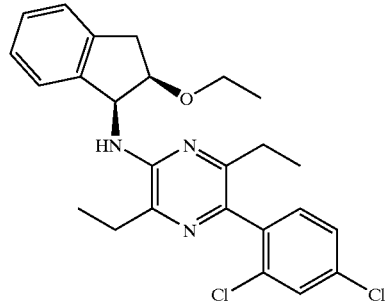

Following the procedure for the preparation of 5-(2,4-dichlorophenyl)-3,6-diethyl-N-[(1S,2R)-2-methoxy-2,3-dihydro-1H-inden-1-yl]pyrazin-2-amine but substituting (1S,2R)-1-{[5-(2,4-dichlorophenyl)-3,6-diethylpyrazin-2-yl]amino}-2,3-dihydro-1H-inden-2-ol and iodoethane and making non-critical variations provided the title compound as a solid: MS (ESI+) for C₂₅H₂₇Cl₂N₃O m/z 457 (M+H)⁺.

Example 127

5-(2,4-dichlorophenyl)-N-[(1S,2S)-2-ethoxy-2,3-dihydro-1H-inden-1-yl]-3,6-diethylpyrazin-2-amine

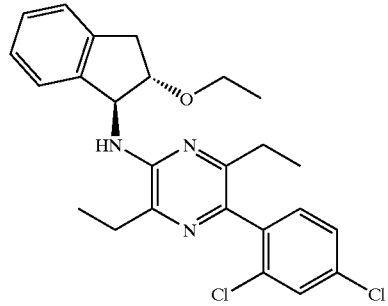

Following the procedure for the preparation of 5-(2,4-dichlorophenyl)-3,6-diethyl-N-[(1S,2S)-2-methoxy-2,3-dihydro-1H-inden-1-yl]pyrazin-2-amine but substituting (1S,2S)-1-{[5-(2,4-dichlorophenyl)-3,6-diethylpyrazin-2-yl]amino}-2,3-dihydro-1H-inden-2-ol and iodoethane and making non-critical variations provided the title compound as a solid: $^1$H NMR (CDCl₃) δ 0.81, 1.17–1.21, 1.30–1.34, 1.51–1.59, 1.98, 3.90–3.96, 4.02–4.08, 6.71–6.73, 7.04–7.07, 7.19; MS (ESI+) for C₂₅H₂₇Cl₂N₃O m/z 457 (M+H)⁺.

Example 128

5-(2,4-dichlorophenyl)-3,6-diethyl-N-[(1S,2S)-2-(2-fluoroethoxy)-2,3-dihydro-1H-inden-1-yl]pyrazin-2-amine

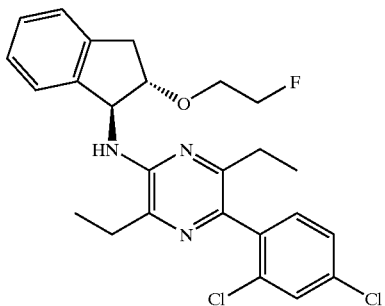

Following the procedure for the preparation of 5-(2,4-dichlorophenyl)-3,6-diethyl-N-[(1S,2S)-2-methoxy-2,3-dihydro-1H-inden-1-yl]pyrazin-2-amine but substituting (1S,2S)-1-{[5-(2,4-dichlorophenyl)-3,6-diethylpyrazin-2-yl]amino}-2,3-dihydro-1H-inden-2-ol and 1-bromo-2-fluoroethane and making non-critical variations provided the title compound as a solid: MS (ESI+) for $C_{25}H_{26}Cl_2FN_3O$ m/z 475 (M+H)$^+$.

Preparation 182

(1R,2S)-1-[(6-chloropyrazin-2-yl)amino]-2,3-dihydro-1H-inden-2-ol

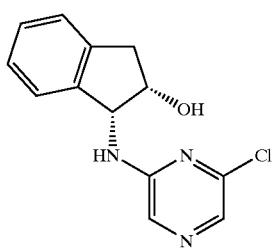

To a solution of 2,6-dichloropyrazine (5.0 g, 34 mmol) in n-BuOH (30 mL) was added triethylamine (6.8 g, 9.4 mL, 67 mmol) and (1R,2S)-(+)-cis-1-amino-2-indanol (5.0 g, 34 mmol). The mixture was heated at 115° C. overnight. The solution was cooled to rt and concentrated. Dissolve material in EtOAc (200 mL) and remove insoluble material by vacuum filtration. Wash filtrate sequentially with 4 N NaOH and sat. aq. NaCl. Dry organic extract over MgSO$_4$, filter and concentrate. Purify by biotage MPLC (90 g column, 10% ethyl acetate/hexanes) to afford 4.85 g (57%) of (1R,2S)-1-[(6-chloropyrazin-2-yl)amino]-2,3-dihydro-1H-inden-2-ol as a solid: $^1$H NMR (CDCl$_3$) δ 2.83–2.87, 3.08–3.13, 3.32, 4.54, 5.11, 5.28–5.31, 7.18–7.28, 7.73, 8.12; MS (ESI+) for $C_{13}H_{12}ClN_3O$ m/z 262 (M+H)$^+$.

Preparation 183 methyl 6-{[(1R,2S)-2-hydroxy-2,3-dihydro-1H-inden-1-yl]amino}pyrazine-2-carboxylate

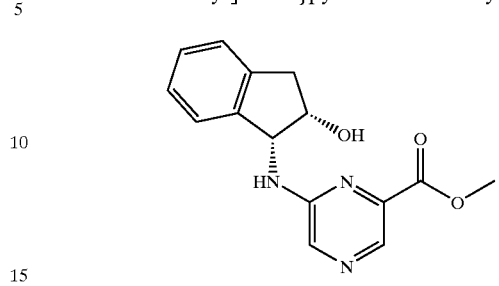

An autoclave was charged with (1R,2S)-1-[(6-chloropyrazin-2-yl)amino]-2,3-dihydro-1H-inden-2-ol (1.7 g, 6.5 mmol), MeOH (20 mL), triethylamine (1.1 mL, 7.8 mmol), bis(diphenylphosphino)ferrocene (21.6 mg, 39 μmol), PdCl$_2$(PhCN)$_2$ (12.5 mg, 32.5 μmol) and dried, powdered 4 Å molecular sieves (2.8 g). Evacuate and charge (3×) with carbon monoxide (350 psi). Heat at 145° C. for 18 hours. Cool to rt, release pressure and remove solids by filtration. The mixture was diluted with CH$_2$Cl$_2$ and washed with water. The organic extract was dried over MgSO$_4$, filtered and concentrated. Purify by biotage MPLC (90 g column, 50% ethyl acetate/hexanes) to afford 1.4 g (77%) of methyl 6-{[(1R,2S)-2-hydroxy-2,3-dihydro-1H-inden-1-yl]amino}pyrazine-2-carboxylate as a solid: $^1$H NMR (CDCl$_3$) δ 2.84–2.88, 3.09–3.14, 3.85, 4.55–4.57, 5.41–5.44, 7.14–7.28, 7.61–7.63, 8.30, 8.39; MS (ESI+) for $C_{15}H_{15}N_3O_3$ m/z 286 (M+H)$^+$.

Preparation 184 methyl 3-bromo-6-{[(1R,2S)-2-hydroxy-2,3-dihydro-1H-inden-1-yl]amino}pyrazine-2-carboxylate

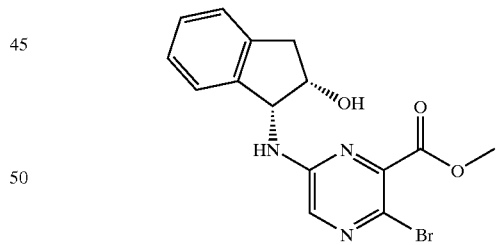

To a solution of methyl 6-{[(1R,2S)-2-hydroxy-2,3-dihydro-1H-inden-1-yl]amino}pyrazine-2-carboxylate (1.0 g, 3.5 mmol) in CH$_2$Cl$_2$ (35 mL) was added N-bromsuccinimide (0.69 g, 3.86 mmol). Stir at t for 2 hr. Wash the reaction with sat. aq. NaHCO$_3$. The organic extract was dried over MgSO$_4$, filtered and concentrated. Purify by biotage MPLC (90 g column, 20% ethyl acetate/hexanes) to afford 380 mg (30%) of methyl 3-bromo-6-{[(1R,2S)-2-hydroxy-2,3-dihydro-1H-inden-1-yl]amino}pyrazine-2-carboxylate as a solid: $^1$H NMR (CDCl$_3$) δ 3.01–3.06, 3.24–3.29, 4.00, 4.75–4.78, 5.45–5.46, 7.25–7.32, 7.94; MS (ESI+) for $C_{15}H_{14}BrN_3O_3$ m/z 386 (M+H)$^+$.

Preparation 185 methyl 3-(2,4-dichlorophenyl)-6-{[(1R,2S)-2-hydroxy-2,3-dihydro-1H-inden-1-yl]amino}pyrazine-2-carboxylate

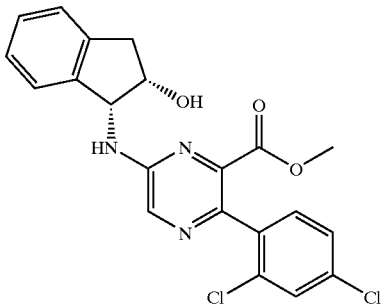

Charge a Kimble vial with methyl 3-bromo-6-{[(1R,2S)-2-hydroxy-2,3-dihydro-1H-inden-1-yl]amino}pyrazine-2-carboxylate (0.45 g, 1.14 mmol), Pd(PPh$_3$)$_4$ (198 mg, 0.17 mmol), and 2,4-dichlorophenylboronic acid (325 mg, 1.71 mmol). Flush with N$_2$ and add DMF (4 mL) and 2 M Na$_2$CO$_3$ (1.1 mL). The resulting mixture was heated at 85° C. overnight. The mixture was diluted with sat. aq. NaHCO$_3$. Extract with Et2O. The organic extract was dried over MgSO$_4$, filtered and concentrated. Purify by biotage MPLC (90 g column, 30% ethyl acetate/hexanes) to afford 290 mg (59%) of methyl 3-(2,4-dichlorophenyl)-6-{[(1R,2S)-2-hydroxy-2,3-dihydro-1H-inden-1-yl]amino}pyrazine-2-carboxylate as a solid: $^1$H NMR (CDCl$_3$) δ 3.06–3.09, 3.27–3.32, 3.80, 4.09–4.15, 4.84, 5.58, 7.28–7.49, 8.25; MS (ESI+) for C$_{21}$H$_{17}$Cl$_2$N$_3$O$_3$ m/z 430 (M+H)$^+$.

Preparation 186 methyl 5-bromo-3-(2,4-dichlorophenyl)-6-{[(1R,2S)-2-hydroxy-2,3-dihydro-1H-inden-1-yl]amino}pyrazine-2-carboxylate

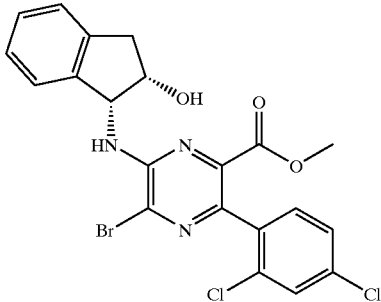

Following the procedure for the preparation of methyl 3-bromo-6-{[(1R,2S)-2-hydroxy-2,3-dihydro-1H-inden-1-yl]amino}pyrazine-2-carboxylate but substituting methyl 3-(2,4-dichlorophenyl)-6-{[(1R,2S)-2-hydroxy-2,3-dihydro-1H-inden-1-yl]amino}pyrazine-2-carboxylate and making non-critical variations provided the title compound as a solid: $^1$H NMR (CDCl$_3$) δ 2.99–3.04, 3.20–3.25, 3.70, 3.99–4.08, 4.77, 5.59–5.62, 6.11, 7.24–7.38; MS (ESI+) for C$_{21}$H$_{16}$BrCl$_2$N$_3$O$_3$ m/z 509 (M+H)$^+$.

Preparation 187 ethyl 3-(2,4-dichlorophenyl)-6-{[(1R,2S)-2-hydroxy-2,3-dihydro-1H-inden-1-yl]amino}-5-methoxypyrazine-2-carboxylate

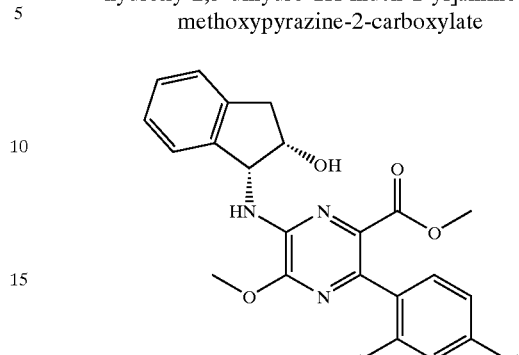

To a solution of methyl 5-bromo-3-(2,4-dichlorophenyl)-6-{[(1R,2S)-2-hydroxy-2,3-dihydro-1H-inden-1-yl]amino}pyrazine-2-carboxylate (0.19 g, 0.37 mmol) in MeOH (3.7 mL) was added NaOMe (60 mg, 1.1 mmol). The mixture was heated at reflux for 3 hr. Cool to rt, and dilute with EtOAc. Wash with sat. aq. NaHCO$_3$. Dry organic extract over MgSO$_4$, filter and concentrate. Purify by biotage MPLC (90 g column, 25% ethyl acetate/hexanes) to afford 0.15 g (73%) of ethyl 3-(2,4-dichlorophenyl)-6-{[(1R,2S)-2-hydroxy-2,3-dihydro-1H-inden-1-yl]amino}-5-methoxypyrazine-2-carboxylate as a solid: $^1$H NMR (CDCl$_3$) δ 3.07–3.12, 3.25–3.31, 3.76, 4.04, 4.85–4.89, 5.68–5.76, 7.28–7.49; MS (ESI+) for C$_{22}$H$_{19}$Cl$_2$N$_3$O$_4$ m/z 460 (M+H)$^+$.

Example 129 methyl 3-(2,4-dichlorophenyl)-6-{[(1R,2S)-2-ethoxy-2,3-dihydro-1H-inden-1-yl]amino}-5-methoxypyrazine-2-carboxylate

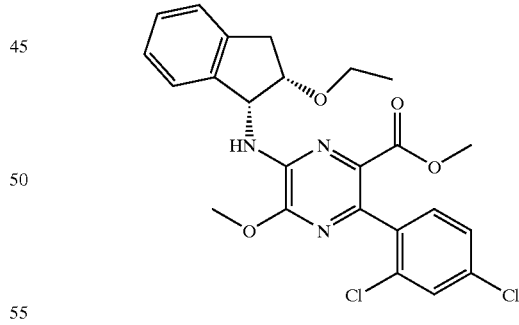

Following the procedure for the preparation of 5-(2,4-dichlorophenyl)-3,6-diethyl-N-[(1S,2S)-2-methoxy-2,3-dihydro-1H-inden-1-yl]pyrazin-2-amine but substituting methyl 3-(2,4-dichlorophenyl)-6-{[(1R,2S)-2-hydroxy-2,3-dihydro-1H-inden-1-yl]amino}-5-methoxypyrazine-2-carboxylate and making non-critical variations provided the title compound as a solid: $^1$H NMR (CDCl$_3$) δ 1.13–0.20, 3.15, 3.55–3.58, 3.66–3.70, 3.76, 4.02, 4.41, 5.75–5.79, 6.16, 7.25–7.34, 7.48, 7.59–7.61; MS (ESI+) for C$_{24}$H$_{23}$Cl$_2$N$_3$O$_4$ m/z 488 (M+H)$^+$.

Example 130 methyl 6-{[(1R,2S)-2-(acetyloxy)-2,3-dihydro-1H-inden-1-yl]amino}-3-(2,4-dichlorophenyl)-5-methoxypyrazine-2-carboxylate

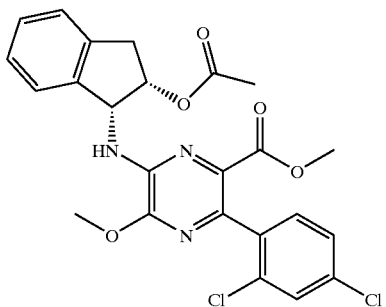

Following the procedure for the preparation of (1R,2S)-1-{[5-(2,4-dichlorophenyl)-3,6-diethylpyrazin-2-yl]amino}-2,3-dihydro-1H-inden-2-yl acetate but substituting methyl 3-(2,4-dichlorophenyl)-6-{[(1R,2S)-2-ethoxy-2,3-dihydro-1H-inden-1-yl]amino}-5-methoxypyrazine-2-carboxylate and making non-critical variations provided the title compound as a solid: $^1$H NMR (CDCl$_3$) δ 2.03, 3.10–3.14 3.31–3.36, 3.75, 4.05, 5.68–5.77, 6.07–6.11, 7.31–7.48; MS (ESI+) for $C_{24}H_{21}Cl_2N_3O_5$ m/z 502 (M+H)$^+$.

Preparation 186

(1R,2S)-1-[(6-methoxypyrazin-2-yl)amino]-2,3-dihydro-1H-inden-2-ol

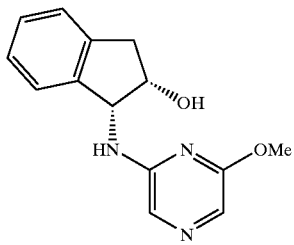

To a solution of (1R,2S)-1-[(6-chloropyrazin-2-yl)amino]-2,3-dihydro-1H-inden-2-ol (2 g, 7.6 mmol) in MeOH (26 mL) was added a solution of NaOMe (1.3 g, 23 mmol) in MeOH (40 mL). The mixture was heated at reflux for 24 hr. Additional NaOMe (1.3 g) was added. Continue heating at reflux for 24 hr, and then add additional NaOMe (1.3 g). Continue heating at reflux for 24 hr and cool to rt. Dilute with EtOAc and was with sat. aq. NaHCO$_3$. The solids were removed by filtration. Separate phases and wash organic extract with additional sat. aq. NaHCO$_3$. Dry organic extracts over MgSO$_4$, filter and concentrate. Purify by biotage MPLC (90 g column, 25% ethyl acetate/hexanes) to afford 1.4 g (71%) of (1R,2S)-1-[(6-methoxypyrazin-2-yl)amino]-2,3-dihydro-1H-inden-2-ol as an oil: $^1$H NMR (CDCl$_3$) δ 3.04–3.08, 3.23–3.29, 3.91, 4.75–4.78, 5.18, 5.42–5.45, 7.25–7.34, 7.57–7.61; MS (ESI+) for $C_{14}H_{15}N_3O_2$ m/z 258 (M+H)$^+$.

Preparation 187

(1R,2S)-1-[(5-bromo-6-methoxypyrazin-2-yl)amino]-2,3-dihydro-1H-inden-2-ol

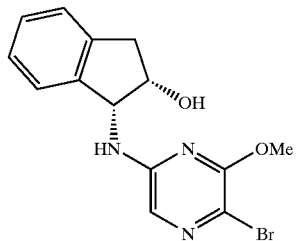

Following the procedure for the preparation of methyl 3-bromo-6-{[(1R,2S)-2-hydroxy-2,3-dihydro-1H-inden-1-yl]amino}pyrazine-2-carboxylate but substituting methyl (1R,2S)-1-[(6-methoxypyrazin-2-yl)amino]-2,3-dihydro-1H-inden-2-ol and making non-critical variations provided the title compound as a solid: $^1$H NMR (CDCl$_3$) δ 2.07, 3.03–3.07, 3.25–3.30, 3.98, 4.76, 5.38, 7.26–7.32, 7.45; MS (ESI+) for $C_{14}H_{14}BrN_3O_2$ m/z 336 (M+H)$^+$.

Preparation 188

(1R,2S)-1-{[5-(2,4-dichlorophenyl)-6-methoxypyrazin-2-yl]amino}-2,3-dihydro-1H-inden-2-ol

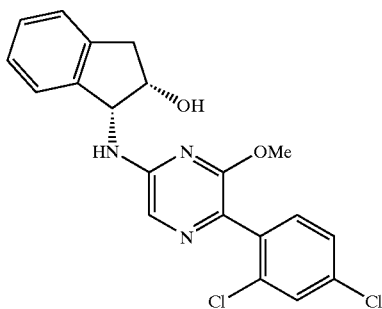

A Kimble vial was charged with (1R,2S)-1-[(5-bromo-6-methoxypyrazin-2-yl)amino]-2,3-dihydro-1H-inden-2-ol (0.55 g, 1.63 mmol), Pd$_2$(dba)$_3$ (33 mg, 35 μmol), dicyclohexyl[2-(9-phenanthryl)phenyl]phosphine (64 mg), 2,4-dichlorophenylboronic acid (567 mg, 2.67 mmol), K$_3$PO$_4$ (1.13 g, 5.34 mmol) and toluene (15 mL). The vial was flushed with N2, sealed and heated at 110° C. for 6 hr. Cool to rt, add additional Pd$_2$(dba)$_3$ (33 mg) and 2,4-dichlorophenylboronic acid (0.5 g, 2.7 mmol). Continue heating overnight. Add additional Pd$_2$(dba)$_3$ (33 mg) and 2,4-dichlorophenylboronic acid (0.5 g, 2.7 mmol) and continue heating for 5 hr. Add additional Pd$_2$(dba)$_3$ (33 mg) and 2,4-dichlorophenylboronic acid (0.5 g, 2.7 mmol) and continue heating overnight. The reaction was cooled to rt, diluted with CH$_2$Cl$_2$, washed with sat. aq NaHCO$_3$ and sat. aq. NaCl. Dry organic extract over MgSO$_4$, filter and concentrate. Purify by biotage MPLC (90 g column, 30% ethyl acetate/hexanes) to afford 0.2 g (31%) of (1R,2S)-1-{[5-(2,4-dichlorophenyl)-6-methoxypyrazin-2-yl]amino}-2,3-dihydro-1H-inden-2-ol as an oil: $^1$H NMR (CDCl$_3$) δ 3.06–3.10, 3.26–3.32, 3.92, 4.79, 5.33, 5.49–5.50, 7.28–7.41, 7.50, 7.74; MS (ESI+) for $C_{20}H_{17}Cl_2N_3O_2$ m/z 402 (M+H)$^+$.

243

Preparation 189

(1R,2S)-1-{[3-bromo-5-(2,4-dichlorophenyl)-6-methoxypyrazin-2-yl]amino}-2,3-dihydro-1H-inden-2-ol

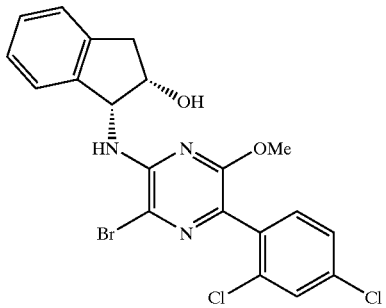

Following the procedure for the preparation of methyl 3-bromo-6-{[(1R,2S)-2-hydroxy-2,3-dihydro-1H-inden-1-yl]amino}pyrazine-2-carboxylate but substituting (1R,2S)-1-{[5-(2,4-dichlorophenyl)-6-methoxypyrazin-2-yl]amino}-2,3-dihydro-1H-inden-2-ol and making non-critical variations provided the title compound as a solid: $^1$H NMR (CDCl$_3$) δ 3.09–3.13, 3.29–3.34, 3.92, 4.81, 5.60–5.63, 5.99, 7.33–7.42, 7.49; MS (ESI+) for C$_{20}$H$_{16}$BrCl$_2$N$_3$O$_2$ m/z 479 (M+H)$^+$.

Preparation 190

(1R,2S)-1-{[5-(2,4-dichlorophenyl)-6-methoxy-3-vinylpyrazin-2-yl]amino}-2,3-dihydro-1H-inden-2-ol

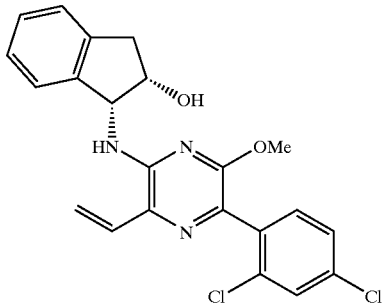

To a solution of (1R,2S)-1-{[3-bromo-5-(2,4-dichlorophenyl)-6-methoxypyrazin-2-yl]amino}-2,3-dihydro-1H-inden-2-ol (150 mg, 0.31 mmol) in DMF (1.6 mL) is added Pd(PPh$_3$)$_4$ (7 mg, 6 µmol), and tributyl vinyl tin (114 mg, 0.36 mmol). The reaction is heated at 120° C. overnight. Sat. aq. KF (15 mL) is added and the mixture is stirred at rt for 1 hr. Extract with CH$_2$Cl$_2$ (5×30 mL). The combined organic extracts were dried over MgSO$_4$, filtered and concentrated. Purify by biotage MPLC (90 g column, 15% ethyl acetate/hexanes) to afford 132 mg (38%) of (1R,2S)-1-{[5-(2,4-dichlorophenyl)-6-methoxy-3-vinylpyrazin-2-yl]amino}-2,3-dihydro-1H-inden-2-ol as a solid: $^1$H NMR (CDCl$_3$) δ 3.08–3.12, 3.28–3.34, 3.93, 4.82, 5.46–5.49, 5.54–5.67, 6.09–6.13, 6.77–6.84, 7.28–7.50; MS (ESI+) for C$_{20}$H$_{17}$Cl$_2$N$_3$O$_2$ m/z 402 (M+H)$^+$.

244

Example 131

5-(2,4-dichlorophenyl)-N-[(1R,2S)-2-ethoxy-2,3-dihydro-1H-inden-1-yl]-6-methoxy-3-vinylpyrazin-2-amine

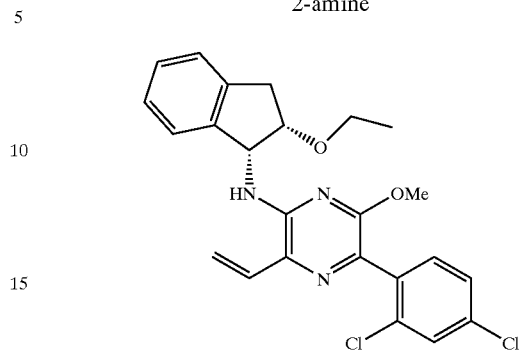

Following the procedure for the preparation of 5-(2,4-dichlorophenyl)-3,6-diethyl-N-[(1S,2S)-2-methoxy-2,3-dihydro-1H-inden-1-yl]pyrazin-2-amine but substituting (1R,2S)-1-{[5-(2,4-dichlorophenyl)-6-methoxy-3-vinylpyrazin-2-yl]amino}-2,3-dihydro-1H-inden-2-ol and making non-critical variations provided the title compound as a solid: $^1$H NMR (CDCl$_3$) δ 1.11–1.14, 3.04–3.08, 3.37–3.44, 3.60–3.68, 3.84, 4.28–4.30, 5.34–5.37, 5.68–5.71, 5.90–5.99, 6.66–6.73, 7.14–7.26, 7.32–7.40; MS (ESI+) for C$_{24}$H$_{23}$Cl$_2$N$_3$O$_2$ m/z 456 (M+H)$^+$.

What is claimed is:
1. A compound of Formula I

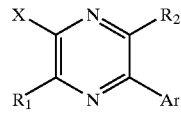

Formula I or a stereoisomer thereof, a pharmaceutically acceptable salt thereof, wherein in Formula I, X is —NR$_3$R$_4$, Ar is selected from aryl or substituted aryl;

R$_1$, R$_2$, and are independently selected from halogen, —NO$_2$, —CN, —R$_a$, —OR$_a$, —S(O)$_m$R$_a$, —NR$_a$R$_a$, —C(O)NR$_a$R$_a$, —C(S)NR$_a$R$_a$—S(O)$_m$NR$_a$R$_a$, —NR$_a$S(O)$_m$R$_a$, —NR$_a$C(O)OR$_a$, —OC(O)NR$_a$R$_a$, —NR$_a$C(O)NR$_a$R$_a$, —NR$_a$C(S)NR$_a$R$_a$, —C(O)OR$_a$, —C(S)OR$_a$, or —OC(O)OR$_a$;

R$_3$ and R$_4$ are independently selected from heteroaryl, substituted heteroaryl, aryl cycloalkyl, substituted aryl cycloalkyl, heteroaryl cycloalkyl, substituted heteroaryl cycloalkyl, aryl heterocycloalkyl, substituted aryl heterocycloalkyl, heteroaryl heterocycloalkyl, substituted heteroaryl heterocycloalkyl, R$_a$ and

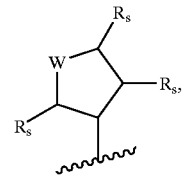

wherein W is O, NR$_p$, or S(O)$_m$,

R$_p$ is independently selected from —R$_a$, —S(O)$_m$R$_a$, —C(O)NR$_a$R$_a$, —C(S)NR$_a$R$_a$—S(O)$_m$NR$_a$R$_a$, —C(O)

$OR_a$, or —$C(S)OR_a$; m is 0,1 or 2, and $R_s$ each is independently selected from halogen, —$NO_2$, —CN, —$R_a$, —$OR_a$, —$S(O)_mR_a$, —$NR_aR_a$, —$C(O)NR_aR_a$, —$C(S)NR_aR_a$—$S(O)_mNR_aR_a$, —$NR_aS(O)_mR_a$, —$NR_aC(O)OR_a$, —$OC(O)NR_aR_a$, —$NR_aC(O)NR_aR_a$, —$NR_aC(S)NR_aR_a$, —$C(O)OR_a$, —$C(S)OR_a$, or —$OC(O)OR_a$; substituted heteroaryl, substituted aryl, aryl cycloalkyl, substituted aryl cycloalkyl, heteroaryl cycloalkyl, substituted heteroaryl cycloalkyl, aryl heterocycloalkyl, substituted aryl heterocycloalkyl, heteroaryl heterocycloalkyl, or substituted heteroaryl heterocycloalkyl provided at least one of $R_3$ and $R_4$ is

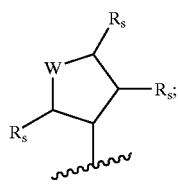

$R_a$ each is selected from H, alkyl, cycloalkyl, haloalkyl, aryl, heteroaryl, or heterocycloalkyl optionally substituted with 1 to 5 of $R_t$, —$OR_t$, —$S(O)_mR_t$, $NR_tR_t$, oxo (=O), thione (=S), phenyl, heteroaryl, or heterocycloalkyl where phenyl, heteroaryl, and heterocycloalkyl are optionally substituted with 1 to 5 independently taken from $R_t$; and $R_t$ each is selected from H, halogen, —$NO_2$, —$NH_2$, —OH, —SH, —CN, —$C(O)NH_2$, —C(O)—NHalkyl, —C(O)Nalkylalkyl, —Oalkyl, NHalkyl, Nalkylalkyl, —$S(O)_m$alkyl, $SO_2NH_2$, $SO_2$NHalkyl and $SO_2$Nalkylalkyl, alkyl, cycloalkyl, haloalkyl, phenyl, benzyl, heteroaryl, or heterocycloalkyl where phenyl, benzyl heteroaryl and heterocycloalkyl may be optionally substituted with alkyl or halogen, provided that the compound is not.

2. A compound of Formula II

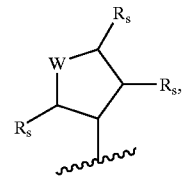

Formula II or a stereoisomer thereof, a pharmaceutically acceptable salt thereof, wherein in Formula II, Ar is selected from aryl or substituted aryl;

m is 0,1 or 2;

$R_1$ and $R_2$ are independently selected from halogen, —$NO_2$, —CN, —$R_a$, —$OR_a$, —$S(O)_mR_a$, —$NR_aR_a$, —$C(O)NR_aR_a$, —$C(S)NR_aR_a$—$S(O)_mNR_aR_a$, —$NR_aS(O)_mR_a$, —$NR_aC(O)OR_a$, —$OC(O)NR_aR_a$, —$NR_aC(O)NR_aR_a$, —$NR_aC(S)NR_aR_a$, —$C(O)OR_a$, —$C(S)OR_a$, or —$OC(O)OR_a$;

$R_3$ and $R_4$ are independently selected from heteroaryl, substituted heteroaryl, aryl cycloalkyl, substituted aryl cycloalkyl, heteroaryl cycloalkyl, substituted heteroaryl cycloalkyl, aryl heterocycloalkyl, substituted aryl heterocycloalkyl, heteroaryl heterocycloalkyl, substituted heteroaryl heterocycloalkyl and

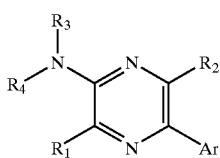

wherein W is O, $NR_p$, or $S(O)_m$, $R_p$ is independently selected from —$R_a$, —$S(O)_mR_a$, —$C(O)NR_aR_a$, —$C(S)NR_aR_a$—$S(O)_mNR_aR_a$, —$C(O)OR_a$, or —$C(S)OR_a$; m is 0,1 or 2, and $R_s$ each is independently selected from halogen, —$NO_2$, —CN, —$R_a$, —$OR_a$, —$S(O)_mR_a$, —$NR_aR_a$, —C(O)$NR_aR_a$, —$C(S)NR_aR_a$—$S(O)_mNR_aR_a$, —$NR_aS(O)_mR_a$, —$NR_aC(O)OR_a$, —$OC(O)NR_aR_a$, —$NR_aC(O)NR_aR_a$, $NR_aC(S)NR_aR_a$, —$C(O)OR_a$, —$C(S)OR_a$, or —$OC(O)OR_a$; substituted heteroaryl, substituted aryl, aryl cycloalkyl, substituted aryl cycloalkyl, heteroalkyl, cycloalkyl, substituted heteroaryl cycloalkyl, aryl heterocycloalkyl, substituted aryl heterocycloalkyl, heteroaryl heterocycloalkyl, or substituted heteroaryl heterocycloalkyl provided at least one of $R_3$ and $R_4$ is

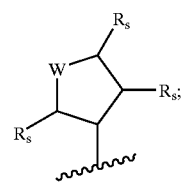

$R_a$ each is independently selected from H, alkyl, cycloalkyl, haloalkyl, aryl, heteroaryl, or heterocycloalkyl optionally substituted with 1 to 5 of $R_t$, —$OR_t$, —$S(O)_mR_t$, $NR_tR_t$, oxo (=O), thione (=S) phenyl, heteroaryl, or heterocycloalkyl where phenyl, heteroaryl, and heterocycloalkyl are optionally substituted with 1 to 5 independently taken from $R_t$; and $R_t$ each is independently selected from H, halogen, —$NH_2$, —OH, —SH, —CN, —$C(O)NH_2$, —C(O)—NHalkyl, —C(O)Nalkylalkyl, —Olakyl, NHalkyl, Nalkylalkyl, —$S(O)_m$alkyl, $SO_2NH_2$, $SO_2$NHalkyl and $SO_2$Nalkylalkyl, alkyl, cycloalkyl, haloalkyl, phenyl, benzyl, heteroaryl, or heterocycloalkyl where phenyl, benzyl heteroaryl and heterocycloalkyl may be optionally substituted with alkyl or halogen.

3. A compound of Formula III

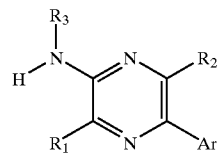

Formula III or a stereoisomer thereof, a pharmaceutically acceptable salt thereof, wherein in Formula III, Ar is selected from aryl or substituted aryl;

m is 0,1 or 2;

$R_1$ and $R_2$ are independently selected from halogen, —$NO_2$, —CN, —$R_a$, —$OR_a$, —$S(O)_mR_a$, —$NR_aR_a$, —$C(O)NR_aR_a$, —$C(S)NR_aR_a$—$S(O)_mNR_aR_a$, —$NR_aS(O)_mR_a$, —$NR_aC(O)OR_a$, —$OC(O)NR_aR_a$, —$NR_aC(O)NR_aR_a$, —$NR_aC(S)NR_aR_a$, —$C(O)OR_a$, —$C(S)OR_a$, or —$OC(O)OR_a$;

$R_3$ is selected from heteroaryl, substituted heteroaryl, aryl cycloalkyl, substituted aryl cycloalkyl, heteroaryl cycloalkyl, substituted heteroaryl cycloalkyl, aryl heterocycloalkyl, substituted aryl heterocycloalkyl, heteroaryl heterocycloalkyl, substituted heteroaryl heterocycloalkyl, or

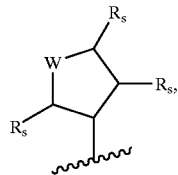

wherein W is O, $NR_p$, or $S(O)_m$, $R_p$ is independently selected from —$R_a$, —$S(O)_mR_a$, —$C(O)NR_aR_a$, —$C(S)NR_aR_a$—$S(O)_mNR_aR_a$, —$C(O)OR_a$, or —$C(S)OR_a$; m is 0,1 or 2, and $R_s$ each is independently selected from halogen, —$NO_2$, —CN, —$R_a$, —$OR_a$, —$S(O)_mR_a$, —$NR_aR_a$, —$C(O)NR_aR_a$, —$C(S)NR_aR_a$—$S(O)_mNR_aR_a$, —$NR_aC(O)OR_a$, —$OC(O)NR_aR_a$, —$NR_aC(O)NR_aR_a$, —$NR_aC(S)NR_aR_a$, —$C(O)OR_a$, —$C(S)OR_a$, or —$OC(O)OR_a$;

$R_a$ each is independently selected from H, alkyl, cycloalkyl, haloalkyl, aryl, heteroaryl, or heterocycloalkyl optionally substituted with 1 to 5 of $R_t$, —$OR_t$, —$S(O)_mR_t$, $NR_tR_t$, oxo (═O), thione (═S) phenyl, heteroaryl, or heterocycloalkyl where phenyl, heteroaryl, and heterocycloalkyl are optionally substituted with 1 to 5 independently taken from $R_t$; and $R_t$ each is independently selected from H, halogen, —$NO_2$, —$NH_2$, —OH, —SH, —CN, —$C(O)NH_2$, —C(O)—NHalkyl, —C(O)Nalkylalkyl, —Oalkyl, NHalkyl, Nalkylalkyl, —$S(O)_m$alkyl, $SO_2NH_2$, $SO_2$NHalkyl and $SO_2$Nalkylalkyl, alkyl, cycloalkyl, haloalkyl, phenyl, benzyl, heteroaryl, or heterocycloalkyl where phenyl, benzyl heteroaryl and heterocycloalkyl may be optionally substituted with alkyl or halogen.

4. A compound of claim 1 wherein in Formula I R3 is

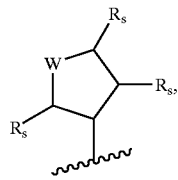

wherein W is O, $NR_p$, or $S(O)_m$, $R_p$ is independently selected from —$R_a$, —$S(O)_mR_a$, —$C(O)NR_aR_a$, —$C(S)NR_aR_a$—$S(O)_mNR_aR_a$, —$C(O)OR_a$, or —$C(S)OR_a$; m is 0,1 or 2, and $R_s$ each is independently selected from halogen, —$NO_2$, —CN, —$R_a$, —$OR_a$, —$S(O)_mR_a$, —$NR_aR_a$, —$C(O)NR_aR_a$, —$C(S)NR_aR_a$—$S(O)_mNR_aR_a$, —$NR_aS(O)_mR_a$, —$NR_aC(O)OR_a$, —$OC(O)NR_aR_a$, —$NR_aC(O)NR_aR_a$, $NR_aC(S)NR_aR_a$, —$C(O)OR_a$, —$C(S)OR_a$, or —$OC(O)OR_a$; substituted heteroaryl, substituted aryl, aryl cycloalkyl, substituted aryl cycloalkyl, heteroalkyl, cycloalkyl, substituted heteroaryl cycloalkyl, aryl heterocycloalkyl, substituted aryl heterocycloalkyl, heteroaryl heterocycloalkyl, or substituted heteroaryl heterocycloalkyl and R4 is hydrogen, or R4 is

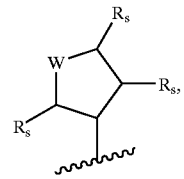

wherein W is O, $NR_p$, or $S(O)_m$, $R_p$ is independently selected from —$R_a$, —$S(O)_mR_a$, —$C(O)NR_aR_a$, —$C(S)NR_aR_a$—$S(O)_mNR_aR_a$, —$C(O)OR_a$, or —$C(S)OR_a$; m is 0,1 or 2, and $R_s$ each is independently selected from halogen, —$NO_2$, —CN, —$R_a$, —$OR_a$, —$S(O)_mR_a$, —$NR_aR_a$, —$C(O)NR_aR_a$, —$C(S)NR_aR_a$—$S(O)_mNR_aR_a$, —$NR_aS(O)_mR_a$, —$NR_aC(O)OR_a$, —$OC(O)NR_aR_a$, —$NR_aC(O)NR_aR_a$, $NR_aC(S)NR_aR_a$, —$C(O)OR_a$, —$C(S)OR_a$, or —$OC(O)OR_a$; substituted heteroaryl, substituted aryl, aryl cycloalkyl, substituted aryl cycloalkyl, heteroalkyl, cycloalkyl, substituted heteroaryl cycloalkyl, aryl heterocycloalkyl, substituted aryl heterocycloalkyl, heteroaryl heterocycloalkyl, or substituted heteroaryl heterocycloalkyl and R3 is hydrogen.

5. A compound of Formula VII

Formula VII

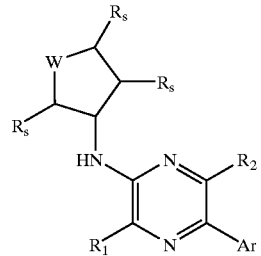

or a stereoisomer thereof, a pharmaceutically acceptable salt thereof, wherein in Formula VII, Ar is selected from aryl or substituted aryl;

W is O, $NR_p$, or $S(O)_m$;

m is 0,1 or 2;

$R_s$ each is independently selected from halogen, —$NO_2$, —CN, —$R_a$, —$OR_a$, —$S(O)_mR_a$, —$NR_aR_a$, —$C(O)NR_aR_a$, —$C(S)NR_aR_a$—$S(O)_mNR_aR_a$, —$NR_aS(O)_mR_a$, —$NR_aC(O)OR_a$, —$OC(O)NR_aR_a$, —$NR_aC(O)NR_aR_a$, —$NR_aC(S)NR_aR_a$, —$C(O)OR_a$, —$C(S)OR_a$, or —$OC(O)OR_a$;

$R_1$ and $R_2$ are independently selected from halogen, —$NO_2$, —CN, —$R_a$, —$OR_a$, —$S(O)_mR_a$, —$NR_aR_a$, —$C(O)NR_aR_a$, —$C(S)NR_aR_a$—$S(O)_mNR_aR_a$, —$NR_aS(O)_mR_a$, —$NR_aC(O)OR_a$, —$OC(O)NR_aR_a$, —$NR_aC(O)NR_aR_a$, —$NR_aC(S)NR_aR_a$, —$C(O)OR_a$, —$C(S)OR_a$, or —$OC(O)OR_a$;

$R_p$ each is independently selected from —$R_a$, —$S(O)_mR_a$, —$C(O)NR_aR_a$, —$C(S)NR_aR_a$—$S(O)_mNR_aR_a$, —$C(O)OR_a$, or —$C(S)OR_a$;

$R_a$ each is independently selected from H, alkyl, cycloalkyl, haloalkyl, aryl, heteroaryl, or heterocycloalkyl optionally substituted with 1 to 5 of $R_t$, —$OR_t$, —$S(O)_mR_t$, —$NR_tR_t$, oxo (═O), thione (═S), phenyl, heteroaryl, or heterocycloalkyl where phenyl, heteroaryl, and heterocycloalkyl are optionally substituted with 1 to 5 independently taken from $R_t$; and $R_t$ each is independently selected from H, halogen, —$NO_2$, —$NH_2$, —OH, —SH, —CN, —C(O)$NH_2$, —C(O)—NHalkyl, —C(O)Nalkylalkyl, —Oalkyl, NHalkyl, Nalkylalkyl, —S(O)$_m$alkyl, $SO_2NH_2$, $SO_2$NHalkyl and $SO_2$Nalkylalkyl, alkyl, cycloalkyl, haloalkyl, phenyl, benzyl, heteroaryl, or heterocycloalkyl where phenyl, benzyl heteroaryl and heterocycloalkyl may be optionally substituted with alkyl or halogen.

6. A compound of Formula VIII

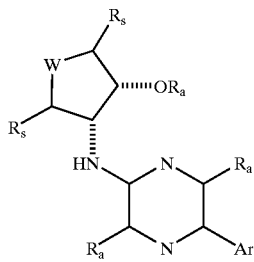

Formula VIII or a stereoisomer thereof, a pharmaceutically acceptable salt thereof, wherein in Formula VIII, Ar is selected from aryl or substituted aryl;

W is O, $NR_p$, or $S(O)_m$, m is 0,1 or 2;

$R_a$ each is independently selected from halogen, —$NO_2$, —CN, —$R_a$, —$OR_a$, —$S(O)_mR_a$, —$NR_aR_a$, —C(O)$NR_aR_a$, —C(S)$NR_aR_a$—$S(O)_mNR_aR_a$, —$NR_aS(O)_mR_a$, —$NR_aC(O)OR_a$, —OC(O)$NR_aR_a$, —$NR_aC(O)NR_aR_a$, —$NR_aC(S)NR_aR_a$, —C(O)$OR_a$, —C(S)$OR_a$, or —OC(O)$OR_a$;

$R_p$ is independently selected from —$R_a$, —$S(O)_mR_a$, —C(O)$NR_aR_a$,—C(S)$NR_aR_a$—$S(O)_mNR_aR_a$, —C(O)$OR_a$, or —C(S)$OR_a$;

$R_a$ each is independently selected from H, alkyl, cycloalkyl, haloalkyl, aryl, heteroaryl, or heterocycloalkyl optionally substituted with 1 to 5 of $R_t$, —$OR_t$, —$S(O)_mR_t$, $NR_tR_t$, oxo (═O), thione (═S), phenyl, heteroaryl, or heterocycloalkyl where phenyl, heteroaryl, and heterocycloalkyl are optionally substituted with 1 to 5 independently taken from $R_t$; and $R_t$ each is independently selected from H, halogen, —$NO_2$, —$NH_2$, —OH, —SH, —CN, —C(O)$NH_2$, —C(O)—NHalkyl, —C(O)Nalkylalkyl, —Oalkyl, NHalkyl, Nalkylalkyl, —S(O)$_m$alkyl, $SO_2NH_2$, $SO_2$NHalkyl and $SO_2$Nalkylalkyl, alkyl, cycloalkyl, haloalkyl, phenyl, benzyl, heteroaryl, or heterocycloalkyl where phenyl, benzyl heteroaryl and heterocycloalkyl may be optionally substituted with alkyl or halogen.

7. A compound of claim 6 which is 5-(2,4-dichlorophenyl)-N-[(cis)-4-ethoxy-1-propionylpyrrolidin-3-yl]-3,6-diethylpyrazin-2-amine, ethyl (cis)-3-{[5-(2,4-dichlorophenyl)-3,6-diethylpyrazin-2-yl]amino}-4-ethoxypyrrolidine-1-carboxylate, benzyl (3R,4S)-3-{[5-(2,4-dichlorophenyl)-3,6-diethylpyrazin-2-yl]amino}-4-ethoxypyrrolidine-1-carboxylate, methyl (3R,4S)-3-{[5-(2,4-dichlorophenyl)-3,6-diethylpyrazin-2-yl]amino}-4-ethoxypyrrolidine-1-carboxylate, methyl (3R,4S)-3-{[5-(2-chloro-4-methoxyphenyl)-3,6-diethylpyrazin-2-yl]amino}-4-ethoxypyrrolidine-1-carboxylate, benzyl (3R,4S)-3-{[5-(2-chloro-4-methoxyphenyl)-3,6-diethylpyrazin-2-yl]amino}-4-ethoxypyrrolidine-1-carboxylate, cis-(+/−)-5-chloro-(2-chloro-4-methoxyphenyl)-3,6-diethyl-N-[4-propoxytetrahydrofuran-3-yl]pyrazin-2-amine or a pharmaceutically acceptable salt thereof.

8. A compound of Formula IX

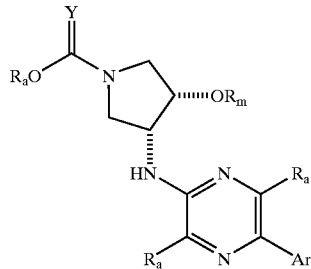

Formula IX or a stereoisomer thereof, a pharmaceutically acceptable salt thereof, wherein in Formula IX, Ar is selected from aryl or substituted aryl;

m is 0,1 or 2;

Y=O or S $R_m$ is $C_1$–$C_6$ alkyl substituted with from 1–2 of halogen, —$NO_2$, —$NH_2$, —OH, —SH, —CN, —C(O)$NH_2$, —C(O)—NHalkyl, —C(O)Nalkylalkyl, —Oalkyl, NHalkyl, Nalkylalkyl, —S(O)$_m$alkyl, $SO_2NH_2$, $SO_2$NHalkyl and $SO_2$Nalkylalkyl, oxo (═O), thione (═S), heterocycloalkyl, or substituted heterocycloalkyl;

$R_a$ each is independently selected from H, alkyl, cycloalkyl, haloalkyl, aryl, heteroaryl, or heterocycloalkyl optionally substituted with 1 to 5 of $R_t$, —$OR_t$, —$S(O)_mR_t$, —$NR_tR_t$, oxo (═O), thione (═S), phenyl, heteroaryl, or heterocycloalkyl where phenyl, heteroaryl, and heterocycloalkyl are optionally substituted with 1 to 5 independently taken from $R_t$; and $R_t$ each is independently selected from H, halogen, —$NO_2$, —$NH_2$, —OH, —SH, —CN, —C(O)$NH_2$, —C(O)—NHalkyl, —C(O)Nalkylalkyl, —Oalkyl, NHalkyl, Nalkylalkyl, —S(O)$_m$alkyl, $SO_2NH_2$, $SO_2$NHalkyl and $SO_2$Nalkylalkyl, alkyl, cycloalkyl, haloalkyl, phenyl, benzyl, heteroaryl, or heterocycloalkyl where phenyl, benzyl heteroaryl and heterocycloalkyl may be optionally substituted with alkyl or halogen.

9. A compound of claim 8 which is benzyl (3R,4S)-3-{[5-(2,4-dichlorophenyl)-3,6-diethylpyrazin-2-yl]amino}-4-(2-fluoroethoxy)pyrrolidine-1-carboxylate, methyl (3R,4S)-3-{[5-(2-chloro-4-methoxyphenyl)-3,6-diethylpyrazin-2-yl]amino}-4-(2-fluoroethoxy)pyrrolidine-1-carboxylate, benzyl (3R,4S)-3-{[5-(2-chloro-4-methoxyphenyl)-3,6-diethylpyrazin-2-yl]amino}-4-(2-fluoroethoxy)pyrrolidine-1-carboxylate, methyl (3R,4S)-3-{[5-(2-chloro-4-methoxyphenyl)-3,6-diethylpyrazin-2-yl]amino}-4-(2-fluoroethoxy)pyrrolidine-1-carboxylate, methyl (3S,4R)-3-(acetyloxy)-4-{[5-(2-chloro-4-methoxyphenyl)-3,6-diethylpyrazin-2-yl]amino}pyrrolidine-1-carboxylate, methyl (3S,4R)-3-(acetyloxy)-4-{[5-(2,4-dichlorophenyl)-3,6-diethylpyrazin-2-yl]amino}pyrrolidine-1-carboxylate, ethyl (3R,4S)-3-{[5-(2-chloro-4-methoxyphenyl)-3,6-diethylpyrazin-2-yl]amino}-4-(2-fluoroethoxy)pyrrolidine-1-carboxylate, or ethyl (3R,4S)-3-{[5-(2,4-dichlorophenyl)-3,6-diethylpyrazin-2-yl]amino}-4-(2-fluoroethoxy)pyrrolidine-1-carboxylate, or a pharmaceutically acceptable salt of any said compound.

10. A compound of Formula II

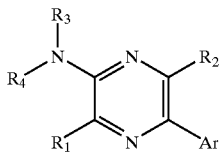

Formula II or a stereoisomer thereof, a pharmaceutically acceptable salt thereof, wherein in Formula II, Ar is selected from aryl or substituted aryl;

m is 0,1 or 2;

$R_1$ and $R_2$ are independently selected from halogen, —$NO_2$, —CN, —$R_a$, —$OR_a$, —$S(O)_mR_a$, —$NR_aR_a$, —$C(O)NR_aR_a$, —$C(S)NR_aR_a$—$S(O)_mNR_aR_a$, —$NR_aS(O)_mR_a$, —$NR_aC(O)OR_a$, —$OC(O)NR_aR_a$, —$NR_aC(O)NR_aR_a$, —$NR_aC(S)NR_aR_a$, —$C(O)OR_a$, —$C(S)OR_a$, or —$OC(O)OR_a$;

$R_3$ and $R_4$ are independently selected from heteroaryl, substituted heteroaryl, aryl cycloalkyl, substituted aryl cycloalkyl, heteroaryl cycloalkyl, substituted heteroaryl cycloalkyl, aryl heterocycloalkyl, substituted aryl heterocycloalkyl, heteroaryl heterocycloalkyl, substituted heteroaryl heterocycloalkyl and

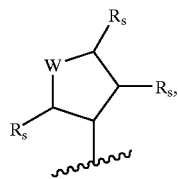

wherein W is O, $NR_p$, or $S(O)_m$, $R_p$ is independently selected from —$R_a$, —$S(O)_mR_a$, —$C(O)NR_aR_a$, —$C(S)NR_aR_a$—$S(O)_mNR_aR_a$, —$C(O)OR_a$, or —$O(S)OR_a$; m is 0,1 or 2, and $R_s$ each is independently selected from halogen, —$NO_2$, —CN, —$R_a$, —$OR_a$, —$S(O)_mR_a$, —$NR_aR_a$, —$C(O)NR_aR_a$, —$C(S)NR_aR_a$—$S(O)_mNR_aR_a$, —$NR_aS(O)_mR_a$, —$NR_aC(O)OR_a$, —$OC(O)NR_aR_a$, —$NR_aC(O)NR_aR_a$, —$NR_aC(S)NR_aR_a$, —$C(O)OR_a$, —$C(S)OR_a$, or —$OC(O)OR_a$; substituted heteroaryl, substituted aryl, aryl cycloalkyl, substituted aryl cycloalkyl, heteroaryl cycloalkyl, substituted heteroaryl cycloalkyl, aryl heterocycloalkyl, substituted aryl heterocycloalkyl, heteroaryl heterocycloalkyl, or substituted heteroaryl heterocycloalkyl provided at least one of $R_3$ and $R_4$ are heteroaryl, substituted heteroaryl, aryl cycloalkyl, substituted aryl cycloalkyl, heteroaryl cycloalkyl, substituted heteroaryl cycloalkyl, aryl heterocycloalkyl, substituted aryl heterocycloalkyl, heteroaryl heterocycloalkyl, or substituted heteroaryl heterocycloalkyl, and provided that at least one of $R_3$ and $R_4$ is

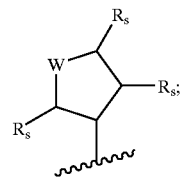

$R_a$ each is independently selected from H, alkyl, cycloalkyl, haloalkyl, aryl, heteroaryl, or heterocycloalkyl optionally substituted with 1 to 5 of $R_t$, —$OR_t$, —$S(O)_mR_t$, $NR_tR_t$, oxo (=O), thione (=S), phenyl, heteroaryl, or heterocycloalkyl where phenyl, heteroaryl, and heterocycloalkyl are optionally substituted with 1 to 5 independently taken from $R_t$; and $R_t$ each is independently selected from H, halogen, —$NO_2$, —$NH_2$, —OH, —SH, —CN, —$C(O)NH_2$, —C(O)—NHalkyl, —C(O)Nalkylalkyl, —Oalkyl, NHalkyl, Nalkylalkyl, —$S(O)_m$alkyl, $SO_2NH_2$, $SO_2NH$alkyl and $SO_2N$alkylalkyl, alkyl, cycloalkyl, haloalkyl, phenyl, benzyl, heteroaryl, or heterocycloalkyl where phenyl, benzyl heteroaryl and heterocycloalkyl may be optionally substituted with alkyl or halogen.

11. A compound which is:

benzyl (cis)-3-{[5-(2,4-dichlorophenyl)-3,6-diethylpyrazin-2-yl]amino}-4-ethoxypyrrolidine-1-carboxylate;

5-(2,4-dichlorophenyl)-N-[(cis)-4-ethoxypyrrolidine-3-yl]-3,6-diethylpyrazin-2-amine;

N-[(cis)-1-acetyl-4-ethoxypyrrolidine-3-yl]-5-(2,4-dichlorophenyl)-3,6-diethylpyrazin-2-amine;

methyl (cis)-3-{[5-(2,4-dichlorophenyl)-3,6-diethylpyrazin-2-yl]amino}-4-ethoxypyrrolidine-1-carboxylate;

5-(2,4-dichlorophenyl)-N-[(cis)-4-ethoxy-1-(methylsulfonyl)pyrrolidin-3-yl]-3,6-diethylpyrazin-2-amine;

(cis)-3-{[5-(2,4-dichlorophenyl)-3,6-diethylpyrazin-2-yl]amino}-4-ethoxy-N,N-dimethylpyrrolidine-1-carboxamide;

(cis)-3-{[5-(2,4-dichlorophenyl)-3,6-diethylpyrazin-2-yl]amino}-4-ethoxy-N,N-dimethylpyrrolidine-1-carbothioamide;

isopropyl (cis)-3-{[5-(2,4-dichlorophenyl)-3,6-diethylpyrazin-2-yl]amino}-4-ethoxypyrrolidine-1-carboxylate;

(cis)-3-{[5-(2,4-dichlorophenyl)-3,6-diethylpyrazin-2-yl]amino}-4-ethoxy-N-methylpyrrolidine-1-carbothioamide;

5-(2,4-dichlorophenyl)-N-[(cis)-4-ethoxy-1-(morpholin-4-ylcarbonyl)pyrrolidin-3-yl]-3,6-diethylpyrazin-2-amine;

2-fluoroethyl (cis)-3-{[5-(2,4-dichlorophenyl)-3,6-diethylpyrazin-2-yl]amino}-4-ethoxypyrrolidine-1-carboxylate;

5-(2,4-dichlorophenyl)-N-[(3R,4S)-4-ethoxypyrrolidin-3-yl]-3,6-diethylpyrazin-2-amine;

5-(2,4-dichlorophenyl)-3,6-diethyl-N-[(3R,4S)-4-(2-fluoroethoxy)pyrrolidin-3-yl]pyrazin-2-amine;

methyl(3R,4S)-3-{[3,6-diethyl-5-(4-methoxy-2-methylphenyl)pyrazin-2-yl]amino}-4-(2-fluoroethoxy)pyrrolidine-1-carboxylate;

methyl (3R,4S)-3-({5-[2-chloro-4-(dimethylamino)phenyl]-3,6-diethylpyrazin-2-yl}amino)-4-(2-fluoroethoxy)pyrrolidine-1-carboxylate;

benzyl (3R,4S)-3-{[5-(2-chloro-4-methoxyphenyl)-3,6-diethylpyrazin-2-yl]amino}-4-hydroxypyrrolidine-1-carboxylate;

5-(2-chloro-4-methoxyphenyl)-N-[(3R,4S)-4-ethoxypyrrolidin-3-yl]-3,6-diethylpyrazin-2-amine;

5-(2-chloro-4-methoxyphenyl)-3,6-diethyl-N-[(3R,4S)-4-(2-fluoroethoxy)pyrrolidin-3-yl]pyrazin-2-amine;

trans-(+/−)-N-[4-ethoxytetrahydrofuran-3-yl]-3,6-diethyl-5-(4-methoxy-2-methylphenyl)pyrazin-2-amine;

cis-(+/−)-N-[4-ethoxytetrahydrofuran-3-yl]-3,6-diethyl-5-(4-methoxy-2-methylphenyl)pyrazin-2-amine;

cis-(+/−)-5-(2-chloro-4-methoxyphenyl)-3,6-diethyl-N-[4-methoxytetrahydrofuran-3-yl]pyrazin-2-amine;

cis-(+/−)-5-(2-chloro-4-methoxyphenyl)-N-[4-ethoxytetrahydrofuran-3-yl]-3,6-diethylpyrazin-2-amine;

5-(2-chloro-4-methoxyphenyl)-3,6-diethyl-N-[(3S,4S)-4-propoxytetrahydrofuran-3-yl]pyrazin-2-amine;

5-(2-chloro-4-methoxyphenyl)-3,6-diethyl-N-[(3S,4S)-4-propoxytetrahydrofuran-3-yl]pyrazin-2-amine;

(+/−)-5-(2-chloro-4-methoxyphenyl)-3,6-diethyl-N-[cis-4-(3-fluoropropoxy)tetrahydrofuran-3-yl]pyrazin-2-amine;

methyl (3R,4S)-3-{[5-(2,4-dichlorophenyl)-3,6-diethylpyrazin-2-yl]amino}-4-propoxypyrrolidine-1-carboxylate;

methyl (3R,4S)-3-{[5-(2,4-dichlorophenyl)-3,6-diethylpyrazin-2-yl]amino}-4-(3-fluoropropoxy)pyrrolidine-1-carboxylate;

methyl (3R,4S)-3-{[5-(2-chloro-4-methoxyphenyl)-3,6-diethylpyrazin-2-yl]amino}-4-(3-fluoropropoxy)pyrrolidine-1-carboxylate;

methyl (3R,4S)-3-{[5-(2-chloro-4-methoxyphenyl)-3,6-diethylpyrazin-2-yl]amino}-4-propoxypyrrolidine-1-carboxylate;

methyl (3R,4S)-3-{[5-(2-chloro-4-methoxyphenyl)-3,6-diethylpyrazin-2-yl]amino}-4-(propionyloxy)pyrrolidine-1-carboxylate;

methyl (3R,4S)-3-{[5-(2,4-dichlorophenyl)-3,6-diethylpyrazin-2-yl]amino}-4-(propionyloxy)pyrrolidine-1-carboxylate;

methyl (3R,4S)-3-{[5-(2,4-dichlorophenyl)-3,6-diethylpyrazin-2-yl]amino}-4-(propionylamino)pyrrolidine-1-carboxylate;

methyl (3S,4R)-3-(acetylamino)-4-{[5-(2,4-dichlorophenyl)-3,6-diethylpyrazin-2-yl]amino}pyrrolidine-1-carboxylate;

methyl (3R,4S)-3-{[5-(2,4-dichlorophenyl)-3,6-diethylpyrazin-2-yl]amino}-4-(ethylamino)pyrrolidine-1-carboxylate;

methyl (3R,4S)-3-{[5-(2,4-dichlorophenyl)-3,6-diethylpyrazin-2-yl]amino}-4-(propylamino)pyrrolidine-1-carboxylate;

O-methyl (3R,4S)-3-{[5-(2,4-dichlorophenyl)-3,6-diethylpyrazin-2-yl]amino}-4-2-fluoroethoxy)pyrrolidine-1-carbothioate;

O-methyl (3R,4S)-3-{[5-(2,4-dichlorophenyl)-3,6-diethylpyrazin-2-yl]amino}-4-ethoxypyrrolidine-1-carbothioate;

O-methyl (3R,4S)-3-{[5-(2-chloro-4-methoxyphenyl)-3,6-diethylpyrazin-2-yl]amino}-4-(3-fluoropropoxy)pyrrolidine-1-carbothioate;

pyridin-2-ylmethyl (3R,4S)-3-{[5-(2,4-dichlorophenyl)-3,6-diethylpyrazin-2-yl]amino}-4-(2-fluoroethoxy)pyrrolidine-1-carboxylate;

pyridin-3-ylmethyl (3R,4S)-3-{[5-(2,4-dichlorophenyl)-3,6-diethylpyrazin-2-yl]amino}-4-(2-fluoroethoxy)pyrrolidine-1-carboxylate;

pyridin-4-ylmethyl (3R,4S)-3-{[5-(2-chloro-4-methoxyphenyl)-3,6-diethylpyrazin-2-yl]amino}-4-(2-fluoroethoxy)pyrrolidine-1-carboxylate;

2-piperidin-1-ylethyl (3R,4S)-3-{[5-(2-chloro-4-methoxyphenyl)-3,6-diethylpyrazin-2-yl]amino}-4-(2-fluoroethoxy)pyrrolidine-1-carboxylate;

2-morpholin-4-ylethyl (3R,4S)-3-{[5-(2,4-dichlorophenyl)-3,6-diethylpyrazin-2-yl]amino}-4-(2-fluoroethoxy)pyrrolidine-1-carboxylate;

2-morpholin-4-ylethyl (3R,4S)-3-{[5-(2,4-dichlorophenyl)-3,6-diethylpyrazin-2-yl]amino}-4-(propionyloxy)pyrrolidine-1-carboxylat;

2-(dimethylamino)ethyl (3R,4S)-3-{[5-(2,4-dichlorophenyl)-3,6-diethylpyrazin-2-yl]amino}-4-(3-fluoropropoxy)pyrrolidine-1-carboxylate;

2-pyrrolidin-1-ylethyl (3R,4S)-3-{[5-(2,4-dichlorophenyl)-3,6-diethylpyrazin-2-yl]amino}-4-(3-fluoropropoxy)pyrrolidine-1-carboxylate;

2-(1H-imidazol-1-yl)ethyl (3R,4S)-3-{[5-(2,4-dichlorophenyl)-3,6-diethylpyrazin-2-yl]amino}-4-(2-fluoroethoxy)pyrrolidine-1-carboxylate;

2-(methylamino)ethyl (3R,4S)-3-{[5-(2,4-dichlorophenyl)-3,6-diethylpyrazin-2-yl]amino}-4-(2-fluoroethoxy)pyrrolidine-1-carboxylate;

2-aminoethyl (3R,4S)-3-{[5-(2,4-dichlorophenyl)-3,6-diethylpyrazin-2-yl]amino}-4-(2-fluoroethoxy)pyrrolidine-1-carboxylate;

2-hydroxyethyl (3R,4S)-3-{[5-(2,4-dichlorophenyl)-3,6-diethylpyrazin-2-yl]amino}-4-(2-fluoroethoxy)pyrrolidine-1-carboxylate;

2-methoxyethyl (3R,4S)-3-{[5-(2,4-dichlorophenyl)-3,6-diethylpyrazin-2-yl]amino}-4-(2-fluoroethoxy)pyrrolidine-1-carboxylate;

2-(2-oxopyrrolidin-1-yl)ethyl (3R,4S)-3-{[5-(2,4-dichlorophenyl)-3,6-diethylpyrazin-2-yl]amino}-4-ethoxypyrrolidine-1-carboxylate;

2-(2-oxopyridin-1(2H)-yl)ethyl (3R,4S)-3-{[5-(2,4-dichlorophenyl)-3,6-diethylpyrazin-2-yl]amino}-4-ethoxypyrrolidine-1-carboxylate;

(3S,4S)-3-{[5-(2,4-dichlorophenyl)-3,6-diethylpyrazin-2-yl]amino}-4-ethoxypyrrolidin-2-one (3S,4S)-3-{[5-(2,4-dichlorophenyl)-3,6-diethylpyrazin-2-yl]amino}-4-ethoxy-1-methylpyrrolidin-2-one;

(3S,4S)-1-benzyl-3-{[5-(2,4-dichlorophenyl)-3,6-diethylpyrazin-2-yl]amino}-4-(2-fluoroethoxy)pyrrolidin-2-one;

(3R,4R)-4-{[5-(2,4-dichlorophenyl)-3,6-diethylpyrazin-2-yl]amino}-3-(2-fluoroethoxy)pyrrolidin-2-one;

(3R,4R)-4-{[5-(2,4-dichlorophenyl)-3,6-diethylpyrazin-2-yl]amino}-3-(2-fluoroethoxy)-1-methylpyrrolidin-2-one;

(3R,4R)-1-benzyl-4-{[5-(2,4-dichlorophenyl)-3,6-diethylpyrazin-2-yl]amino}-3-(2-fluoroethoxy)pyrrolidin-2-one;

5-(2,4-dichlorophenyl)-3,6-diethyl-N-[(2S)-2-(methoxymethyl)pyrrolidin-1-yl]pyrazin-2-amine;

5-(2,4-dichlorophenyl)-3,6-diethyl-N-[(2R)-2-(methoxymethyl)pyrrolidin-1-yl]pyrazin-2-amine;

5-(2,4-dichlorophenyl)-N-[(2R)-2-(ethoxymethyl)pyrrolidin-1-yl]-3,6-diethylpyrazin-2-amine;

5-(2,4-dichlorophenyl)-3,6-diethyl-N-[(2R)-2-(propoxymethyl)pyrrolidin-1-yl]pyrazin-2-amine;

5-(2-chloro-4-methoxyphenyl)-3,6-diethyl-N-{(2R)-2-[(2-fluoroethoxy)methyl]pyrrolidin-1-yl}pyrazin-2-amine;

5-(2-chloro-4-methoxyphenyl)-N-[(2R)-2-(ethoxymethyl)pyrrolidin-1-yl]-3,6-diethylpyrazin-2-amine;

methyl (3R,4S)-3-{[5-(2,4-dichlorophenyl)-3,6-bis(methoxymethyl)pyrazin-2-yl]amino}-4-(2-fluoroethoxy)pyrrolidine-1-carboxylate;

methyl (3R,4S)-3-{[5-(2-chloro-4-methoxyphenyl)-3,6-bis(methoxymethyl)pyrazin-2-yl]amino}-4-(2-fluoroethoxy)pyrrolidine-1-carboxylate;

(3R,4R)-4-{[5-(2-chloro-4-methoxyphenyl)-3,6-diethylpyrazin-2-yl]amino}tetrahydrofuran-3-yl acetate;

(3R,4R)-4-{[5-(2,4-dichlorophenyl)-3,6-diethylpyrazin-2-yl]amino}tetrahydrofuran-3-yl acetate;

(3R,4R)-4-{[5-(2-chloro-4-methoxyphenyl)-3,6-diethylpyrazin-2-yl]amino}tetrahydrofuran-3-yl propionate;

(3R,4R)-4-{[5-(2,4-dichlorophenyl)-3,6-diethylpyrazin-2-yl]amino}tetrahydrofuran-3-yl propionate;

5-(2,4-dichlorophenyl)-3,6-diethyl-N-[(3R,4R)-4-propoxytetrahydrofuran-3-yl]pyrazin-2-amine;

5-(2,4-dichlorophenyl)-3,6-diethyl-N-[(3R,4R)-4-(3-fluoropropoxy)tetrahydrofuran-3-yl]pyrazin-2-amine;

(3S,4R)-3-{[5-(2-chloro-4-methoxyphenyl)-3,6-diethylpyrazin-2-yl]amino}-4-(2-fluoroethoxy)dihydrofuran-2(3H)-one;

(3S,4R)-3-{[5-(2-chloro-4-methoxyphenyl)-3,6-diethylpyrazin-2-yl]amino}-4-ethoxydihydrofuran-2(3H)-one;

(3R,4S)-4-{[5-(2-chloro-4-methoxyphenyl)-3,6-diethylpyrazin-2-yl]amino}-5-oxotetrahydrofuran-3-yl acetate;

(3R,4S)-4-{[5-(2-chloro-4-methoxyphenyl)-3,6-diethylpyrazin-2-yl]amino}-5-oxotetrahydrofuran-3-yl propionate;

(3S,4R)-3-{[5-(2-chloro-4-methoxyphenyl)-3,6-diethylpyrazin-2-yl]amino}-4-propoxydihydrofuran-2(3H)-one;

(3S,4R)-3-{[5-(2-chloro-4-methoxyphenyl)-3,6-diethylpyrazin-2-yl]amino}-4-(3-fluoropropoxy)dihydrofuran-2(3H)-one; or a pharmaceutically acceptable salt of any said compound.

12. A compound of claim 1 wherein the compound exhibits an $IC_{50}$ for CRF receptor binding of 1 micromolar or less in a CRF binding assay using IMR-32 human neuroblastoma cells.

13. A compound of claim 12 wherein the compound exhibits an $IC_{50}$ for CRF receptor binding of 100 nanomolar or less.

14. A compound of claim 12 wherein the compound exhibits an $IC_{50}$ for CRF receptor binding of 10 nanomolar or less.

15. A pharmaceutical composition comprising a compound of claim 1 and a pharmaceutically acceptable carrier or excipient.

16. A method of inhibiting the binding of CRF to the $CRF_1$ receptor, the method comprising contacting, in the presence of CRF, a solution comprising a compound of claim 1 with cells expressing the $CRF_1$ receptor, wherein the compound is present in the solution at a concentration sufficient to reduce levels of CRF binding to the cells in vitro.

17. An article of manufacture comprising: a) a packaging material; b) a compound of claim 1, and c) a label or package insert contained within said packaging material indicating that said compound is effective for treating affective disorder, anxiety or depression.

18. A method of treating a disorder in a mammal, comprising administering to the mammal in need thereof an effective amount of a compound of claim 1, wherein the disorder is selected from social anxiety disorder; anxiety with co-morbid depressive illness; anxiety; depression; post-traumatic stress disorder; drug or alcohol withdrawal symptoms; generalized anxiety disorder; bipolar disorders.

19. The method of claim 18 wherein the mammal is a human.

20. The method according to claim 19 wherein the disorder is selected from anxiety, and depression.

* * * * *